(12) United States Patent
Blank et al.

(10) Patent No.: US 9,890,166 B2
(45) Date of Patent: Feb. 13, 2018

(54) IMIDAZOPYRROLIDINE DERIVATIVES AND THEIR USE IN THE TREATMENT OF DISEASE

(71) Applicants: Jutta Blank, Binzen (DE); Guido Bold, Gipf-Oberfrick (CH); Simona Cotesta, Basel (CH); Vito Guagnano, Basel (CH); Heinrich Rueeger, Flueh (CH); Andrea Vaupel, Riehen (CH)

(72) Inventors: Jutta Blank, Binzen (DE); Guido Bold, Gipf-Oberfrick (CH); Simona Cotesta, Basel (CH); Vito Guagnano, Basel (CH); Heinrich Rueeger, Flueh (CH); Andrea Vaupel, Riehen (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/892,616

(22) PCT Filed: May 26, 2014

(86) PCT No.: PCT/IB2014/061715
§ 371 (c)(1),
(2) Date: Nov. 20, 2015

(87) PCT Pub. No.: WO2014/191894
PCT Pub. Date: Dec. 4, 2014

(65) Prior Publication Data
US 2016/0108047 A1 Apr. 21, 2016

(30) Foreign Application Priority Data

May 27, 2013 (EP) .................................. 13169390
Jul. 23, 2013 (EP) .................................. 13177676

(51) Int. Cl.
| | | |
|---|---|---|
| *C07D 487/04* | (2006.01) | |
| *C07D 471/04* | (2006.01) | |
| *A61K 31/4192* | (2006.01) | |
| *A61K 31/4439* | (2006.01) | |
| *A61K 31/444* | (2006.01) | |
| *A61K 31/5025* | (2006.01) | |
| *A61K 31/513* | (2006.01) | |
| *A61K 31/5377* | (2006.01) | |

(52) U.S. Cl.
CPC ........ *C07D 487/04* (2013.01); *A61K 31/4192* (2013.01); *A61K 31/444* (2013.01); *A61K 31/4439* (2013.01); *A61K 31/5025* (2013.01); *A61K 31/513* (2013.01); *A61K 31/5377* (2013.01); *C07D 471/04* (2013.01)

(58) Field of Classification Search
CPC ........................... C07D 487/04; C07D 471/04
See application file for complete search history.

(56) References Cited

U.S. PATENT DOCUMENTS

| | | |
|---|---|---|
| 3,829,420 A | 8/1974 | Inaba et al. |
| 3,865,827 A | 2/1975 | Yamamoto et al. |
| 3,923,710 A | 12/1975 | Ishizumi et al. |
| 4,099,002 A | 7/1978 | Inaba et al. |
| 4,258,187 A | 3/1981 | Middleton |
| 4,335,127 A | 6/1982 | Vandenberk et al. |
| 4,695,633 A | 9/1987 | Berneth et al. |
| 6,479,499 B1 | 11/2002 | Kuo et al. |
| 6,734,302 B2 | 5/2004 | Kong et al. |
| 7,541,354 B2 | 6/2009 | Fancelli et al. |
| 8,101,644 B2 | 1/2012 | Kai et al. |
| 8,222,288 B2 | 7/2012 | Wang et al. |
| 8,440,693 B2 | 5/2013 | Berghausen et al. |
| 8,815,926 B2 * | 8/2014 | Furet .............................. 514/393 |
| 2003/0153580 A1 | 8/2003 | Kong et al. |
| 2006/0069085 A1 | 3/2006 | Zhao et al. |
| 2008/0153791 A1 | 6/2008 | Wilckens |
| 2009/0163545 A1 | 6/2009 | Goldfarb |

(Continued)

FOREIGN PATENT DOCUMENTS

| | | |
|---|---|---|
| EP | 1657238 A1 | 5/2006 |
| EP | 2 143 713 A1 | 1/2010 |

(Continued)

OTHER PUBLICATIONS

No Author Listed, National Cancer Institute. "Drugs Approved for Leukemia." © 2013. Available from: http://www.cancer.gov/cancertopics/druginfo/leukemia/print >.
Richter et al., An Optimised Small-Molecule Stabiliser of the 14-3-3-PMA2 Protein-Protein Interaction. Chem. Eur. J. 2012;18(21):6520-7.
Sun et al., Single-Nucleotide Polymorphisms in p53 Pathway and Aggressiveness of Prostate Cancer in a Caucasian Population. Clin. Cancer Res. 2010;16:5244-51.
Vanotti et al., Cdc7 Kinase Inhibitors: Pyrrolopyrimidinones as Potential Antitumor Agents. 1. Synthesis and Structure-Activity Relationships. Journal of Medicinal Chemistry. 2008;51:487-501.
Wade et al., Targeting Mdm2 and Mdmx in Cancer Therapy: Better Living through Medicinal Chemistry? Mol. Cancer Res. 2009;7:1-11.
Wang et al., Benzimidazole-2-one: A novel anchoring principle for antagonizing p53-Mdm2. Bioorganic & Medicinal Chemistry 2013;21:3982-95.
Westphal The formation of pyrrolo[3,4-c]pyrazoles. Journal for Practical Chemistry. 1969;311:379-84.

(Continued)

*Primary Examiner* — Laura L. Stockton
(74) *Attorney, Agent, or Firm* — Asimina T. Georges Evangelinos

(57) ABSTRACT

The present invention provides a compound of formula (I) or a pharmaceutically acceptable salt thereof; a method for manufacturing the compounds of the invention, and its therapeutic uses. The present invention further provides a combination of pharmacologically active agents and a pharmaceutical composition.

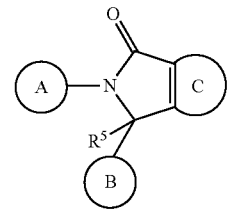

13 Claims, No Drawings

(56) References Cited

U.S. PATENT DOCUMENTS

| | | |
|---|---|---|
| 2010/0160356 A1 | 6/2010 | Heinrich et al. |
| 2010/0210632 A1 | 8/2010 | Hiroyuki et al. |
| 2011/0183939 A1 | 7/2011 | Kai et al. |
| 2011/0230457 A1 | 9/2011 | Berghausen et al. |
| 2011/0301133 A1 | 12/2011 | Wu et al. |
| 2012/0065210 A1 | 3/2012 | Chu et al. |
| 2013/0245036 A1 | 9/2013 | Berghausen et al. |
| 2013/0281396 A1 | 10/2013 | McLure et al. |
| 2013/0281473 A1 | 10/2013 | Berghausen et al. |
| 2013/0317024 A1 | 11/2013 | Cotesta et al. |
| 2014/0011798 A1 | 1/2014 | Furet et al. |
| 2014/0135306 A1 | 5/2014 | Buschmann et al. |

FOREIGN PATENT DOCUMENTS

| | | |
|---|---|---|
| JP | 45-16950 A | 6/1970 |
| JP | 46-15500 A | 4/1971 |
| JP | 57021388 | 2/1982 |
| JP | 2001302515 A | 10/2001 |
| JP | 2005-511766 A | 4/2005 |
| JP | 2006-524228 | 10/2006 |
| JP | 2014-533745 | 12/2014 |
| WO | 1993/04047 A1 | 3/1993 |
| WO | 1995/19362 A1 | 7/1995 |
| WO | 1998/01467 A2 | 1/1998 |
| WO | 1998/19362 A1 | 5/1998 |
| WO | 1998/45276 A2 | 10/1998 |
| WO | 2000/066560 A1 | 11/2000 |
| WO | 2002/012242 A2 | 2/2002 |
| WO | 2003/051359 | 6/2003 |
| WO | 2003/062392 A2 | 7/2003 |
| WO | 2003/095625 A2 | 11/2003 |
| WO | 2003/101985 A1 | 12/2003 |
| WO | 2004/014916 | 2/2004 |
| WO | 2004/014916 A1 | 2/2004 |
| WO | 2004/094421 A1 | 11/2004 |
| WO | 2004/094429 A1 | 11/2004 |
| WO | 2004/096134 A2 | 11/2004 |
| WO | 2005/027882 A1 | 3/2005 |
| WO | 2005/051922 A1 | 6/2005 |
| WO | 2005/110996 A1 | 11/2005 |
| WO | 2005/117876 A1 | 12/2005 |
| WO | 2006/024837 A1 | 3/2006 |
| WO | 2006/074262 A1 | 7/2006 |
| WO | 2006/097337 A1 | 9/2006 |
| WO | 2006/100038 A1 | 9/2006 |
| WO | 2006/136606 A2 | 12/2006 |
| WO | 2007/068637 A1 | 6/2007 |
| WO | 2007/096334 A1 | 8/2007 |
| WO | 2007/144384 A1 | 12/2007 |
| WO | 2008/034039 A2 | 3/2008 |
| WO | 2008/045529 A1 | 4/2008 |
| WO | 2008/120725 A1 | 10/2008 |
| WO | 2008/130614 A2 | 10/2008 |
| WO | 2010/007116 A2 | 1/2010 |
| WO | 2010/035727 A1 | 4/2010 |
| WO | 2010/047956 A1 | 4/2010 |
| WO | 2010/141738 A2 | 12/2010 |
| WO | 2011/076786 A1 | 6/2011 |
| WO | 2011/161031 A1 | 12/2011 |
| WO | 2012/034954 A1 | 3/2012 |
| WO | 2012/046030 A2 | 4/2012 |
| WO | 2012/065022 A2 | 5/2012 |
| WO | 2012/151512 A2 | 11/2012 |
| WO | 2012/174487 A2 | 12/2012 |
| WO | 2012/175487 A2 | 12/2012 |
| WO | 2012/175520 A1 | 12/2012 |
| WO | 2013/027168 A1 | 2/2013 |
| WO | 2013/033268 A2 | 3/2013 |
| WO | 2013/033270 A2 | 3/2013 |
| WO | 2013/080141 A1 | 6/2013 |
| WO | 2013/097052 A1 | 7/2013 |
| WO | 2013/111105 A1 | 8/2013 |
| WO | 2013/156869 A1 | 10/2013 |
| WO | 2013/158952 A1 | 10/2013 |
| WO | 2013/175281 A1 | 11/2013 |
| WO | 2013/175417 A1 | 11/2013 |
| WO | 2014/191894 A1 | 12/2014 |

OTHER PUBLICATIONS

Gein et al, "Synthesis and analgesic activity of 5-aryl-4-heteroyl-3-hydroxy-1-(2-thiazolyl)-3-pyrrolin-2-ones and their derivatives" Perm State Pharmaceutical Academy, Perm, 614990, Russia; Pharmaceutical Chemistry Journal (2014), 47(10), 539-543.

Acharya, B.P. et al., "Friedel-Crafts Acylation with 2-Isocyanatobenzoyl Chlorides: The Structure of the Intermediate Complex," Journal of Chemical Research, Synopses, (4):96-7 (1987)[Abstract only].

Bahloul, A. et al., "1,3-Dipolar Cycloaddition of Diarylnitrilimines with 4-Arylidene-1,2-Diphenyl-1,4-Dihydro-3(2H)-Isoquinolin-3-Ones," Journal de la Societe Marocaine de Chimie, 2(1):12-17 (French)(1993)[Abstract only].

Chen, R. et al., "Ytterbium(III) Triflate-Catalyzed Stereoselective Synthesis of Beta-lactams via [2+2] Cyclocondensation in Ionic Liquid," Synthetic Communications, 36(21):3167-3174, Taylor & Francis Group, LLC (English)(2006).

De Luca et al., "3D Pharmacophore Models for 1,2,3,4-Tetrahydroisoquinoline Derivatives Acting as Anticonvulsant Agents" Arch. Pharm. Chem. Life Sci., 2006, 339, 388-400.

Dietz, G. et al.; "Synthesis and Conversion of 3,4-Dihydroquinazolin-4-ols. Part 2: Conversion of 3,4-Dihydroquinazolin-4-ols;" Direktionsber. Forsch. Entwickl., VEB Pharm. Komb. Germed Dresden, Dresden, Ger. Dem. Rep.; Pharmazie; 35(12):751-5 (German)(1980)[Abstract only].

Dudkina, Anna S. et al. "Small Molecule Protein-Protein Inhibitors for the p53-MDM2 Interaction", Current Topics in Medicinal Chemistry, 2007, 7, pp. 952-960.

Ishiwaka, N. et al., "o-Aminobenzophenone Derivatives. V. Reactions of 2-Amino-5-Chloro-Benzophenone with Isocyanates and Isothiocyanates," Kagaku Zasshi, 90(9):917-20 (Japanese)(1969)[Abstract only].

Ishiwaka, N. et al., "Reaction of 2-Amino-5-Chlorobenzophenone with P-Substituted Phenyl Isocyanates," Kagaku Zasshi, 91(10):994-7 (Japanese)(1970)[Abstract only].

Ivanov et al., Polyphosphoric acid-induced construction of quinazolinone skeleton from 1-(3,4-dimethoxyphenyl)-3-phenylurea and carboxylic acids. Heterocycles. May 12, 2006;68(7):1443-9.

Ivanov, I., "Synthesis of 6,7-Dimethoxy-3,4-Diphenyl-2(1H)-Quinazolinone from 1-(3,4-Dimethoxyphenyl)Urea and Benzoic Acid in Polyphosphoric Acid," Molbank M492/1-M492/2 (English)(2006)[Abstract only].

Mollov, N.M. et al., "Internal Alpha-Amidoalkylation Leading to 1,4-Dihydro-3(2H)-Isoquinolinones," Acta Chimica Academiae Scientiarum Hungaricae, 98(3):315-19 (English)(1978).

Mollov, N.M. et al., "Reactivity of Adducts Obtained from Arylacetyl Chloride and Aromatic Schiff Bases," Izvestiya po Khimiya, 10(4):616-20 (English)(1977).

Mollov, N. M. et al., "Synthesis of 3(2H)-isoquinolinones by Means of Inner Alpha-Amidoalkylation," Doklady Bolgarskoi Akademii Nauk, 28(8):1055-7 (English)(1975)[Abstract only].

Mumm, O. et al., "Diacylamides," Berichte der Deutschen Chemischen Gesellschaft, 48:379-91 (1915)[Abstract only].

Pfeiffer, P. et al., "Autoxidation Phenomena in the Anils of the Indandione Series. II," Journal fuer Praktische Chemie (Leipzig), 159:13-35 (1941)[Abstract and Article].

Pfeiffer, P. et al., "Autoxidation Phenomena. VI," Justus Liebigs Annalen der Chemie, 563:73-85 (1949)[Abstract and Article].

Pfeiffer, P. et al., "Autoxidation Reactions. VII," Justus Liebigs Annalen der Chemie, 581:149-59 (1953)[Abstract and Article].

Richter, D., "Anthraquinone Coloring Matters: Ruberythric Acid," Journal of the Chemical Society, 1701-3 (1936).

Richter, P. et al., "Synthesis of Derivatives of 2-Hydrazino-1,4- or 3,4-Dihydroquinazolines," Pharmazie, 45(10):721-4 (German)(1990)[Abstract only].

Schonberg, A. et al., "Autoxidation Effects in the Indone Series," Naturwissenschaften, 24:620 (1936)[Abstract only].

(56) References Cited

OTHER PUBLICATIONS

Schonberg, A. et al., "Autoxidation Phenomena and Valency Tautomerism in the Indone Series," Journal of the Chemical Society, 109-12 (1937).
Shangary, Sanjeev et al., "Targeting the MDM2-p53 Interaction for Cancer Therapy", Clin. Cancer Res., 2008, 14, 5318-5324.
Venkov, A. et al., "An Improved Synthesis of N-Substituted 1-Aryl-3-Oxo-1,2,3,4-Tetrahydroisoquinolines," Synthesis, 216-17, Stuttgart, New York (English)(1982).
Ventsov, A. et al., "Synthesis of N-Substituted 1,4-Dihydro-3(2H)-Isoquinolinones from 3,4,5-Trimethoxyphenylacetyl chloride and Schiff Bases," Bolgarskoi Akademii Nauk, 34(10):1405-7 (English)(1981)[Abstract only].
Yamamoto, M. et al., "Synthetic Studies on Quinazoline Derivatives. II. The Reactions of 2-Trichloro- and 2-Trifluoroacetamidobenzophenones with Primary Amines," Chemical & Pharmaceutical Bulletin, 29(8):2135-56 (English)(1981).
Zhang, Y. et al., "Superacid-Promoted Reactions of N-Acyliminium Ions: An Effective Route to Substituted 3-Oxo-1,2,3,4-Tetrahydroisoquinolines and Related Products," Synthesis (11):1775-1780 (English)(2006).
Zin'Kovskaya, V.R. et al., "Ring-chain transformations involving the carbonyl group. XVI. Amides of 2-benzoylphenyl-Alpha,Alpha-dimethylacetic acid," Latvijas PSR Zinatnu, Akademijas Vestis, Kimijas Serija, (1)65-8 (Russian)(1976)[Abstract only].
Sheng, R. et al, Pharmacophore model construction of p53-MDM2 binding inhibitors, Acta Physico-Chimica Sinica, Aug. 6, 2007, vol. 23, No. 11,p. 1815-1820.
Aebi, A. et al, Pharmaceutica Acta Helvetiae, vol. 38, Issue: 7-8, pp. 616-622, Journal, 1963.
Shams El-Dine, S. A et al Pharmazie, vol. 56, Issue: 12, pp. 933-937, Journal, 2001.
Chaudhari, P.V., Oriental Journal of Chemistry (2012), 28(1), 507-512.
Journal of Enzyme Inhibition and Medicinal Chemistry (2011), 26(4), 472-479.
J. D. Akbari et al.: Indian Journal of Chemistry, Section B: Organic Chemistry Including Medicinal Chemistry (2008), 47B(3), 477-480.
Raj et al.: Organic Chemistry: An Indian Journal (2007), 3(4),176-179.
Ahmed Kamal et al.: Expert opinion on therapeutic patents 2012, vol. 22, No. 2, pp. 95-105, XP055107028.
Chung et al., Fragment-based discovery of bromodomain inhibitors part 1: inhibitor binding modes and implications for lead discovery. J Med Chem. Jan. 26, 2012;55(2):576-86.
Filippakopoulos et al., Benzodiazepines and benzotriazepines as protein interaction inhibitors targeting bromodomains of the BET family. Bioorg Med Chem. Mar. 15, 2012;20(6):1878-86.
Filippakopoulos et al., Selective inhibition of BET bromodomains. Nature. Dec. 23, 2010;468(7327):1067-73.
Hackam et al., Translation of research evidence from animals to humans. JAMA. Oct. 11, 2006;296(14):1731-2.
Jordan, Tamoxifen: a most unlikely pioneering medicine. Nat Rev Drug Discov. Mar. 2003;2(3):205-13.
Wu et al., The double bromodomain-containing chromatin adaptor Brd4 and transcriptional regulation. J Biol Chem. May 4, 2007;282(18):13141-5.
Andreichikov et al., Chemistry of Oxalyl Derivatives of Methyl Ketones XLIV. Synthesis of 4-Aroyl-1,5-Diphenyltetrahydropyrrole-2,3-Diones and their Reaction with Amines and Hydrazine. Journal of Organic Chemistry 1986;22(8):1572-7.
Dohrn et al., Berichte der Deutschen Chemischen Gesellschaft [Abteilung] B: Abhandlungen. 1931;64B:2863-5.
Gein et al., Reactions of 4-Acyl-1-alkoxyaryl-5-aryl-3-hydroxy-2,5-dihydro-1 H-pyrrol-2-ones with Nucleophilic Reagents. Russian Journal of Organic Chemistry. 2011;47(1):95-9.
Gein et al., 5-Membered 2,3-Dioxoheterocyclic Compounds. Journal of General Chemistry. 1993;63(10):2324-8.
Lee et al., Novel Pyrrolopyrimidine-Based alpha-Helix Mimetics: Cell Permeable Inhibitors of Protein-Protein Interactions. Journal of the American Chemical Society. 2010;133:676-9.
Miyazaki et al., Lead optimization of novel p53-MDM2 interaction inhibitors possessing dihydroimidazothiazole scaffold. Bioorganic and Medicinal Chemistry Letters. 2013;23:728-32.
No Auhtor Listed, WedMD "Leukemia." Available from: <http://www.webmd.com/cancer/tc/leukemia-prevention?print=true#> @2010.
No Author Listed, American Cancer Society. "Leukemia—Acute Myeloid (Myelogenous)." © 2013. Available from: <http://www.cancer.org/cancer/leukemia-acutemyeloidaml/detailedguide/leukemia-acute-myeloid-myelogenous-what-is-aml >.
No Author Listed, Mayo Clinic "Leukemia Medications." Available from: <http://www.drugs.com/condition/leukemia.html> @2013.

* cited by examiner

IMIDAZOPYRROLIDINE DERIVATIVES AND THEIR USE IN THE TREATMENT OF DISEASE

This application is a U.S. National Phase filing of International Application No. PCT/182014/061715 filed 26 May 2014, which claims priority to EP Application No. 13169390.5 filed 27 May 2013 and EP Application No. 13177676.7 filed Jul. 23, 2013.

FIELD OF THE INVENTION

The invention provides imidazopyrrolidinone derivatives and their use as BET inhibitors, for the treatment of conditions or diseases such as cancer.

BACKGROUND OF THE INVENTION

BET proteins are proteins encoded by either of the genes BRD2, BRD3, BRD4, or BRDT. Each of these proteins bears two N-terminal bromodomains. Bromodomains comprise of a conserved ~110 amino acid segment found in at least 42 diverse proteins that specifically interact with acetylated lysines that occur for example on histone tails (Filippakopoulos and Knapp, FEBS Letters, 586 (2012), 2692-2704). Histones are a constituent part of chromatin and their covalent modifications including lysine acetylation regulate gene transcription. Bromodomains are thus believed to regulate transcription by recruiting proteins to genes that are marked with specific patterns of lysine acetylation.

Several published reports have linked the BET protein family to diseases including cancer, metabolic disease and inflammation. Oncogenic fusions of BRD4 or BRD3 and the Nuclear protein in Testis (NUT) gene caused by chromosomal translocations are underlying an aggressive cancer named NUT midline carcinoma (French et al., J Clin Oncol, 22 (2004), 4135-9; French et al., J Clin Pathol, 63 (2008), 492-6). The BRD3/4 bromodomains are preserved in these fusion proteins, and their inhibition either by knockdown or with the selective BET bromodomain inhibitor JQ1 leads to death and/or differentiation of these cancer cells both in vitro and in animal tumour models (Filippakopoulos et al., Nature, 468 (2010), 1067-73). JQ1 and several other selective BET inhibitors have been shown to bind to BET bromodomains and thereby prevent acetyl-lysine binding, which prevents BET proteins from interacting with chromatin and thereby regulating transcription. BRD4 was also identified from an RNAi screen as a target in acute myeloid leukemia (AML) (Zuber et al., Nature, 478 (2011), 524-8). This finding was validated in vitro and in vivo using the BET inhibitor JQ1 and another selective BET inhibitor named I-BET151 that is chemically unrelated to JQ1 (Dawson et al., Nature, 478 (2011), 529-33). These and other studies showed that BET inhibitors have broad anti-cancer activity in acute leukemias, multiple myeloma and other hematological malignancies. In several cancer models an acute downregulation of the oncogenic transcription factor Myc upon BET inhibition has been observed (Delmore et al., Cell, 146 (2011), 904-17; Mertz et al., Proc Natl Acad Sci USA, 108 (2011), 16669-74). More recent studies suggest that the therapeutic potential of BET inhibitors extends to other cancer indications, for example lung and brain cancer.

Another BET inhibitor named I-BET762 that is closely related to JQ1 in chemical structure and the manner in which it binds to BET bromodomains, was reported to modulate expression of key inflammatory genes and thereby protect against endotoxic shock and bacteria-induced sepsis in mouse models (Nicodeme et al., Nature, 468 (2010), 1119-23). This body of data has been used to support the clinical evaluation of the BET inhibitor RVX-208 in clinical trials in patients suffering from atherosclerosis, coronary artery disease, dyslipidemia, diabetes, and other cardiovascular diseases (McNeill, Curr Opin Investig Drugs, 3 (2010), 357-64 and clinicaltrials.gov), Both RVX-208 and I-BET762 have been shown to upregulate Apolipoprotein A-I, which is critically involved in reducing the tissue levels of cholesterol. Finally, BET proteins have been linked to propagation and transcription regulation of several viruses, and therefore it is believed that BET inhibitors could have anti-viral activity (Weidner-Glunde, Frontiers in Bioscience 15 (2010), 537-549).

In summary, inhibitors of BET bromodomains have therapeutic potential in several human diseases.

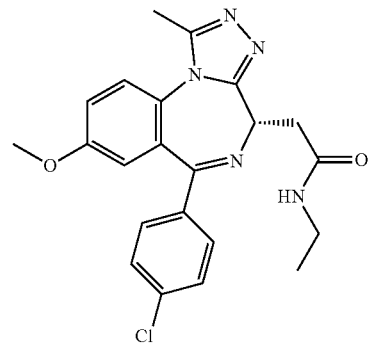

I-BET 762

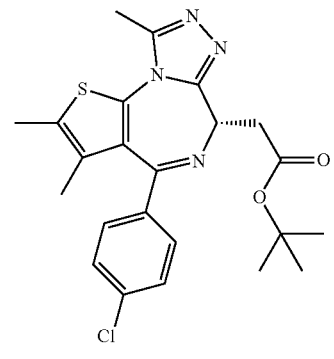

JQ1

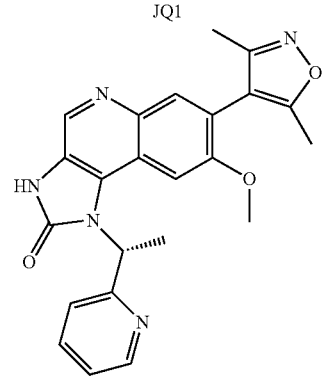

I-BET 151

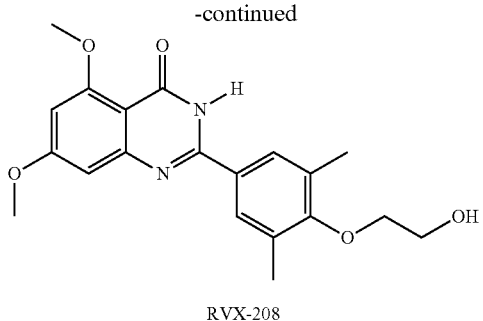

RVX-208

SUMMARY OF THE INVENTION

There remains a need for new treatments and therapies for the treatment of cancer. The invention provides compounds as BET inhibitors, pharmaceutically acceptable salts thereof, pharmaceutical compositions thereof and combinations thereof. The invention further provides methods of treating, preventing or ameliorating cancer, comprising administering to a subject in need thereof an effective amount of a BET inhibitor.

Various embodiments of the invention are described herein. Particularly interesting compounds of the invention have good potency in the biological assays described herein. In another aspect they should have a favourable safety profile. In another aspect, they should possess favourable pharmacokinetic properties.

According to a first aspect of the invention, Embodiment 1, there is provided a compound of formula (I) or a salt thereof,

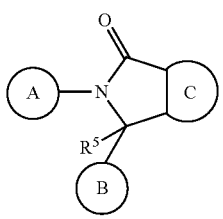

(I)

wherein
A is selected from:

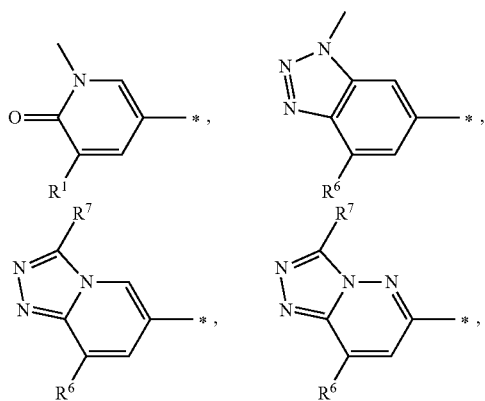

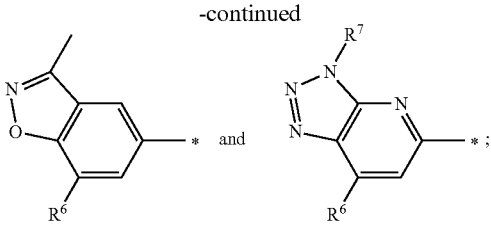

B is selected from

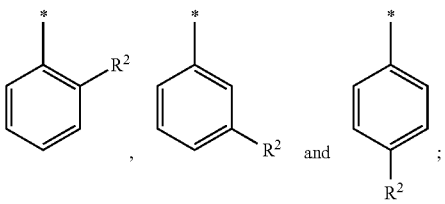

C is selected from:

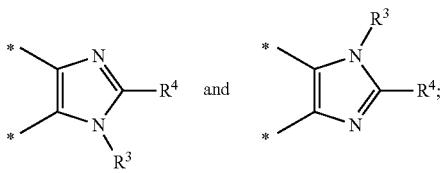

$R^1$ is selected from H, halo and methyl;
$R^2$ is selected from halo, cyano, methyl, —$CF_3$ and —O($C_1$-$C_4$alkyl);
$R^3$ is selected from H, methyl, ethyl, n-propyl, iso-propyl, n-butyl, sec-butyl, iso-butyl, tert-butyl, cyclopropyl, cyclobutyl, cyclopentyl, methoxyethyl-, and

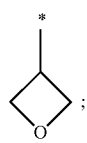

;

$R^4$ is selected from:
H;
$C_1$-$C_4$alkyl;
$C_3$-$C_6$cycloalkyl;
pyridine, optionally substituted with one or two substituents selected from halo, cyano, —OH, —$C_1$-$C_4$alkyl, halo$C_1$-$C_4$alkyl, —O(halo$C_1$-$C_4$alkyl) and —$C_1$-$C_4$alkoxy;
pyrimidin-5-yl, optionally substituted with one or two substituents selected from halo, cyano, —OH, —$C_1$-$C_4$alkyl, halo$C_1$-$C_4$alkyl, —O(halo$C_1$-$C_4$alkyl) and —$C_1$-$C_4$alkoxy;
a 5- or 6-membered saturated or partially unsaturated heterocyclic ring containing 1 oxygen or 1 nitrogen atom or 1 oxygen and 1 nitrogen atom, and optionally substituted with one —$C_1$-$C_6$alkyl substituent, or optionally substituted with 1, 2, 3 or 4 methyl substituents, or optionally substituted with one substituent selected from —C(O) $C_1$-$C_4$alkyl, —C(O)O$C_1$-$C_4$alkyl, —C(O)NH$C_1$-$C_4$alkyl, and —S(O)$_2$$C_1$-$C_4$alkyl;

a 5-membered heteroaryl ring containing 1 or 2 nitrogen atoms, and optionally substituted with —C$_1$-C$_4$alkyl;
a 5-membered heteroaryl ring containing 1 nitrogen atom and 1 oxygen or 1 sulphur atom, optionally substituted with one or two C$_1$-C$_4$alkyl; and

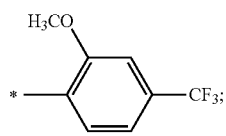

R$^5$ is H;
R$^6$ is selected from methyl and methoxy; and
R$^7$ is selected from methyl, —CH$_2$F and —CHF$_2$;
provided that when
A is

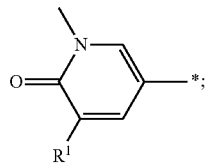

B is

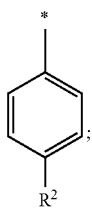

C is

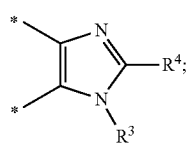

R$^2$ is selected from chloro, fluoro, trifluoromethyl, methyl and cyano; and
R$^3$ is isopropyl, isobutyl, cyclopropyl, cyclobutyl or cyclopentyl; then
R$^4$ is selected from:
H;
C$_1$-C$_4$alkyl;
C$_3$-C$_6$cycloalkyl;
a 5- or 6-membered saturated or partially unsaturated heterocyclic ring containing 1 or 2 heteroatoms selected from oxygen, sulphur and nitrogen, and optionally substituted with C$_1$-C$_4$alkyl; or a 5- or 6-membered saturated or partially unsaturated heterocyclic ring containing 1 oxygen or 1 nitrogen atom, and optionally substituted with one C$_1$-C$_4$alkyl substituent or optionally substituted with 1, 2, 3 or 4 methyl substituents; or a 5- or 6-membered saturated or partially unsaturated heterocyclic ring containing 1 oxygen or 1 nitrogen atom, or 1 oxygen and 1 nitrogen atom, and optionally substituted with one —C$_1$-C$_6$alkyl substituent, or optionally substituted with 1, 2, 3 or 4 methyl substituents, or optionally substituted with one substituent selected from —C(O) C$_1$-C$_4$alkyl, —C(O) OC$_1$-C$_4$alkyl, —C(O)NHC$_1$-C$_4$alkyl, and —S(O)$_2$C$_1$-C$_4$alkyl;
a 5-membered heteroaryl ring containing 1 or 2 nitrogen atoms, and optionally substituted with C$_1$-C$_4$alkyl;
a 5-membered heteroaryl ring containing 1 nitrogen atom and 1 oxygen or 1 sulphur atom, optionally substituted with one or two C$_1$-C$_4$alkyl;

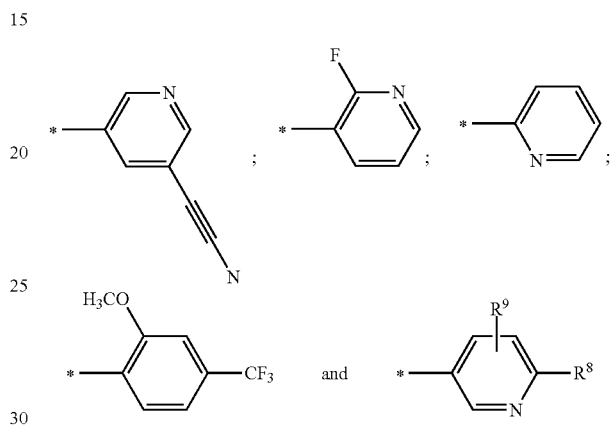

wherein R$^8$ is selected from OCH$_3$, OH and OCF$_3$; and R$^9$ is halo; and wherein * indicates the point of attachment to the remainder of the molecule.

In another embodiment, the invention provides a pharmaceutical composition comprising a therapeutically effective amount of a compound according to the definition of formula (I), or a salt thereof, or subformulae thereof and one or more pharmaceutically acceptable carriers.

In another embodiment, the invention provides a combination, in particular a pharmaceutical combination, comprising a therapeutically effective amount of the compound according to the definition of formula (I), or a salt thereof, or subformulae thereof and one or more therapeutically active agents.

DETAILED DESCRIPTION

Described below are a number of embodiments (E) of the first aspect of the invention, where for convenience Embodiment 1 is identical thereto.

Unless specified otherwise, the term "compounds of the present invention" refers to compounds of formula (I) and subformulae thereof, and salts thereof, as well as all stereoisomers (including diastereoisomers and enantiomers), rotamers, tautomers and isotopically labeled compounds (including deuterium substitutions), as well as inherently formed moieties.

Unless specified otherwise, the term "compounds of the present invention" refers to compounds of formula (I) and subformulae thereof, and salts thereof, as well as all stereoisomers (including diastereoisomers and enantiomers), rotamers, tautomers and isotopically labeled compounds (including deuterium substitutions), as well as inherently formed moieties.

As used herein, the term "C$_{1-6}$alkyl" refers to a fully saturated branched or unbranched hydrocarbon moiety having 1 to 6 carbon atoms. Representative examples of $C_{1-6}$alkyl include methyl, ethyl, n-propyl, iso-propyl, n-butyl, sec-butyl, iso-butyl, tert-butyl, neopentyl (or 2,2-dimethylpropyl). As used herein, the term "$C_{1-4}$alkyl" refers to a fully saturated branched or unbranched hydrocarbon moiety having 1 to 4 carbon atoms. Representative examples of $C_{1-4}$alkyl include methyl, ethyl, n-propyl, iso-propyl, n-butyl, sec-butyl, iso-butyl and tert-butyl.

As used herein, the term "halo$C_{1-4}$alkyl" refers to a $C_{1-4}$alkyl group as defined herein, wherein at least one of the hydrogen atoms is replaced by a halo atom. The halo$C_{1-4}$alkyl group can be monohalo$C_{1-4}$alkyl, dihalo$C_{1-4}$alkyl or polyhalo$C_{1-4}$alkyl including perhalo$C_{1-4}$alkyl. A monohalo$C_{1-4}$alkyl can have one iodo, bromo, chloro or fluoro within the alkyl group. Dihalo$C_{1-4}$alkyl and polyhalo$C_{1-4}$alkyl groups can have two or more of the same halo atoms or a combination of different halo groups within the alkyl. Typically the polyhalo$C_{1-4}$alkyl group contains up to 8, or 6, or 4, or 3, or 2 halo groups. Non-limiting examples of halo$C_{1-4}$alkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo$C_{1-4}$alkyl group refers to an $C_{1-4}$alkyl group having all hydrogen atoms replaced with halo atoms.

As used herein, the term "$C_{3-6}$cycloalkyl" refers to saturated or unsaturated monocyclic, bicyclic or tricyclic hydrocarbon groups of 3-6 carbon atoms. Exemplary $C_{3-6}$cycloalkyl groups include, but are not limited to, cyclopropyl, cyclobutyl, cyclopentyl, cyclopentenyl, cyclohexyl and cyclohexenyl As used herein, the term "heterocyclic ring", "heterocyclyl" or "heterocyclo" refers to a saturated or unsaturated non-aromatic ring or ring system, which is a 5- or 6-membered monocyclic ring containing 1 or 2 heteroatoms selected from O, S and N. The heterocyclic group can be attached via a heteroatom or a carbon atom. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane and thiomorpholine.

As used herein, the term "heteroaryl" refers to a 5- or 6-membered monocyclic aromatic ring containing 1, 2 or 3 heteroatoms selected from O, S and N. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl and 2-, 4-, or 5-pyrimidinyl.

Various embodiments of the invention are described herein. It will be recognized that features specified in each embodiment may be combined with other specified features to provide further embodiments of the present invention.

The invention therefore provides a compound of the formula (I) as described hereinabove as Embodiment 1.

Embodiment 1.1. A compound of formula (I) or a salt thereof, (I)

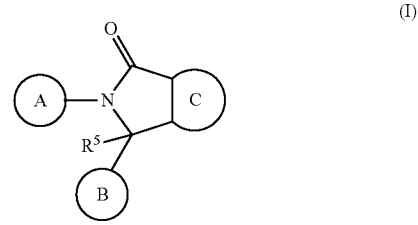

wherein
A is selected from:

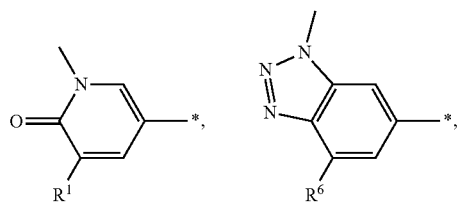

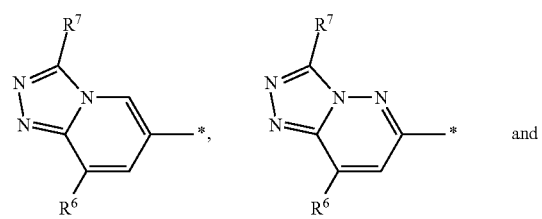

and

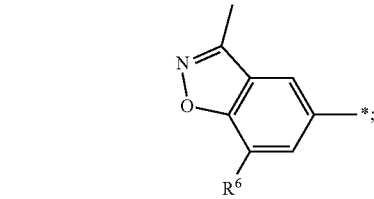

;

B is selected from

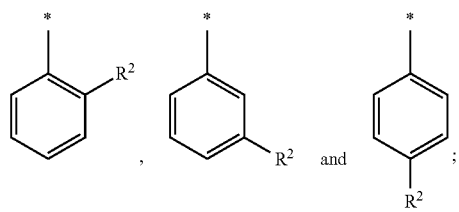

C is selected from:

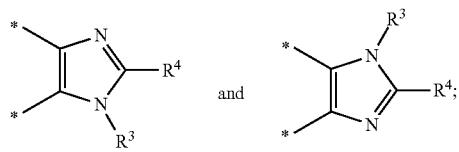

$R^1$ is selected from H, halo and methyl;
$R^2$ is selected from halo, cyano, methyl, —$CF_3$ and —$O(C_1$-$C_4$alkyl);
$R^3$ is selected from H, methyl, ethyl, n-propyl, iso-propyl, n-butyl, sec-butyl, iso-butyl, tert-butyl, cyclopropyl, cyclobutyl, cyclopentyl and methoxyethyl-;
$R^4$ is selected from:
  H;
  $C_1$-$C_4$alkyl;
  $C_3$-$C_6$cycloalkyl;
  pyridine, optionally substituted with one or two substituents selected from halo, cyano, —OH, $C_1$-$C_4$alkyl, halo$C_1$-$C_4$alkyl, and —O(halo$C_1$-$C_4$alkyl);
  pyrimidin-5-yl, optionally substituted with one or two substituents selected from halo, cyano, —OH, $C_1$-$C_4$alkyl, halo$C_1$-$C_4$alkyl, and —O(halo$C_1$-$C_4$alkyl);
  a 5- or 6-membered saturated or partially unsaturated heterocyclic ring containing 1 oxygen or 1 nitrogen atom, and optionally substituted with one $C_1$-$C_4$alkyl substituent or optionally substituted with 1, 2, 3 or 4 methyl substituents;
  a 5-membered heteroaryl ring containing 1 or 2 nitrogen atoms, and optionally substituted with $C_1$-$C_4$alkyl; and
  a 5-membered heteroaryl ring containing 1 nitrogen atom and 1 oxygen or 1 sulphur atom, optionally substituted with one or two $C_1$-$C_4$alkyl;
$R^5$ is H.
$R^6$ is selected from methyl and methoxy; and
$R^7$ is selected from methyl, —$CH_2F$ and —$CHF_2$;
provided that when
A is

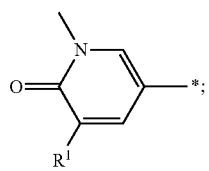

B is

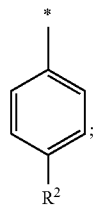

C is

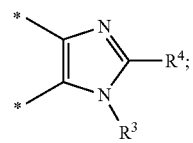

$R^2$ is selected from chloro, fluoro, trifluoromethyl, methyl and cyano; and $R^3$ is isopropyl, isobutyl, cyclopropyl, cyclobutyl or cyclopentyl; then
$R^4$ is selected from:
  H;
  $C_1$-$C_4$alkyl;
  $C_3$-$C_6$cycloalkyl;
  a 5- or 6-membered saturated or partially unsaturated heterocyclic ring containing 1 or 2 heteroatoms selected from oxygen, sulphur and nitrogen, and optionally substituted with $C_1$-$C_4$alkyl; or a 5- or 6-membered saturated or partially unsaturated heterocyclic ring containing 1 oxygen or 1 nitrogen atom, and optionally substituted with one $C_1$-$C_4$alkyl substituent or optionally substituted with 1, 2, 3 or 4 methyl substituents;
  a 5-membered heteroaryl ring containing 1 or 2 nitrogen atoms, and optionally substituted with $C_1$-$C_4$alkyl;
  a 5-membered heteroaryl ring containing 1 nitrogen atom and 1 oxygen or 1 sulphur atom, optionally substituted with one or two $C_1$-$C_4$alkyl;

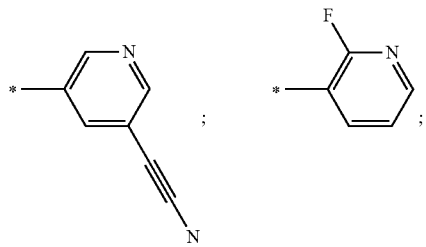

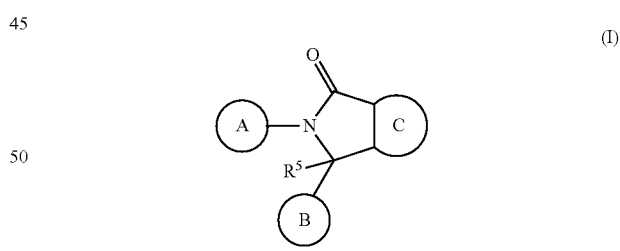

wherein $R^8$ is selected from $OCH_3$, OH and $OCF_3$; and $R^9$ is halo; and wherein * indicates the point of attachment to the remainder of the molecule.

Embodiment 1.2. A compound of formula (I) or a salt thereof,

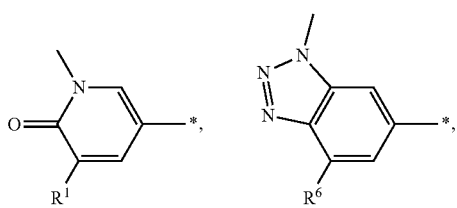

(I)

wherein
A is selected from:

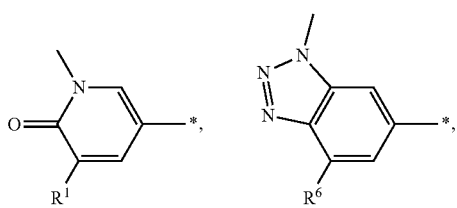

-continued

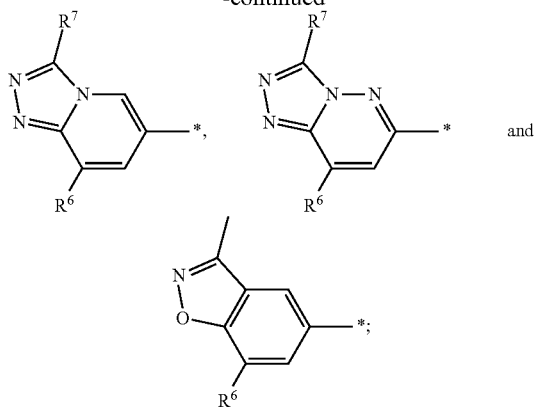

B is selected from

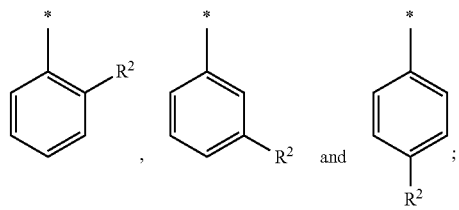

C is selected from:

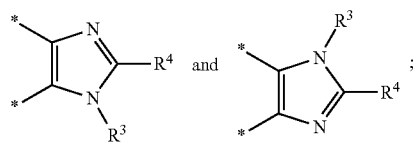

R¹ is selected from H, halo and methyl;
R² is selected from halo, cyano, methyl, —CF₃ and —O(C₁-C₄alkyl);
R³ is selected from H, methyl, ethyl, n-propyl, iso-propyl, n-butyl, sec-butyl, iso-butyl, tert-butyl, cyclopropyl, cyclobutyl, cyclopentyl and methoxyethyl-;
R⁴ is selected from:
H;
C₁-C₄alkyl;
C₃-C₆cycloalkyl;
pyridine, optionally substituted with one or two substituents selected from halo, cyano, —OH, C₁-C₄alkyl, haloC₁-C₄alkyl, and —O(haloC₁-C₄alkyl);
pyrimidin-5-yl, optionally substituted with one or two substituents selected from halo, cyano, —OH, C₁-C₄alkyl, haloC₁-C₄alkyl, and —O(haloC₁-C₄alkyl);
a 5- or 6-membered saturated or partially unsaturated heterocyclic ring containing 1 oxygen or 1 nitrogen atom, and optionally substituted with C₁-C₄alkyl;
a 5-membered heteroaryl ring containing 1 or 2 nitrogen atoms, and optionally substituted with C₁-C₄alkyl; and
a 5-membered heteroaryl ring containing 1 nitrogen atom and 1 oxygen or 1 sulphur atom, optionally substituted with one or two C₁-C₄alkyl;

R⁵ is H.
R⁶ is selected from methyl and methoxy; and
R⁷ is selected from methyl, —CH₂F and —CHF₂;
provided that when
A is

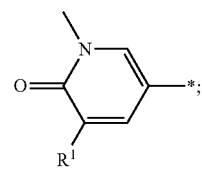

B is

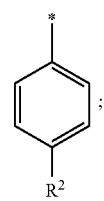

C is

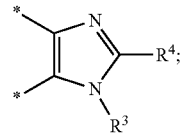

R² is selected from chloro, fluoro, trifluoromethyl, methyl and cyano; and
R³ is isopropyl, isobutyl, cyclopropyl, cyclobutyl or cyclopentyl; then
R⁴ is selected from:
H;
C₁-C₄alkyl;
C₃-C₆cycloalkyl;
a 5- or 6-membered saturated or partially unsaturated heterocyclic ring containing 1 or 2 heteroatoms selected from oxygen, sulphur and nitrogen, and optionally substituted with C₁-C₄alkyl;
a 5-membered heteroaryl ring containing 1 or 2 nitrogen atoms, and optionally substituted with C₁-C₄alkyl;
a 5-membered heteroaryl ring containing 1 nitrogen atom and 1 oxygen or 1 sulphur atom, optionally substituted with one or two C₁-C₄alkyl;

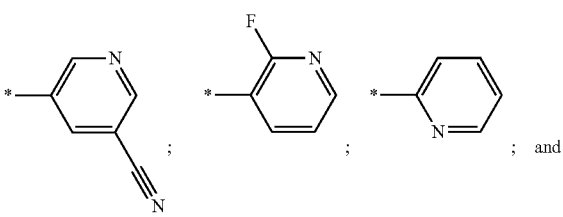

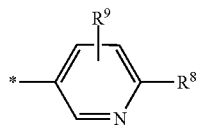

wherein R$^8$ is selected from OCH$_3$, OH and OCF$_3$; and R$^9$ is halo; and wherein * indicates the point of attachment to the remainder of the molecule.

Embodiment 2. A compound of formula (I), or a salt thereof, according to Embodiment 1, 1.1 or 1.2, which is of the formula (Ia):

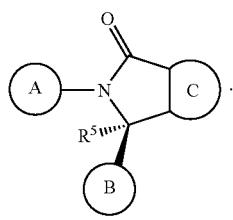

(Ia)

Embodiment 3. A compound of formula (I), or a salt thereof, according to Embodiment 1, 1.1, 1.2 or 2, which is of the formula (II) or (IIa):

(II)

(IIa)

Embodiment 4. A compound of formula (I), or a salt thereof, according to Embodiment 1, 1.1, 1.2 or 2, which is of the formula (III) or (IIIa):

(III)

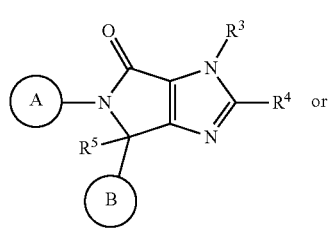

(IIIa)

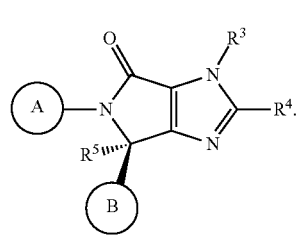

Embodiment 5. A compound of formula (I), or a salt thereof, according to any preceding Embodiment, wherein when A is

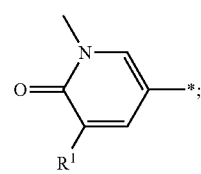

B is

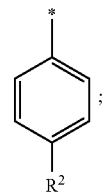

R$^2$ is selected from chloro, fluoro, trifluoromethyl, methyl and cyano; and

R$^3$ is isopropyl, isobutyl, cyclopropyl, cyclobutyl or cyclopentyl; then

R$^4$ is selected from:

H;

C$_1$-C$_4$alkyl;

C$_3$-C$_6$cycloalkyl;

a 5- or 6-membered saturated or partially unsaturated heterocyclic ring containing 1 or 2 heteroatoms selected from oxygen, sulphur and nitrogen, and optionally substituted with C$_1$-C$_4$alkyl; or a 5- or 6-membered saturated or partially unsaturated heterocyclic ring containing 1 oxygen or 1 nitrogen atom, and optionally substituted with one C$_1$-C$_4$alkyl substituent or optionally substituted with 1, 2, 3 or 4 methyl substituents;

a 5-membered heteroaryl ring containing 1 or 2 nitrogen atoms, and optionally substituted with C$_1$-C$_4$alkyl;

a 5-membered heteroaryl ring containing 1 nitrogen atom and 1 oxygen or 1 sulphur atom, optionally substituted with one or two C$_1$-C$_4$alkyl;

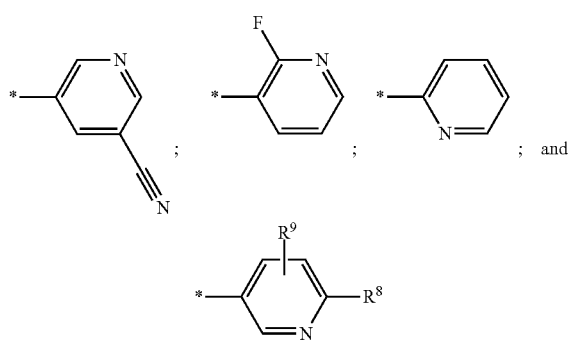
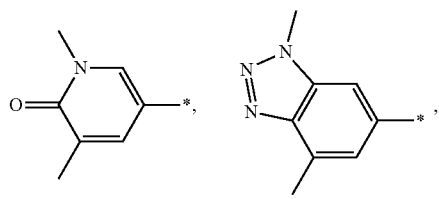
wherein $R^8$ is selected from $OCH_3$, OH and $OCF_3$; and $R^9$ is halo;
Embodiment 6. A compound of formula (I), or a salt thereof, according to any preceding Embodiment, wherein A is selected from:
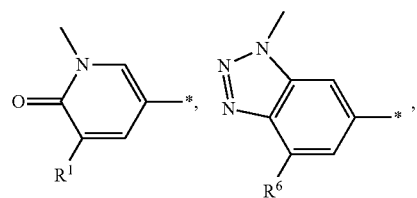
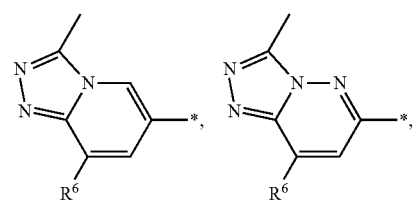
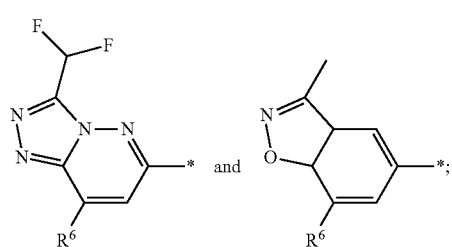
or A is selected from
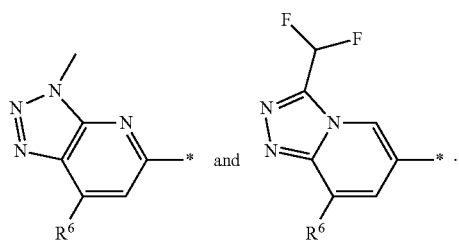
Embodiment 7. A compound of formula (I), or a salt thereof, according to any preceding Embodiment, wherein A is selected from:
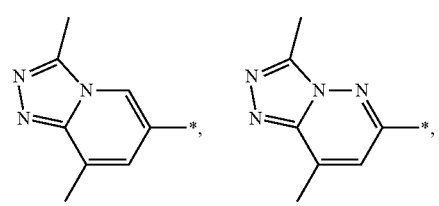
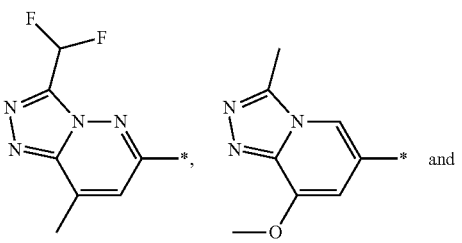
or A is selected from
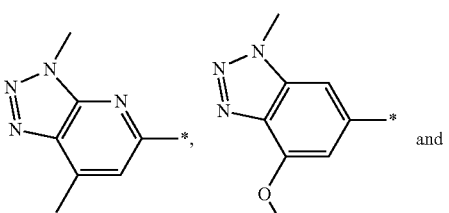
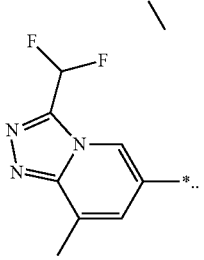

Embodiment 8. A compound of formula (I), or a salt thereof, according to any preceding Embodiment, wherein B is

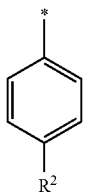

Embodiment 9. A compound of formula (I), or a salt thereof, according to any preceding Embodiment, wherein $R^2$ is selected from chloro, fluoro, bromo, cyano and —$CF_3$.

Embodiment 10. A compound of formula (I), or a salt thereof, according to any preceding Embodiment, wherein $R^2$ is chloro.

Embodiment 11. A compound of formula (I), or a salt thereof, according to any preceding Embodiment, wherein $R^3$ is selected from H, methyl, ethyl, n-propyl, isopropyl, cyclopropyl and t-butyl; or $R^3$ is

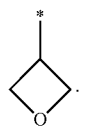

Embodiment 12. A compound of formula (I), or salt thereof, according to any preceding Embodiment, wherein $R^4$ is selected from:

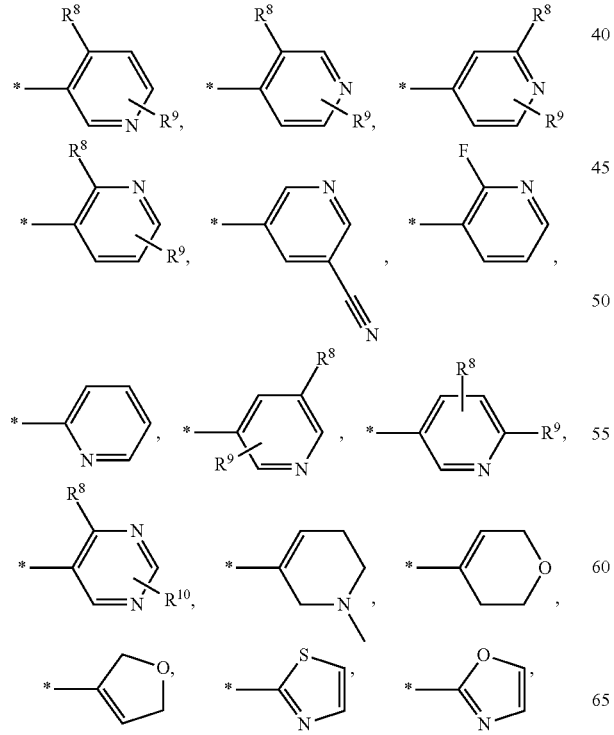

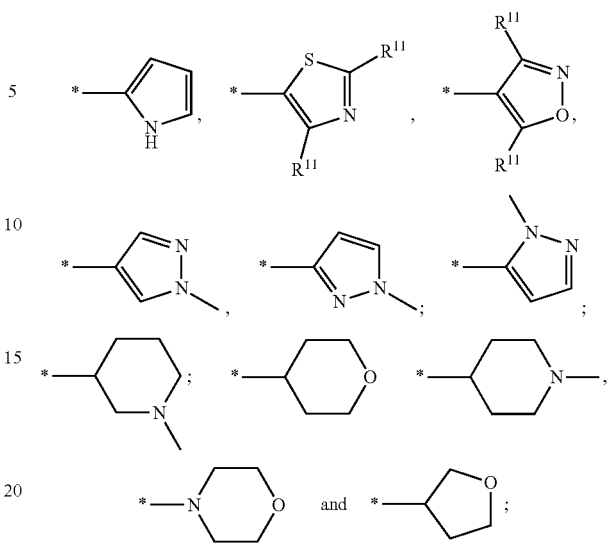

wherein
$R^8$ is independently selected from $OCH_3$, OH and $OCF_3$;
$R^9$ is selected from H and halo;
$R^{10}$ is selected from H, $O(C_1\text{-}C_4)$alkyl, and OH;
each $R^{11}$ is independently selected from H, and $CH_3$;

Embodiment 13. A compound of formula (I), or salt thereof, according to any preceding Embodiment, wherein $R^4$ is selected from: methyl, cyclopropyl, cyclobutyl, cyclopentyl,

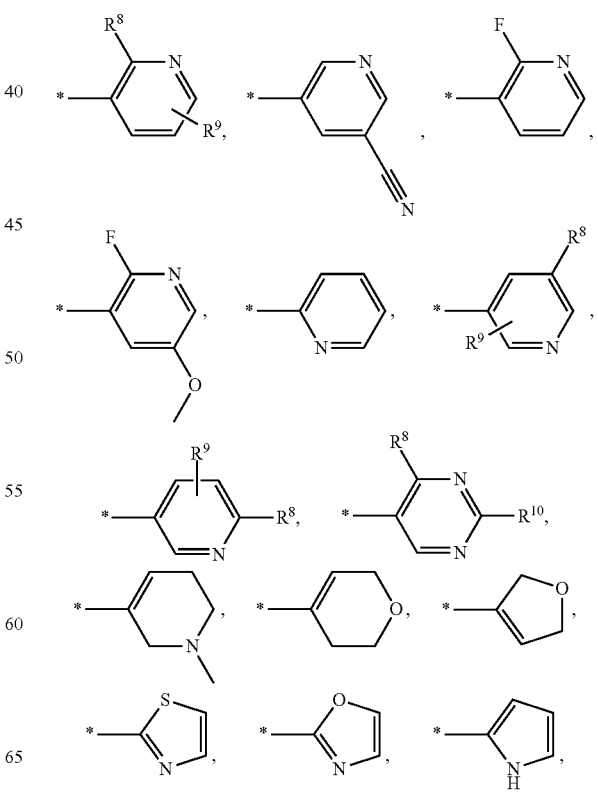

-continued
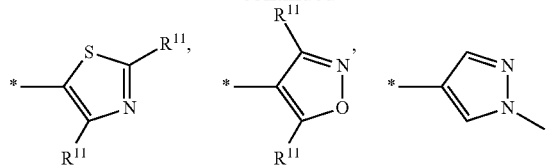
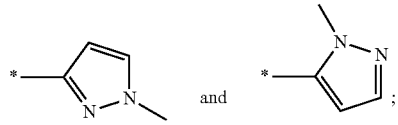
or R⁴ is selected from
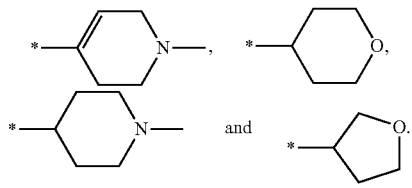
Embodiment 14. A compound of formula (I), or a salt thereof, according to any preceding Embodiment, wherein R⁴ is selected from: methyl, cyclopropyl, cyclopentyl,
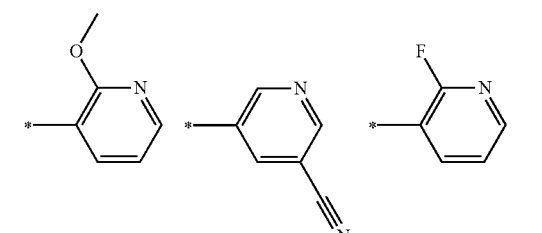
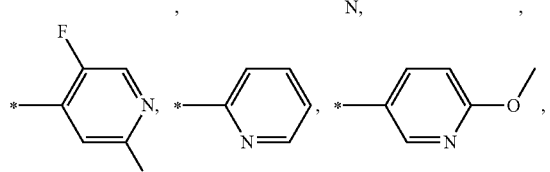
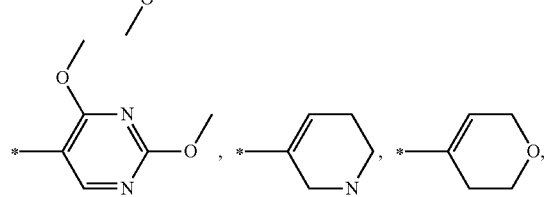
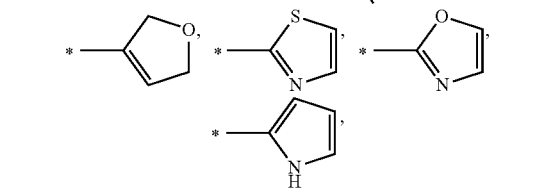
-continued
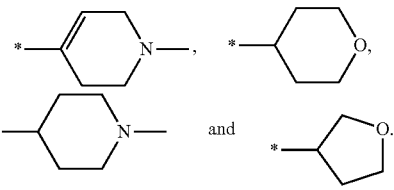
or R⁴ is selected from
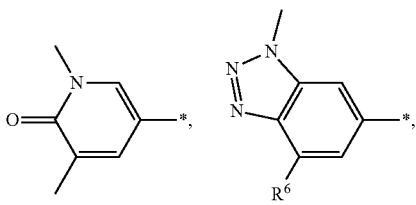
Embodiment 15. A compound of formula (I) or a salt thereof, according to Embodiment 1 wherein A is selected from:
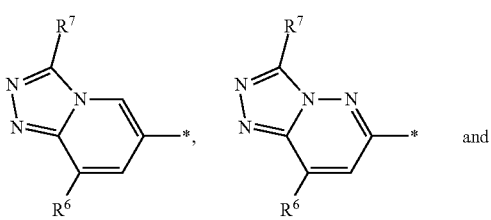
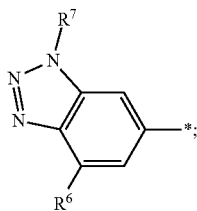
B is
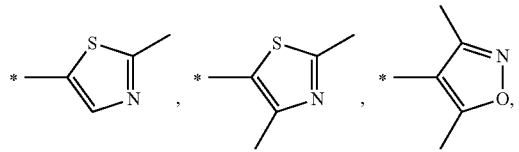
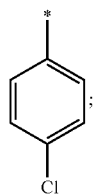

C is selected from:

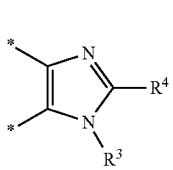 and 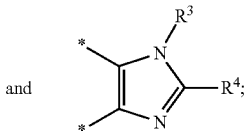

R³ is selected from H, isopropyl and

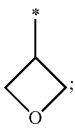 [SMILES: *C1COC1]

R⁴ is selected from:
  $C_1$-$C_4$alkyl;
  $C_3$-$C_6$cycloalkyl;
  pyridine, optionally substituted with one or two substituents selected from halo, cyano, —OH, —$C_1$-$C_4$alkyl, halo$C_1$-$C_4$alkyl, —O(halo$C_1$-$C_4$alkyl) and —$C_1$-$C_4$alkoxy;
  a 5- or 6-membered saturated or partially unsaturated heterocyclic ring containing 1 oxygen or 1 nitrogen atom or 1 oxygen and 1 nitrogen atom, and optionally substituted with one —$C_1$-$C_6$alkyl substituent, or optionally substituted with 1, 2, 3 or 4 methyl substituents;
R⁶ is selected from methyl and methoxy; and
R⁷ is selected from methyl, —$CH_2F$ and —$CHF_2$;
provided that when
A is

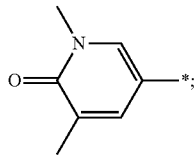

C is

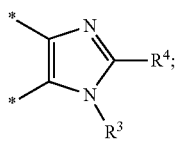

and
R³ is isopropyl; then
R⁴ is selected from:
  $C_1$-$C_4$alkyl;
  $C_3$-$C_6$cycloalkyl;
  a 5- or 6-membered saturated or partially unsaturated heterocyclic ring containing 1 or 2 heteroatoms selected from oxygen, sulphur and nitrogen, and optionally substituted with $C_1$-$C_4$alkyl; or a 5- or 6-membered saturated or partially unsaturated heterocyclic ring containing 1 oxygen or 1 nitrogen atom, and optionally substituted with one $C_1$-$C_4$alkyl substituent or optionally substituted with 1, 2, 3 or 4 methyl substituents;
and wherein * indicates the point of attachment to the remainder of the molecule.

Embodiment 16. A compound of formula (I) or a salt thereof, according to any one of Embodiments 1 or 3 to 15, wherein the compound is present as the racemate of the 2 enantiomeric forms (Ia) and (Ib) disclosed herein.

Embodiment 17. A compound of formula (I), or a salt thereof, according to Embodiment 1, which is selected from:
Example 1: 6-(4-chlorophenyl)-5-(3,7-dimethyl-3H-benzo[d][1,2,3]triazol-5-yl)-2-methyl-5,6-dihydropyrrolo[3,4-d]imidazol-4(1H)-one;
Example 2: 6-(4-chlorophenyl)-5-(3,7-dimethyl-3H-benzo[d][1,2,3]triazol-5-yl)-1-isopropyl-2-methyl-5,6-dihydropyrrolo[3,4-d]imidazol-4(1H)-one;
Example 3: 6-(4-chlorophenyl)-5-(3,7-dimethyl-3H-benzo[d][1,2,3]triazol-5-yl)-3-isopropyl-2-methyl-5,6-dihydropyrrolo[3,4-d]imidazol-4(3H)-one;
Example 4: 6-(4-chlorophenyl)-5-(1,5-dimethyl-6-oxo-1,6-dihydropyridin-3-yl)-2-(6-methoxypyridin-3-yl)-5,6-dihydropyrrolo[3,4-d]imidazol-4(1H)-one;
Example 5: (R)-6-(4-chlorophenyl)-5-(1,5-dimethyl-6-oxo-1,6-dihydropyridin-3-yl)-2-(6-methoxypyridin-3-yl)-5,6-dihydropyrrolo[3,4-d]imidazol-4(1H)-one;
Example 6: 6-(4-chlorophenyl)-5-(1,5-dimethyl-6-oxo-1,6-dihydropyridin-3-yl)-2-(6-methoxypyridin-3-yl)-3-methyl-5,6-dihydropyrrolo[3,4-d]imidazol-4(3H)-one;
Example 7: (R)-6-(4-chlorophenyl)-5-(1,5-dimethyl-6-oxo-1,6-dihydropyridin-3-yl)-2-(6-methoxypyridin-3-yl)-3-methyl-5,6-dihydropyrrolo[3,4-d]imidazol-4(3H)-one;
Example 8: 6-(4-chlorophenyl)-5-(1,5-dimethyl-6-oxo-1,6-dihydropyridin-3-yl)-2-(6-methoxypyridin-3-yl)-1-methyl-5,6-dihydropyrrolo[3,4-d]imidazol-4(1H)-one;
Example 9: 6-(4-chlorophenyl)-5-(3,8-dimethyl-[1,2,4]triazolo[4,3-a]pyridin-6-yl)-1-isopropyl-2-(6-methoxypyridin-3-yl)-5,6-dihydropyrrolo[3,4-d]imidazol-4(1H)-one;
Example 10: 6-(4-chlorophenyl)-2-(2,4-dimethoxypyrimidin-5-yl)-5-(3,8-dimethyl-[1,2,4]triazolo[4,3-a]pyridin-6-yl)-1-isopropyl-5,6-dihydropyrrolo[3,4-d]imidazol-4(1H)-one;
Example 11: 6-(4-chlorophenyl)-2-(2,5-dihydrofuran-3-yl)-5-(3,8-dimethyl-[1,2,4]triazolo[4,3-a]pyridin-6-yl)-1-isopropyl-5,6-dihydropyrrolo[3,4-d]imidazol-4(1H)-one;
Example 12: 6-(4-chlorophenyl)-5-(3,8-dimethyl-[1,2,4]triazolo[4,3-a]pyridin-6-yl)-1-isopropyl-2-(1-methyl-1,2,5,6-tetrahydropyridin-3-yl)-5,6-dihydropyrrolo[3,4-d]imidazol-4(1H)-one;
Example 13: 6-(4-chlorophenyl)-2-cyclopropyl-5-(3,8-dimethyl-[1,2,4]triazolo[4,3-a]pyridin-6-yl)-1-isopropyl-5,6-dihydropyrrolo[3,4-d]imidazol-4(1H)-one;
Example 14: 6-(4-chlorophenyl)-2-(3,6-dihydro-2H-pyran-4-yl)-5-(3,8-dimethyl-[1,2,4]triazolo[4,3-a]pyridin-6-yl)-1-isopropyl-5,6-dihydropyrrolo[3,4-d]imidazol-4(1H)-one;
Example 15: 6-(4-chlorophenyl)-5-(3,8-dimethyl-[1,2,4]triazolo[4,3-a]pyridin-6-yl)-1-isopropyl-2-(oxazol-2-yl)-5,6-dihydropyrrolo[3,4-d]imidazol-4(1H)-one;
Example 16: 6-(4-chlorophenyl)-5-(3,8-dimethyl-[1,2,4]triazolo[4,3-a]pyridin-6-yl)-2-(6-methoxypyridin-3-yl)-1-methyl-5,6-dihydropyrrolo[3,4-d]imidazol-4(1H)-one;
Example 17: 6-(4-chlorophenyl)-2-cyclopropyl-1-isopropyl-5-(8-methoxy-3-methyl-[1,2,4]triazolo[4,3-a]pyridin-6-yl)-5,6-dihydropyrrolo[3,4-d]imidazol-4(1H)-one;

Example 18: 6-(4-chlorophenyl)-5-(3,8-dimethyl-[1,2,4]triazolo[4,3-b]pyridazin-6-yl)-1-isopropyl-2-methyl-5,6-dihydropyrrolo[3,4-d]imidazol-4(1H)-one;
Example 19: 6-(4-chlorophenyl)-1-isopropyl-2-(isoxazol-4-yl)-5-(1-methyl-6-oxo-1,6-dihydropyridin-3-yl)-5,6-dihydropyrrolo[3,4-d]imidazol-4(1H)-one;
Example 20: 6-(4-chlorophenyl)-1-isopropyl-5-(1-methyl-6-oxo-1,6-dihydropyridin-3-yl)-2-(pyridin-2-yl)-5,6-dihydropyrrolo[3,4-d]imidazol-4(1H)-one;
Example 21: 6-(4-chlorophenyl)-1-isopropyl-2-(1-methyl-1H-pyrazol-5-yl)-5-(1-methyl-6-oxo-1,6-dihydropyridin-3-yl)-5,6-dihydropyrrolo[3,4-d]imidazol-4(1H)-one;
Example 22: 6-(4-chlorophenyl)-1-isopropyl-2-(1-methyl-1H-pyrazol-3-yl)-5-(1-methyl-6-oxo-1,6-dihydropyridin-3-yl)-5,6-dihydropyrrolo[3,4-d]imidazol-4(1H)-one;
Example 23: 6-(4-chlorophenyl)-5-(1,5-dimethyl-6-oxo-1,6-dihydropyridin-3-yl)-1-isopropyl-2-(thiazol-2-yl)-5,6-dihydropyrrolo[3,4-d]imidazol-4(1H)-one;
Example 24: (R)-6-(4-chlorophenyl)-5-(1,5-dimethyl-6-oxo-1,6-dihydropyridin-3-yl)-1-isopropyl-2-(thiazol-2-yl)-5,6-dihydropyrrolo[3,4-d]imidazol-4(1H)-one;
Example 25: 6-(4-chlorophenyl)-5-(1,5-dimethyl-6-oxo-1,6-dihydropyridin-3-yl)-2-(2,4-dimethylthiazol-5-yl)-1-isopropyl-5,6-dihydropyrrolo[3,4-d]imidazol-4(1H)-one;
Example 26: 6-(4-chlorophenyl)-5-(1,5-dimethyl-6-oxo-1,6-dihydropyridin-3-yl)-1-isopropyl-2-(thiazol-5-yl)-5,6-dihydropyrrolo[3,4-d]imidazol-4(1H)-one;
Example 27: 6-(4-chlorophenyl)-5-(1,5-dimethyl-6-oxo-1,6-dihydropyridin-3-yl)-2-(3,5-dimethylisoxazol-4-yl)-1-isopropyl-5,6-dihydropyrrolo[3,4-d]imidazol-4(1H)-one;
Example 28: 6-(4-chlorophenyl)-2-cyclopropyl-5-(1,5-dimethyl-6-oxo-1,6-dihydropyridin-3-yl)-1-isopropyl-5,6-dihydropyrrolo[3,4-d]imidazol-4(1H)-one;
Example 29: 6-(4-chlorophenyl)-5-(1,5-dimethyl-6-oxo-1,6-dihydropyridin-3-yl)-1-isopropyl-2-(2-methylthiazol-5-yl)-5,6-dihydropyrrolo[3,4-d]imidazol-4(1H)-one;
Example 30: 6-(4-chlorophenyl)-5-(1,5-dimethyl-6-oxo-1,6-dihydropyridin-3-yl)-1-isopropyl-2-(1H-pyrrol-2-yl)-5,6-dihydropyrrolo[3,4-d]imidazol-4(1H)-one;
Example 31: 6-(4-chlorophenyl)-2-cyclopentyl-5-(1,5-dimethyl-6-oxo-1,6-dihydropyridin-3-yl)-1-isopropyl-5,6-dihydropyrrolo[3,4-d]imidazol-4(1H)-one;
Example 32: 6-(4-chlorophenyl)-5-(1,5-dimethyl-6-oxo-1,6-dihydropyridin-3-yl)-2-(2-fluoropyridin-3-yl)-1-methyl-5,6-dihydropyrrolo[3,4-d]imidazol-4(1H)-one;
Example 33: 1-(tert-butyl)-6-(4-chlorophenyl)-2-cyclopropyl-5-(1,5-dimethyl-6-oxo-1,6-dihydropyridin-3-yl)-5,6-dihydropyrrolo[3,4-d]imidazol-4(1H)-one;
Example 34: 6-(4-chlorophenyl)-2-(2,4-dimethoxypyrimidin-5-yl)-5-(3,7-dimethylbenzo[d]-isoxazol-5-yl)-1-isopropyl-5,6-dihydropyrrolo[3,4-d]imidazol-4(1H)-one;
Example 35: 6-(4-chlorophenyl)-5-(3,7-dimethylbenzo[d]isoxazol-5-yl)-1-isopropyl-2-(6-methoxypyridin-3-yl)-5,6-dihydropyrrolo[3,4-d]imidazol-4(1H)-one;
Example 36: 6-(4-chlorophenyl)-5-(1,5-dimethyl-6-oxo-1,6-dihydropyridin-3-yl)-2-(5-fluoro-2-methoxypyridin-4-yl)-3-propyl-5,6-dihydropyrrolo[3,4-d]imidazol-4(3H)-one;
Example 37: 5-(4-(4-chlorophenyl)-5-(1,5-dimethyl-6-oxo-1,6-dihydropyridin-3-yl)-6-oxo-1-propyl-1,4,5,6-tetrahydropyrrolo[3,4-d]imidazol-2-yl)nicotinonitrile;
Example 38: 6-(4-chlorophenyl)-5-(1,5-dimethyl-6-oxo-1,6-dihydropyridin-3-yl)-3-ethyl-2-(6-methoxypyridin-3-yl)-5,6-dihydropyrrolo[3,4-d]imidazol-4(3H)-one;
Example 39: (R)-6-(4-chlorophenyl)-5-(1,5-dimethyl-6-oxo-1,6-dihydropyridin-3-yl)-3-ethyl-2-(6-methoxypyridin-3-yl)-5,6-dihydropyrrolo[3,4-d]imidazol-4(3H)-one;
Example 40: 6-(4-chlorophenyl)-5-(1,5-dimethyl-6-oxo-1,6-dihydropyridin-3-yl)-3-ethyl-2-(2-methoxypyridin-3-yl)-5,6-dihydropyrrolo[3,4-d]imidazol-4(3H)-one;
Example 41: (R)-6-(4-chlorophenyl)-5-(1,5-dimethyl-6-oxo-1,6-dihydropyridin-3-yl)-3-ethyl-2-(2-methoxypyridin-3-yl)-5,6-dihydropyrrolo[3,4-d]imidazol-4(3H)-one;
Example 42: 6-(4-chlorophenyl)-5-(1,5-dimethyl-6-oxo-1,6-dihydropyridin-3-yl)-3-ethyl-2-(1-methyl-1H-pyrazol-5-yl)-5,6-dihydropyrrolo[3,4-d]imidazol-4(3H)-one;
Example 43: 6-(4-chlorophenyl)-1-cyclopropyl-5-(1,5-dimethyl-6-oxo-1,6-dihydropyridin-3-yl)-2-(thiazol-2-yl)-5,6-dihydropyrrolo[3,4-d]imidazol-4(1H)-one;
Example 44: 6-(4-chlorophenyl)-5-(1,5-dimethyl-6-oxo-1,6-dihydropyridin-3-yl)-3-isopropyl-2-(2-methoxypyridin-3-yl)-5,6-dihydropyrrolo[3,4-d]imidazol-4(3H)-one;
Example 45: (R)-6-(4-chlorophenyl)-5-(1,5-dimethyl-6-oxo-1,6-dihydropyridin-3-yl)-3-isopropyl-2-(2-methoxypyridin-3-yl)-5,6-dihydropyrrolo[3,4-d]imidazol-4(3H)-one;
Example 46: 6-(4-chlorophenyl)-2-cyclopropyl-5-(1,5-dimethyl-6-oxo-1,6-dihydropyridin-3-yl)-5,6-dihydropyrrolo[3,4-d]imidazol-4(3H)-one;
Example 47: R-6-(4-chlorophenyl)-2-cyclopropyl-5-(1,5-dimethyl-6-oxo-1,6-dihydropyridin-3-yl)-5,6-dihydropyrrolo[3,4-d]imidazol-4(3H)-one;
Example 48: (R)-6-(4-chlorophenyl)-2-(2,5-dihydrofuran-3-yl)-5-(3,8-dimethyl-[1,2,4]triazolo[4,3-a]pyridin-6-yl)-1-isopropyl-5,6-dihydropyrrolo[3,4-d]imidazol-4(1H)-one;
Example 49: 6-(4-Chlorophenyl)-5-(3,8-dimethyl-[1,2,4]triazolo[4,3-a]pyridin-6-yl)-1-isopropyl-2-(1,2,3,6-tetrahydropyridin-4-yl)-5,6-dihydropyrrolo[3,4-d]imidazol-4(1H)-one;
Example 50: 6-(4-Chlorophenyl)-5-(3,8-dimethyl-[1,2,4]triazolo[4,3-a]pyridin-6-yl)-1-isopropyl-2-(1-methyl-1,2,3,6-tetrahydropyridin-4-yl)-5,6-dihydropyrrolo[3,4-d]imidazol-4(1H)-one;
Example 51: 6-(4-Chlorophenyl)-5-(3,8-dimethyl-[1,2,4]triazolo[4,3-a]pyridin-6-yl)-1-isopropyl-2-(2,2,6,6-tetramethyl-1,2,3,6-tetrahydropyridin-4-yl)-5,6-di hydropyrrolo[3,4-d]imidazol-4(1H)-one
Example 52: 6-(4-chlorophenyl)-1-isopropyl-5-(8-methoxy-3-methyl-[1,2,4]triazolo[4,3-a]pyridin-6-yl)-2-(6-methoxypyridin-3-yl)-5,6-dihydropyrrolo[3,4-d]imidazol-4(1H)-one;
Example 53: 6-(4-chlorophenyl)-2-(3,6-dihydro-2H-pyran-4-yl)-1-isopropyl-5-(8-methoxy-3-methyl-[1,2,4]triazolo[4,3-a]pyridin-6-yl)-5,6-dihydropyrrolo[3,4-d]imidazol-4(1H)-one;
Example 54: 6-(4-chlorophenyl)-2-(2,4-dimethoxypyrimidin-5-yl)-5-(8-methoxy-3-methyl-[1,2,4]triazolo[4,3-a]pyridin-6-yl)-1-methyl-5,6-dihydropyrrolo[3,4-d]imidazol-4(1H)-one;
Example 55: 6-(4-chlorophenyl)-5-(8-methoxy-3-methyl-[1,2,4]triazolo[4,3-a]pyridin-6-yl)-2-(6-methoxypyridin-3-yl)-1-methyl-5,6-dihydropyrrolo[3,4-d]imidazol-4(1H)-one;
Example 56: 6-(4-chlorophenyl)-2-cyclopropyl-5-(8-methoxy-3-methyl-[1,2,4]triazolo[4,3-a]pyridin-6-yl)-1-methyl-5,6-dihydropyrrolo[3,4-d]imidazol-4(1H)-one;
Example 57: 6-(4-chlorophenyl)-2-cyclopropyl-5-(3,8-dimethyl-[1,2,4]triazolo[4,3-a]pyridin-6-yl)-1-methyl-5,6-dihydropyrrolo[3,4-d]imidazol-4(1H)-one;
Example 58: 6-(4-chlorophenyl)-5-(3,8-dimethyl-[1,2,4]triazolo[4,3-a]pyridin-6-yl)-1-isopropyl-2-methyl-5,6-dihydropyrrolo[3,4-d]imidazol-4(1H)-one;

Example 59: (R)-6-(4-chlorophenyl)-5-(3,8-dimethyl-[1,2,4]triazolo[4,3-a]pyridin-6-yl)-1-isopropyl-2-methyl-5,6-dihydropyrrolo[3,4-d]imidazol-4(1H)-one;

Example 60: 6-(4-chlorophenyl)-2-(3,6-dihydro-2H-pyran-4-yl)-1-isopropyl-5-(4-methoxy-1-methyl-1H-benzo[d][1,2,3]triazol-6-yl)-5,6-dihydropyrrolo[3,4-d]imidazol-4(1H)-one;

Example 61: (R)-6-(4-chlorophenyl)-2-(3,6-dihydro-2H-pyran-4-yl)-1-isopropyl-5-(4-methoxy-1-methyl-1H-benzo[d][1,2,3]triazol-6-yl)-5,6-dihydropyrrolo[3,4-d]imidazol-4(1H)-one;

Example 62: 6-(4-chlorophenyl)-1-isopropyl-5-(4-methoxy-1-methyl-1H-benzo[d][1,2,3]triazol-6-yl)-2-(1-methyl-1,2,5,6-tetrahydropyridin-3-yl)-5,6-dihydropyrrolo[3,4-d]imidazol-4(1H)-one;

Example 63: 6-(4-chlorophenyl)-1-isopropyl-5-(4-methoxy-1-methyl-1H-benzo[d][1,2,3]triazol-6-yl)-2-methyl-5,6-dihydropyrrolo[3,4-d]imidazol-4(1H)-one;

Example 64: 6-(4-chlorophenyl)-1-isopropyl-5-(4-methoxy-1-methyl-1H-benzo[d][1,2,3]triazol-6-yl)-2-(tetrahydro-2H-pyran-4-yl)-5,6-dihydropyrrolo[3,4-d]imidazol-4(1H)-one;

Example 65: methyl 4-(6-(4-chlorophenyl)-5-(3,8-dimethyl-[1,2,4]triazolo[4,3-a]pyridin-6-yl)-1-isopropyl-4-oxo-1,4,5,6-tetrahydropyrrolo[3,4-d]imidazol-2-yl)-5,6-dihydropyridine-1(2H)-carboxylate;

Example 66: 2-(1-acetyl-1,2,3,6-tetrahydropyridin-4-yl)-6-(4-chlorophenyl)-5-(3,8-dimethyl-[1,2,4]triazolo[4,3-a]pyridin-6-yl)-1-isopropyl-5,6-dihydropyrrolo[3,4-d]imidazol-4(1H)-one;

Example 67: 6-(4-chlorophenyl)-5-(3,8-dimethyl-[1,2,4]triazolo[4,3-a]pyridin-6-yl)-1-isopropyl-2-(1-(methylsulfonyl)-1,2,3,6-tetrahydropyridin-4-yl)-5,6-dihydropyrrolo[3,4-d]imidazol-4(1H)-one;

Example 68: 6-(4-chlorophenyl)-5-(3,8-dimethyl-[1,2,4]triazolo[4,3-a]pyridin-6-yl)-2-(1-ethyl-1,2,3,6-tetrahydropyridin-4-yl)-1-isopropyl-5,6-dihydropyrrolo[3,4-d]imidazol-4(1H)-one;

Example 69: isobutyl 4-(6-(4-chlorophenyl)-5-(3,8-dimethyl-[1,2,4]triazolo[4,3-a]pyridin-6-yl)-1-isopropyl-4-oxo-1,4,5,6-tetrahydropyrrolo[3,4-d]imidazol-2-yl)-5,6-dihydropyridine-1(2H)-carboxylate;

Example 70: ethyl 4-(6-(4-chlorophenyl)-5-(3,8-dimethyl-[1,2,4]triazolo[4,3-a]pyridin-6-yl)-1-isopropyl-4-oxo-1,4,5,6-tetrahydropyrrolo[3,4-d]imidazol-2-yl)-5,6-dihydropyridine-1(2H)-carboxylate;

Example 71: isopropyl 4-(6-(4-chlorophenyl)-5-(3,8-dimethyl-[1,2,4]triazolo[4,3-a]pyridin-6-yl)-1-isopropyl-4-oxo-1,4,5,6-tetrahydropyrrolo[3,4-d]imidazol-2-yl)-5,6-dihydropyridine-1(2H)-carboxylate;

Example 72: N-(tert-butyl)-4-(6-(4-chlorophenyl)-5-(3,8-dimethyl-[1,2,4]triazolo[4,3-a]pyridin-6-yl)-1-isopropyl-4-oxo-1,4,5,6-tetrahydropyrrolo[3,4-d]imidazol-2-yl)-5,6-dihydropyridine-1(2H)-carboxamide;

Example 73: 6-(4-chlorophenyl)-1-isopropyl-5-(4-methoxy-1-methyl-1H-benzo[d][1,2,3]triazol-6-yl)-2-(1-methyl-1,2,3,6-tetrahydropyridin-4-yl)-5,6-dihydropyrrolo[3,4-d]imidazol-4(1H)-one;

Example 74: 6-(4-chlorophenyl)-1-isopropyl-5-(4-methoxy-1-methyl-1H-benzo[d][1,2,3]triazol-6-yl)-2-(2-methoxypyridin-3-yl)-5,6-dihydropyrrolo[3,4-d]imidazol-4(1H)-one;

Example 75: 6-(4-chlorophenyl)-5-(3,8-dimethyl-[1,2,4]triazolo[4,3-a]pyridin-6-yl)-1-isopropyl-2-(piperidin-4-yl)-5,6-dihydropyrrolo[3,4-d]imidazol-4(1H)-one;

Example 76: methyl 4-(6-(4-chlorophenyl)-5-(3,8-dimethyl-[1,2,4]triazolo[4,3-a]pyridin-6-yl)-1-isopropyl-4-oxo-1,4,5,6-tetrahydropyrrolo[3,4-d]imidazol-2-yl)piperidine-1-carboxylate;

Example 77: 6-(4-chlorophenyl)-5-(1,4-dimethyl-1H-benzo[d][1,2,3]triazol-6-yl)-1-isopropyl-2-(2-methoxypyridin-3-yl)-5,6-dihydropyrrolo[3,4-d]imidazol-4(1H)-one;

Example 78: 6-(4-chlorophenyl)-5-(1,4-dimethyl-1H-benzo[d][1,2,3]triazol-6-yl)-1-isopropyl-2-(1-methyl-1,2,3,6-tetrahydropyridin-4-yl)-5,6-dihydropyrrolo[3,4-d]imidazol-4(1H)-one;

Example 79: 6-(4-chlorophenyl)-2-(3,6-dihydro-2H-pyran-4-yl)-5-(1,4-dimethyl-1H-benzo[d][1,2,3]triazol-6-yl)-1-isopropyl-5,6-dihydropyrrolo[3,4-d]imidazol-4(1H)-one;

Example 80: 6-(4-chlorophenyl)-5-(1,4-dimethyl-1H-benzo[d][1,2,3]triazol-6-yl)-1-isopropyl-2-(tetrahydro-2H-pyran-4-yl)-5,6-dihydropyrrolo[3,4-d]imidazol-4(1H)-one;

Example 81: (R)-6-(4-chlorophenyl)-2-(3,6-dihydro-2H-pyran-4-yl)-5-(1,4-dimethyl-1H-benzo[d][1,2,3]triazol-6-yl)-1-isopropyl-5,6-dihydropyrrolo[3,4-d]imidazol-4(1H)-one;

Example 82: (R)-6-(4-chlorophenyl)-5-(1,4-dimethyl-1H-benzo[d][1,2,3]triazol-6-yl)-1-isopropyl-2-(tetrahydro-2H-pyran-4-yl)-5,6-dihydropyrrolo[3,4-d]imidazol-4(1H)-one;

Example 83: 6-(4-chlorophenyl)-5-(1,4-dimethyl-1H-benzo[d][1,2,3]triazol-6-yl)-1-isopropyl-2-(6-methoxypyridin-3-yl)-5,6-dihydropyrrolo[3,4-d]imidazol-4(1H)-one;

Example 84: (R)-6-(4-chlorophenyl)-2-(3,6-dihydro-2H-pyran-4-yl)-5-(3,8-dimethyl-[1,2,4]triazolo[4,3-a]pyridin-6-yl)-1-isopropyl-5,6-dihydropyrrolo[3,4-d]imidazol-4(1H)-one;

Example 85: (R)-6-(4-chlorophenyl)-5-(3,8-dimethyl-[1,2,4]triazolo[4,3-a]pyridin-6-yl)-1-isopropyl-2-(1-methyl-1,2,5,6-tetrahydropyridin-3-yl)-5,6-dihydropyrrolo[3,4-d]imidazol-4(1H)-one;

Example 86: 6-(4-chlorophenyl)-5-(3,8-dimethyl-[1,2,4]triazolo[4,3-a]pyridin-6-yl)-1-isopropyl-2-(tetrahydro-2H-pyran-4-yl)-5,6-dihydropyrrolo[3,4-d]imidazol-4(1H)-one;

Example 87: (R)-6-(4-chlorophenyl)-5-(3,8-dimethyl-[1,2,4]triazolo[4,3-a]pyridin-6-yl)-1-isopropyl-2-(tetrahydro-2H-pyran-4-yl)-5,6-dihydropyrrolo[3,4-d]imidazol-4(1H)-one;

Example 88: 6-(4-chlorophenyl)-2-(3,6-dihydro-2H-pyran-4-yl)-5-(3-(fluoromethyl)-8-methyl-[1,2,4]triazolo[4,3-a]pyridin-6-yl)-1-isopropyl-5,6-dihydropyrrolo[3,4-d]imidazol-4(1H)-one;

Example 89: 6-(4-chlorophenyl)-5-(3-(fluoromethyl)-8-methyl-[1,2,4]triazolo[4,3-a]pyridin-6-yl)-1-isopropyl-2-(2-methoxypyridin-3-yl)-5,6-dihydropyrrolo[3,4-d]imidazol-4(1H)-one;

Example 90: 6-(4-chlorophenyl)-5-(3-(fluoromethyl)-8-methyl-[1,2,4]triazolo[4,3-a]pyridin-6-yl)-1-isopropyl-2-(2,2,6,6-tetramethyl-1,2,3,6-tetrahydropyridin-4-yl)-5,6-dihydropyrrolo[3,4-d]imidazol-4(1H)-one;

Example 91: 6-(4-chlorophenyl)-5-(3-(fluoromethyl)-8-methyl-[1,2,4]triazolo[4,3-a]pyridin-6-yl)-1-isopropyl-2-(1-methyl-1,2,5,6-tetrahydropyridin-3-yl)-5,6-dihydropyrrolo[3,4-d]imidazol-4(1H)-one;

Example 92: 6-(4-chlorophenyl)-2-(2,5-dihydrofuran-3-yl)-5-(3-(fluoromethyl)-8-methyl-[1,2,4]triazolo[4,3-a]pyridin-6-yl)-1-isopropyl-5,6-dihydropyrrolo[3,4-d]imidazol-4(1H)-one;

Example 93: 6-(4-chlorophenyl)-2-(3,6-dihydro-2H-pyran-4-yl)-5-(1,4-dimethyl-1H-benzo[d][1,2,3]triazol-6-yl)-1-(oxetan-3-yl)-5,6-dihydropyrrolo[3,4-d]imidazol-4(1H)-one;

Example 94: 6-(4-chlorophenyl)-5-(1,4-dimethyl-1H-benzo[d][1,2,3]triazol-6-yl)-2-methyl-1-(oxetan-3-yl)-5,6-dihydropyrrolo[3,4-d]imidazol-4(1H)-one;

Example 95: 6-(4-chlorophenyl)-2-cyclopropyl-5-(1,4-dimethyl-1H-benzo[d][1,2,3]triazol-6-yl)-1-(oxetan-3-yl)-5,6-dihydropyrrolo[3,4-d]imidazol-4(1H)-one;

Example 96: 6-(4-chlorophenyl)-5-(1,4-dimethyl-1H-benzo[d][1,2,3]triazol-6-yl)-2-(1-methyl-1,2,3,6-tetrahydropyridin-4-yl)-1-(oxetan-3-yl)-5,6-dihydropyrrolo[3,4-d]imidazol-4(1H)-one;

Example 97: 6-(4-chlorophenyl)-1-isopropyl-5-(4-methoxy-1-methyl-1H-benzo[d][1,2,3]triazol-6-yl)-2-(1-methylpiperidin-4-yl)-5,6-dihydropyrrolo[3,4-d]imidazol-4(1H)-one;

Example 98: 6-(4-chlorophenyl)-5-(3,8-dimethyl-[1,2,4]triazolo[4,3-a]pyridin-6-yl)-1-isopropyl-2-(1-methyl piperidin-4-yl)-5,6-dihydropyrrolo[3,4-d]imidazol-4(1H)-one;

Example 99: 6-(4-chlorophenyl)-5-(1,4-dimethyl-1H-benzo[d][1,2,3]triazol-6-yl)-1-isopropyl-2-(tetrahydrofuran-3-yl)-5,6-dihydropyrrolo[3,4-d]imidazol-4(1H)-one;

Example 100: 6-(4-chlorophenyl)-2-(3,6-dihydro-2H-pyran-4-yl)-5-(3,8-dimethyl-[1,2,4]triazolo[4,3-b]pyridazin-6-yl)-1-isopropyl-5,6-dihydropyrrolo[3,4-d]imidazol-4(1H)-one;

Example 101: 6-(4-chlorophenyl)-5-(3,8-dimethyl-[1,2,4]triazolo[4,3-b]pyridazin-6-yl)-1-isopropyl-2-(tetrahydro-2H-pyran-4-yl)-5,6-dihydropyrrolo[3,4-d]imidazol-4(1H)-one;

Example 102: (R)-6-(4-chlorophenyl)-5-(3,8-dimethyl-[1,2,4]triazolo[4,3-b]pyridazin-6-yl)-1-isopropyl-2-(tetrahydro-2H-pyran-4-yl)-5,6-dihydropyrrolo[3,4-d]imidazol-4(1H)-one;

Example 103: (R)-6-(4-chlorophenyl)-2-(3,6-dihydro-2H-pyran-4-yl)-5-(3,8-dimethyl-[1,2,4]triazolo[4,3-b]pyridazin-6-yl)-1-isopropyl-5,6-dihydropyrrolo[3,4-d]imidazol-4(1H)-one;

Example 104: 6-(4-chlorophenyl)-5-(3,8-dimethyl-[1,2,4]triazolo[4,3-a]pyridin-6-yl)-1-isopropyl-2-(1-neopentylpiperidin-4-yl)-5,6-dihydropyrrolo[3,4-d]imidazol-4(1H)-one;

Example 105: 6-(4-chlorophenyl)-5-(1,4-dimethyl-1H-benzo[d][1,2,3]triazol-6-yl)-1-(oxetan-3-yl)-2-(tetrahydro-2H-pyran-4-yl)-5,6-dihydropyrrolo[3,4-d]imidazol-4(1H)-one;

Example 106: 6-(4-chlorophenyl)-5-(1,4-dimethyl-1H-benzo[d][1,2,3]triazol-6-yl)-1-isopropyl-5,6-dihydropyrrolo[3,4-d]imidazol-4(1H)-one;

Example 107: (R)-6-(4-chlorophenyl)-2-cyclopropyl-5-(3,8-dimethyl-[1,2,4]triazolo[4,3-a]pyridin-6-yl)-1-isopropyl-5,6-dihydropyrrolo[3,4-d]imidazol-4(1H)-one;

Example 108: (R)-6-(4-chlorophenyl)-1-isopropyl-5-(4-methoxy-1-methyl-1H-benzo[d][1,2,3]triazol-6-yl)-2-(tetrahydro-2H-pyran-4-yl)-5,6-dihydropyrrolo[3,4-d]imidazol-4(1H)-one;

Example 109: (R)-6-(4-chlorophenyl)-5-(3,7-dimethyl-3H-benzo[d][1,2,3]triazol-5-yl)-1-isopropyl-2-methyl-5,6-dihydropyrrolo[3,4-d]imidazol-4(1H)-one;

Example 110: (R)-6-(4-chlorophenyl)-5-(3,8-dimethyl-[1,2,4]triazolo[4,3-b]pyridazin-6-yl)-1-isopropyl-2-methyl-5,6-dihydropyrrolo[3,4-d]imidazol-4(1H)-one;

Example 111: (R)-6-(4-chlorophenyl)-1-isopropyl-5-(4-methoxy-1-methyl-1H-benzo[d][1,2,3]triazol-6-yl)-2-(2-methoxypyridin-3-yl)-5,6-dihydropyrrolo[3,4-d]imidazol-4(1H)-one;

Example 112: (R)-6-(4-chlorophenyl)-5-(1,4-dimethyl-1H-benzo[d][1,2,3]triazol-6-yl)-1-isopropyl-2-(2-methoxypyridin-3-yl)-5,6-dihydropyrrolo[3,4-d]imidazol-4(1H)-one;

Example 113: 6-(4-chlorophenyl)-1-isopropyl-5-(4-methoxy-1-methyl-1H-benzo[d][1,2,3]triazol-6-yl)-2-(6-methoxypyridin-3-yl)-5,6-dihydropyrrolo[3,4-d]imidazol-4(1H)-one;

Example 114: (R)-6-(4-chlorophenyl)-1-isopropyl-5-(4-methoxy-1-methyl-1H-benzo[d][1,2,3]triazol-6-yl)-2-(6-methoxypyridin-3-yl)-5,6-dihydropyrrolo[3,4-d]imidazol-4(1H)-one;

Example 115: 6-(4-chlorophenyl)-3-cyclopropyl-5-(3,8-dimethyl-[1,2,4]triazolo[4,3-a]pyridin-6-yl)-2-methyl-5,6-dihydropyrrolo[3,4-d]imidazol-4(3H)-one;

Example 116: 6-(4-chlorophenyl)-2-(3,6-dihydro-2H-pyran-4-yl)-5-(3,8-dimethyl-[1,2,4]triazolo[4,3-a]pyridin-6-yl)-5,6-dihydropyrrolo[3,4-d]imidazol-4(1H)-one;

Example 117: 6-(4-chlorophenyl)-5-(3,8-dimethyl-[1,2,4]triazolo[4,3-a]pyridin-6-yl)-2-(6-methoxypyridin-3-yl)-5,6-dihydropyrrolo[3,4-d]imidazol-4(1H)-one;

Example 118: (R)-6-(4-chlorophenyl)-5-(3,7-dimethyl-3H-benzo[d][1,2,3]triazol-5-yl)-3-isopropyl-2-methyl-5,6-dihydropyrrolo[3,4-d]imidazol-4(3H)-one;

Example 119: 6-(4-chlorophenyl)-5-(3,7-dimethyl-3H-benzo[d][1,2,3]triazol-5-yl)-3-ethyl-2-methyl-5,6-dihydropyrrolo[3,4-d]imidazol-4(3H)-one;

Example 120: (R)-6-(4-chlorophenyl)-5-(3,7-dimethyl-3H-benzo[d][1,2,3]triazol-5-yl)-1-ethyl-2-methyl-5,6-dihydropyrrolo[3,4-d]imidazol-4(1H)-one;

Example 121: 6-(4-chlorophenyl)-5-(3,7-dimethyl-3H-benzo[d][1,2,3]triazol-5-yl)-3-ethyl-2-methyl-5,6-dihydropyrrolo[3,4-d]imidazol-4(3H)-one;

Example 122: (R)-6-(4-chlorophenyl)-5-(3,7-dimethyl-3H-benzo[d][1,2,3]triazol-5-yl)-3-ethyl-2-methyl-5,6-dihydropyrrolo[3,4-d]imidazol-4(3H)-one;

Example 123: 6-(4-chlorophenyl)-5-(3,8-dimethyl-[1,2,4]triazolo[4,3-a]pyridin-6-yl)-2-(2-methoxypyridin-3-yl)-5,6-dihydropyrrolo[3,4-d]imidazol-4(1H)-one;

Example 124: 6-(4-chlorophenyl)-2-(2,4-dimethoxypyrimidin-5-yl)-5-(3,8-dimethyl-[1,2,4]triazolo[4,3-a]pyridin-6-yl)-5,6-dihydropyrrolo[3,4-d]imidazol-4(1H)-one;

Example 125: 6-(4-chlorophenyl)-5-(8-methoxy-3-methyl-[1,2,4]triazolo[4,3-a]pyridin-6-yl)-2-(6-methoxypyridin-3-yl)-5,6-dihydropyrrolo[3,4-d]imidazol-4(1H)-one;

Example 126: (R)-6-(4-chlorophenyl)-5-(8-methoxy-3-methyl-[1,2,4]triazolo[4,3-a]pyridin-6-yl)-2-(6-methoxypyridin-3-yl)-5,6-dihydropyrrolo[3,4-d]imidazol-4(1H)-one;

Example 127: 6-(4-chlorophenyl)-2-(2,4-dimethoxypyrimidin-5-yl)-5-(8-methoxy-3-methyl-[1,2,4]triazolo[4,3-a]pyridin-6-yl)-5,6-dihydropyrrolo[3,4-d]imidazol-4(1H)-one;

Example 128: (R)-6-(4-chlorophenyl)-2-(2,4-dimethoxypyrimidin-5-yl)-5-(8-methoxy-3-methyl-[1,2,4]triazolo[4,3-a]pyridin-6-yl)-5,6-dihydropyrrolo[3,4-d]imidazol-4(1H)-one;

Example 129: (R)-6-(4-chlorophenyl)-5-(3,8-dimethyl-[1,2,4]triazolo[4,3-a]pyridin-6-yl)-2-(6-methoxypyridin-3-yl)-5,6-dihydropyrrolo[3,4-d]imidazol-4(1H)-one;

Example 130: 6-(4-chlorophenyl)-5-(1,5-dimethyl-6-oxo-1,6-dihydropyridin-3-yl)-1-methyl-2-morpholino-5,6-dihydropyrrolo[3,4-d]imidazol-4(1H)-one;

Example 131: 6-(4-chlorophenyl)-5-(3-(difluoromethyl)-8-methyl-[1,2,4]triazolo[4,3-a]pyridin-6-yl)-1-isopropyl-2-methyl-5,6-dihydropyrrolo[3,4-d]imidazol-4(1H)-one;

Example 132: 6-(4-chlorophenyl)-5-(3-(difluoromethyl)-8-methyl-[1,2,4]triazolo[4,3-a]pyridin-6-yl)-1-isopropyl-2-(2-methoxypyridin-3-yl)-5,6-dihydropyrrolo[3,4-d]imidazol-4(1H)-one;

Example 133: 6-(4-chlorophenyl)-5-(3,7-dimethyl-3H-benzo[d][1,2,3]triazol-5-yl)-2-(2-methoxypyridin-3-yl)-5,6-dihydropyrrolo[3,4-d]imidazol-4(1H)-one;

Example 134: 6-(4-chlorophenyl)-2-(3,6-dihydro-2H-pyran-4-yl)-5-(1,5-dimethyl-6-oxo-1,6-dihydropyridin-3-yl)-5,6-dihydropyrrolo[3,4-d]imidazol-4(1H)-one;

Example 135: 6-(4-chlorophenyl)-5-(1,5-dimethyl-6-oxo-1,6-dihydropyridin-3-yl)-2-(1-methyl-1,2,3,6-tetrahydropyridin-4-yl)-5,6-dihydropyrrolo[3,4-d]imidazol-4(1H)-one;

Example 136: 6-(4-chlorophenyl)-5-(3,8-dimethyl-[1,2,4]triazolo[4,3-a]pyridin-6-yl)-2-(2-methoxy-4-(trifluoromethyl)phenyl)-5,6-dihydropyrrolo[3,4-d]imidazol-4(1H)-one;

Example 137: 6-(4-chlorophenyl)-5-(3,8-dimethyl-[1,2,4]triazolo[4,3-a]pyridin-6-yl)-2-(4-fluoro-2-methoxyphenyl)-5,6-dihydropyrrolo[3,4-d]imidazol-4(1H)-one;

Example 138: 6-(4-chlorophenyl)-5-(3,7-dimethyl-3H-[1,2,3]triazolo[4,5-b]pyridin-5-yl)-1-isopropyl-2-(6-methoxypyridin-3-yl)-5,6-dihydropyrrolo[3,4-d]imidazol-4(1H)-one;

Example 139: 6-(4-chlorophenyl)-5-(3-(difluoromethyl)-8-methyl-[1,2,4]triazolo[4,3-a]pyridin-6-yl)-2-methyl-5,6-dihydropyrrolo[3,4-d]imidazol-4(1H)-one;

Example 140: 6-(4-chlorophenyl)-5-(3-(difluoromethyl)-8-methyl-[1,2,4]triazolo[4,3-a]pyridin-6-yl)-2-(2-methoxypyridin-3-yl)-5,6-dihydropyrrolo[3,4-d]imidazol-4(1H)-one;

Example 141: 6-(4-chlorophenyl)-5-(3-(difluoromethyl)-8-methyl-[1,2,4]triazolo[4,3-a]pyridin-6-yl)-2-(6-methoxypyridin-3-yl)-5,6-dihydropyrrolo[3,4-d]imidazol-4(1H)-one;

Example 142: (R)-6-(4-chlorophenyl)-5-(3,8-dimethyl-[1,2,4]triazolo[4,3-a]pyridin-6-yl)-2-(2-methoxypyridin-3-yl)-5,6-dihydropyrrolo[3,4-d]imidazol-4(1H)-one;

Example 143: 6-(4-chlorophenyl)-5-(3-(difluoromethyl)-8-methyl-[1,2,4]triazolo[4,3-a]pyridin-6-yl)-2-(2,4-dimethoxypyrimidin-5-yl)-1-isopropyl-5,6-dihydropyrrolo[3,4-d]imidazol-4(1H)-one;

Example 144: 6-(4-chlorophenyl)-5-(3-(difluoromethyl)-8-methyl-[1,2,4]triazolo[4,3-a]pyridin-6-yl)-1-isopropyl-2-(2-methoxy-4-(trifluoromethyl)phenyl)-5,6-dihydropyrrolo[3,4-d]imidazol-4(1H)-one;

Example 145: 6-(4-chlorophenyl)-2-cyclopropyl-5-(3-(difluoromethyl)-8-methyl-[1,2,4]triazolo[4,3-a]pyridin-6-yl)-1-isopropyl-5,6-dihydropyrrolo[3,4-d]imidazol-4(1H)-one;

Example 146: (R)-6-(4-chlorophenyl)-5-(3-(difluoromethyl)-8-methyl-[1,2,4]triazolo[4,3-a]pyridin-6-yl)-1-isopropyl-2-methyl-5,6-dihydropyrrolo[3,4-d]imidazol-4(1H)-one;

Example 147: 6-(4-chlorophenyl)-5-(3-(difluoromethyl)-8-methyl-[1,2,4]triazolo[4,3-a]pyridin-6-yl)-2-(3,6-dihydro-2H-pyran-4-yl)-1-isopropyl-5,6-dihydropyrrolo[3,4-d]imidazol-4(1H)-one;

Example 148: 6-(4-chlorophenyl)-5-(3-(difluoromethyl)-8-methyl-[1,2,4]triazolo[4,3-b]pyridazin-6-yl)-1-isopropyl-2-(2-methoxypyridin-3-yl)-5,6-dihydropyrrolo[3,4-d]imidazol-4(1H)-one;

Example 149: 6-(4-chlorophenyl)-5-(3-(difluoromethyl)-8-methyl-[1,2,4]triazolo[4,3-b]pyridazin-6-yl)-1-isopropyl-2-(6-methoxypyridin-3-yl)-5,6-dihydropyrrolo[3,4-d]imidazol-4(1H)-one;

Example 150: 6-(4-chlorophenyl)-5-(3-(difluoromethyl)-8-methyl-[1,2,4]triazolo[4,3-b]pyridazin-6-yl)-1-isopropyl-2-methyl-5,6-dihydropyrrolo[3,4-d]imidazol-4(1H)-one;

Example 151: (R)-6-(4-chlorophenyl)-5-(3-(difluoromethyl)-8-methyl-[1,2,4]triazolo[4,3-a]pyridin-6-yl)-1-isopropyl-2-(2-methoxypyridin-3-yl)-5,6-dihydropyrrolo[3,4-d]imidazol-4(1H)-one;

Example 152: (R)-6-(4-chlorophenyl)-2-(3,6-dihydro-2H-pyran-4-yl)-5-(1,5-dimethyl-6-oxo-1,6-dihydropyridin-3-yl)-5,6-dihydropyrrolo[3,4-d]imidazol-4(1H)-one;

Example 153: (R)-6-(4-chlorophenyl)-5-(3-(difluoromethyl)-8-methyl-[1,2,4]triazolo[4,3-a]pyridin-6-yl)-2-(2-methoxypyridin-3-yl)-5,6-dihydropyrrolo[3,4-d]imidazol-4(1H)-one;

Example 154: (R)-6-(4-chlorophenyl)-5-(3,7-dimethyl-3H-[1,2,3]triazolo[4,5-b]pyridin-5-yl)-1-isopropyl-2-(6-methoxypyridin-3-yl)-5,6-dihydropyrrolo[3,4-d]imidazol-4(1H)-one;

Example 155: 6-(4-chlorophenyl)-5-(1,5-dimethyl-6-oxo-1,6-dihydropyridin-3-yl)-2-(2-methoxypyridin-3-yl)-5,6-dihydropyrrolo[3,4-d]imidazol-4(1H)-one;

Example 156: (R)-6-(4-chlorophenyl)-5-(1,5-dimethyl-6-oxo-1,6-dihydropyridin-3-yl)-2-(2-methoxypyridin-3-yl)-5,6-dihydropyrrolo[3,4-d]imidazol-4(1H)-one;

Example 157: 6-(4-chlorophenyl)-5-(3,7-dimethyl-3H-[1,2,3]triazolo[4,5-b]pyridin-5-yl)-1-isopropyl-2-(2-methoxypyridin-3-yl)-5,6-dihydropyrrolo[3,4-d]imidazol-4(1H)-one;

Example 158: (R)-6-(4-chlorophenyl)-5-(3,7-dimethyl-3H-[1,2,3]triazolo[4,5-b]pyridin-5-yl)-1-isopropyl-2-(2-methoxypyridin-3-yl)-5,6-dihydropyrrolo[3,4-d]imidazol-4(1H)-one;

Example 159: (R)-6-(4-chlorophenyl)-5-(3-(difluoromethyl)-8-methyl-[1,2,4]triazolo[4,3-a]pyridin-6-yl)-2-(2,4-dimethoxypyrimidin-5-yl)-1-isopropyl-5,6-dihydropyrrolo[3,4-d]imidazol-4(1H)-one;

Example 160: 6-(4-chlorophenyl)-2-(3,6-dihydro-2H-pyran-4-yl)-5-(3,7-dimethyl-3H-[1,2,3]triazolo[4,5-b]pyridin-5-yl)-1-isopropyl-5,6-dihydropyrrolo[3,4-d]imidazol-4(1H)-one;

Example 161: 6-(4-chlorophenyl)-5-(3-(difluoromethyl)-8-methyl-[1,2,4]triazolo[4,3-b]pyridazin-6-yl)-2-(3,6-dihydro-2H-pyran-4-yl)-1-isopropyl-5,6-dihydropyrrolo[3,4-d]imidazol-4(1H)-one;

Example 162: 6-(4-chlorophenyl)-2-(3,6-dihydro-2H-pyran-4-yl)-5-(3,7-dimethyl-3H-[1,2,3]triazolo[4,5-b]pyridin-5-yl)-5,6-dihydropyrrolo[3,4-d]imidazol-4(1H)-one;

Example 163: 6-(4-chlorophenyl)-5-(3,7-dimethyl-3H-[1,2,3]triazolo[4,5-b]pyridin-5-yl)-2-(2-methoxypyridin-3-yl)-5,6-dihydropyrrolo[3,4-d]imidazol-4(1H)-one;

Example 164: (R)-6-(4-chlorophenyl)-2-(3,6-dihydro-2H-pyran-4-yl)-5-(3,7-dimethyl-3H-[1,2,3]triazolo[4,5-b]pyridin-5-yl)-1-isopropyl-5,6-dihydropyrrolo[3,4-d]imidazol-4(1H)-one;

Example 165: (R)-6-(4-chlorophenyl)-2-(3,6-dihydro-2H-pyran-4-yl)-5-(3,7-dimethyl-3H-[1,2,3]triazolo[4,5-b]pyridin-5-yl)-5,6-dihydropyrrolo[3,4-d]imidazol-4(1H)-one;

Example 166: (R)-6-(4-chlorophenyl)-5-(3,7-dimethyl-3H-[1,2,3]triazolo[4,5-b]pyridin-5-yl)-2-(2-methoxypyridin-3-yl)-5,6-dihydropyrrolo[3,4-d]imidazol-4(1H)-one:

Example 167: (R)-6-(4-chlorophenyl)-2-(3,6-dihydro-2H-pyran-4-yl)-5-(3,8-dimethyl-[1,2,4]triazolo[4,3-a]pyridin-6-yl)-5,6-dihydropyrrolo[3,4-d]imidazol-4(1H)-one;

Example 168: (R)-6-(4-chlorophenyl)-5-(3-(difluoromethyl)-8-methyl-[1,2,4]triazolo[4,3-b]pyridazin-6-yl)-1-isopropyl-2-(2-methoxypyridin-3-yl)-5,6-dihydropyrrolo[3,4-d]imidazol-4(1H)-one;

Example 169: 6-(4-chlorophenyl)-5-(3,8-dimethyl-[1,2,4]triazolo[4,3-b]pyridazin-6-yl)-1-isopropyl-2-(1-methylpiperidin-4-yl)-5,6-dihydropyrrolo[3,4-d]imidazol-4(1H)-one;

Example 170: 6-(4-chlorophenyl)-5-(3,8-dimethyl-[1,2,4]triazolo[4,3-b]pyridazin-6-yl)-1-isopropyl-2-(tetrahydrofuran-3-yl)-5,6-dihydropyrrolo[3,4-d]imidazol-4(1H)-one;

Example 171: (6R)-6-(4-chlorophenyl)-5-(3,8-dimethyl-[1,2,4]triazolo[4,3-b]pyridazin-6-yl)-1-isopropyl-2-(tetrahydrofuran-3-yl)-5,6-dihydropyrrolo[3,4-d]imidazol-4(1H)-one; and Example 172: (6R)-6-(4-chlorophenyl)-5-(1,4-dimethyl-1H-benzo[d][1,2,3]triazol-6-yl)-1-isopropyl-2-(tetrahydrofuran-3-yl)-5,6-dihydropyrrolo[3,4-d]imidazol-4(1H)-one.

Embodiment 18. A compound of formula (I), or a salt thereof, according to Embodiment 1, which is selected from:

Example 18: 6-(4-chlorophenyl)-5-(3,8-dimethyl-[1,2,4]triazolo[4,3-b]pyridazin-6-yl)-1-isopropyl-2-methyl-5,6-dihydropyrrolo[3,4-d]imidazol-4(1H)-one;

Example 47: R-6-(4-chlorophenyl)-2-cyclopropyl-5-(1,5-dimethyl-6-oxo-1,6-dihydropyridin-3-yl)-5,6-dihydropyrrolo[3,4-d]imidazol-4(3H)-one;

Example 77: 6-(4-chlorophenyl)-5-(1,4-dimethyl-1H-benzo[d][1,2,3]triazol-6-yl)-1-isopropyl-2-(2-methoxypyridin-3-yl)-5,6-dihydropyrrolo[3,4-d]imidazol-4(1H)-one;

Example 78: 6-(4-chlorophenyl)-5-(1,4-dimethyl-1H-benzo[d][1,2,3]triazol-6-yl)-1-isopropyl-2-(1-methyl-1,2,3,6-tetrahydropyridin-4-yl)-5,6-dihydropyrrolo[3,4-d]imidazol-4(1H)-one;

Example 81: (R)-6-(4-chlorophenyl)-2-(3,6-dihydro-2H-pyran-4-yl)-5-(1,4-dimethyl-1H-benzo[d][1,2,3]triazol-6-yl)-1-isopropyl-5,6-dihydropyrrolo[3,4-d]imidazol-4(1H)-one;

Example 82: (R)-6-(4-chlorophenyl)-5-(1,4-dimethyl-1H-benzo[d][1,2,3]triazol-6-yl)-1-isopropyl-2-(tetrahydro-2H-pyran-4-yl)-5,6-dihydropyrrolo[3,4-d]imidazol-4(1H)-one;

Example 93: 6-(4-chlorophenyl)-2-(3,6-dihydro-2H-pyran-4-yl)-5-(1,4-dimethyl-1H-benzo[d][1,2,3]triazol-6-yl)-1-(oxetan-3-yl)-5,6-dihydropyrrolo[3,4-d]imidazol-4(1H)-one;

Example 95: 6-(4-chlorophenyl)-2-cyclopropyl-5-(1,4-dimethyl-1H-benzo[d][1,2,3]triazol-6-yl)-1-(oxetan-3-yl)-5,6-dihydropyrrolo[3,4-d]imidazol-4(1H)-one;

Example 102: (R)-6-(4-chlorophenyl)-5-(3,8-dimethyl-[1,2,4]triazolo[4,3-b]pyridazin-6-yl)-1-isopropyl-2-(tetrahydro-2H-pyran-4-yl)-5,6-dihydropyrrolo[3,4-d]imidazol-4(1H)-one;

Example 103: (R)-6-(4-chlorophenyl)-2-(3,6-dihydro-2H-pyran-4-yl)-5-(3,8-dimethyl-[1,2,4]triazolo[4,3-b]pyridazin-6-yl)-1-isopropyl-5,6-dihydropyrrolo[3,4-d]imidazol-4(1H)-one;

Example 111: (R)-6-(4-chlorophenyl)-1-isopropyl-5-(4-methoxy-1-methyl-1H-benzo[d][1,2,3]triazol-6-yl)-2-(2-methoxypyridin-3-yl)-5,6-dihydropyrrolo[3,4-d]imidazol-4(1H)-one;

Example 112: (R)-6-(4-chlorophenyl)-5-(1,4-dimethyl-1H-benzo[d][1,2,3]triazol-6-yl)-1-isopropyl-2-(2-methoxypyridin-3-yl)-5,6-dihydropyrrolo[3,4-d]imidazol-4(1H)-one;

Example 138: 6-(4-chlorophenyl)-5-(3,7-dimethyl-3H-[1,2,3]triazolo[4,5-b]pyridin-5-yl)-1-isopropyl-2-(6-methoxypyridin-3-yl)-5,6-dihydropyrrolo[3,4-d]imidazol-4(1H)-one;

Example 151: (R)-6-(4-chlorophenyl)-5-(3-(difluoromethyl)-8-methyl-[1,2,4]triazolo[4,3-a]pyridin-6-yl)-1-isopropyl-2-(2-methoxypyridin-3-yl)-5,6-dihydropyrrolo[3,4-d]imidazol-4(1H)-one;

Example 156: (R)-6-(4-chlorophenyl)-5-(1,5-dimethyl-6-oxo-1,6-dihydropyridin-3-yl)-2-(2-methoxypyridin-3-yl)-5,6-dihydropyrrolo[3,4-d]imidazol-4(1H)-one;

Example 158: (R)-6-(4-chlorophenyl)-5-(3,7-dimethyl-3H-[1,2,3]triazolo[4,5-b]pyridin-5-yl)-1-isopropyl-2-(2-methoxypyridin-3-yl)-5,6-dihydropyrrolo[3,4-d]imidazol-4(1H)-one;

Example 164: (R)-6-(4-chlorophenyl)-2-(3,6-dihydro-2H-pyran-4-yl)-5-(3,7-dimethyl-3H-[1,2,3]triazolo[4,5-b]pyridin-5-yl)-1-isopropyl-5,6-dihydropyrrolo[3,4-d]imidazol-4(1H)-one;

Example 165: (R)-6-(4-chlorophenyl)-2-(3,6-dihydro-2H-pyran-4-yl)-5-(3,7-dimethyl-3H-[1,2,3]triazolo[4,5-b]pyridin-5-yl)-5,6-dihydropyrrolo[3,4-d]imidazol-4(1H)-one;

Example 168: (R)-6-(4-chlorophenyl)-5-(3-(difluoromethyl)-8-methyl-[1,2,4]triazolo[4,3-b]pyridazin-6-yl)-1-isopropyl-2-(2-methoxypyridin-3-yl)-5,6-dihydropyrrolo[3,4-d]imidazol-4(1H)-one;

Example 169: 6-(4-chlorophenyl)-5-(3,8-dimethyl-[1,2,4]triazolo[4,3-b]pyridazin-6-yl)-1-isopropyl-2-(1-methylpiperidin-4-yl)-5,6-dihydropyrrolo[3,4-d]imidazol-4(1H)-one; and Example 172: (6R)-6-(4-chlorophenyl)-5-(1,4-dimethyl-1H-benzo[d][1,2,3]triazol-6-yl)-1-isopropyl-2-(tetrahydrofuran-3-yl)-5,6-dihydropyrrolo[3,4-d]imidazol-4(1H)-one.

The present disclosure includes compounds of stereochemistry is as shown in formula (Ib):

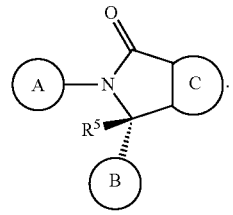

(Ib)

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

In another aspect, the present invention provides compounds of formula I in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{123}$I, $^{124}$I, $^{125}$I respectively. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by BET proteins, or (ii) associated with BET protein activity, or (iii) characterized by activity (normal or abnormal) of BET proteins; or (2) reduce or inhibit the activity of BET proteins; or (3) reduce or inhibit the expression of BET. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of BET proteins; or at least partially reducing or inhibiting the expression of BET proteins.

A "BET protein" is a protein encoded by either of the genes BRD2, BRD3, BRD4, or BRDT". Unless indicated otherwise "BET proteins" or "BET protein" are used herein in the singular and plural forms interchangeably, and the use of either is not limiting. Unless indicated otherwise "BET proteins" includes all, or any combination of, such encoded proteins.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R, S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Compositions:

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The compounds of formula I in free form or in pharmaceutically acceptable salt form, exhibit valuable pharmacological properties, e.g. BET protein modulating properties, e.g. as indicated in tests as provided in the next sections, and are therefore indicated for therapy or for use as research chemicals, e.g. as tool compounds.

Having regard to their activity as BET inhibitors, compounds of the formula (I) in free or pharmaceutically acceptable salt form, are useful in the treatment of conditions which are mediated by the activity of BET proteins, such as cancer, and/or that are responsive (meaning especially in a therapeutically beneficial way) to inhibition of a BET protein, most especially a disease or disorder as mentioned herein below.

Compounds of the invention are believed to be useful in the treatment of diseases or disorders such as cancer. In particular, such cancers include benign or malignant tumours, a soft tissue sarcoma or a sarcoma such as liposarcoma, rhabdomyosarcoma or bone cancer, e.g. osteosarcoma, a carcinoma, such as of the brain, kidney, liver, adrenal gland, bladder, breast, gastric, ovary, colon, rectum, prostate, pancreas, lung (including small cell lung cancer), vagina or thyroid, a glioblastoma, meningioma, glioma, mesothelioma, a neuroendocrine tumor such as neuroblastoma, a multiple myeloma, a gastrointestinal cancer, especially colon carcinoma or colorectal adenoma, a tumor of the head and neck, a melanoma, a prostate hyperplasia, a neoplasia, a neoplasia of epithelial character, a neoplasia originating from blood or bone marrow, a leukemia such as acute myeloid leukemia (AML) or acute lymphoblastic leukemia (ALL) or B-cell chronic lymphocytic leukemia, a lymphoma, such as of B- or T-cell origin, such as diffuse large B cell lymphoma (DLBCL), NUT midline carcinoma or any other neoplasia with chromosomal rearrangements of the BET genes, and metastases in other organs. In particular, compounds of the invention are believed to be useful in a cancer selected from a neoplasia originating from blood or bone marrow; a leukemia such as acute myeloid leukemia (AML) or acute lymphoblastic leukemia (ALL) or B-cell chronic lymphocytic leukemia; a lymphoma, such as of B- or T-cell origin, such as diffuse large B cell lymphoma (DLBCL); NUT midline carcinoma or any other neoplasia with chromosomal rearrangements of the BET genes, a neuroendocrine tumor such as neuroblastoma; a multiple myeloma; a lung cancer (including small cell lung cancer); and a colon cancer.

Compounds of the invention may also be of use in the treatment of atherosclerosis, coronary artery disease, dyslipidemia, diabetes, and other cardiovascular diseases, and/or as antiviral agents.

Thus, as a further embodiment, the present invention provides the use of a compound of formula (I) or a salt thereof, in therapy. In a further embodiment, the therapy is selected from a disease which may be treated by inhibition of BET proteins. In another embodiment, the disease is a cancer disease selected from the afore-mentioned list.

Thus, as a further embodiment, the present invention provides a compound of formula (I) or a salt thereof, for use in therapy. In a further embodiment, the therapy is selected from a disease which may be treated by inhibition of a BET protein. In another embodiment, the disease is a cancer disease selected from the afore-mentioned list.

In another embodiment, the invention provides a method of treating a disease which is treated by inhibition of a BET protein, comprising administration of a therapeutically acceptable amount of a compound of formula (I) or salt thereof. In a further embodiment, the disease is a cancer disease selected from the afore-mentioned list.

Thus, as a further embodiment, the present invention provides the use of a compound of formula (I) or salt thereof, for the manufacture of a medicament. In a further embodiment, the medicament is for treatment of a disease which may be treated by inhibition of a BET protein. In another embodiment, the disease is a cancer disease selected from the afore-mentioned list.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

Combinations

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by a BET protein. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by a BET protein, wherein the medicament is prepared for administration with another therapeutic agent. The invention also provides the use of another therapeutic agent for treating a disease or condition mediated by a BET protein, wherein the medicament is administered with a compound of formula (I).

The invention also provides a compound of formula (I) for use in a method of treating a disease or condition mediated by a BET protein, wherein the compound of formula (I) is prepared for administration with another therapeutic agent. The invention also provides another therapeutic agent for use in a method of treating a disease or condition mediated by a BET protein, wherein the other therapeutic agent is prepared for administration with a compound of formula (I). The invention also provides a compound of formula (I) for use in a method of treating a disease or condition mediated by a BET protein, wherein the compound of formula (I) is administered with another therapeutic agent. The invention also provides another therapeutic agent for use in a method of treating a disease or condition mediated by a BET protein, wherein the other therapeutic agent is administered with a compound of formula (I).

The invention also provides the use of a compound of formula (I) for treating a disease or condition mediated by a BET protein, wherein the patient has previously (e.g. within 24 hours) been treated with another therapeutic agent. The invention also provides the use of another therapeutic agent for treating a disease or condition mediated by a BET protein, wherein the patient has previously (e.g. within 24 hours) been treated with a compound of formula (I).

In one embodiment, the other therapeutic agent is an anticancer agent.

In a further embodiment, the other therapeutic agent is a modulator of a target in the field of epigenetics, such as an inhibitor of histone deacetylase (HDAC), or an inhibitor of histone methyltransferase (HMT).

Generic Schemes

Typically, the compounds of formula (I) can be prepared according to the Schemes provided infra, wherein $R^1$, $R^2$, $R^3$ and $R^4$ are as defined in Embodiment 1 and A is

, as defined in Embodiment 1.

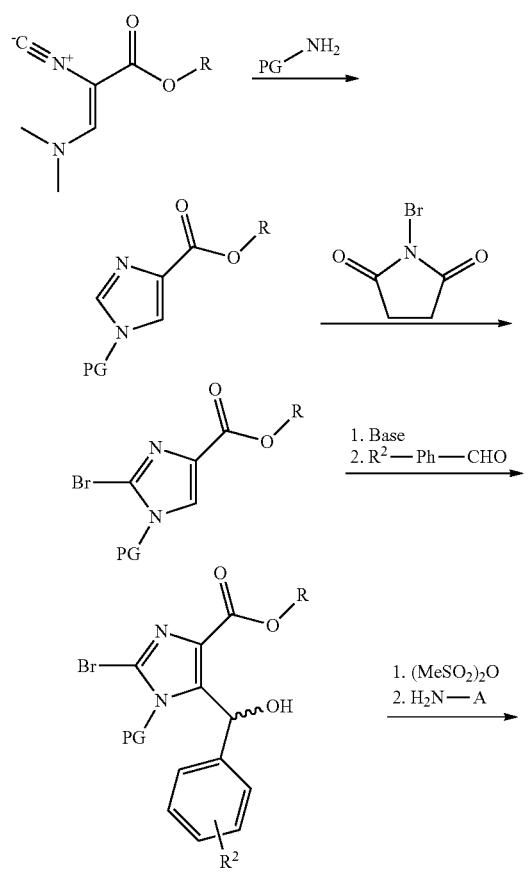

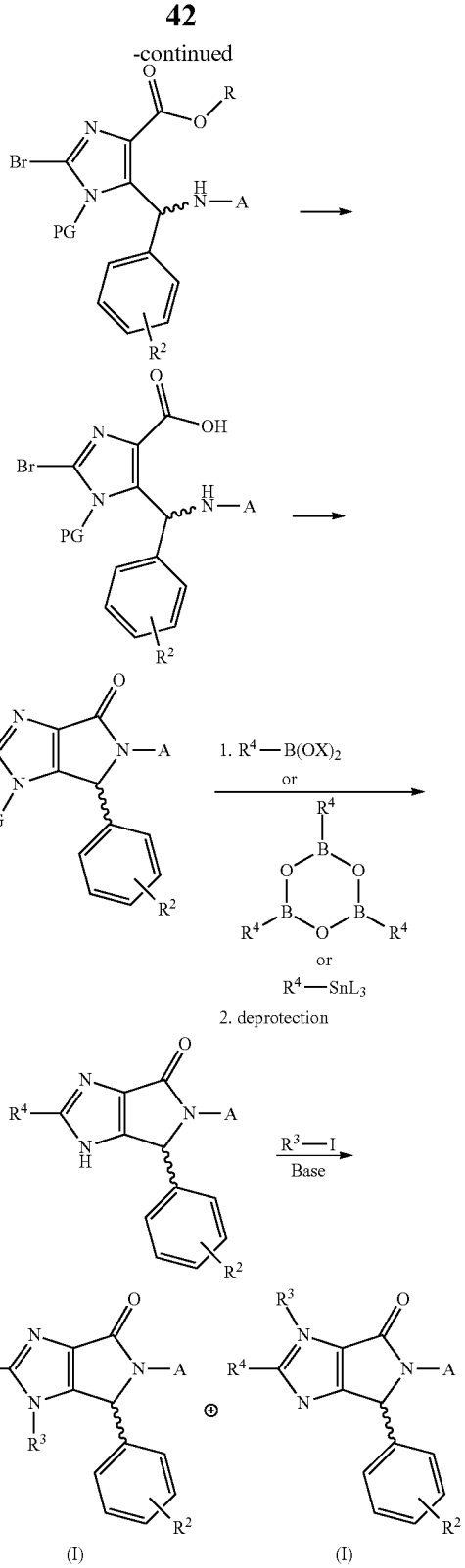

wherein R is $C_1$-$C_4$alkyl, suitable methyl; PG is a suitable protecting group (PG) such as allyl, para-methoxybenzyl or 3,4-dimethoxybenzyl; $B(OX)_3$ is a suitable boronic acid or boronic ester such as aryl- or heteroarylboronic esters, -acids, or trialkyl-boroxines; and $SnL_3$ is a suitable tin reagent, such as $SnBu_3$.

Scheme 1 illustrates a method for preparing compounds of the invention (e.g. Examples 1-8, 45). The commercially available isonitrile derivative is reacted with an amine suitable for introduction of an appropriate protecting group (PG) such as allyl, para-methoxybenzyl or 3,4-dimethoxybenzyl to generate the respective imidazole ester. Bromination with N-bromo-succinimide leads to the 2-bromo-imidazole. Deprotonation of the imidazole with strong bases, as exemplified with lithium-diisopropylamide, and reaction with 4-substituted benzaldehyde provides the corresponding alcohol. Conversion of the secondary alcohol into a leaving group, for example with (a) methanesulfonyl chloride or methanesulfonic anhydride in the presence of an organic base such as pyridine (together with a catalytic amount of 4-dimethylaminopyridine) or triethylamine or (b) 1-chloro-N,N,2-trimethylpropylamine, followed by reaction with an amine at temperatures between −30° C. and 50° C. results in the introduction of moiety A. Cyclization to the lactam can be effected either (a) directly from the amino-ester using either trimethylaluminium, dimethylaluminium chloride or diethylaluminium chloride or (b) in two steps by initial saponification of the ester group on treatment with a base such as an alkali metal hydroxide (e.g. lithium hydroxide or sodium hydroxide) in a solvent such as wet cycloalkylether or alcohol (e.g. dioxane/water or methanol/water), at a temperature between 20° C. and 100° C., preferably between 20° C. and 50° C. The amino-acid intermediate obtained after neutralization of the reaction mixture with an acid (such as a mineral acid, e.g. hydrochloric acid or a weak organic acid, e.g. citric acid), extraction and evaporation to dryness is then submitted to intramolecular cyclization using peptide coupling reagents such as O-(7-azabenzotriazol-1-yl)-N,N,N',N'-tetramethyluronium-hexafluorophosphate (HATU), O-benzotriazolyl tetramethylisouronium tetrafluoroborate (TBTU), 1,3,5,2,4,6-trioxatriphosphorinan-2,4,6-tripropyl-2,4,6-trioxid (propsal), or 1-chloro-N,N,2-trimethylpropylamine. Cross coupling reactions of the resulting 2-bromo-5,6-dihydropyrrolo[3,4-d]imidazol-4-(3H)-one intermediates with aryl- or heteroarylboronic esters, -acids, or trialkyl-boroxines ($R^4B(OX)_2$; e.g. $R^4$—$B(OH)_2$) or tin reagents ($R^4SnL_3$; e.g. $R^4$—$Sn(n\text{-butyl})_3$) are conducted under either Suzuki- or Stille-type conditions, i.e. utilizing catalysts such as $Pd(PPh_3)_4$, $(Ph_3P)_2PdCl_2$ or $Pd(dppf)Cl_2 \cdot CH_2Cl_2$ complex in the presence of excess of an inorganic base (e.g. $K_3PO_4$) in solvent systems such as dioxane/water or wet toluene in a temperature range from 80° C. to 120° C. These conditions can typically affect the concomitant cleavage of the N-allyl protecting group of the imidazole providing the unsubstituted N—H imidazole or needs to be followed by a separate deprotection step (e.g. treatment with TFA or hydrogenation). The N-unsubstituted imidazoles subsequently can be subjected to alkylation with alkyl iodides in the presence of a mineral base (e.g. $K_2CO_3$; $Cs_2CO_3$) in solvents such as acetonitrile to afford 2 regioisomeric products.

Scheme 2

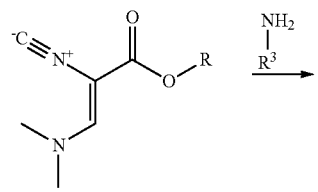

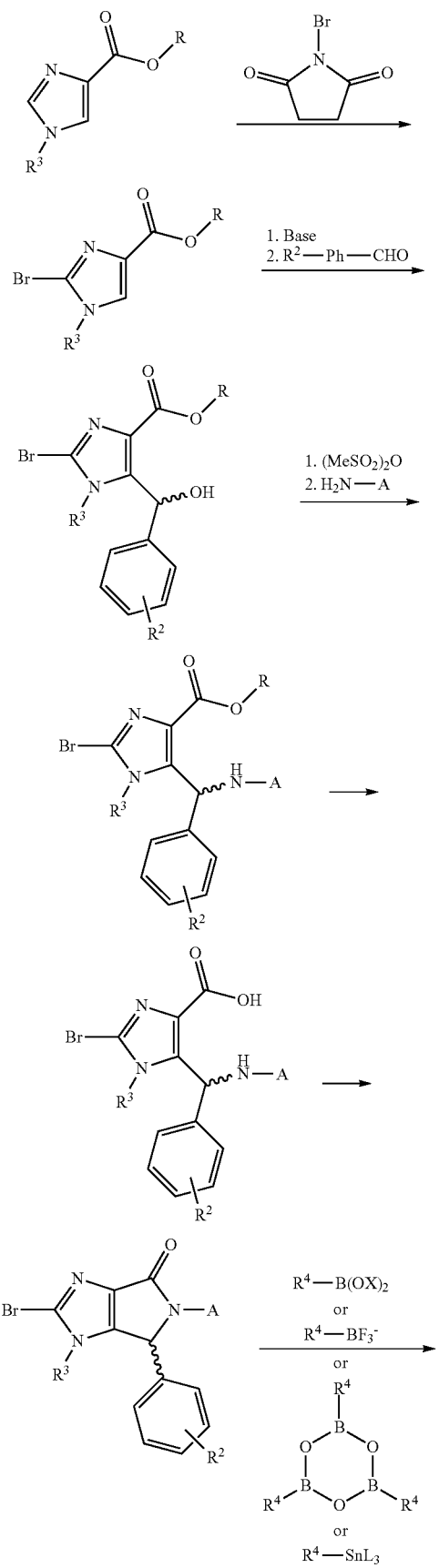

-continued

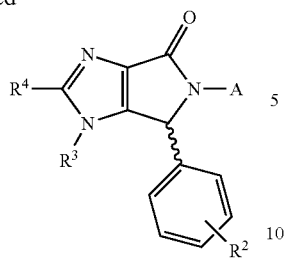

Scheme 3

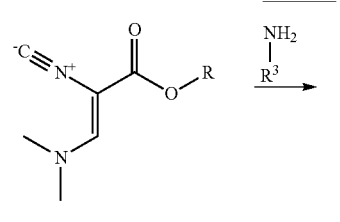

wherein R, B(OX)$_3$ and SnL$_3$ are as defied in Scheme 1.

Scheme 2 illustrates a variation of the method depicted in Scheme 1 for preparing compounds of the invention (e.g. Examples 9-17, 19-35, 43). The commercially available isonitrile derivative is reacted with an amino-alkane to generate the respective imidazole. Bromination with N-bromo-succinimide leads to the 2-bromo-imidazole. Deprotonation of the imidazole with strong bases, as exemlified with lithium-diisopropylamide, and reaction with 4-substituted benzaldehyde provides the corresponding alcohol. Conversion of the secondary alcohol into a leaving group, for example with (a) methanesulfonyl chloride or methanesulfonic anhydride in the presence of an organic base such as pyridine (together with a catalytic amount of 4-dimethylaminopyridine) or triethylamine or (b) 1-chloro-N,N,2-trimethylpropenylamine, followed by reaction with an amine at temperatures between −30° C. and 50° C. results in the introduction of moiety A. Cyclization to the lactam can be effected either (a) directly from the amino-ester using either trimethylaluminium, dimethylaluminium chloride or diethylaluminium chloride or (b) in two steps by initial saponification of the ester group on treatment with a base such as an alkali metal hydroxide (e.g. lithium hydroxide or sodium hydroxide) in a solvent such as wet cycloalkylether or alcohol (e.g. dioxane/water or methanol/water), at a temperature between 20° C. and 100° C., preferably between 20° C. and 50° C. The amino-acid intermediate obtained after neutralization of the reaction mixture with an acid (such as a mineral acid, e.g. hydrochloric acid or a weak organic acid, e.g. citric acid), extraction and evaporation to dryness is then submitted to intramolecular cyclization using peptide coupling reagents such as O-(7-azabenzotriazol-1-yl)-N,N,N',N'-tetramethyluronium-hexafluorophosphate (HATU), O-benzotriazolyl tetramethylisouronium tetrafluoroborate (TBTU), 1,3,5,2,4,6-trioxatriphosphorinan-2,4,6-tripropyl-2,4,6-trioxid (propsal), or 1-chloro-N,N,2-trimethylpropenylamine. Cross coupling reactions of the resulting 2-bromo-5,6-dihydropyrrolo[3,4-d]imidazol-4(3H)-one intermediates with aryl- or heteroarylboronic esters, -acids, alkyl-trifluoroborates (R$^4$—BF$_3$) or trialkyl-boroxines (R$^4$B(OX)$_2$; e.g. R$^4$B(OH)$_2$) or tin reagents (R$^4$SnL$_3$; e.g. R$^4$Sn(n-butyl)$_3$) are conducted under either Suzuki- or Stille-type conditions, i.e. utilizing catalysts such as Pd(PPh$_3$)$_4$, (Ph$_3$P)$_2$PdCl$_2$ or Pd(dppf)Cl$_2$.CH$_2$Cl$_2$ complex in the presence of excess of an inorganic base (e.g. K$_3$PO$_4$ or Cs$_2$CO$_3$) in solvent systems such as dioxane/water or wet toluene in a temperature range from 80° C. to 120° C.

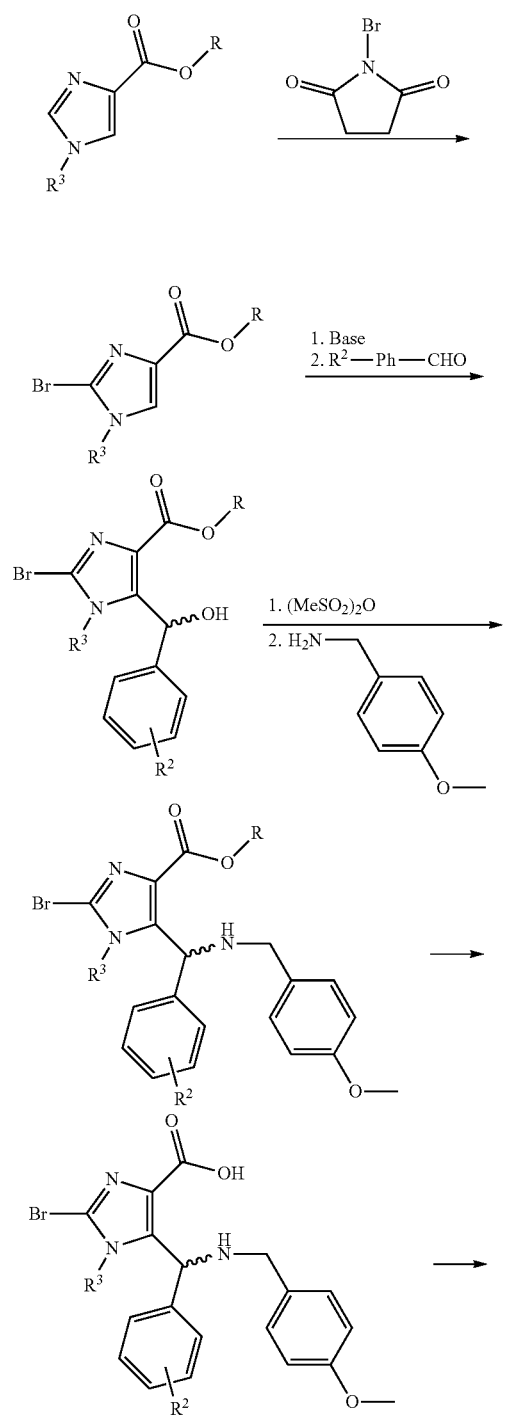

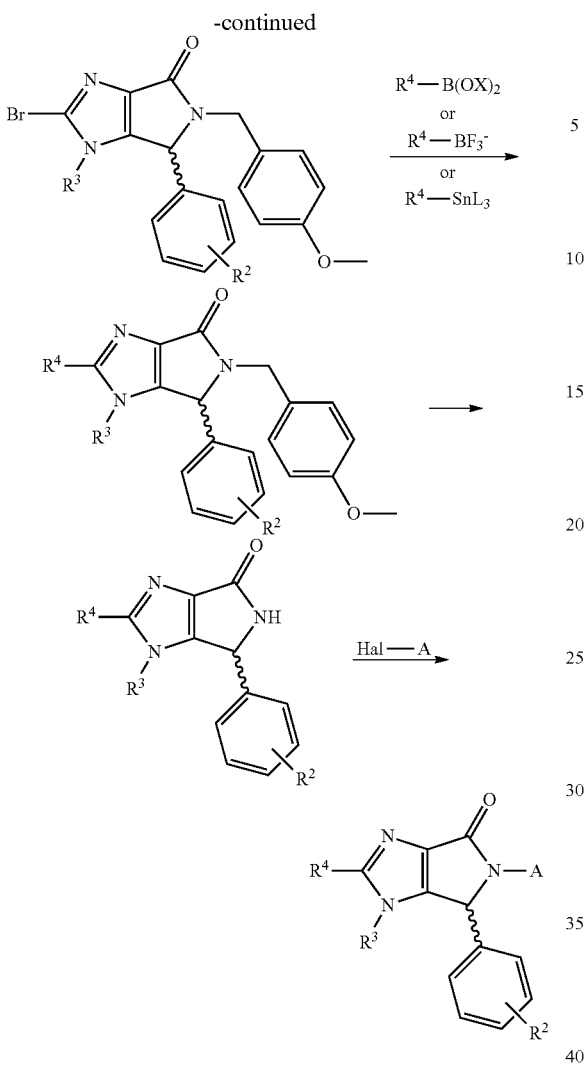

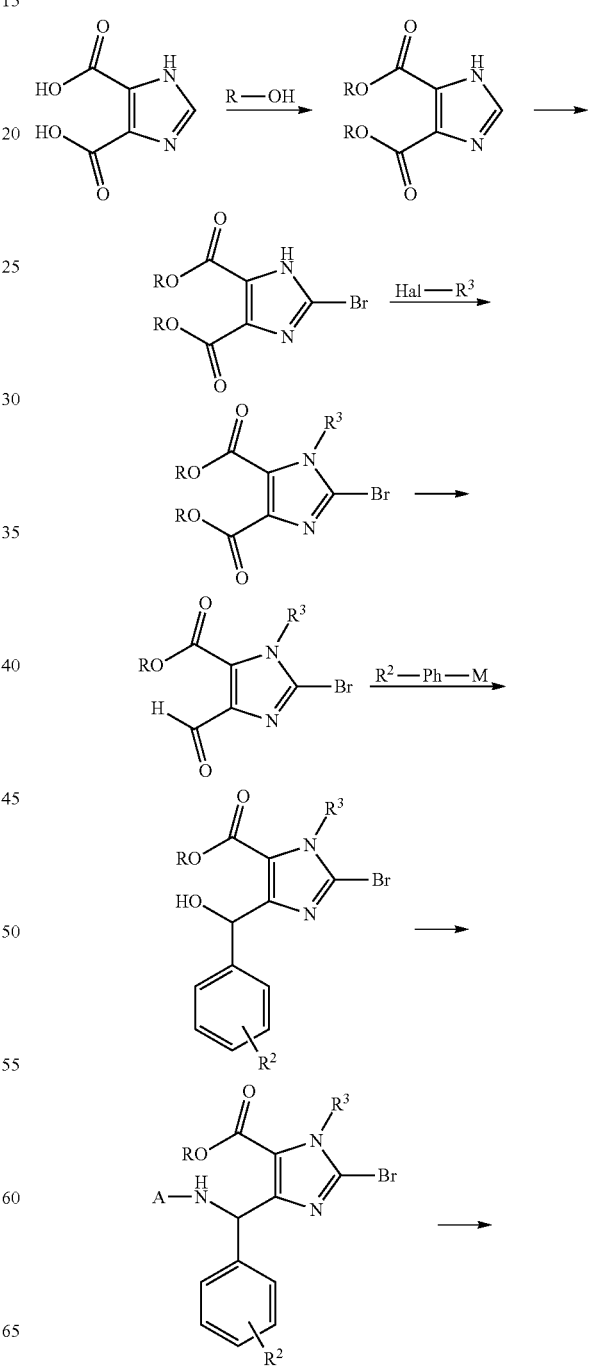

tetramethylisouronium tetrafluoroborate (TBTU), 1,3,5,2,4,6-trioxatriphosphorinan-2,4,6-tripropyl-2,4,6-trioxid (propsal), or 1-chloro-N,N,2-trimethylpropenylamine. Cross coupling reactions are performed in a analogy to the conditions described in Schemes 1 and 2. Cleavage of the para-methoxy benzyl (PMB) group can be effected by treatment with neat triflouoroacetic acid under microwave irradiation at a temperature of 140° C. N-heteroarylation of the resulting unsubstituted lactam by heteroaryl halides (Hal-A) can be promoted by Palladium (e.g. $Pd_2(dba)_3$/xantphos) or copper (e.g. Cham-Lam conditions) catalysis.

Scheme 4 wherein R, $B(OX)_3$ and $SnL_3$ are as defined in Scheme 1.

Scheme 3 illustrates another variation of the method depicted in Scheme 1 for preparing compounds of the invention (e.g. Example 18). The initial steps of this procedure follow the same sequence as outlined in Scheme 1 and 2 (R being suitably $C_1$ to $C_4$ alkyl). Conversion of the secondary alcohol into a leaving group, for example with (a) methanesulfonyl chloride or methanesulfonic anhydride in the presence of an organic base such as pyridine (together with a catalytic amount of 4-dimethylaminopyridine) or triethylamine or (b) 1-chloro-N,N,2-trimethylpropenylamine, followed by reaction with 4-methoxybenzylamine at temperatures between 0° C. and rt affords aminoesters. Cyclization to the lactam is be effected by saponification of the ester group on treatment with a base such as an alkali metal hydroxide (e.g. lithium hydroxide or sodium hydroxide) in a solvent such as wet cycloalkylether or alcohol (e.g. dioxane/water or methanol/water), at a temperature between 20° C. and 100° C., preferably between 20° C. and 50° C. The amino-acid intermediate obtained after neutralization of the reaction mixture with an acid (such as a mineral acid, e.g. hydrochloric acid or a weak organic acid, e.g. citric acid), extraction and evaporation to dryness is then submitted to intramolecular cyclization using peptide coupling reagents such as O-(7-azabenzotriazol-1-yl)-N,N,N',N'-tetramethyluronium-hexafluorophosphate (HATU), O-benzotriazolyl

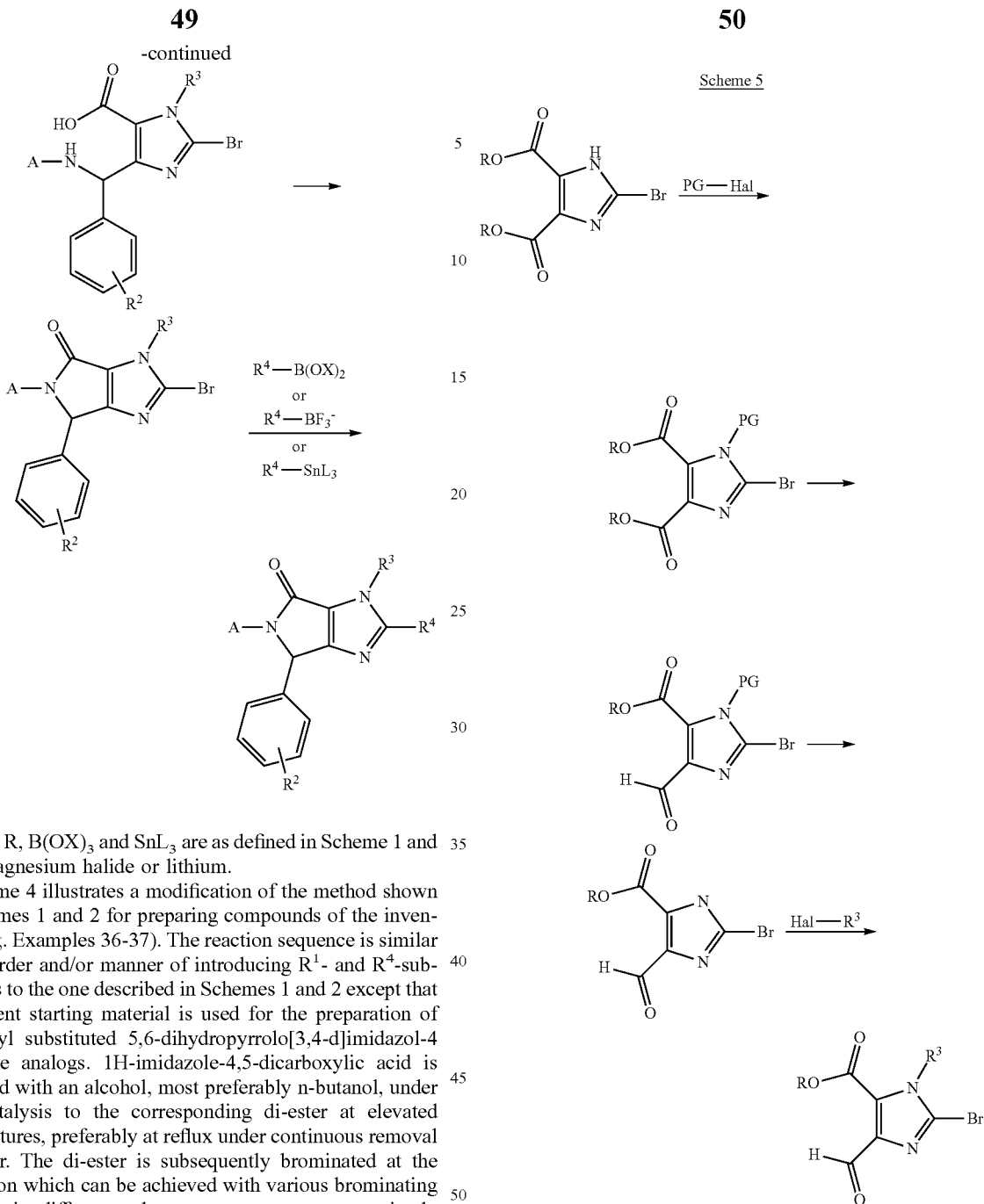

wherein R, B(OX)$_3$ and SnL$_3$ are as defined in Scheme 1 and M is magnesium halide or lithium.

Scheme 4 illustrates a modification of the method shown in Schemes 1 and 2 for preparing compounds of the invention (e.g. Examples 36-37). The reaction sequence is similar in the order and/or manner of introducing R$^1$- and R$^4$-substituents to the one described in Schemes 1 and 2 except that a different starting material is used for the preparation of N-3-alkyl substituted 5,6-dihydropyrrolo[3,4-d]imidazol-4 (3H)-one analogs. 1H-imidazole-4,5-dicarboxylic acid is esterified with an alcohol, most preferably n-butanol, under acid catalysis to the corresponding di-ester at elevated temperatures, preferably at reflux under continuous removal of water. The di-ester is subsequently brominated at the 2-position which can be achieved with various brominating reagents in different solvent systems, most conveniently with bromine and K$_2$CO$_3$ in acetonitrile at ambient temperature. The N-unsubstituted imidazole intermediate is subsequently reacted with a halogenated reagent R$^3$-Hal wherein Hal refers to halogen preferably iodine or bromine, e.g. n-propyl iodide, in N,N-dimethylformamide at elevated temperature, preferably 50-80° C. Selective reduction of the distal ester functionality to the aldehyde can be achieved with a metal hydride reagent, preferably with diisobutylaluminium hydride in tetrahydrofuran at low temperature, ideally between −78° C. and −20° C. The resulting aldehyde intermediate can be further processed by reaction with commercially available metallated aryl (R$^2$—Ph-M) Grignard or lithium reagents (e.g. M being magnesium-halogen or lithium) to afford the corresponding secondary alcohols which can be transformed to the final compounds in analogy to the sequence as outlined in Schemes 1 and 2.

wherein R is C$_1$-C$_4$alkyl, suitable methyl; and PG is a suitable protecting group, suitably an acid cleavable protecting group such as 4-methoxybenzyl (PMB).

Scheme 5 illustrates a modification of the method shown in Scheme 4 for preparing compounds of the invention (e.g. Examples 38-42). This method is similar to the one described in Scheme 4 except that the R$^3$-group can be varied after the synthesis of the aldehyde-ester intermediate. Instead of insertion of the R$^3$-group at the beginning, a protection group is attached, most preferably an acid cleavable protecting such as 4-methoxybenzyl (PMB), which can be removed after generation of the aldehyde-ester intermediate to allow alkylation with a halogenated R$^3$-reagent at N3- as well as at N1-position of the imidazole derivative.

Scheme 6
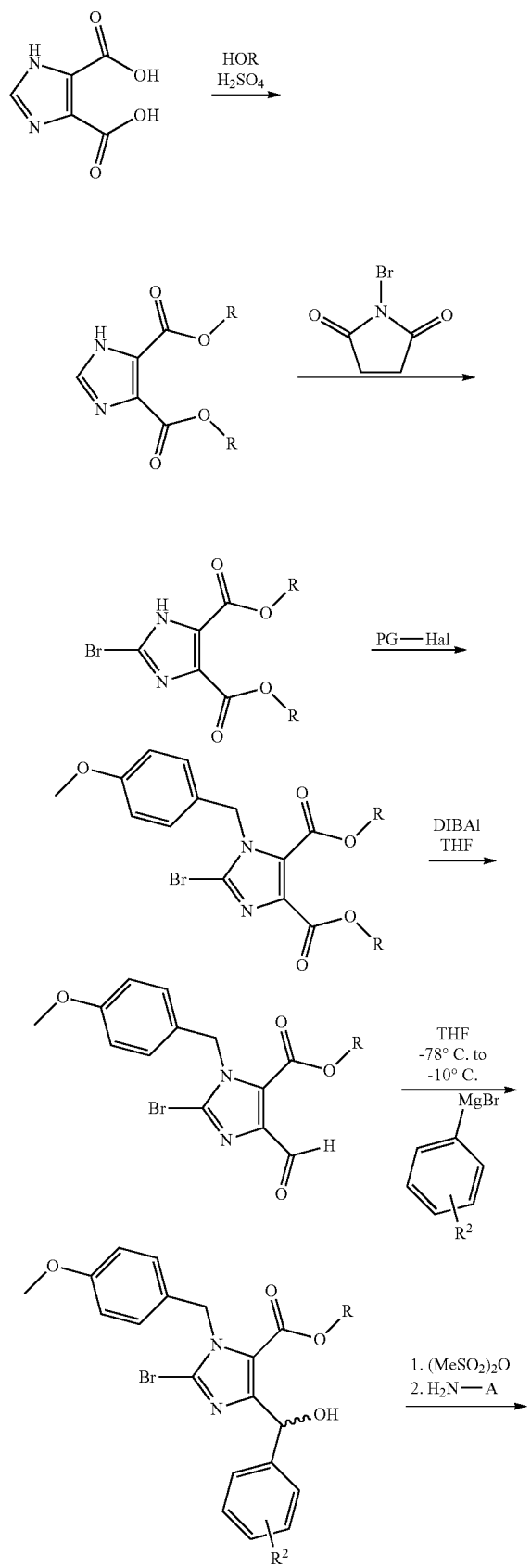
wherein R is $C_1$-$C_4$alkyl, suitable methyl; PG is a is a suitable protecting group, suitably an acid cleavable protecting group such as 4-methoxybenzyl (PMB); $B(OX)_3$ is a suitable boronic acid or boronic ester such as aryl- or heteroarylboronic esters, -acids, or trialkyl-boroxines; and SnL₃ is a suitable tin reagent, such as SnBu₃.

Scheme 6 illustrates another modification of the method shown in Scheme 4 for preparing compounds of the invention (e.g. Examples 46). The reaction sequence utilizes as in Scheme 4 the similar sequence/manner for the introduction of $R^1$- and $R^4$-substituents to the one described in Schemes 1 and 2 except that the same material is used for the preparation of N-3-alkyl substituted 5,6-dihydropyrrolo[3,4-d]imidazol-4(3H)-one intermediate as described in Scheme 4 following the similar order of synthetic steps. The N-unsubstituted imidazole intermediate is reacted with 4-methoxy benzylchloride in N,N-dimethylformamide at elevated temperature, preferably 50-80° C. in the presence of a mineral base (e. g. $K_2CO_3$). The further sequence is conducted in a similar manner as outlined in Scheme 4. After Suzuki or Stille type coupling for introduction of $R^4$ as outlined in previous schemes; the imidazole nitrogen is debenzylated which can be effected by treatment with e. g. TFA at elevated temperatures, typically 100-140° C.

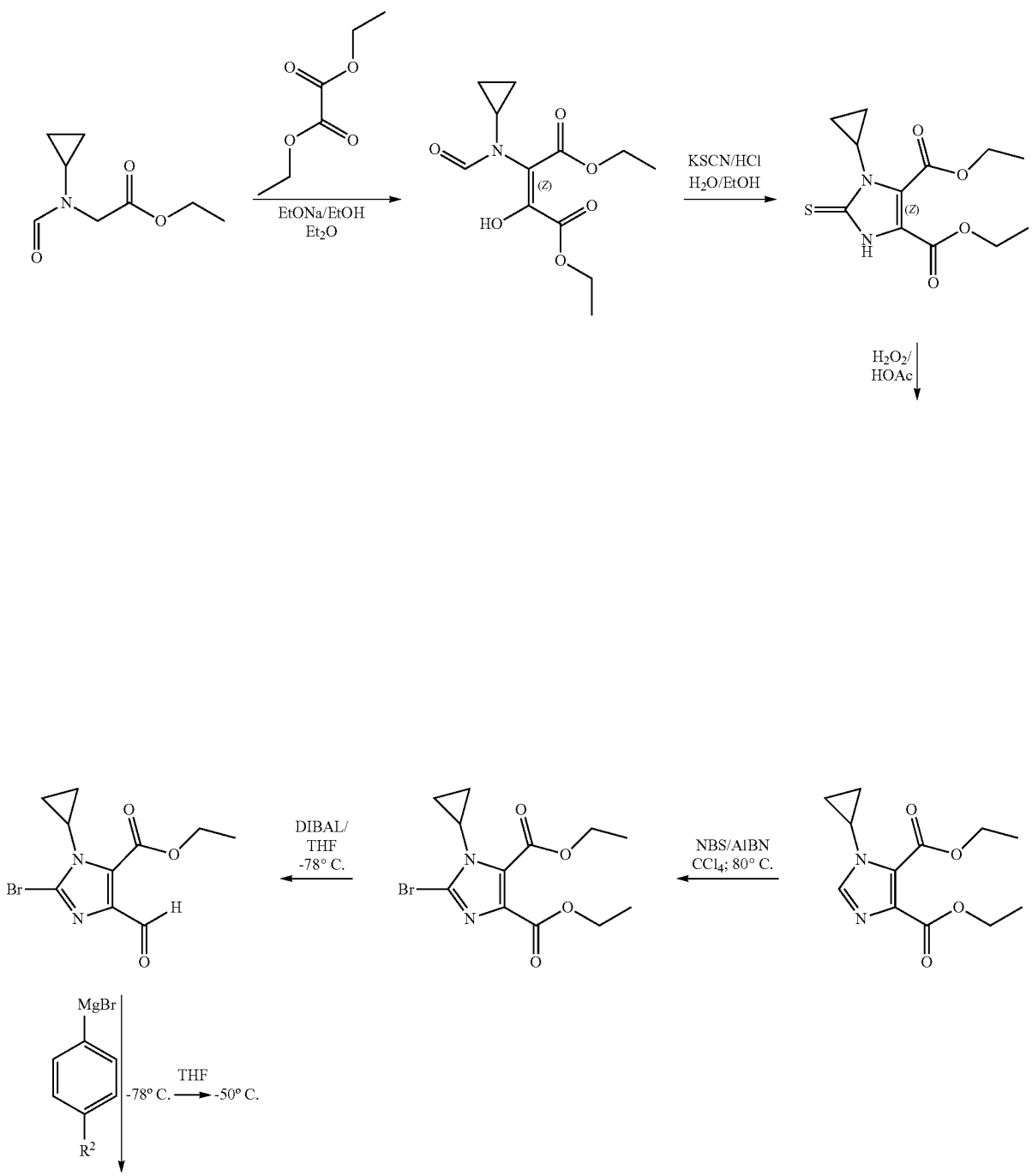

Scheme 7

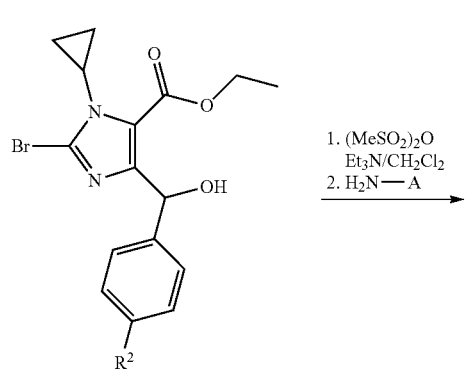
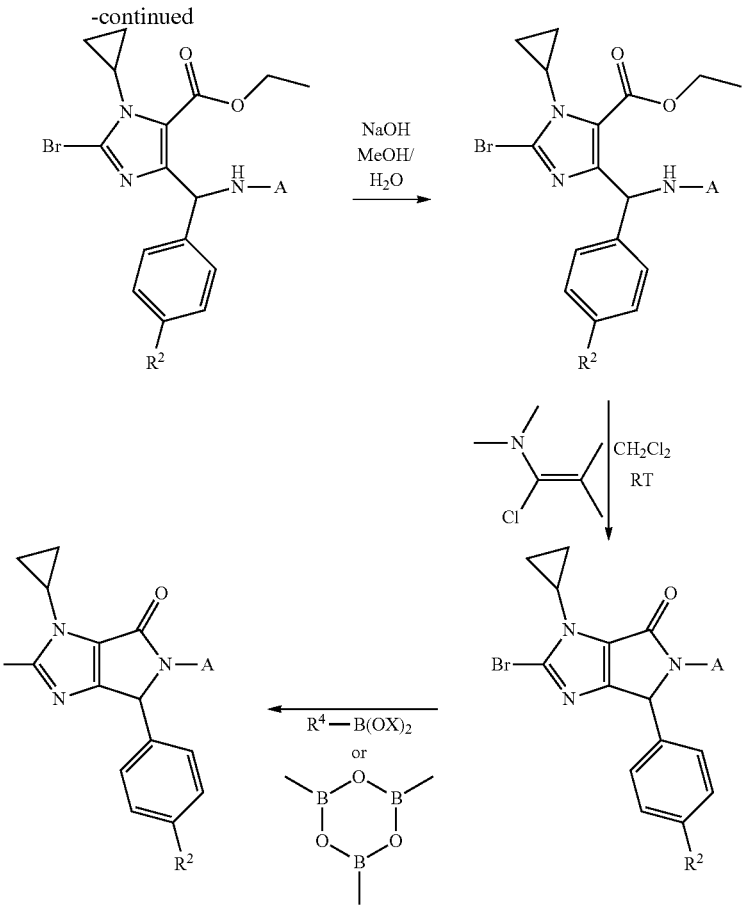

Scheme 7 illustrates another modification of the method shown in Scheme 4 for preparing compounds of the invention (e.g. Examples 115). The reaction sequence utilizes as in Scheme 4 the similar sequence/manner for the introduction of A- and $R^4$-substituents to the one described in Schemes 1 and 2 except that the intermediate 2-bromo-1-cycloalkyl-1H-imidazole-4,5-dicarboxylic acid ester is prepared differently. The product of the condensation of the N-formyl-gylcine derivative with oxalic acid ester is cyclized with KSCN to the corresponding 2-thioxo-2,3-dihydro-1H-imidazole-4,5-dicarboxylic acid ester. Desulfurization with $H_2O_2$/HOAc and bromination gives the 2-bromo-1-cycloalkyl-1H-imidazole-4,5-dicarboxylic acid ester derivative.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

Synthetic Methods

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

Abbreviations
$Ac_2O$ acetic anhydride
AcOH acetic acid
ACN acetonitrile
aq. aqueous
Ar argon
Boc tert-butoxycarbonyl
Brine saturated (at rt) sodium chloride solution
br. s broad singlet
cc concentrated
$CH_2Cl_2$ dichloromethane
$CH_3CN$ acetonitrile
$CS_2CO_3$ cesium carbonate
d doublet
DIBAL-H diisobutylaluminium hydride
DIPEA N,N-Diisopropylethylamine
DMA dimethylacetamide
DMAP 4-dimethylaminopyridine DMF N,N-dimethylformamide
DMSO dimethylsulfoxide
EP ethylpyridine
ESI-MS electrospray ionization mass spectrometry
$Et_2O$ diethylether
EtOAc ethyl acetate
EtOH ethanol
hr hour(s)
HCl hydrochloric acid
$HNO_3$ nitric acid
$H_2SO_4$ sulfuric acid
HPLC high-performance liquid chromatography
IPAm isopropylamine
$iPr_2O$ diisopropylether
iPrOH isopropylalcohol
$K_2CO_3$ potassium carbonate
$K_3PO_4$ potassium phosphate
LDA lithium diisopropylamine
m multiplet
MeOH methanol
$MgSO_4$ magnesium sulfate
min minute(s)
mL milliliter(s)
MS mass Spectrometry
$Ms_2O$ methanesulfonic anhydride
MW microwave
NaH sodium hydride
$NaHCO_3$ sodium bicarbonate
NaOAc natrium acetate
NaOH sodium hydroxide
$Na_2SO_4$ sodium sulfate
$Na_2S_2O_3$ sodium thiosulfate
NBS N-bromosuccinimide
n-BuOH n-butanol
$NH_4Cl$ ammonium chloride
NMP N-methyl-2-pyrrolidone
NMR nuclear magnetic resonance
$Pd_2(dba)_3.HCCl_3$ Tris(dibenzylideneacetone)dipalladium $HCCl_3$ complex
$Pd(OAc)_2$ palladium (II) acetate
$Pd(PBu_3)_2$ di-(tributylphosphine)palladium(0)
$Pd(PPh_3)_4$ tetrakis(triphenylphosphine)palladium(0)
ppm parts per million
PPU propyl-pyridyl-urea
propsal 1,3,5,2,4,6-trioxatriphosphorinan-2,4,6-tripropyl-2,4,6-trioxid (50% in DMF)
$R_f$ ratio of fronts
rt (or RT) room temperature
RuPhos 2-dicyclohexylphosphino-2',6'-diisopropoxybiphenyl
s singlet
$scCO_2$ supercritical carbon dioxide
SFC supercritical fluid chromatography
t triplet
TBME tert-butylmethylether
$t_R$ time of retention
TFA trifluoroacetic acid
THF tetrahydrofuran
TLC thin layer chromatography
XantPhos 4,5-bis(diphenylphosphino)-9,9-dimethylxanthene HPLC Methods:
HPLC 1: Column: Nucleosil 100-3 C18 HD, 4.6×70 mm. Flow: 1 mL/min. Column temperature: 30° C. Gradient: 20% to 100% B in 5 min, 100% B for 1.5 min, 100% to 20% B in 0.5 min; A=0.1% TFA in water, B=0.1% TFA in ACN.

LC-MS Methods:
LC-MS 1:
Column: Waters Acquity HSS T3, 1.8 μm, 2.1×50 mm, oven at 50° C. Flow: 1.2 mL/min. Gradient: 2% to 98% B in 1.40 min, then 98% B for 0.40 min, 98% to 2% B in 0.10 min, 2% B for 0.10 min; A=water+0.05% formic acid+3.75 mM ammonium acetate, B=ACN+0.04% formic acid. Detection UV/VIS (DAD), ESI (+/−). Mass spectrometer range: 100-1600 Da.

LC-MS 2:
Column: Waters Acquity HSS T3, 1.8 μm, 2.1×50 mm, oven at 60° C. Flow: 1.0 mL/min. Gradient: 5% to 98% B in 1.40 min, then 98% B for 0.40 min, 98% to 5% B in 0.10 min, 5% B for 0.10 min; A=water+0.05% formic acid+3.75 mM ammonium acetate, B=ACN+0.04% formic acid. Detection UV/VIS (DAD), ESI (+/−). Mass spectrometer range: 100-1200 Da.

EXAMPLE 1

6-(4-chlorophenyl)-5-(3,7-dimethyl-3H-benzo[d][1,2,3]triazol-5-yl)-2-methyl-5,6-dihydropyrrolo[3,4-d]imidazol-4(1H)-one

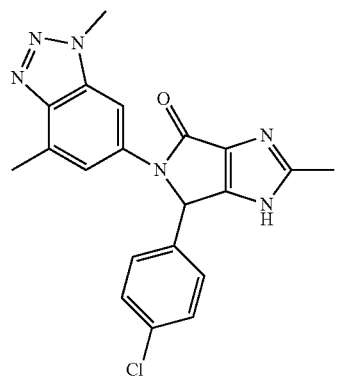

To a stirred mixture of 1-allyl-2-bromo-6-(4-chlorophenyl)-5-(3,7-dimethyl-3H-benzo[d][1,2,3]triazol-5-yl)-5,6-dihydropyrrolo[3,4-d]imidazol-4(1H)-one (Step 1.11) (80 mg, 0.161 mmol) in Dioxane (1.1 mL) and water (400 μL) under Ar were added $K_3PO_4$ (136 mg, 0.643 mmol), $PdCl_2$(dppf).$CH_2Cl_2$ adduct (20 mg, 0.0.24 mmol) and trimethylboroxine (45 μL, 0.32 mmol). The resulting mixture was heated up and stirred at 100° C. overnight. $PdCl_2$(dppf).$CH_2Cl_2$ adduct (20 mg, 0.0.24 mmol) and trimethylboroxine (45 μL, 0.32 mmol) were added and the reaction was stirred 1.5 hr at 100° C. $PdCl_2$(dppf).$CH_2Cl_2$ (20 mg, 0.0.24 mmol) adduct and trimethylboroxine trimethylboroxine (45 μL, 0.32 mmol) were added and the reaction was stirred 5.5 hr at 100° C. The reaction was cooled down to RT, diluted with water and the aq. layer was extracted twice with EtOAc. Combined extracts were dried over $Na_2SO_4$, filtered and concentrated under reduced pressure. The crude product was purified by preparative HPLC (gradient 35-55% $CH_3CN$ in 16 min) followed by basic workup to afford the title product (5 mg, 0.012 mmol, 7.52% yield). $t_R$: 0.80 min (LC-MS 2); ESI-MS: 393 [M+H]$^+$; ESI-MS: 391 [M−H]$^−$ (LC-MS 2).

Step 1.1: 5-bromo-N,3-dimethyl-2-nitroaniline

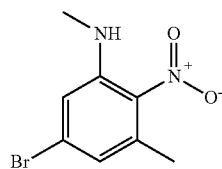

A MW vial was charged with 5-bromo-1-fluoro-3-methyl-2-nitrobenzene (500 mg, 2.137 mmol) and methylamine 2M in THF (5 mL, 10.0 mmol). The MW vial was sealed and the reaction mixture was submitted to MW irradiation for 30 min at 100° C. The reaction was cooled down to RT and concentrated under reduced pressure to afford the title product (520 mg, 2.122 mmol, 99% yield) as yellow solid. $t_R$: 1.19 min (LC-MS 2); ESI-MS: no ionisation (LC-MS 2). $^1$H NMR (400 MHz, CDCl3) δ ppm 2.46 (s, 3H) 2.92 (d, J=5.1 Hz, 3H) 6.68 (d, J=2.34 Hz, 1H), 6.73-6.87 (m, 2H).

Step 1.2: 5-bromo-N1,3-dimethylbenzene-1,2-diamine

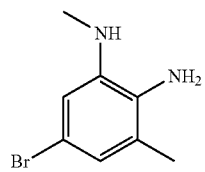

To a solution of 5-bromo-N,3-dimethyl-2-nitroaniline (Step 1.1) (2.7 g, 11.02 mmol) in THF (100 mL) and MeOH (100 mL) was added Raney Nickel (189 mg, 2.203 mmol) and the resulting mixture was stirred under hydrogen atmosphere at RT for 16 hr. The reaction was filtered through a pad of Celite and the resulting filtrate was concentrated under reduced pressure to afford the title product (2.5 g, 10.56 mmol, 96% yield) as off-white solid. $t_R$: 0.94 min (LC-MS 2); ESI-MS: 214 [M+H]$^+$ (LC-MS 2).

Step 1.3: 6-bromo-1,4-dimethyl-1H-benzo[d][1,2,3]triazole

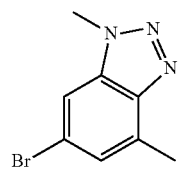

To a solution of 5-bromo-N1,3-dimethylbenzene-1,2-diamine (Step 1.2) (2.5 g, 11.62 mmol) in HCl cc (15 mL, 494 mmol) cooled down to 0° C. was slowly added a solution of NaNO$_2$ (0.962 g, 13.95 mmol) in water (25 mL). The resulting mixture was allowed to warm up and stir at RT for 2 hr. NaOH was added until basic pH and a precipitate occurred. The resulting solid was filtrated off, washed with water and dried under reduced pressure to afford the title product (2.5 g, 9.95 mmol, 86% yield) as beige solid. $t_R$: 0.93 min (LC-MS 2); ESI-MS: 228 [M+H]$^+$ (LC-MS 2).

Step 1.4: 1,4-dimethyl-1H-benzo[d][1,2,3]triazol-6-amine

A MW vial was charged with 6-bromo-1,4-dimethyl-1H-benzo[d][1,2,3]triazole (Step 1.3) (200 mg, 0.86 mmol), copper(II) oxide (6.33 mg, 0.04 mmol) and aq. NH$_3$ (1.5 mL, 17.69 mmol) and few drops of NMP were added. The MW vial was sealed and the reaction was submitted to MW irradiation at 100° C. for 1 hr then, 140° C. for 30 min. Cupper(I) iodide (around 6 mg) was added to the reaction and the mixture was submitted to MW irradiation at 150° C. for 1.5 hr. The reaction mixture was diluted with water and extracted with EtOAc. The organic layer was dried over Na$_2$SO$_4$ and concentrated under reduced pressure to afford the title product (90 mg, 0.50 mmol, 56.5% yield) as orange solid. $t_R$: 0.47 min (LC-MS 2); ESI-MS: 163.1 [M+H]$^+$ (LC-MS 2).

Step 1.5: (Z)-ethyl 3-(dimethylamino)-2-isocyanoacrylate

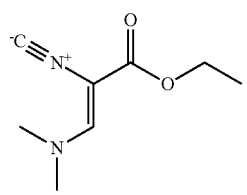

To a dark brown solution of ethylisocyanoacetate (1000 g, 8.6 mol) in EtOH (11.3 L) under nitrogen, cooled down to −5° C. was added N,N-dimethylformamide diethyl acetal (2.0 L, 11.3 mol) over a period of 30 min, keeping the internal temperature below 0° C. The dark brown solution was warmed up to 25° C. and stirred for 4 hr. The reaction was concentrated under reduced pressure. The crude product was dissolved in TBME (3 L), 1 kg silica gel was added and the resulting mixture was stirred for 15 min, filtered through a pad of silica gel (0.5 kg) and washed with TBME (5×0.3 L). The filtrate was concentrated under reduced pressure and the resulting crude product was purified by silica gel column chromatography (heptane/EtOAc 6:4) to afford the title product (1078 g, 6.4 mol, 74.0% yield) as yellow amorphous crystals.

Step 1.6: ethyl 1-allyl-1H-imidazole-4-carboxylate

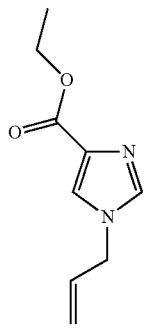

To a brown solution of (Z)-ethyl 3-(dimethylamino)-2-isocyanoacrylate (Step 1.5) (255 g, 1.5 mol) in EtOH (600 mL) under nitrogen and cooled down to 11° C. was added dropwise allylamine (567 mL, 7.6 mol). The resulting mixture was allowed to warm up and stir at RT overnight. The reaction mixture was cooled down to RT and concentrated under reduced pressure to afford the title product (281.1 g, 1.5 mol, 98% yield) as brown oil without further purification.

Step 1.7: ethyl 1-allyl-2-bromo-1H-imidazole-4-carboxylate

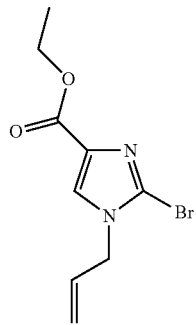

To a brown solution of ethyl 1-allyl-1H-imidazole-4-carboxylate (Step 1.6) (280 g, 1.5 mol) in THF (3 L) under nitrogen was added NBS (277 g, 1.5 mol) portionwise over 15 minutes at RT (exothermic reaction, flask was cooled down with ice/water bath). The resulting mixture was stirred overnight at RT. NBS (138 g, 777 mmol) was added portionwise over 5 minutes at RT and the reaction mixture was stirred for further 5 hr. The mixture was filtered through a pad of silica gel and the pad was washed with EtOAc (ca 0.5 L). The resulting filtrate was concentrated under reduced pressure, diluted with EtOAc (2 L) and washed with a saturated aq. NaHCO$_3$ solution (1×2 L and 1×1 L). The combined aq. layers were extracted with EtOAc (0.5 L). Combined extracts were washed with brine (1 L), dried over anhydrous Na$_2$SO$_4$, filtered and concentrated under reduced pressure. The crude product was dissolved in heptane/EtOAc (1:1) (1 L) and CH$_2$Cl$_2$ (200 mL) and the resulting solution was filtered through a pad of silica gel. The pad was washed several times with heptane/EtOAc (1:1) (total 8 L), and the filtrate containing the desired product was concentrated under reduced pressure. The crude product was purified by silica gel column chromatography (toluene/EtOAc 10-40%) to afford the title product (130.6 g, 487 mmol, 28.9% yield) as yellow oil. t$_R$: 0.79 min (LC-MS 2); ESI-MS: 259/261 [M+H]$^+$ (LC-MS 2).

Step 1.8: ethyl 1-allyl-2-bromo-5-((4-chlorophenyl)(hydroxy)methyl)-1H-imidazole-4-carboxylate

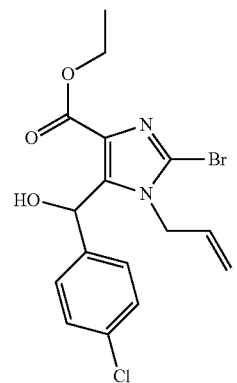 [SMILES: C=CCn1c(Br)nc(C(=O)OCC)c1C(O)c1ccc(Cl)cc1]

Ethyl 1-allyl-2-bromo-1H-imidazole-4-carboxylate (Step 1.7) (6 g, 23.2 mmol) was dissolved in THF (230 mL) under Ar, 4-chlorobenzaldehyde (3.42 g, 24.3 mmol) was added and the resulting mixture was cooled down to −78° C. 2M LDA (23.16 mL, 46.3 mmol) was added dropwise over 1.5 hr, the reaction mixture was stirred at −78° C. for 1 hr. The reaction was allowed to warm up and stir to −20° C. and quenched with aq. NH$_4$Cl solution. EtOAc was added, both phases were separated and the aq. layer was extracted three times with EtOAc. Combined extracts were dried over Na$_2$SO$_4$, filtered and concentrated under reduced pressure. The crude product was purified by silica gel column chromatography (hexane/EtOAc 0-50% EtOAc) to afford the title product (3.2 g, 7.61 mmol, 32.8% yield) as yellow solid. t$_R$: 1.13 min (LC-MS 2); ESI-MS: 399/401 [M+H]$^+$ (LC-MS 2).

Step 1.9: ethyl 1-allyl-2-bromo-54(4-chlorophenyl)((1,4-dimethyl-1H-benzo[d][1,2,3]triazol-6-yl)amino)methyl)-1H-imidazole-4-carboxylate

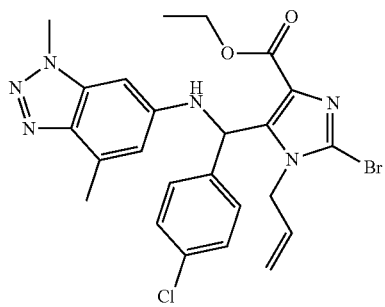 [SMILES: C=CCn1c(Br)nc(C(=O)OCC)c1C(Nc1cc(C)c2nnn(C)c2c1)c1ccc(Cl)cc1]

Ethyl 1-allyl-2-bromo-5-((4-chlorophenyl)(hydroxy)methyl)-1H-imidazole-4-carboxylate (Step 1.8) (130 mg, 0.33 mmol) was dissolved in CH$_2$Cl$_2$ (3.2 mL) under Ar, TEA (227 μL, 1.63 mmol) was added and the resulting mixture was cooled down to 5° C. Methanesulfonic anhydride (142 mg, 0.81 mmol) was added and the reaction mixture was allowed to warm up and stir at RT for 30 min. The reaction was cooled down to 5° C., 1,4-dimethyl-1H-benzo[d][1,2,3]triazol-6-amine (Step 1.4) (63.3 mg, 0.39 mmol) was added and the reaction mixture was allowed to warm up and stir at RT for 16 hr. The reaction was washed with 1N HCl and aq. NaHCO$_3$ solution, dried over Na$_2$SO$_4$, filtered and concentrated under reduced pressure to afford the title product (190 mg, 0.29 mmol, 88% yield) as yellow resin. $t_R$: 1.19 min (LC-MS 2); ESI-MS: 543/545 [M+H]$^+$ (LC-MS 2).

Step 1.10: 1-allyl-2-bromo-5-((4-chlorophenyl)((1,4-dimethyl-1H-benzo[d][1,2,3]triazol-6-yl)amino)methyl)-1H-imidazole-4-carboxylic acid

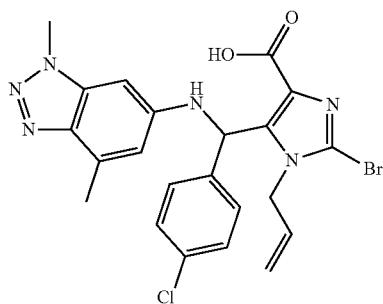 [SMILES: C=CCn1c(Br)nc(C(=O)O)c1C(Nc1cc(C)c2nnn(C)c2c1)c1ccc(Cl)cc1]

Ethyl 1-allyl-2-bromo-5((4-chlorophenyl)((1,4-dimethyl-1H-benzo[d][1,2,3]triazol-6-yl)amino methyl)-1H-imidazole-4-carboxylate (Step 1.9) (190 mg, 0.290 mmol) was dissolved in MeOH (3 mL) and THF (3 mL), 2N NaOH (2.2 mL, 4.4 mmol) was added and the resulting mixture was stirred at RT for 1 hr. The reaction was concentrated under reduced pressure and the aq. layer was cooled down with an ice/water bath and stirred, 2N HCl (ca 2.2 mL) was slowly added, ice/water bath was removed and the resulting mixture was stirred at RT overnight. The resulting solid was filtered off and dried under reduced pressure to afford the title product (142 mg, 0.23 mmol, 81% yield) as pale yellow solid. $t_R$: 1.00 min (LC-MS 2); ESI-MS: 515/517 [M+H]$^+$; ESI-MS: 513/515 [M−H]$^-$ (LC-MS 2).

Step 1.11: 1-allyl-2-bromo-6-(4-chlorophenyl)-5-(3,7-dimethyl-3H-benzo[d][1,2,3]triazol-5-yl)-5,6-dihydropyrrolo[3,4-d]imidazol-4(1H)-one

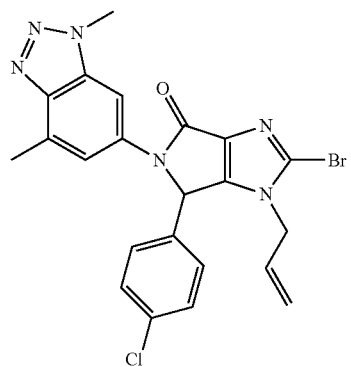 [SMILES: C=CCn1c(Br)nc2c1C(c1ccc(Cl)cc1)N(c1cc(C)c3nnn(C)c3c1)C2=O]

1-Allyl-2-bromo-5((4-chlorophenyl)((1,4-dimethyl-1H-benzo[d][1,2,3]triazol-6-yl)amino)methyl)-1H-imidazole-4-carboxylic acid (Step 1.10) (142 mg, 0.26 mmol) was dissolved in CH$_2$Cl$_2$ (2.8 mL) under Ar and the mixture was cooled down to 5° C. 1-chloro-N,N,2-trimethylprop-1-en-1-amine (73 µL, 0.55 mmol) was added and the reaction mixture was allowed to warm up and stir at RT for 1 hr. The reaction was diluted with water and extracted twice with CH$_2$Cl$_2$. Combined extracts were dried over Na$_2$SO$_4$, filtered and concentrated under reduced pressure. The crude product was triturated with Et$_2$O, sonicated and the resulting solid was filtered off and dried under reduced pressure to afford the title product (82 mg, 0.156 mmol, 56.8% yield) as beige solid. $t_R$: 1.06 min (LC-MS 2); ESI-MS: 497/499 [M+H]$^+$ (LC-MS 2).

EXAMPLE 2

6-(4-chlorophenyl)-5-(3,7-dimethyl-3H-benzo[d][1,2,3]triazol-5-yl)-1-isopropyl-2-methyl-5,6-dihydropyrrolo[3,4-d]imidazol-4(1H)-one

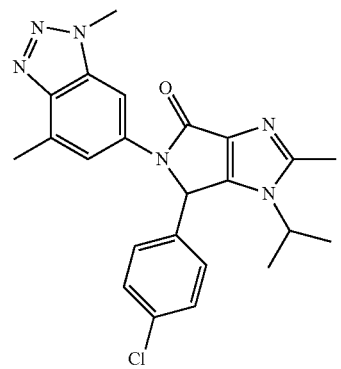

6-(4-Chlorophenyl)-5-(3,7-dimethyl-3H-benzo[d][1,2,3]triazol-5-yl)-2-methyl-5,6dihydropyrrolo[3,4-d]imidazol-4(1H)-one (Example 1) (200 mg, 0.51 mmol) was dissolved in CH$_3$CN (5 mL). K$_2$CO$_3$ (148 mg, 1.1 mmol) and isopropyl iodide (255 µL, 2.5 mmol) were successively added and the resulting mixture was heated up and stirred at 90° C. for 5 hr. The reaction was cooled down to RT and water was added. The aq. layer was extracted twice with EtOAc. Combined extracts were dried over Na$_2$SO$_4$, filtered and concentrated under reduced pressure. The crude product was triturated with CH$_3$CN/MeOH, the solid was filtered off and the filtrate was concentrated under reduced pressure. The residue was purified by silica gel column chromatography (CH$_2$Cl$_2$/MeOH 0-10% MeOH) followed by trituration in MeOH to afford the title product (23 mg, 0.05 mmol, 9.9% yield) as pale yellow solid. $t_R$: 0.94 min (LC-MS 2); ESI-MS: 435/437 [M+H]$^+$ (LC-MS 2).

EXAMPLE 3

6-(4-chlorophenyl)-5-(3,7-dimethyl-3H-benzo[d][1,2,3]triazol-5-yl)-3-isopropyl-2-methyl-5,6-dihydropyrrolo[3,4-d]imidazol-4(3H)-one

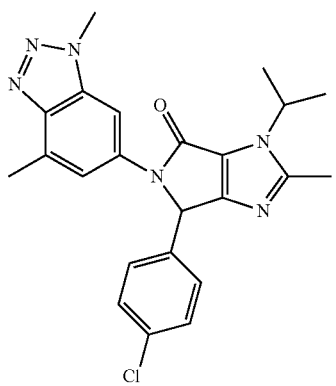

The title compound was prepared in analogy to the procedure described in Example 2 using 6-(4-chlorophenyl)-5-(3,7-dimethyl-3H-benzo[d][1,2,3]triazol-5-yl)-2-methyl-5,6dihydropyrrolo[3,4-d]imidazol-4(1H)-one (Example 1). The crude product was triturated with $CH_3CN$/MeOH, the resulting solid was filtered off and dried under reduced pressure. The solid was further purified by silica gel column chromatography ($CH_2Cl_2$/MeOH 0-10% MeOH) to afford the title product (54 mg, 0.12 mmol, 22.9% yield) as colorless foam. $t_R$: 1.00 min (LC-MS 2); ESI-MS: 435 [M+H]+ (LC-MS 2).

EXAMPLE 4

6-(4-chlorophenyl)-5-(1,5-dimethyl-6-oxo-1,6-dihydropyridin-3-yl)-2-(6-methoxypyridin-3-yl)-5,6-dihydropyrrolo[3,4-d]imidazol-4(1H)-one

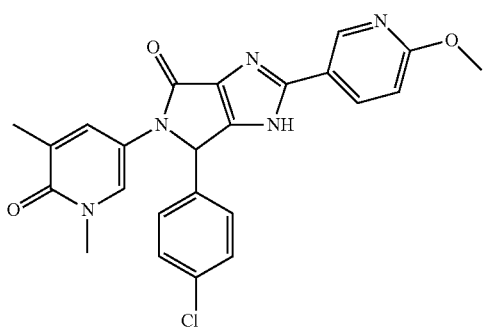 [SMILES: COc1ccc(-c2nc3c([nH]2)C(c2ccc(Cl)cc2)N(c2cc(C)c(=O)n(C)c2)C3=O)cn1]

The title compound was prepared in analogy to the procedure described in Example 1 using 1-allyl-2-bromo-6-(4-chlorophenyl)-5-(1,5-dimethyl-6-oxo-1,6-dihydropyridin-3-yl)-5,6-dihydropyrrolo[3,4-d]imidazol-4(1H)-one (Step 4.6) and 6-methoxy-3-pyridinylboronic acid at 100° C. for 16 hr. After workup, the palladium was removed using a polymer supported benzyl mercaptan resin (PL-BnSH MP-resin) and the resulting crude product was purified by silica gel column chromatography (EtOAc/MeOH 0-10% MeOH).

$t_R$: 0.85 min (LC-MS 2); ESI-MS: 462 [M+H]+ (LC-MS 2).

Step 4.1: 3-methyl-5-nitropyridin-2-ol

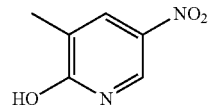

To a stirred solution of 3-methylpyridin-2-ol (280 g, 2.56 mol) in $H_2SO_4$ (750 mL) cooled down to 0° C. was added $H_2SO_4$ (180 mL) and 70% $HNO_3$ (180 mL) dropwise to keep the temperature at 20-25° C. The resulting solution was stirred at RT for 2 hr, 70% $HNO_3$ (180 mL) was added dropwise keeping the temperature below 35° C., water (500 mL) was added dropwise keeping the temperature below 50-60° C. The resulting mixture was heated up and stirred 2 hr at 115° C. The reaction was cooled down to RT then, to 0° C. by adding ice into it. The resulting solid was filtrated off, washed with cold $Et_2O$ and dried under reduced pressure to afford the title product (362 g, 2.35 mol, 92% yield). $^1$H NMR (DMSO-$d_6$, 400 MHz) δ ppm 12.55 (s, 1H), 8.56-8.54 (d, J=3.2 Hz, 1H), 8.05 (s, 1H), 2.04 (s, 3H).

Step 4.2: 1,3-dimethyl-5-nitropyridin-2(1H)-one

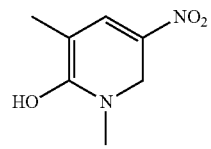

To a stirred suspension of 3-methyl-5-nitropyridin-2-ol (Step 4.1) (360 g, 2.34 mol) and $K_2CO_3$ (645.8 g, 4.68 mol) in DMF (4 L) under nitrogen and cooled down to 0° C. was added dropwise methyl iodide (498.4 g, 3.51 mol). The resulting mixture was allowed to warm up and stirred at RT for 1 hr. The reaction mixture was concentrated under reduced pressure, diluted with water and extracted with EtOAc. The organic layers were combined and washed with brine, dried over $Na_2SO_4$, filtered and concentrated under reduced pressure to afford the title product (357 g, 2.13 mol, 91% yield). $^1$H NMR (DMSO-$d_6$, 400 MHz) δ ppm 9.10-9.09 (d, J=2.4 Hz, 1H), 8.08-8.09 (m, J=1.2 Hz, 1H), 3.57 (s, 3H), 2.08 (s, 3H).

Step 4.3: 5-amino-1,3-dimethylpyridin-2(1H)-one

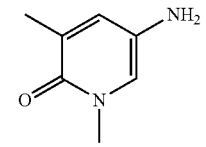

To a stirred solution of 1,3-dimethyl-5-nitropyridin-2 (1H)-one (Step 4.2) (335 g, 1.9 mol) and $NH_4Cl$ (1054.7 g, 19.9 mol) in EtOH (3.5 L) was added iron (334.3 g, 5.9 mol) portionwise. The resulting mixture was heated up and stirred at reflux for 1 hr. The reaction was filtered and concentrated under reduced pressure. The crude product was purified by silica gel column chromatography (NH$_3$ 1%/CH$_2$Cl$_2$/MeOH 2-6%) to afford the title product (113.7 g, 0.82 mol, 41.6% yield). $^1$H NMR (DMSO-d$_6$, 400 MHz) δ ppm 6.95-6.95 (d, J=1.6 Hz, 1H), 6.70 (s, 1H), 4.16 (s, 2H), 3.31 (s, 3H), 1.94 (S, 3H).

Step 4.4: ethyl 1-allyl-2-bromo-54(4-chlorophenyl) ((1,5-dimethyl-6-oxo-1,6-dihydropyridin-3-yl) amino)methyl)-1H-imidazole-4-carboxylate

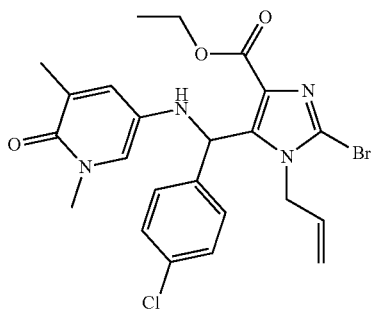 [SMILES: C=CCn1c(Br)nc(C(=O)OCC)c1C(Nc1cc(C)c(=O)n(C)c1)c1ccc(Cl)cc1]

The title compound was prepared in analogy to the procedure described in Step 1.9 using ethyl 1-allyl-2-bromo-5-((4-chlorophenyl)(hydroxy)methyl)-1H-imidazole-4-carboxylate (Step 1.8) and 5-amino-1,3-dimethylpyridin-2(1H)-one (Step 4.3). The crude product was purified by silica gel column chromatography (CH$_2$Cl$_2$/MeOH 0-15% MeOH) to afford the title product as brownish foam. t$_R$: 1.07 min (LC-MS 2); ESI-MS: 519/521 [M+H]$^+$ (LC-MS 2).

Step 4.5: 1-allyl-2-bromo-54(4-chlorophenyl)((1,5-dimethyl-6-oxo-1,6-dihydropyridin-3-yl)amino) methyl)-1H-imidazole-4-carboxylic acid

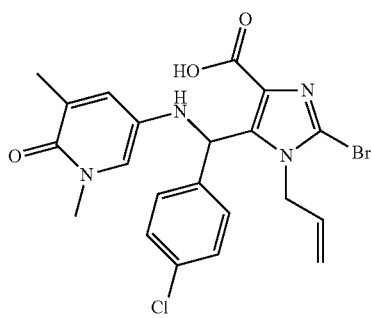 [SMILES: C=CCn1c(Br)nc(C(=O)O)c1C(Nc1cc(C)c(=O)n(C)c1)c1ccc(Cl)cc1]

The title compound was prepared in analogy to the procedure described in Step 1.10 using ethyl 1-allyl-2-bromo-54(4-chlorophenyl)((1,5-dimethyl-6-oxo-1,6-dihydropyridin-3-yl)amino)methyl)-1H-imidazole-4-carboxylate (Step 4.4). t$_R$: 0.87 min (LC-MS 2); ESI-MS: 491/493 [M+H]$^+$; ESI-MS: 489/491 [M−H]$^-$ (LC-MS 2).

Step 4.6: 1-allyl-2-bromo-6-(4-chlorophenyl)-5-(1,5-dimethyl-6-oxo-1,6-dihydropyridin-3-yl)-5,6-dihydropyrrolo[3,4-d]imidazol-4(1H)-one

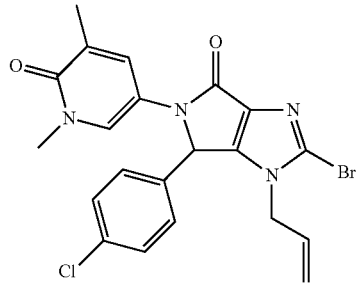 [SMILES: C=CCn1c(Br)nc2c1C(c1ccc(Cl)cc1)N(c1cc(C)c(=O)n(C)c1)C2=O]

The title compound was prepared in analogy to the procedure described in Step 1.11 using 1-allyl-2-bromo-5-((4-chlorophenyl)((1,5-dimethyl-6-oxo-1,6-dihydropyridin-3-yl)amino)methyl)-1H-imidazole-4-carboxylic acid (Step 4.5). t$_R$: 0.90 min (LC-MS 2); ESI-MS: 473/475 [M+H]$^+$ (LC-MS 2).

EXAMPLE 5

(R)-6-(4-chlorophenyl)-5-(1,5-dimethyl-6-oxo-1,6-dihydropyridin-3-yl)-2-(6-methoxypyridin-3-yl)-5,6-dihydropyrrolo[3,4-d]imidazol-4(1H)-one

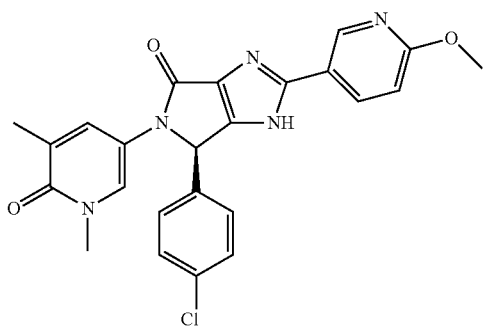

The title compound (12 mg, 0.025 mmol, 38% yield) was obtained enantiomerically pure (ee>99.5%) after chiral preparative chromatography (System: Gilson PLC 2020 HPLC system; column: Chiralpak IC 5 μm, 20×250 mm; mobile phase: heptane/EtOH/MeOH 75:15:10 isocratic; flow rate: 11 mL/min; detection 210 nm) of the racemic mixture of 6-(4-chlorophenyl)-5-(1,5-dimethyl-6-oxo-1,6-dihydropyridin-3-yl)-2-(6-methoxypyridin-3-yl)-5,6-dihydropyrrolo[3,4-d]imidazol-4(1H)-one (Example 4) (30 mg, 0.065 mmol). t$_R$: 0.85 min (LC-MS 2); ESI-MS: 462/464 [M+H]$^+$ (LC-MS 2). The second enantiomer 6-(4-chlorophenyl)-5-(1,5-dimethyl-6-oxo-1,6-dihydropyridin-3-yl)-2-(6-methoxypyridin-3-yl)-5,6-dihydropyrrolo[3,4-d]imidazol-4(1H)-one (13 mg, 0.03 mmol, 41% yield) was obtained enantiomerically pure (ee>99.5%) via the same separation.

EXAMPLE 6

6-(4-chlorophenyl)-5-(1,5-dimethyl-6-oxo-1,6-dihydropyridin-3-yl)-2-(6-methoxypyridin-3-yl)-3-methyl-5,6-dihydropyrrolo[3,4-d]imidazol-4(3H)-one

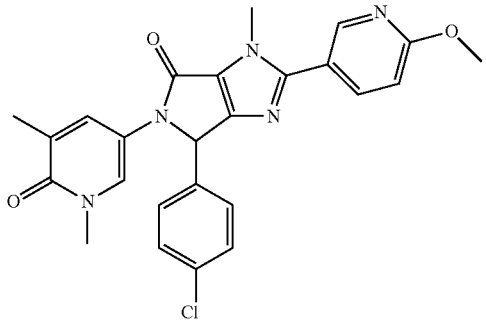

The title compound was prepared in analogy to the procedure described in Example 2 using 6-(4-chlorophenyl)-5-(1,5-dimethyl-6-oxo-1,6-dihydropyridin-3-yl)-2-(6-methoxypyridin-3-yl)-5,6-dihydropyrrolo[3,4-d]imidazol-4(1H)-one (Example 4) and methyl iodide at RT for 2 hr. The crude product was purified by preparative HPLC (gradient 20 to 40% CH$_3$CN in 20 min), followed by basic workup to afford the title product as yellow solid. t$_R$: 0.90 min (LC-MS 2); ESI-MS: 476 [M+H]$^+$ (LC-MS 2).

EXAMPLE 7

(R)-6-(4-chlorophenyl)-5-(1,5-dimethyl-6-oxo-1,6-dihydropyridin-3-yl)-2-(6-methoxypyridin-3-yl)-3-methyl-5,6-dihydropyrrolo[3,4-d]imidazol-4(3H)-one

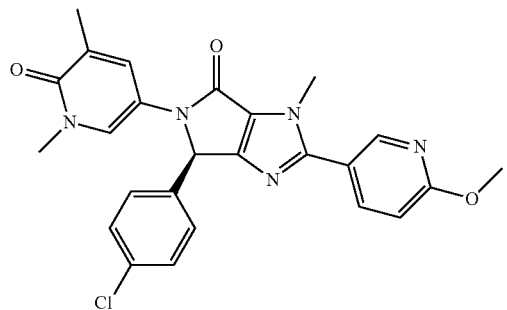 [SMILES: COc1ccc(-c2nc3c(n2C)C(=O)N(c2cc(C)c(=O)n(C)c2)[C@@H]3c2ccc(Cl)cc2)cn1]

The title compound (13 mg, 0.026 mmol, 37.4% yield) was obtained enantiomerically pure (ee>99.5%) after chiral preparative chromatography (System: Gilson PLC 2020 HPLC system; column: Phenomenex Lux Cel-2 (=Chiralcel OZ—H) 5 μm, 21.2×250 mm; mobile phase: EtOH/MeOH 50:50 isocratic; flow rate: 10 mL/min; detection 220 nm) of the racemic mixture of 6-(4-chlorophenyl)-5-(1,5-dimethyl-6-oxo-1,6-dihydropyridin-3-yl)-2-(6-methoxypyridin-3-yl)-3-methyl-5,6-dihydropyrrolo[3,4-d]imidazol-4(3H)-one (Example 6) (33 mg, 0.069 mmol). White foam. t$_R$: 0.90 min (LC-MS 2); ESI-MS: 476 [M+H]$^+$ (LC-MS 2).

The second enantiomer (S)-6-(4-chlorophenyl)-5-(1,5-dimethyl-6-oxo-1,6-dihydropyridin-3-yl)-2-(6-methoxypyridin-3-yl)-3-methyl-5,6-dihydropyrrolo[3,4-d]imidazol-4(3H)-one (12 mg, 0.024 mmol, 34.5% yield) was obtained enantiomerically pure (ee>99.5%) via the same separation.

EXAMPLE 8

6-(4-chlorophenyl)-5-(1,5-dimethyl-6-oxo-1,6-dihydropyridin-3-yl)-2-(6-methoxypyridin-3-yl)-1-methyl-5,6-dihydropyrrolo[3,4-d]imidazol-4(1H)-one

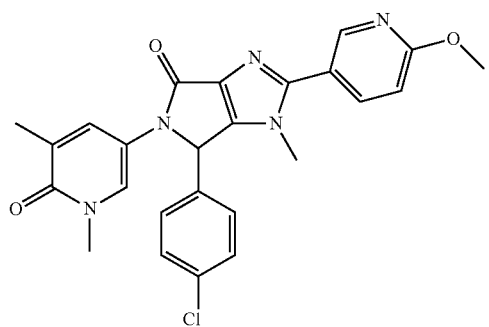

The title compound was obtained as second product in Example 6. The crude product was purified by preparative HPLC (gradient 20 to 40% CH$_3$CN in 20 min), followed by basic workup and trituration in EtOAc to afford the title product as yellow solid. t$_R$: 0.87 min (LC-MS 2); ESI-MS: 476 [M+H]$^+$ (LC-MS 2).

EXAMPLE 9

6-(4-chlorophenyl)-5-(3,8-dimethyl-[1,2,4]triazolo[4,3-a]pyridin-6-yl)-1-isopropyl-2-(6-methoxypyridin-3-yl)-5,6-dihydropyrrolo[3,4-d]imidazol-4(1H)-one

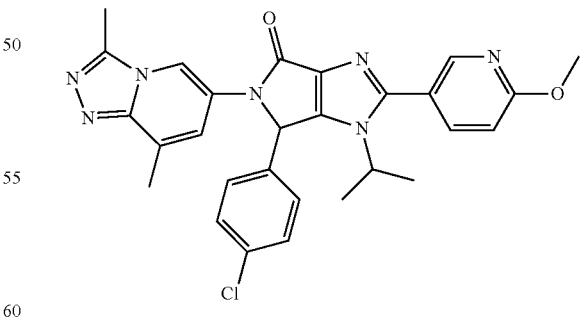

The title compound was prepared in analogy to the procedure described for Example 1 using 2-bromo-6-(4-chlorophenyl)-5-(3,8-dimethyl-[1,2,4]triazolo[4,3-a]pyridin-6-yl)-1-isopropyl-5,6-dihydropyrrolo[3,4-d]imidazol-4(1H)-one (step 9.9) and 2-methoxy-5-pyridineboronic acid at 86° C. for 1.5 hr. The crude product was purified by preparative achiral SFC (column 4-EP, gradient 19-24% over 6 min; total 11 min). $t_R$: 0.95 min (LC-MS 2); ESI-MS: 528 [M+H]$^+$ (LC-MS 2).

Step 9.1: 2-hydrazinyl-3-methyl-5-nitropyridine

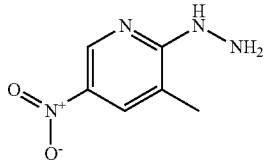

To a solution of 2-chloro-3-methyl-5-nitropyridine (35 g, 200 mmol) in EtOH (400 mL) was added hydrazine hydrate (30.0 g, 600 mmol) and the resulting reaction mixture was stirred at 60° C. for 1 hr. The reaction mixture was cooled down with an ice bath, the resulting precipitate was filtrated off, washed with cold H$_2$O and Et$_2$O and dried at 50° C. under reduced pressure to afford the title product (25.40 g, 113 mmol, 98% yield) as a yellow solid. $t_R$: 0.43 min (LC-MS 2); ESI-MS: 169 [M+H]$^+$; ESI-MS: 167 [M−H]$^−$ (LC-MS 2).

Step 9.2: 3,8-dimethyl-6-nitro-[1,2,4]triazolo[4,3-a]pyridine

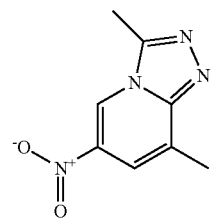

To a suspension 2-hydrazinyl-3-methyl-5-nitropyridine (Step 9.1) (33.2 g, 198 mmol) in dioxane (175 mL) was added Ac$_2$O (20.5 mL, 217 mmol) and the reaction was stirred at RT for 30 min. After addition of AcOH (35 mL) the reaction mixture was stirred for 3 hr at 100° C. The reaction mixture was cooled RT and the crystallization was facilitated by the addition of Et$_2$O (700 mL) over a period of 3 hr. After stirring the suspension for 3 hr at 0° C., the crystals were collected, washed with Et$_2$O and dried to afford the title product (23.4 g, 119 mmol, 60% yield) as a light yellow solid. $t_R$: 0.51 min (LC-MS 2); ESI-MS: 193 [M+H]$^+$ (LC-MS 2); TLC (EtOAc/MeOH 9:1) R$_f$=0.35; $^1$H NMR (400 MHz, DMSO-d$_6$) δ ppm 2.60 (s, 3H) 2.80 (s, 3H) 7.87 (d, J=1.9 Hz, 1H) 9.45 (d, J=1.8 Hz, 1H).

Step 9.3: 3,8-dimethyl-[1,2,4]triazolo[4,3-a]pyridin-6-amine

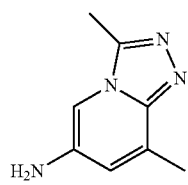

A suspension of 3,8-dimethyl-6-nitro-[1,2,4]triazolo[4,3-a]pyridine (Step 9.2) (14.1 g, 71.9 mmol) and 10% Pd/C (2.75 g, 25.9 mmol) in MeOH (300 mL) was shaken for 5 h under 4 bar hydrogen atmosphere at RT. Further 10% Pd/C was added and the reaction mixture was shaken another 1 hr under hydrogen atmosphere. The mixture was filtered through Celite. The pad of Celite was washed with MeOH and the resulting filtrate was concentrated under reduced pressure. The crude product was purified by silica gel column chromatography (hexane/(CH$_2$Cl$_2$-MeOH 19:1) 50-100% (CH$_2$Cl$_2$-MeOH 19:1)) to afford the title product as yellow solid. $t_R$: 0.29 min (LC-MS 2); ESI-MS: 163 [M+H]$^+$ (LC-MS 2); TLC (CH$_2$Cl$_2$-MeOH 9:1) R$_f$=0.26; $^1$H NMR (400 MHz, DMSO-d$_6$) δ ppm 2.43 (s, 3H) 2.54 (s, 3H) 5.05 (br. s, 2H) 6.75 (br. s, 1H) 7.18 (br. s, 1H).

Step 9.4: ethyl 1-isopropyl-1H-imidazole-4-carboxylate

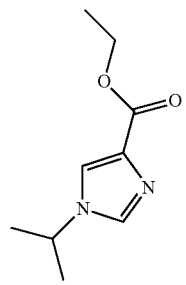

To a stirred solution of (Z)-ethyl 3-(dimethylamino)-2-isocyanoacrylate (Step 1.5) (500 g, 2.973 mol) in n-BuOH (5 L) at RT was added isopropylamine (2.53 L, 29.73 mol) over 45 min. The resulting mixture was heated up and stirred at 70° C. overnight. The reaction was concentrated under reduced pressure to 2 L volume and diluted with EtOAc (15 L), 1N HCl (2 L) and water (1 L) and both phases were separated. The aq. layer was extracted with EtOAc (2×5 L). Combined extracts were washed with brine (2 L). The aq. layer was basified to pH 6 with 2N NaOH and extracted with EtOAc (2×5 L). Combined extracts were washed with brine, dried over Na$_2$SO$_4$, filtered and concentrated under reduced pressure to afford the title product (459.7 g, 2.52 mol, 85% yield) as yellow oil. $t_R$: 0.64 min (LC-MS 1); ESI-MS: 183 [M+H]$^+$ (LC-MS 1).

Step 9.5: ethyl 2-bromo-1-isopropyl-1H-imidazole-4-carboxylate

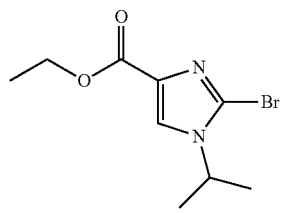

The title compound was prepared in analogy to the procedure described in Step 1.7 using ethyl 1-isopropyl-1H-imidazole-4-carboxylate (Step 9.4). $t_R$: 0.84 min (LC-MS 1); ESI-MS: 261/263 [M+H]$^+$ (LC-MS 1).

Step 9.6: ethyl 2-bromo-5((4-chlorophenyl)(hydroxy)methyl)-1-isopropyl-1H-imidazole-4-carboxylate

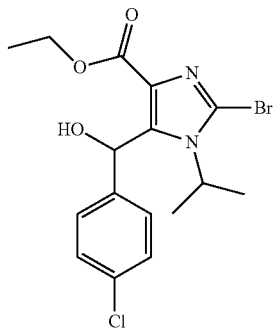 [SMILES: CCOC(=O)c1nc(Br)n(C(C)C)c1C(O)c1ccc(Cl)cc1]

Ethyl 2-bromo-1-isopropyl-1H-imidazole-4-carboxylate (Step 9.5) (10 g, 38.3 mmol) was dissolved in THF (200 mL) under Ar and cooled to −78° C. Then 2M LDA (26.8 mL, 53.6 mmol) was added dropwise during 10 min. The reaction mixture was stirred at −78° C. for 1¼ hr. 4-Chlorobenzaldehyde (7.3 g, 50 mmol), dissolved in THF (50 mL), was added during 10 min. The reaction was stirred for 30 min at −78° C. and then warmed up to −20° C. 10% aq. NH$_4$Cl solution (250 mL) was added dropwise. The resulting mixture was extracted three times with EtOAc. Combined extracts were washed with brine, dried over Na$_2$SO$_4$, filtered and concentrated under reduced pressure. Crystallization from iPr$_2$O (100 mL) afforded the title product (12.5 g, 31.1 mmol, 81% yield). $t_R$: 1.16 min (LC-MS 2); ESI-MS: 401/403 [M+H]$^+$ (LC-MS 2).

Step 9.7: ethyl 2-bromo-5-((4-chlorophenyl)((3,8-dimethyl-[1,2,4]triazolo[4,3-a]pyridin-6-yl)amino)methyl)-1-isopropyl-1H-imidazole-4-carboxylate

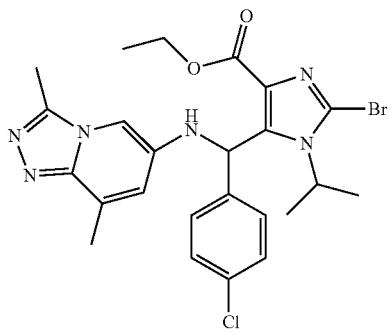 [SMILES: CCOC(=O)c1nc(Br)n(C(C)C)c1C(Nc1cc(C)c2nnc(C)n2c1)c1ccc(Cl)cc1]

The title compound was prepared in analogy to the procedure described for Step 1.9 using ethyl 2-bromo-5-((4-chlorophenyl)(hydroxy)methyl)-1-isopropyl-1H-imidazole-4-carboxylate (Step 9.6) and 3,8-dimethyl-[1,2,4]triazolo[4,3-a]pyridin-6-amine (Step 9.3). Crystallization in iPr$_2$O to afford the product as orange crystals. $t_R$: 1.07 min (LC-MS 2); ESI-MS: 545/547 [M+H]$^+$ (LC-MS 2).

Step 9.8: 2-bromo-54(4-chlorophenyl)((3,8-dimethyl-[1,2,4]triazolo[4,3-a]pyridin-6-yl)amino)methyl)-1-isopropyl-1H-imidazole-4-carboxylic acid

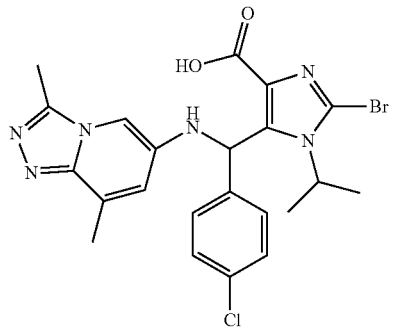 [SMILES: Cc1cc(NC(c2ccc(Cl)cc2)c2c(C(=O)O)nc(Br)n2C(C)C)cn2c(C)nnc12]

The title compound was prepared in analogy to the procedure described in Step 1.10 using ethyl 2-bromo-54(4-chlorophenyl)((3,8-dimethyl-[1,2,4]triazolo[4,3-a]pyridin-6-yl)amino)methyl)-1-isopropyl-1H-imidazole-4-carboxylate (Step 9.7). The crude product was diluted with CH$_2$Cl$_2$/MeOH 5:1 and sonicated. The resulting solid was filtered off, washed with CH$_2$Cl$_2$/MeOH 5:1 and the combined filtrates were concentrated under reduced pressure to afford the desired product. $t_R$: 0.90 min (LC-MS 2); ESI-MS: 515/517 [M+H]$^+$ (LC-MS 2).

Step 9.9: 2-bromo-6-(4-chlorophenyl)-5-(3,8-dimethyl-[1,2,4]triazolo[4,3-a]pyridin-6-yl)-1-isopropyl-5,6-dihydropyrrolo[3,4-d]imidazol-4(1H)-one

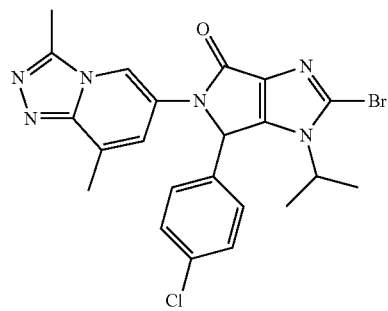 [SMILES: Cc1cc(N2C(=O)c3nc(Br)n(C(C)C)c3C2c2ccc(Cl)cc2)cn2c(C)nnc12]

The title compound was prepared in analogy to the procedure described in Step 1.11 using 2-bromo-5-((4-chlorophenyl)((3,8-dimethyl-[1,2,4]triazolo[4,3-a]pyridin-6-yl)amino)methyl)-1-isopropyl-1H-imidazole-4-carboxylic acid (Step 9.8). Crystallization in MeOH/sonication afforded the desired product as beige crystals. $t_R$: 0.92 min (LC-MS 2); ESI-MS: 499/501 [M+H]$^+$ (LC-MS 2).

EXAMPLE 10

6-(4-chlorophenyl)-2-(2,4-dimethoxypyrimidin-5-yl)-5-(3,8-dimethyl-[1,2,4]triazolo[4,3-a]pyridin-6-yl)-1-isopropyl-5,6-dihydropyrrolo[3,4-d]imidazol-4(1H)-one

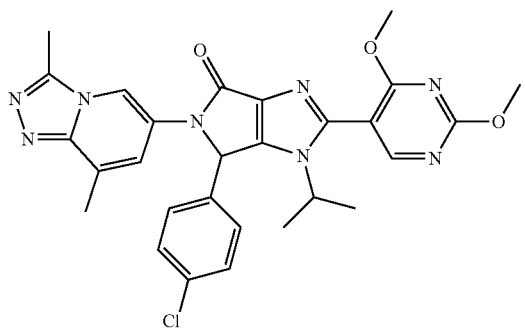 [SMILES: COc1ncc(-c2nc3c(n2C(C)C)C(c2ccc(Cl)cc2)N(c2cc(C)c4nnc(C)n4c2)C3=O)c(OC)n1]

The title compound was prepared in analogy to the procedure described for Example 1 using 2-bromo-6-(4-chlorophenyl)-5-(3,8-dimethyl-[1,2,4]triazolo[4,3-a]pyridin-6-yl)-1-isopropyl-5,6-dihydropyrrolo[3,4-d]imidazol-4(1H)-one (Step 9.9) and 2,4-dimethoxypyrimidine-5-boronic acid at 85° C. for 4.5 hr. The crude product was purified by silica gel column chromatography (CH$_2$Cl$_2$/MeOH 0-10% MeOH) followed by precipitation in CH$_2$Cl$_2$/iPr$_2$O. t$_R$: 0.92 min (LC-MS 2); ESI-MS: 559 [M+H]$^+$ (LC-MS 2).

EXAMPLE 11

6-(4-chlorophenyl)-2-(2,5-dihydrofuran-3-yl)-5-(3,8-dimethyl-[1,2,4]triazolo[4,3-a]pyridin-6-yl)-1-isopropyl-5,6-dihydropyrrolo[3,4-d]imidazol-4(1H)-one

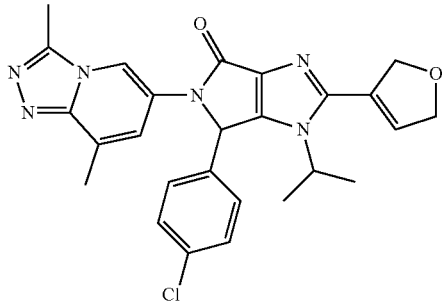 [SMILES: Cc1cc(N2C(=O)c3nc(C4=CCOC4)n(C(C)C)c3C2c2ccc(Cl)cc2)cn2c(C)nnc12]

The title compound was prepared in analogy to the procedure described for Example 1 using 2-bromo-6-(4-chlorophenyl)-5-(3,8-dimethyl-[1,2,4]triazolo[4,3-a]pyridin-6-yl)-1-isopropyl-5,6-dihydropyrrolo[3,4-d]imidazol-4(1H)-one (Step 9.9) and 2-(2,5-dihydrofuran-3-yl)-4,4,5,5-tetramethyl-1,3,2-dioxaborolane at 90° C. for 2 hr. The crude product was purified by silica gel column chromatography (CH$_2$Cl$_2$/MeOH 0-10% MeOH). t$_R$: 0.85 min (LC-MS 2); ESI-MS: 489 [M+H]$^+$ (LC-MS 2).). $^1$H NMR (400 MHz, DMSO-d$_6$) δ ppm 0.72 (d, J=6.7 Hz, 3 H) 1.51 (d, J=6.7 Hz, 3 H) 2.45 (s, 3 H) 2.66 (s, 3 H) 4.7-5.0 (m, 4 H) 5.05 (m, 1 H) 6.48 (s, 1 H) 6.73 (s, 1H) 7.40 (m, 5H) 8.41 (s, 1 H).

EXAMPLE 12

6-(4-chlorophenyl)-5-(3,8-dimethyl-[1,2,4]triazolo[4,3-a]pyridin-6-yl)-1-isopropyl-2-(1-methyl-1,2,5,6-tetrahydropyridin-3-yl)-5,6-dihydropyrrolo[3,4-d]imidazol-4(1H)-one

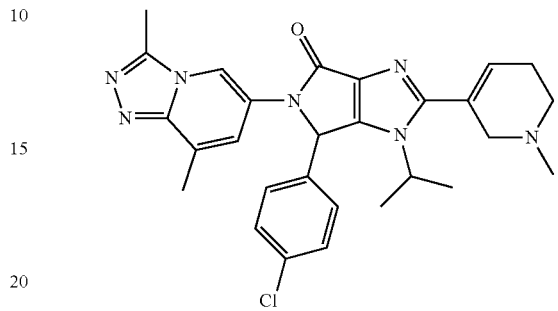

The title compound was prepared in analogy to the procedure described for Example 1 using 2-bromo-6-(4-chlorophenyl)-5-(3,8-dimethyl-[1,2,4]triazolo[4,3-a]pyridin-6-yl)-1-isopropyl-5,6-dihydropyrrolo[3,4-d]imidazol-4(1H)-one (Step 9.9) and 1-methyl-5-(4,4,5,5-tetramethyl-1,3,2-dioxaborolan-2-yl)-1,2,3,6-tetrahydropyridine at 90° C. for 4 hr. The crude product was purified by silica gel column chromatography (CH$_2$Cl$_2$/MeOH 5-30% MeOH). t$_R$: 0.65 min (LC-MS 2); ESI-MS: 516 [M+H]$^+$ (LC-MS 2).

EXAMPLE 13

6-(4-chlorophenyl)-2-cyclopropyl-5-(3,8-dimethyl-[1,2,4]triazolo[4,3-a]pyridin-6-yl)-1-isopropyl-5,6-dihydropyrrolo[3,4-d]imidazol-4(1H)-one

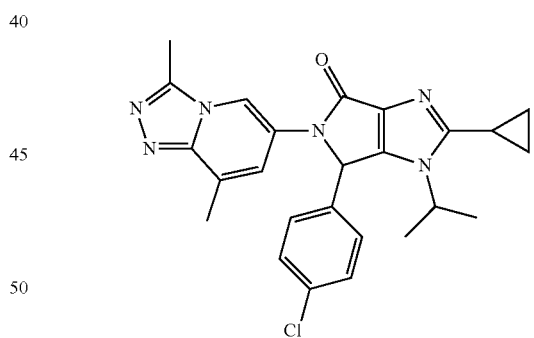

A MW vial was charged with 2-bromo-6-(4-chlorophenyl)-5-(3,8-dimethyl-[1,2,4]triazolo[4,3-a]pyridin-6-yl)-1-isopropyl-5,6-dihydropyrrolo[3,4-d]imidazol-4(1H)-one (Step 9.9) (420 mg, 0.84 mmol), potassium cyclopropyltrifluoroborate (249 mg, 1.68 mmol), RuPhos (49 mg, 0.10 mmol) and K$_3$PO$_4$ (535 mg, 2.5 mmol) in toluene (10 mL) and water (0.5 mL). The mixture was flushed with Ar, Pd(OAc)$_2$ (11 mg, 0.05 mmol) was added, the MW vial was sealed and the reaction mixture was submitted to MW irradiation at 115° C. for 2 hr. The reaction mixture was cooled down. A second portion of potassium cyclopropyltrifluoroborate (125 mg, 0.84 mmiol), RuPhos (25 mg; 0.05 mmol) and Pd(OAc)$_2$ (6 mg; 0.03 mmol) was added and MW irradiation at 115° C. was continued for 2 hr. The reaction mixture was diluted with CH$_2$Cl$_2$ (100 mL), water (20 mL) and sat. NaHCO$_3$ solution (10 mL). The aq. layer was separated off and extracted twice with CH$_2$Cl$_2$. Combined extracts were dried over Na$_2$SO$_4$, filtered and concentrated under reduced pressure. The crude product was purified by preparative achiral SFC (col. 2-EP/grad isocratic 10% over 18 min_total 22 min) to afford the title product (139 mg, 36% yield) as a white solid. t$_R$: 0.89 min (LC-MS 2); ESI-MS: 461 [M+H]$^+$ (LC-MS 2). $^1$H NMR (400 MHz, DMSO-d$_6$) δ ppm 0.72 (d, J=6.5 Hz, 3 H) 0.85-1.05 (m, 4 H) 1.45 (d, J=6.5 Hz, 3 H) 2.12 (m, 1H) 2.44 (s, 3 H) 2.64 (s, 3 H) 4.74 (m, 1 H) 6.63 (s, 1 H) 7.38 (m, 5 H) 8.36 (s, 1 H).

EXAMPLE 14

6-(4-chlorophenyl)-2-(3,6-dihydro-2H-pyran-4-yl)-5-(3,8-dimethyl-[1,2,4]triazolo[4,3-a]pyridin-6-yl)-1-isopropyl-5,6-dihydropyrrolo[3,4-d]imidazol-4(1H)-one

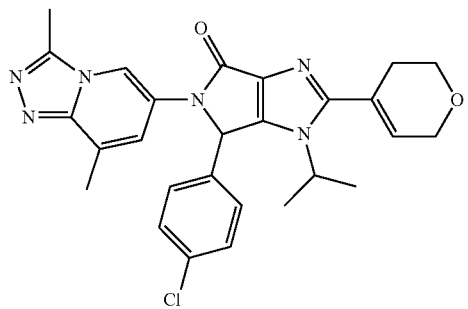 [SMILES: Cc1cc(N2C(=O)c3nc(C4=CCOCC4)n(C(C)C)c3C2c2ccc(Cl)cc2)cn2c(C)nnc12]

The title compound was prepared in analogy to the procedure described for Example 13 using 2-bromo-6-(4-chlorophenyl)-5-(3,8-dimethyl-[1,2,4]triazolo[4,3-a]pyridin-6-yl)-1-isopropyl-5,6-dihydropyrrolo[3,4-d]imidazol-4(1H)-one (Step 9.9) and potassium 3,6-dihydro-2H-pyran-4-trifluoroborate under MW irradiation at 125° C. for 2 hr. The reaction mixture was diluted with a saturated aq. NaHCO$_3$ solution and extracted twice with EtOAc. Combined extracts were washed with brine, dried over Na$_2$SO$_4$, filtered and concentrated under reduced pressure. The crude product was purified by preparative HPLC (gradient 5-100% CH$_3$CN in 20 min), followed by basic workup to afford the desired product as white solid. t$_R$: 0.86 min (LC-MS 2); ESI-MS: 503 [M+H]$^+$ (LC-MS 2). $^1$H NMR (400 MHz, DMSO-d$_6$) δ ppm 0.64 (d, J=6.8 Hz, 3 H) 1.48 (d, J=6.8 Hz, 3 H) 2.42 (m, 1 H) 2.45 (s, 3 H) 2.62 (m, 1 H) 2.65 (s, 3 H) 3.79 (m, 1 H) 3.88 (m, 1 H) 4.25 (m, 2 H) 4.65 (sept, J=6.8 Hz, 1 H) 6.11 (s, 1 H) 6.70 (s, 1H) 7.41 (m, 5H) 8.40 (s, 1 H).

EXAMPLE 15

6-(4-chlorophenyl)-5-(3,8-dimethyl-[1,2,4]triazolo[4,3-a]pyridin-6-yl)-1-isopropyl-2-(oxazol-2-yl)-5,6-dihydropyrrolo[3,4-d]imidazol-4(1H)-one

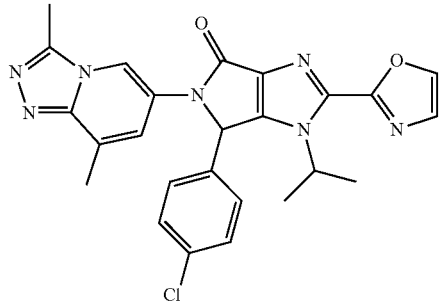 [SMILES: Cc1cc(N2C(=O)c3nc(-c4ncco4)n(C(C)C)c3C2c2ccc(Cl)cc2)cn2c(C)nnc12]

A MW vial was charged with 2-bromo-6-(4-chlorophenyl)-5-(3,8-dimethyl-[1,2,4]triazolo[4,3-a]pyridin-6-yl)-1-isopropyl-5,6-dihydropyrrolo[3,4-d]imidazol-4(1H)-one (Step 9.9) (90 mg, 0.180 mmol) and 2-tributylstannyloxazole (94 μL, 0.45 mmol) in DMF (2 mL). The mixture was flushed with Ar, Pd(PPh$_3$)$_4$ (41.6 mg, 0.04 mmol) was added, the vial was sealed and the reaction mixture was heated up and stirred at 86° C. overnight. The reaction was cooled down to RT, diluted with brine and extracted twice with EtOAc. Combined extracts were dried over Na$_2$SO$_4$, filtered and concentrated under reduced pressure. The crude product was purified by preparative achiral SFC (column 2-EP, gradient 15% isocratic over 10 min_total 14 min) to afford the title product (10 mg, 11% yield) as white solid. t$_R$: 0.92 min (LC-MS 2); ESI-MS: 488 [M+H]$^+$ (LC-MS 2).

EXAMPLE 16

6-(4-chlorophenyl)-5-(3,8-dimethyl-[1,2,4]triazolo[4,3-a]pyridin-6-yl)-2-(6-methoxypyridin-3-yl)-1-methyl-5,6-dihydropyrrolo[3,4-d]imidazol-4(1H)-one

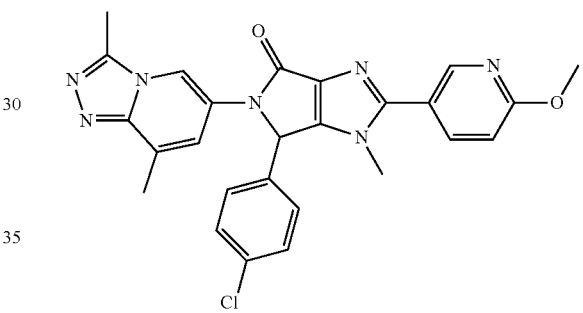

The title compound was prepared in analogy to the procedure described in Example 1 using 2-bromo-6-(4-chlorophenyl)-5-(3,8-dimethyl-[1,2,4]triazolo[4,3-a]pyridin-6-yl)-1-methyl-5,6-dihydropyrrolo[3,4-d]imidazol-4(1H)-one (Step 16.6) and 2-methoxy-5-pyridineboronic acid at 85° C. for 1 hr. The crude product was purified by preparative achiral SFC (column NH$_2$, gradient 24-29% over 6 min_total 11 min) to afford the desired product as pale brown solid. t$_R$: 0.96 min (LC-MS 2); ESI-MS: 500 [M+H]$^+$ (LC-MS 2).

Step 16.1: ethyl 1-methyl-1H-imidazole-4-carboxylate

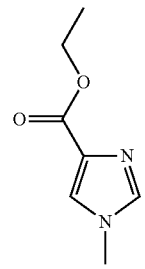

A flask was charged with 2-dimethylamino-3-isocyanato-acrylic acid ethyl ester (50 g, 297 mmol) and methylamine in EtOH and the resulting mixture was stirred at 0° C. until exothermic ceased then RT overnight. The reaction mixture was concentrated under reduced pressure to afford the title product (54 g, 280 mmol, 94% yield) as orange solid. $t_R$: 0.44 min (LC-MS 2); ESI-MS: 155 [M+H]$^+$ (LC-MS 2).

Step 16.2: ethyl 2-bromo-1-methyl-1H-imidazole-4-carboxylate

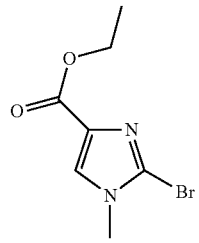

To a stirred mixture of ethyl 1-methyl-1H-imidazole-4-carboxylate (Step 16.1) (24.5 g, 159 mmol) in THF (490 mL) cooled down to 0° C. was added NBS (29.7 g, 167 mmol) portionwise over 1.5 hr period. The reaction mixture was allowed to warm up and stir at RT for 16 hr. Water and ice were added to the reaction mixture, diluted with aq. NaHCO$_3$ solution and the resulting aq. layer was extracted with EtOAc. The organic phase was dried over Na$_2$SO$_4$, filtered and concentrated under reduced pressure. The crude product was purified by silica gel column chromatography to afford the title product as pale yellow solid. $t_R$: 0.62 min (LC-MS 2); ESI-MS: 233/235 [M+H]$^+$ (LC-MS 2).

Step 16.3: ethyl 2-bromo-5-((4-chlorophenyl)(hydroxy)methyl)-1-methyl-1H-imidazole-4-carboxylate

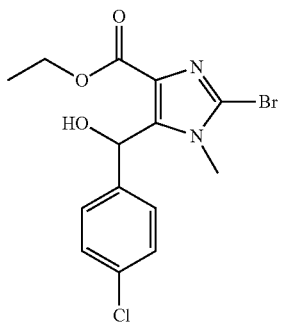 [SMILES: CCOC(=O)c1nc(Br)n(C)c1C(O)c1ccc(Cl)cc1]

The title compound was prepared in analogy to the procedure described in Step 9.6 using ethyl 2-bromo-1-methyl-1H-imidazole-4-carboxylate (Step 16.2). Part of the title product was obtained by trituration of the crude product in Et$_2$O, mixture sonicated and the resulting solid was filtrated off and washed with Et$_2$O. The mother liquor was concentrated under reduced pressure and purified by silica gel column chromatography (hexane/EtOAc 5-50% EtOAc) to recover the rest of the desired product. $t_R$: 1.03 min (LC-MS 2); ESI-MS: 373/375 [M+H]$^+$ (LC-MS 2).

Step 16.4: ethyl 2-bromo-54(4-chlorophenyl)((3,8-dimethyl-[1,2,4]triazolo[4,3-a]pyridin-6-yl)amino)methyl)-1-methyl-1H-imidazole-4-carboxylate

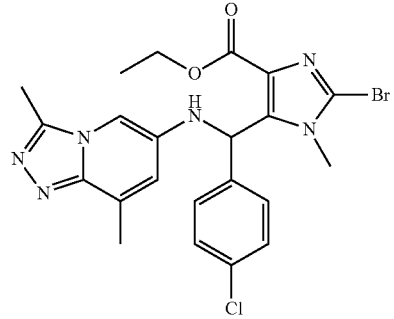 [SMILES: CCOC(=O)c1nc(Br)n(C)c1C(Nc1cc(C)c2nnc(C)n2c1)c1ccc(Cl)cc1]

The title compound was prepared in analogy to the procedure described for Step 1.9 using ethyl 2-bromo-5-((4-chlorophenyl)(hydroxy)methyl)-1-methyl-1H-imidazole-4-carboxylate (Step 16.3) and 3,8-dimethyl-[1,2,4]triazolo[4,3-a]pyridin-6-amine (Step 9.3). Crystallization in Et$_2$O afforded brownish crystals. $t_R$: 0.97 min (LC-MS 2); ESI-MS: 517/519 [M+H]$^+$ (LC-MS 2).

Step 16.5: 2-bromo-54(4-chlorophenyl)((3,8-dimethyl-[1,2,4]triazolo[4,3-a]pyridin-6-yl)amino)methyl)-1-methyl-1H-imidazole-4-carboxylic acid

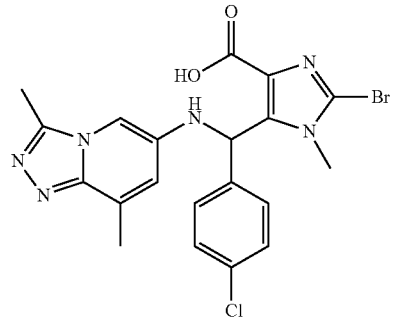 [SMILES: Cc1cc(NC(c2ccc(Cl)cc2)c2c(C(=O)O)nc(Br)n2C)cn2c(C)nnc12]

The title compound was prepared in analogy to the procedure described in Step 9.8 using ethyl 2-bromo-5-((4-chlorophenyl)((3,8-dimethyl-[1,2,4]triazolo[4,3-a]pyridin-6-yl)amino)methyl)-1-methyl-1H-imidazole-4-carboxylate (Step 16.4). $t_R$: 0.80 min (LC-MS 2); ESI-MS: 489/491 [M+H]$^+$; ESI-MS: 487/489 [M–H]$^-$ (LC-MS 2).

Step 16.6: 2-bromo-6-(4-chlorophenyl)-5-(3,8-dimethyl-[1,2,4]triazolo[4,3-a]pyridin-6-yl)-1-methyl-5,6-dihydropyrrolo[3,4-d]imidazol-4(1H)-one

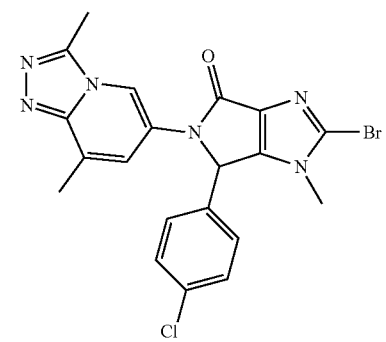 [SMILES: Cc1cc(N2C(=O)c3nc(Br)n(C)c3C2c2ccc(Cl)cc2)cn2c(C)nnc12]

The title compound was prepared in analogy to the procedure described in Step 1.11 using 2-bromo-5-((4-chlorophenyl)((3,8-dimethyl-[1,2,4]triazolo[4,3-a]pyridin-6-yl)amino)methyl)-1-methyl-1H-imidazole-4-carboxylic acid (Step 16.5). The crude product was triturated in iPr$_2$O, sonicated and the resulting solid was filtrated off and washed with iPr$_2$O to afford the title product as brownish crystals. $t_R$: 0.81 min (LC-MS 2); ESI-MS: 471/473 [M+H]$^+$ (LC-MS 2).

EXAMPLE 17

6-(4-chlorophenyl)-2-cyclopropyl-1-isopropyl-5-(8-methoxy-3-methyl-[1,2,4]triazolo[4,3-a]pyridin-6-yl)-5,6-dihydropyrrolo[3,4-d]imidazol-4(1H)-one

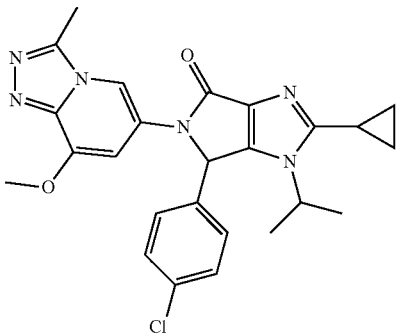 [SMILES: COc1cc(N2C(=O)c3nc(C4CC4)n(C(C)C)c3C2c2ccc(Cl)cc2)cn2c(C)nnc12]

The title compound was prepared in analogy to the procedure described for Example 13 using 2-bromo-6-(4-chlorophenyl)-1-isopropyl-5-(8-methoxy-3-methyl-[1,2,4]triazolo[4,3-a]pyridin-6-yl)-5,6-dihydropyrrolo[3,4-d]imidazol-4(1H)-one (Step 17.7) at 125° C. for 3.5 hr. The reaction was diluted with EtOAc and water and both phases were separated. The aq. layer was extracted with EtOAc. Combined extracts were dried over Na$_2$SO$_4$, filtered and concentrated under reduced pressure. The crude product was purified by preparative achiral SFC (column 2-EP, gradient 15-20% over 6 min_total 11 min). $t_R$: 0.90 min (LC-MS 2); ESI-MS: 477 [M+H]$^+$ (LC-MS 2).

Step 17.1: 2-hydrazinyl-3-methoxy-5-nitropyridine

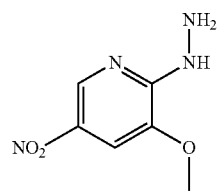

The title compound was prepared in analogy to the procedure described in Step 9.1 using 2-chloro-3-methoxy-5-nitropyridine. $t_R$: 0.46 min (LC-MS 2); ESI-MS: 185 [M+H]$^+$ (LC-MS 2); ESI-MS: 183 [M–H]$^-$ (LC-MS 2).

Step 17.2: N'-(3-methoxy-5-nitropyridin-2-yl)acetohydrazide

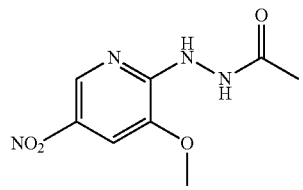 [SMILES: COc1cc([N+](=O)[O-])cnc1NNC(C)=O]

To a suspension of 2-hydrazinyl-3-methoxy-5-nitropyridine (Step 17.1) (20 g, 106 mmol) in dioxane (170 mL) was added at RT Ac$_2$O (13.1 mL, 138 mmol) and the reaction mixture was stirred for 1 hr at RT. The reaction mixture was poured onto ice-water (700 mL) and stirred for 1 hr at 0° C. The precipitate was collected by filtration, washed with H$_2$O and Et$_2$O, and dried under reduced pressure at 50° C. to afford the title product (23.3 g, 101 mmol, 95% yield) as a yellow solid. $t_R$: 0.45 min (LC-MS 2); ESI-MS: 227 [M+H]$^+$ (LC-MS 2); ESI-MS: 225 [M–H]$^-$ (LC-MS 2).

Step 17.3: 8-methoxy-3-methyl-6-nitro-[1,2,4]triazolo[4,3-a]pyridine

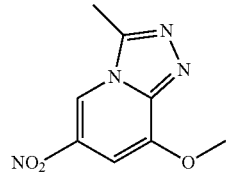

To a suspension of N'-(3-methoxy-5-nitropyridin-2-yl)acetohydrazide (Step 17.2) (23.3 g, 84 mmol) in ACN (200 mL) was added DIPEA (11.1 mL, 63.3 mmol) and dropwise POCl$_3$ (11.8 mL, 127 mmol) and the reaction mixture was stirred for 3.5 hr at 90° C. The cooled mixture was slowly added to water (600 mL), stirred for 30 min before the mixture was neutralized with solid NaHCO$_3$ to pH 6.5. The product was extracted with CH$_2$Cl$_2$/MeOH 6:1. Combined extracts were washed with H$_2$O, dried over MgSO$_4$, filtered and concentrated under reduced pressure. The crude material was purified by silica gel column chromatography (hexane/EtOAc/MeOH 50:50:5 to 0:50:5) followed by recrystallization from CH$_2$Cl$_2$/EtOAc/Et$_2$O. $t_R$: 0.49 min (LC-MS 2); ESI-MS: 209 [M+H]$^+$ (LC-MS 2); $^1$H NMR (400 MHz, DMSO-d$_6$) δ ppm 2.79 (s, 3H) 4.10 (s, 3H) 7.29 (d, J=1.7 Hz, 1H) 9.25 (d, J=1.7 Hz, 1H).

Step 17.4: 8-methoxy-3-methyl-[1,2,4]triazolo[4,3-a]pyridin-6-amine

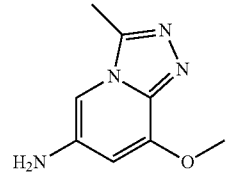

The title compound was prepared in analogy to the procedure described in Step 9.3 using 8-methoxy-3-methyl-6-nitro-[1,2,4]triazolo[4,3-a]pyridine (Step 17.3). The crude product was purified by silica gel column chromatography (CH$_2$Cl$_2$-MeOH 9:1) to afford the title product as yellow solid. TLC (CH$_2$Cl$_2$-MeOH 10:1) R$_f$=0.16; t$_R$: 0.31 min (LC-MS 2); ESI-MS: 179 [M+H]$^+$ (LC-MS 2); $^1$H NMR (400 MHz, DMSO-d$_6$) δ ppm 2.45 (s, 3H) 3.91 (s, 3H) 5.08 (s, 2H) 6.36 (d, J=1.2 Hz, 1H) 6.97 (d, J=1.2 Hz, 1H).

Step 17.5: ethyl 2-bromo-5-((4-chlorophenyl)((8-methoxy-3-methyl-[1,2,4]triazolo[4,3-a]pyridin-6-yl)amino)methyl)-1-isopropyl-1H-imidazole-4-carboxylate

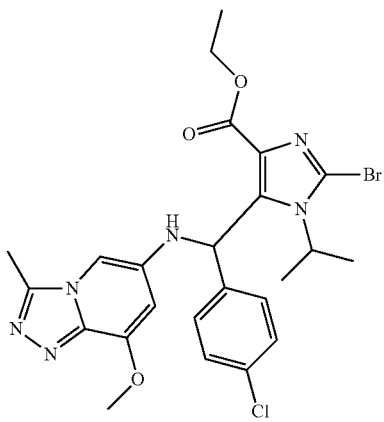 [SMILES: CCOC(=O)c1nc(Br)n(C(C)C)c1C(Nc1cc(OC)c2nnc(C)n2c1)c1ccc(Cl)cc1]

The title compound was prepared in analogy to the procedure described for Step 1.9 using ethyl 2-bromo-5-((4-chlorophenyl)(hydroxy)methyl)-1-isopropyl-1H-imidazole-4-carboxylate (Step 9.6) and 8-methoxy-3-methyl-[1,2,4]triazolo[4,3-a]pyridin-6-amine (Step 17.4). The crude product was purified by preparative HPLC followed by basic workup. t$_R$: 1.06 min (LC-MS 2); ESI-MS: 561/563 [M+H]$^+$ (LC-MS 2).

Step 17.6: 2-bromo-54(4-chlorophenyl)((8-methoxy-3-methyl-[1,2,4]triazolo[4,3-a]pyridin-6-yl)amino)methyl)-1-isopropyl-1H-imidazole-4-carboxylic acid

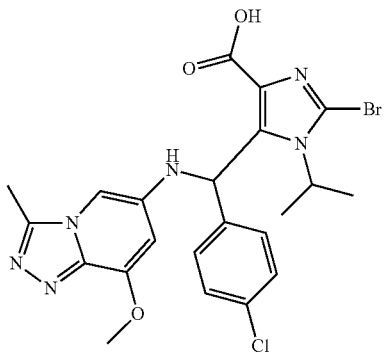 [SMILES: COc1cc(NC(c2ccc(Cl)cc2)c2c(C(=O)O)nc(Br)n2C(C)C)cn2c(C)nnc12]

The title compound was prepared in analogy to the procedure described in Step 9.8 using ethyl 2-bromo-5-((4-chlorophenyl)((8-methoxy-3-methyl-[1,2,4]triazolo[4,3-a]pyridin-6-yl)amino)methyl)-1-isopropyl-1H-imidazole-4-carboxylate (Step 17.5) at 45° C. overnight. t$_R$: 0.88 min (LC-MS 2); ESI-MS: 533/535 [M+H]$^+$; ESI-MS: 531/533 [M–H]$^-$ (LC-MS 2).

Step 17.7: 2-bromo-6-(4-chlorophenyl)-1-isopropyl-5-(8-methoxyl-3-methyl-[1,2,4]triazolo[4,3-a]pyridin-6-yl)-5,6-dihydropyrrolo[3,4-d]imidazol-4(1H)-one

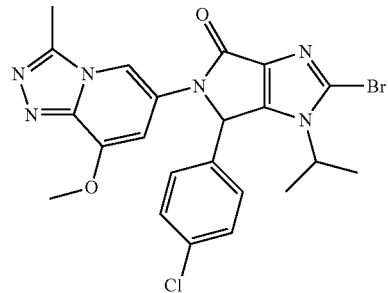 [SMILES: COc1cc(N2C(=O)c3nc(Br)n(C(C)C)c3C2c2ccc(Cl)cc2)cn2c(C)nnc12]

The title compound was prepared in analogy to the procedure described in Step 1.11 using 2-bromo-5-((4-chlorophenyl)((8-methoxy-3-methyl-[1,2,4]triazolo[4,3-a]pyridin-6-yl)amino)methyl)-1-isopropyl-1H-imidazole-4-carboxylic acid (Step 17.6). t$_R$: 0.91 min (LC-MS 2); ESI-MS: 515/517 [M+H]$^+$ (LC-MS 2).

EXAMPLE 18

6-(4-chlorophenyl)-5-(3,8-dimethyl-[1,2,4]triazolo[4,3-b]pyridazin-6-yl)-1-isopropyl-2-methyl-5,6-dihydropyrrolo[3,4-d]imidazol-4(1H)-one

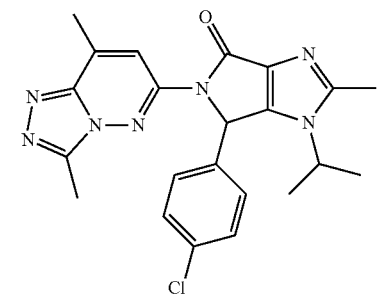 [SMILES: Cc1cc(N2C(=O)c3nc(C)n(C(C)C)c3C2c2ccc(Cl)cc2)nn2c(C)nnc12]

6-(4-chlorophenyl)-1-isopropyl-2-methyl-5,6-dihydropyrrolo[3,4-d]imidazol-4(1H)-one (Step 18.7) (45 mg, 0.155 mmol) was dissolved in Dioxane (2.6 mL) under Ar. 6-chloro-3,8-dimethyl-[1,2,4]triazolo[4,3-b]pyridazine (Step 18.2) (34 mg, 0.186 mmol), Pd$_2$(dba)$_3$ (14.22 mg, 0.016 mmol), xantphos (17.97 mg, 0.031 mmol) and Cs$_2$CO$_3$ (101 mg, 0.311 mmol) were added and the resulting mixture was heated up and stirred at 100° C. for 2 hr. The reaction mixture was diluted with EtOAc and water and both phases separated. The organic layer was dried over Na$_2$SO$_4$, filtered and concentrated under reduced pressure. The crude product was purified by preparative HPLC to afford the title product (27 mg, 0.059 mmol, 37.9% yield) as beige solid. t$_R$: 0.89 min (LC-MS 2); ESI-MS: 436 [M+H]$^+$ (LC-MS 2).

Step 18.1:
6-chloro-3-hydrazinyl-4-methylpyridazine

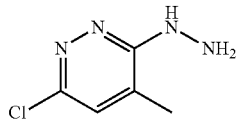

The title compound was prepared in analogy to the procedure described in Step 9.1 using 3,6-dichloro-4-methylpyridazine at 80° C. overnight. The crude product was sonicated in EtOH for 1 hr to afford the title product as white solid. $t_R$: 0.34 min (LC-MS 2); ESI-MS: 159 [M+H]$^+$ (LC-MS 2).

Step 18.2: 6-chloro-3,8-dimethyl-[1,2,4]triazolo[4,3-b]pyridazine

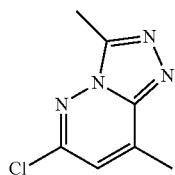

A mixture of 6-chloro-3-hydrazinyl-4-methylpyridazine (Step 18.1) (1.76 g, 11.1 mmol) in AcOH (30 mL) was heated up and stirred at 115° C. for 1 hr. The reaction mixture was cooled down to RT, diluted with CH$_2$Cl$_2$ and saturated aq. NaHCO$_3$ solution and both phases were separated. The aq. layer was extracted twice with CH$_2$Cl$_2$. Combined extracts were dried over Na$_2$SO$_4$, filtered and concentrated under reduced pressure to afford the title product (1.6 g, 7.89 mmol, 71.1% yield) as grey solid. $t_R$: 0.60 min (LC-MS 2); ESI-MS: 183 [M+H]$^+$ (LC-MS 2).

Step 18.3: ethyl 2-bromo-54(4-chlorophenyl)((4-methoxybenzyl)amino)methyl)-1-isopropyl-1H-imidazole-4-carboxylate

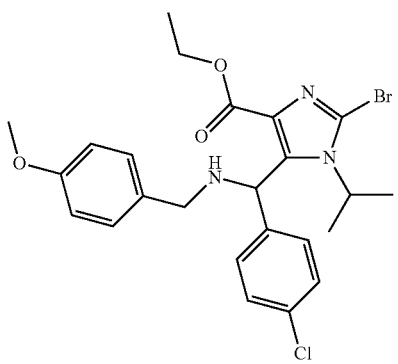 [SMILES: CCOC(=O)c1nc(Br)n(C(C)C)c1C(NCc1ccc(OC)cc1)c1ccc(Cl)cc1]

The title compound was prepared in analogy to the procedure described for Step 1.9 using ethyl 2-bromo-5-((4-chlorophenyl)(hydroxy)methyl)-1-isopropyl-1H-imidazole-4-carboxylate (Step 9.6) and 4-methoxybenzylamine. $t_R$: 1.36 min (LC-MS 2); ESI-MS: 520/522 [M+H]$^+$ (LC-MS 2).

Step 18.4: 2-bromo-54(4-chlorophenyl)((4-methoxybenzyl)amino)methyl)-1-isopropyl-1H-imidazole-4-carboxylic acid

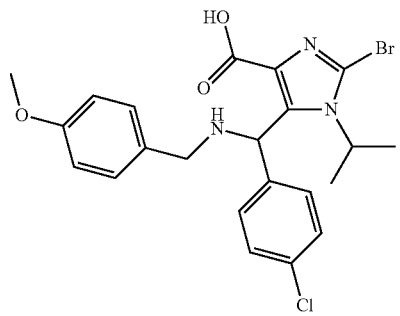 [SMILES: COc1ccc(CNC(c2ccc(Cl)cc2)c2c(C(=O)O)nc(Br)n2C(C)C)cc1]

The title compound was prepared in analogy to the procedure described in Step 1.10 using ethyl 2-bromo-54(4-chlorophenyl)((4-methoxybenzyl)amino)methyl)-1-isopropyl-1H-imidazole-4-carboxylate (Step 18.3). The reaction mixture was concentrated under reduced pressure, neutralized with 2N HCl and extracted with EtOAc. The organic layer was dried over Na$_2$SO$_4$, filtered and concentrated under pressure. $t_R$: 0.86 min (LC-MS 2); ESI-MS: 492/494 [M+H]$^+$; ESI-MS: 490/492 [M–H]$^-$ (LC-MS 2).

Step 18.5: 2-bromo-6-(4-chlorophenyl)-1-isopropyl-5-(4-methoxybenzyl)-5,6-dihydropyrrolo[3,4-d]imidazol-4(1H)-one

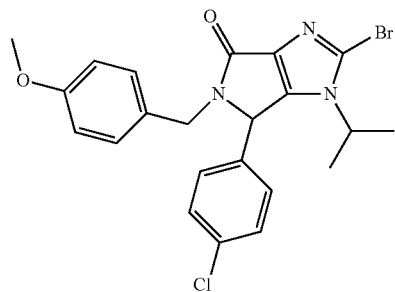 [SMILES: COc1ccc(CN2C(=O)c3nc(Br)n(C(C)C)c3C2c2ccc(Cl)cc2)cc1]

The title compound was prepared in analogy to the procedure described in Step 1.11 using 2-bromo-5-((4-chlorophenyl)((4-methoxybenzyl)amino)methyl)-1-isopropyl-1H-imidazole-4-carboxylic acid (Step 18.4) at RT for 2 hr. $t_R$: 1.19 min (LC-MS 2); ESI-MS: 474/476 [M+H]$^+$ (LC-MS 2).

Step 18.6: 6-(4-chlorophenyl)-1-isopropyl-5-(4-methoxybenzyl)-2-methyl-5,6-dihydropyrrolo[3,4-d]imidazol-4(1H)-one

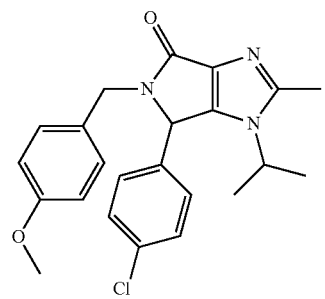 [SMILES: COc1ccc(CN2C(=O)c3nc(C)n(C(C)C)c3C2c2ccc(Cl)cc2)cc1]

The title compound was prepared in analogy to the procedure described for Example 1 using 2-bromo-6-(4-chlorophenyl)-1-isopropyl-5-(4-methoxybenzyl)-5,6-dihydropyrrolo[3,4-d]imidazol-4(1H)-one (Step 18.5). $t_R$: 1.19 min (LC-MS 2); ESI-MS: 410.2 [M+H]$^+$ (LC-MS 2).

Step 18.7: 6-(4-chlorophenyl)-1-isopropyl-2-methyl-5,6-dihydropyrrolo[3,4-d]imidazol-4(1H)-one

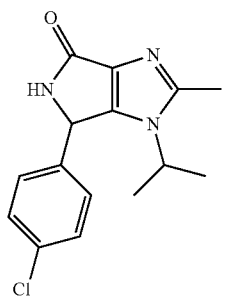 [SMILES: Cc1nc2c(n1C(C)C)C(c1ccc(Cl)cc1)NC2=O]

A MW vial was charged with 6-(4-chlorophenyl)-1-isopropyl-5-(4-methoxybenzyl)-2-methyl-5,6-dihydropyrrolo[3,4-d]imidazol-4(1H)-one (Step 18.6) (270 mg, 0.527 mmol) and TFA (1.218 mL, 15.81 mmol). The MW vial was sealed and the resulting mixture was submitted to MW irradiation at 140° C. for 140 min. The reaction mixture was poured into ice/aq. NaHCO$_3$ solution and extracted with CH$_2$Cl$_2$. The organic layer was dried over Na$_2$SO$_4$, filtered and concentrated under reduced pressure. The crude product was triturated with Et$_2$O and the resulting solid was filtrated off. This solid was purified by silica gel chromatography (EtOAc/MeOH 0-20% MeOH) to afford the title product (58 mg, 0.168 mmol, 31.9% yield) as pale solid. $t_R$: 0.79 min (LC-MS 2); ESI-MS: 290 [M+H]$^+$ (LC-MS 2).

EXAMPLE 19

6-(4-chlorophenyl)-1-isopropyl-2-(isoxazol-4-yl)-5-(1-methyl-6-oxo-1,6-dihydropyridin-3-yl)-5,6-dihydropyrrolo[3,4-d]imidazol-4(1H)-one

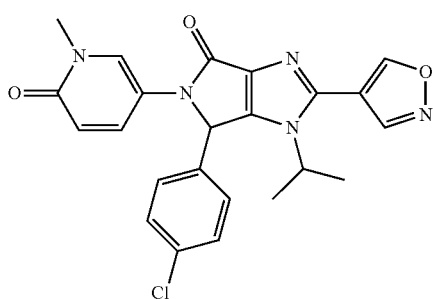 [SMILES: CC(C)n1c(-c2cnoc2)nc2c1C(c1ccc(Cl)cc1)N(c1ccc(=O)n(C)c1)C2=O]

The title compound was prepared in analogy to the procedure described in Example 1 using 2-bromo-6-(4-chlorophenyl)-1-isopropyl-5-(1-methyl-6-oxo-1,6-dihydropyridin-3-yl)-5,6-dihydropyrrolo[3,4-d]imidazol-4(1H)-one (Step 19.4) and isoxazole-4-boronic acid at 110° C. overnight. The crude product was purified by silica gel column chromatography (CH$_2$Cl$_2$/MeOH 0-20% MeOH) to afford a pale brown sticky product. $t_R$: 0.77 min (LC-MS 2); ESI-MS: 450 [M+H]$^+$ (LC-MS 2).

Step 19.1: 5-amino-1-methylpyridin-2(1H)-one

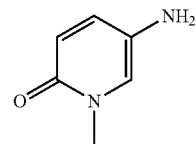

To a solution of 5-nitro-1-methyl-2(1H)-pyridinone (10 g, 64.9 mmol) in THF (130 mL) was added 10% Pd/C (1 g). The resulting suspension was shaken at RT for 7.5 hr under hydrogen atmosphere. The mixture was filtered through a pad of Celite. The pad was washed with THF and the resulting filtrate was concentrated under reduced pressure to afford the title product (8 g, 99% yield) as greenish product, which was directly used for further steps.

Step 19.2: ethyl 2-bromo-5((4-chlorophenyl)(1-methyl-6-oxo-1,6-dihydropyridin-3-ylamino)methyl)-1-isopropyl-1H-imidazole-4-carboxylate

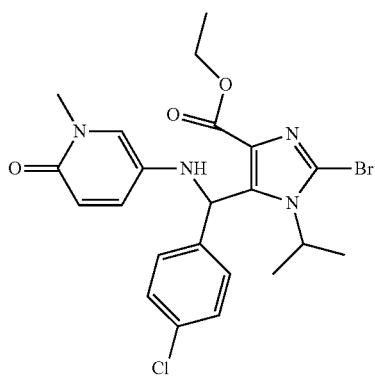 [SMILES: CCOC(=O)c1nc(Br)n(C(C)C)c1C(Nc1ccc(=O)n(C)c1)c1ccc(Cl)cc1]

Ethyl 2-bromo-5-((4-chlorophenyl)(hydroxy)methyl)-1-isopropyl-1H-imidazole-4-carboxylate (Step 9.6) (6 g, 14.94 mmol) was dissolved in CH$_2$Cl$_2$ (60 mL). TEA 812.49 mL, 90 mmol) were added and the resulting mixture was cooled down and stirred at −30° C. Methanesulfonic anhydride (5.36 g, 29.9 mmol) was added portionwise and the mixture was stirred at −30° C. for 30 min, then allowed to warm up and stir at RT for 1 hr. A solution of 5-amino-1-methylpyridin-2(1H)-one (Step 19.1) (2.06 g, 14.94 mmol) in CH$_2$Cl$_2$ (20 mL) was added dropwise and the resulting mixture was stirred at RT for 3 hr. The mixture was washed with water (80 mL). The aq. layer was extracted twice with CH$_2$Cl$_2$. Combined extracts were washed with water and brine, dried over Na$_2$SO$_4$, filtered and concentrated under reduced pressure. The crude product was purified by silica gel column chromatography (EtOAc/MeOH 5-20% MeOH) followed by crystallization in iPr$_2$O to afford the title product (2.22 g, 29% yield) as pale blue-grey crystals. $t_R$: 1.02 min (LC-MS 2); ESI-MS: 507/509 [M+H]$^+$ (LC-MS 2); TLC (EtOAc/MeOH 9:1) $R_f$=0.2.

Step 19.3: sodium 2-bromo-54(4-chlorophenyl)(1-methyl-6-oxo-1,6-dihydropyridin-3-ylamino)methyl)-1-isopropyl-1H-imidazole-4-carboxylate

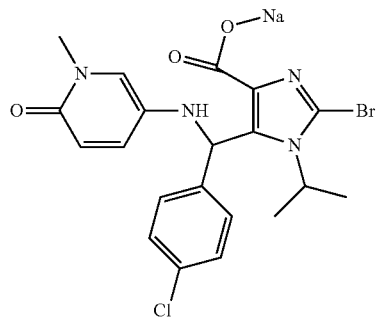

Ethyl 2-bromo-5-((4-chlorophenyl)(1-methyl-6-oxo-1,6-dihydropyridin-3-ylamino)methyl)-1-isopropyl-1H-imidazole-4-carboxylate (Step 19.2) (2.26 g, 4.45 mmol) was dissolved in dioxane (50 mL) and water (25 mL) and 1N NaOH (6.68 mL, 6.68 mmol) was added. The resulting mixture was heated up and stirred at 50° C. for 2 hr. The reaction mixture was concentrated under reduced pressure to afford the title product (2.35 g) as brown sodium salt. $t_R$: 0.85 min (LC-MS 2); ESI-MS: 479/481 [M+H]$^+$; ESI-MS: 477/479 [M−H]$^-$ (LC-MS 2).

Step 19.4: 2-bromo-6-(4-chlorophenyl)-1-isopropyl-5-(1-methyl-6-oxo-1,6-dihydropyridin-3-yl)-5,6-dihydropyrrolo[3,4-d]imidazol-4(1H)-one

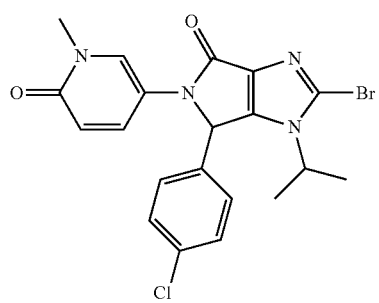 [SMILES: CC(C)n1c(Br)nc2c1C(c1ccc(Cl)cc1)N(c1ccc(=O)n(C)c1)C2=O]

To a solution of sodium 2-bromo-5-((4-chlorophenyl)(1-methyl-6-oxo-1,6-dihydropyridin-3-ylamino)methyl)-1-isopropyl-1H-imidazole-4-carboxylate (Step 19.3) (2.35 g, 4.45 mmol) in DMF (30 mL) were added TEA (13.95 mL, 100 mmol), DMAP (109 mg, 0.89 mmol) and propsal 50% in DMF (11.69 mL, 20.02 mmol). The resulting mixture was stirred 1.5 hr at RT. The reaction mixture was diluted with EtOAc and water and both phases were separated. The organic layer was washed with water and twice with brine. The aq. layer was extracted with EtOAc. Combined extracts were dried over Na$_2$SO$_4$, filtered and concentrated under reduced pressure. The crude product was taken in EtOAc, the resulting solid was filtrated off and washed with EtOAc and hexane. The resulting filtrate was concentrated under reduced pressure and purified by silica gel column chromatography (EtOAc/MeOH 0-30% MeOH) followed by trituration in EtOAc. Solids were combined to afford the title product (1.37 g, 2.9 mmol, 67% yield) as pale beige crystals. $t_R$: 0.86 min (LC-MS 2); ESI-MS: 461/463 [M+H]$^+$ (LC-MS 2).

EXAMPLE 20

6-(4-chlorophenyl)-1-isopropyl-5-(1-methyl-6-oxo-1,6-dihydropyridin-3-yl)-2-(Pyridin-2-yl)-5,6-dihydropyrrolo[3,4-d]imidazol-4(1H)-one

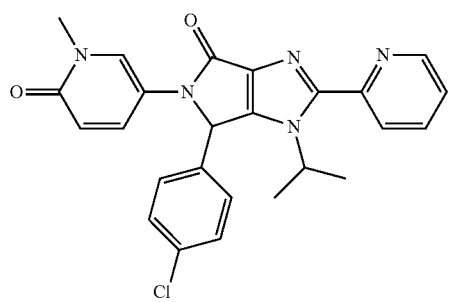 [SMILES: CC(C)n1c(-c2ccccn2)nc2c1C(c1ccc(Cl)cc1)N(c1ccc(=O)n(C)c1)C2=O]

To a solution of 2-bromo-6-(4-chlorophenyl)-1-isopropyl-5-(1-methyl-6-oxo-1,6-dihydropyridin-3-yl)-5,6-dihydropyrrolo[3,4-d]imidazol-4(1H)-one (Step 19.4) (100 mg, 0.217 mmol) in DMA (2.5 mL) under nitrogen were added 2-(tributylstannyl)pyridine (0.351 mL, 0.866 mmol), CsF (132 mg, 0.866 mmol) and Pd(PBu$_3$)$_2$ (33.2 mg, 0.065 mmol). The resulting mixture was heated up and stirred at 100° C. for 4 hr. The reaction was quenched with brine, diluted with EtOAc and water and both phases were separated. The aq. layer was extracted twice with EtOAc. Combined extracts were washed with brine, dried over Na$_2$SO$_4$, filtered and concentrated under reduced pressure. The crude product was purified by preparative HPLC (gradient 5-70% CH$_3$CN in 20 min) followed by basic workup and trituration in iPr$_2$O to afford the title product (27 mg, 26% yield) as beige crystals. $t_R$: 0.95 min (LC-MS 2); ESI-MS: 460 [M+H]$^+$ (LC-MS 2).

EXAMPLE 21

6-(4-chlorophenyl)-1-isopropyl-2-(1-methyl-1H-pyrazol-5-yl)-5-(1-methyl-6-oxo-1,6-dihydropyridin-3-yl)-5,6-dihydropyrrolo[3,4-d]imidazol-4(1H)-one

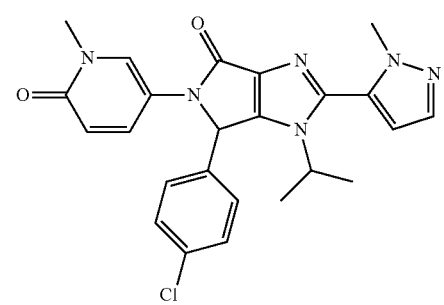 [SMILES: CC(C)n1c(-c2ccnn2C)nc2c1C(c1ccc(Cl)cc1)N(c1ccc(=O)n(C)c1)C2=O]

To a solution of 2-bromo-6-(4-chlorophenyl)-1-isopropyl-5-(1-methyl-6-oxo-1,6-dihydropyridin-3-yl)-5,6-dihydropyrrolo[3,4-d]imidazol-4(1H)-one (Step 19.4) (100 mg, 0.22 mmol) in dioxane (2 mL) and water (0.2 mL) under nitrogen were added 1-methyl-5-(4,4,5,5-tetramethyl-1,3,2-dioxaborolan-2-yl)-1H-pyrazole (Step 21.1) (58.6 mg, 0.28 mmol), Cs₂CO₃ (183 mg, 0.563 mmol) and PdCl₂(dppf).CH₂Cl₂ adduct (26.5 mg, 0.03 mmol). The resulting mixture was flushed with Ar, heated up and stirred at 100° C. for 3 hr. The reaction was cooled down to RT, 1-methyl-5-(4,4,5,5-tetramethyl-1,3,2-dioxaborolan-2-yl)-1H-pyrazole (43 mg) and PdCl₂(dppf).CH₂Cl₂ adduct (20 mg) were added and the resulting mixture was heated up and stirred at 100° C. for 105 min. The reaction mixture was diluted with EtOAc and water and both phases were separated. The aq. layer was extracted twice with EtOAc. Combined extracts were washed with brine, dried over Na₂SO₄, filtered and concentrated under reduced pressure. The crude product was purified by preparative HPLC (gradient 5-100% CH₃CN in 20 min) followed by basic workup and trituration in iPr₂O to afford the title product (44 mg, 44% yield) as pale beige crystals. $t_R$: 0.82 min (LC-MS 2); ESI-MS: 463 [M+H]⁺ (LC-MS 2).

Step 21.1: 1-methyl-5-(4,4,5,5-tetramethyl-1,3,2-dioxaborolan-2-yl)-1H-pyrazole

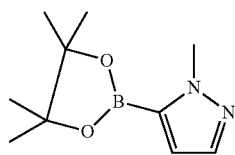

The title compound was prepared following the procedure described in the literature (*J. Heterocyclic Chem*, 41, 931 (2004).

EXAMPLE 22

6-(4-chlorophenyl)-1-isopropyl-2-(1-methyl-1H-pyrazol-3-yl)-5-(1-methyl-6-oxo-1,6-dihydropyridin-3-yl)-5,6-dihydropyrrolo[3,4-d]imidazol-4(1H)-one

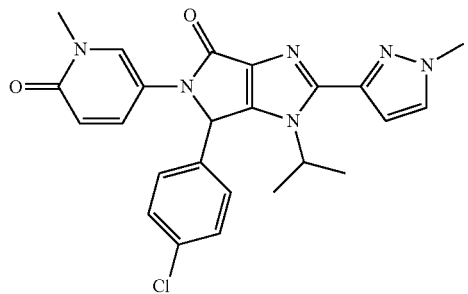 [SMILES: CC(C)n1c(-c2ccn(C)n2)nc2c1C(c1ccc(Cl)cc1)N(c1ccc(=O)n(C)c1)C2=O]

The title compound was prepared in analogy to the procedure described in Example 21 using 2-bromo-6-(4-chlorophenyl)-1-isopropyl-5-(1-methyl-6-oxo-1,6-dihydropyridin-3-yl)-5,6-dihydropyrrolo[3,4-d]imidazol-4(1H)-one (Step 19.4) and 1-methyl-3-(4,4,5,5-tetramethyl-1,3,2-dioxaborolan-2-yl)-1H-pyrazole (Step 22.1) at 100° C. for 7 hr. $t_R$: 0.87 min (LC-MS 2); ESI-MS: 463 [M+H]⁺ (LC-MS 2).

Step 22.1: 1-methyl-3-(4,4,5,5-tetramethyl-1,3,2-dioxaborolan-2-yl)-1H-pyrazole

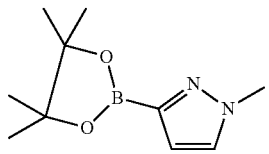

The title compound was prepared in analogy to the procedure described in patent WO 2010075270 p137.

EXAMPLE 23

6-(4-chlorophenyl)-5-(1,5-dimethyl-6-oxo-1,6-dihydropyridin-3-yl)-1-isopropyl-2-(thiazol-2-yl)-5,6-dihydropyrrolo[3,4-d]imidazol-4(1H)-one

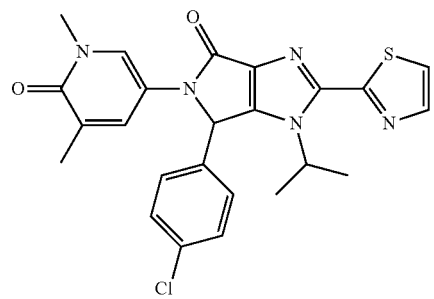 [SMILES: Cc1cc(N2C(=O)c3nc(-c4nccs4)n(C(C)C)c3C2c2ccc(Cl)cc2)cn(C)c1=O]

The title compound was prepared in analogy to the procedure described for Example 15 using 2-bromo-6-(4-chlorophenyl)-5-(1,5-dimethyl-6-oxo-1,6-dihydropyridin-3-yl)-1-isopropyl-5,6-dihydropyrrolo[3,4-d]imidazol-4(1H)-one (Step 23.3) and 2-tributylstannylthiazole. The crude product was diluted with Et₂O, sonicated and the resulting solid was filtrated off and washed with Et₂O. The solid was purified by silica gel column chromatography (CH₂Cl₂/MeOH 2-10% MeOH) to afford the title product (52 mg, 0.108 mmol, 51% yield) as white solid. $t_R$: 1.02 min (LC-MS 2); ESI-MS: 480 [M+H]⁺ (LC-MS 2).

Step 23.1: ethyl 2-bromo-54(4-chlorophenyl)((1,5-dimethyl-6-oxo-1,6-dihydropyridin-3-yl)amino)methyl)-1-isopropyl-1H-imidazole-4-carboxylate

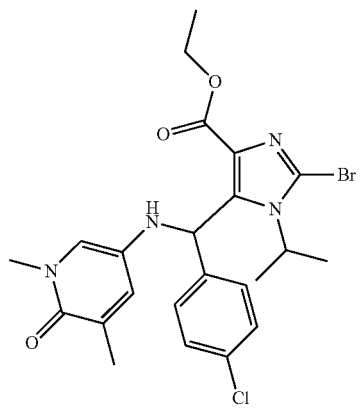 [SMILES: CCOC(=O)c1nc(Br)n(C(C)C)c1C(Nc1cc(C)c(=O)n(C)c1)c1ccc(Cl)cc1]

The title compound was prepared in analogy to the procedure described for Step 1.9 using ethyl 2-bromo-5-((4-chlorophenyl)(hydroxy)methyl)-1-isopropyl-1H-imidazole-4-carboxylate (Step 9.6) and 5-amino-1,3-dimethylpyridin-2(1H)-one (Step 4.3). The crude product was purified by silica gel column chromatography. $t_R$: 1.09 min (LC-MS 2); ESI-MS: 521/523 [M+H]$^+$ (LC-MS 2).

Step 23.2: 2-bromo-54(4-chlorophenyl)((1,5-dimethyl-6-oxo-1,6-dihydropyridin-3-yl)amino)methyl)-1-isopropyl-1H-imidazole-4-carboxylic acid

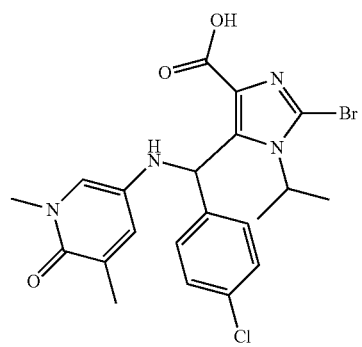 [SMILES: Cc1cc(NC(c2ccc(Cl)cc2)c2c(C(=O)O)nc(Br)n2C(C)C)cn(C)c1=O]

The title compound was prepared in analogy to the procedure described in Step 9.8 using ethyl 2-bromo-5-((4-chlorophenyl)((1,5-dimethyl-6-oxo-1,6-dihydropyridin-3-yl)amino)methyl)-1-isopropyl-1H-imidazole-4-carboxylate (Step 23.1) in MeOH at 40° C. for 1.5 hr. $t_R$: 0.91 min (LC-MS 2); ESI-MS: 493/495 [M+H]$^+$; ESI-MS: 491/493 [M−H]$^−$ (LC-MS 2).

Step 23.3: 2-bromo-6-(4-chlorophenyl)-5-(1,5-dimethyl-6-oxo-1,6-dihydropyridin-3-yl)-1-isopropyl-5,6-dihydropyrrolo[3,4-d]imidazol-4(1H)-one

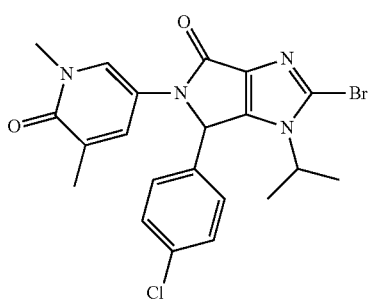 [SMILES: Cc1cc(N2C(=O)c3nc(Br)n(C(C)C)c3C2c2ccc(Cl)cc2)cn(C)c1=O]

The title compound was prepared in analogy to the procedure described in Step 1.11 using 2-bromo-5-((4-chlorophenyl)((1,5-dimethyl-6-oxo-1,6-dihydropyridin-3-yl)amino)methyl)-1-isopropyl-1H-imidazole-4-carboxylic acid (13 mmol; Step 23.2). The reaction mixture was diluted with CH$_2$Cl$_2$ (500 mL) and saturated aq. NaHCO$_3$ solution (100 mL) and both phases were separated. The aq. layer was extracted with CH$_2$Cl$_2$ (50 mL). Combined extracts were dried over Na$_2$SO$_4$, filtered and concentrated under reduced pressure until ca 100 mL volume. The suspension was filtrated off, washed with Et$_2$O and dried under reduced pressure to afford colorless crystals. $t_R$: 0.93 min (LC-MS 2); ESI-MS: 475/477 [M+H]$^+$ (LC-MS 2).

EXAMPLE 24

(R)-6-(4-chlorophenyl)-5-(1,5-dimethyl-6-oxo-1,6-dihydropyridin-3-yl)-1-isopropyl-2-(thiazol-2-yl)-5,6-dihydropyrrolo[3,4-d]imidazol-4(1H)-one

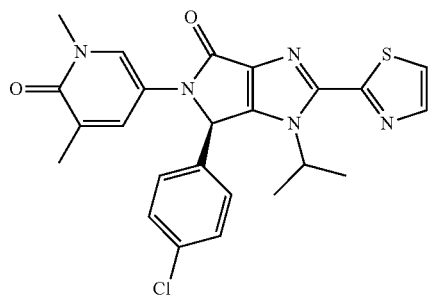 [SMILES: Cc1cc(N2C(=O)c3nc(-c4nccs4)n(C(C)C)c3[C@H]2c2ccc(Cl)cc2)cn(C)c1=O]

The title compound (14 mg, 0.029 mmol, 36.5% yield) was obtained enantiomerically pure (ee>99.5%) after chiral preparative chromatography (System: Gilson PLC 2020 HPLC system; column: Chiralpak IA 5 μm, 250×20 mm; mobile phase: heptane/CH$_2$Cl$_2$/EtOH 55:30:15 isocratic; flow rate: 10 mL/min; detection 312 nm) of the racemic mixture of 6-(4-chlorophenyl)-5-(1,5-dimethyl-6-oxo-1,6-dihydropyridin-3-yl)-1-isopropyl-2-(thiazol-2-yl)-5,6-dihydropyrrolo[3,4-d]imidazol-4(1H)-one (Example 23) (38 mg, 0.079 mmol). The second enantiomer (S)-6-(4-chlorophenyl)-5-(1,5-dimethyl-6-oxo-1,6-dihydropyridin-3-yl)-1-isopropyl-2-(thiazol-2-yl)-5,6-dihydropyrrolo[3,4-d]imidazol-4(1H)-one (17 mg, 44.3% yield) was obtained enantiomerically pure (ee>99.5%) via the same separation.

EXAMPLE 25

6-(4-chlorophenyl)-5-(1,5-dimethyl-6-oxo-1,6-dihydropyridin-3-yl)-2-(2,4-dimethylthiazol-5-yl)-1-isopropyl-5,6-dihydropyrrolo[3,4-d]imidazol-4(1H)-one

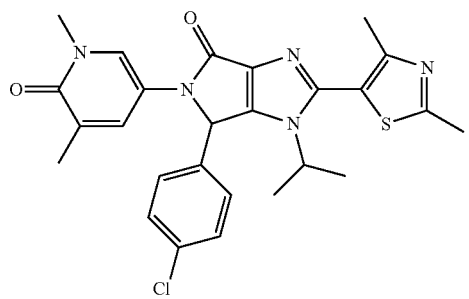 [SMILES: Cc1nc(C)c(-c2nc3c(n2C(C)C)C(c2ccc(Cl)cc2)N(c2cc(C)c(=O)n(C)c2)C3=O)s1]

The title compound was prepared in analogy to the procedure described for Example 21 using 2-bromo-6-(4-chlorophenyl)-5-(1,5-dimethyl-6-oxo-1,6-dihydropyridin-3-yl)-1-isopropyl-5,6-dihydropyrrolo[3,4-d]imidazol-4(1H)-one (Step 23.3) and 2,4-dimethyl-5-(4,4,5,5-tetramethyl-1,3,2-dioxaborolan-2-yl)thiazole. The crude product was purified by silica gel chromatography (CH$_2$Cl$_2$/MeOH 0-10% MeOH) followed by crystallization in iPr$_2$O to afford grey crystals. t$_R$: 0.93 min (LC-MS 2); ESI-MS: 508 [M+H]$^+$ (LC-MS 2).

EXAMPLE 26

6-(4-chlorophenyl)-5-(1,5-dimethyl-6-oxo-1,6-dihydropyridin-3-yl)-1-isopropyl-2-(thiazol-5-yl)-5,6-dihydropyrrolo[3,4-d]imidazol-4(1H)-one

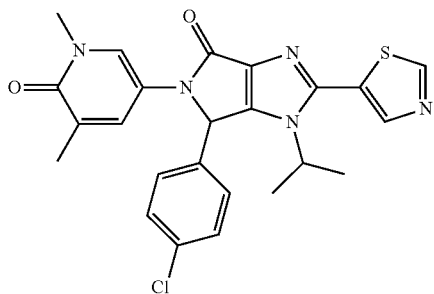 [SMILES: Cc1cc(N2C(=O)c3nc(-c4cncs4)n(C(C)C)c3C2c2ccc(Cl)cc2)cn(C)c1=O]

The title compound was prepared in analogy to the procedure described for Example 15 using 2-bromo-6-(4-chlorophenyl)-5-(1,5-dimethyl-6-oxo-1,6-dihydropyridin-3-yl)-1-isopropyl-5,6-dihydropyrrolo[3,4-d]imidazol-4(1H)-one (Step 23.3) and 5-tributylstannylthiazole. The crude product was first purified by silica gel column chromatography (CH$_2$Cl$_2$/MeOH 0-10% MeOH) followed by preparative achiral SFC (column 2-EP, gradient 14-22% over 6 min_total 11 min) to afford a white solid. t$_R$: 0.81 min (LC-MS 2); ESI-MS: 397 [M+H]$^+$ (LC-MS 2).

EXAMPLE 27

6-(4-chlorophenyl)-5-(1,5-dimethyl-6-oxo-1,6-dihydropyridin-3-yl)-2-(3,5-dimethylisoxazol-4-yl)-1-isopropyl-5,6-dihydropyrrolo[3,4-d]imidazol-4(1H)-one

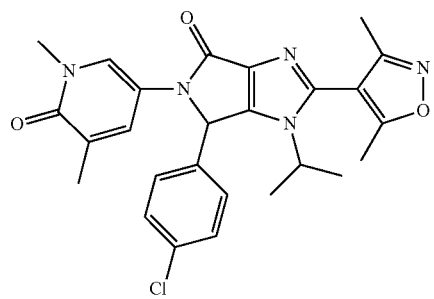 [SMILES: Cc1noc(C)c1-c1nc2c(n1C(C)C)C(c1ccc(Cl)cc1)N(c1cc(C)c(=O)n(C)c1)C2=O]

A MW vial was charged with 2-bromo-6-(4-chlorophenyl)-5-(1,5-dimethyl-6-oxo-1,6-dihydropyridin-3-yl)-1-isopropyl-5,6-dihydropyrrolo[3,4-d]imidazol-4(1H)-one (Step 23.3) (95 mg, 0.2 mmol), 3,5-dimethylisoxazole-4-boronic acid pinacolester (89 mg, 0.40 mmol) and K$_2$CO$_3$ (55.3 mg, 0.40 mmol) in dioxane (1.5 mL) and water (0.3 mL). The mixture was flushed with Ar, Pd(PPh$_3$)$_4$ (14.2 mg, 0.012 mmol) was added, the MW vial was sealed and the resulting mixture was submitted to MW irradiation for 20 min at 100° C., then 40 min at 100° C. The reaction mixture was concentrated under reduced pressure. The residue was diluted with EtOAc (7 mL) and saturated aq. NaHCO$_3$ solution (3 mL) and both phases separated. The aq. layer was extracted with EtOAc (2 mL). Combined extracts were dried over Na$_2$SO$_4$, filtered and concentrated under reduced pressure. The crude product was purified by silica gel column chromatography (CH$_2$Cl$_2$/(CH$_2$Cl$_2$/EtOH 9:1) 3-50% (CH$_2$Cl$_2$/EtOH 9:1)) to afford the title product (45.5 mg, 46% yield) as yellow solid. t$_R$: 0.92 min (LC-MS 2); ESI-MS: 492 [M+H]$^+$ (LC-MS 2).

EXAMPLE 28

6-(4-chlorophenyl)-2-cyclopropyl-5-(1,5-dimethyl-6-oxo-1,6-dihydropyridin-3-yl)-1-isopropyl-5,6-dihydropyrrolo[3,4-d]imidazol-4(1H)-one

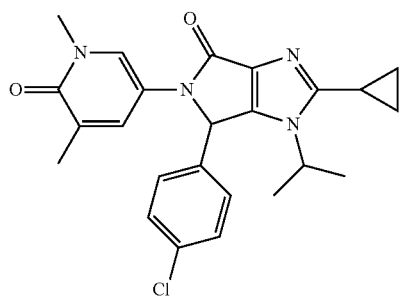 [SMILES: Cc1cc(N2C(=O)c3nc(C4CC4)n(C(C)C)c3C2c2ccc(Cl)cc2)cn(C)c1=O]

The title compound was prepared in analogy to the procedure described for Example 13 using 2-bromo-6-(4-chlorophenyl)-5-(1,5-dimethyl-6-oxo-1,6-dihydropyridin-3-yl)-1-isopropyl-5,6-dihydropyrrolo[3,4-d]imidazol-4(1H)-one (Step 23.3). The crude product was purified by silica gel column chromatography (CH$_2$Cl$_2$/EtOH 0-10% EtOH) to afford a colorless resin. t$_R$: 0.93 min (LC-MS 2); ESI-MS: 437 [M+H]$^+$ (LC-MS 2).

EXAMPLE 29

6-(4-chlorophenyl)-5-(1,5-dimethyl-6-oxo-1,6-dihydropyridin-3-yl)-1-isopropyl-2-(2-methylthiazol-5-yl)-5,6-dihydropyrrolo[3,4-d]imidazol-4(1H)-one

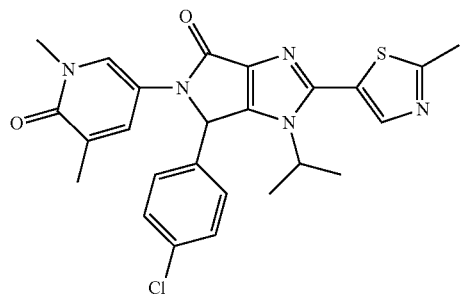 [SMILES: Cc1ncc(-c2nc3c(n2C(C)C)C(c2ccc(Cl)cc2)N(c2cc(C)c(=O)n(C)c2)C3=O)s1]

The title product was prepared in analogy to the procedure described for Example 27 using 2-bromo-6-(4-chlorophenyl)-5-(1,5-dimethyl-6-oxo-1,6-dihydropyridin-3-yl)-1-isopropyl-5,6-dihydropyrrolo[3,4-d]imidazol-4(1H)-one (Step 23.3) and 2-methylthiazole 5-boronic acid pinacol ester under MW irradiation at 100° C. for 9 hr. The crude product was first purified by silica gel column chromatography ((CH$_2$Cl$_2$/(CH$_2$Cl$_2$/EtOH 9:1) 5-60% (CH$_2$Cl$_2$/EtOH 9:1)), followed by preparative achiral SFC (column Silica, gradient isocratic 19% _total 19 min) to afford a colorless resin. t$_R$: 0.90 min (LC-MS 2); ESI-MS: 494 [M+H]$^+$ (LC-MS 2).

EXAMPLE 30

6-(4-chlorophenyl)-5-(1,5-dimethyl-6-oxo-1,6-dihydropyridin-3-yl)-1-isopropyl-2-(1H-pyrrol-2-yl)-5,6-dihydropyrrolo[3,4-d]imidazol-4(1H)-one

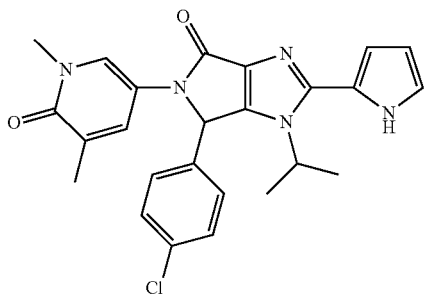 [SMILES: Cc1cc(N2C(=O)c3nc(-c4ccc[nH]4)n(C(C)C)c3C2c2ccc(Cl)cc2)cn(C)c1=O]

The title product was prepared in analogy to the procedure described for Example 27 using 2-bromo-6-(4-chlorophenyl)-5-(1,5-dimethyl-6-oxo-1,6-dihydropyridin-3-yl)-1-isopropyl-5,6-dihydropyrrolo[3,4-d]imidazol-4(1H)-one (Step 23.3) and 1-Boc-pyrrole-2-boronic acid pinacol ester under MW irradiation at 100° C. for 2 hr. The crude product (mixture of the title compound and tert-butyl 2-(6-(4-chlorophenyl)-5-(1,5-dimethyl-6-oxo-1,6-dihydropyridin-3-yl)-1-isopropyl-4-oxo-1,4,5,6-tetrahydropyrrolo[3,4-d]imidazol-2-yl)-1H-pyrrole-1-carboxylate) was first purified by silica gel column chromatography (EtOAc/EtOH 1-10% EtOH), followed by preparative achiral SFC (column PPU, gradient isocratic 10% _total 30 min) to afford a colorless foam. t$_R$: 0.99 min (LC-MS 2); ESI-MS: 462 [M+H]$^+$ (LC-MS 2).

EXAMPLE 31

6-(4-chlorophenyl)-2-cyclopentyl-5-(1,5-dimethyl-6-oxo-1,6-dihydropyridin-3-yl)-1-isopropyl-5,6-dihydropyrrolo[3,4-d]imidazol-4(1H)-one

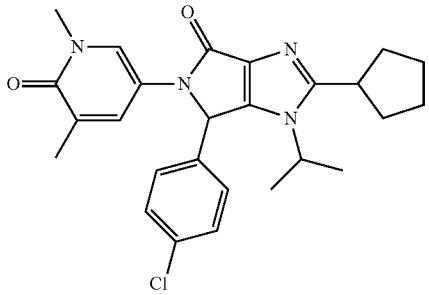 [SMILES: Cc1cc(N2C(=O)c3nc(C4CCCC4)n(C(C)C)c3C2c2ccc(Cl)cc2)cn(C)c1=O]

To a solution of 6-(4-chlorophenyl)-2-(cyclopent-1-en-1-yl)-5-(1,5-dimethyl-6-oxo-1,6-dihydropyridin-3-yl)-1-isopropyl-5,6-dihydropyrrolo[3,4-d]imidazol-4(1H)-one (Step 31.1) (220 mg, 0.475 mmol) in MeOH (5 mL) and THF (2 mL) was added PtO$_2$ (50 mg). The resulting mixture was shaken under hydrogen atmosphere at RT for 10 hr. The reaction mixture was filtered through a PL-thiol SPE cartridge (supplied by Agilent), washed with MeOH and the resulting filtrate was concentrated under reduced pressure. The crude product was purified by preparative achiral SFC (column NH$_2$, gradient 19-24% over 6 min_total 11 min) to afford the title product (95 mg, 0.194 mmol, 40.8% yield) as pale yellowish solid. t$_R$: 1.05 min (LC-MS 2); ESI-MS: 465.4 [M+H]$^+$ (LC-MS 2).

Step 31.1: 6-(4-chlorophenyl)-2-(cyclopent-1-en-1-yl)-5-(1,5-dimethyl-6-oxo-1,6-dihydropyridin-3-yl)-1-isopropyl-5,6-dihydropyrrolo[3,4-d]imidazol-4(1H)-one

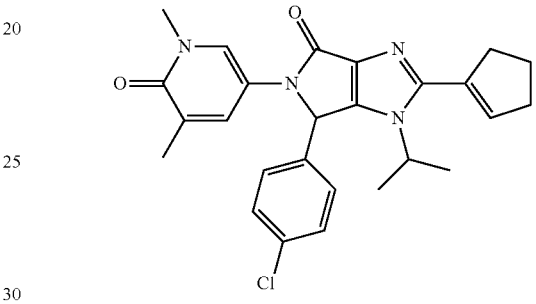

The title compound was prepared in analogy to the procedure described for Example 1 using 2-bromo-6-(4-chlorophenyl)-5-(1,5-dimethyl-6-oxo-1,6-dihydropyridin-3-yl)-1-isopropyl-5,6-dihydropyrrolo[3,4-d]imidazol-4(1H)-one (Step 23.3) and Cyclopenten-1-ylboronic acid at 95° C. for 2 hr. The crude product was filtered through a PL-thiol SPE cartridge, washed with MeOH and the filtrate was concentrated under reduced pressure to afford a beige solid. t$_R$: 1.04 min (LC-MS 2); ESI-MS: 463.3 [M+H]$^+$ (LC-MS 2).

EXAMPLE 32

6-(4-chlorophenyl)-5-(1,5-dimethyl-6-oxo-1,6-dihydropyridin-3-yl)-2-(2-fluoropyridin-3-yl)-1-methyl-5,6-dihydropyrrolo[3,4-d]imidazol-4(1H)-one

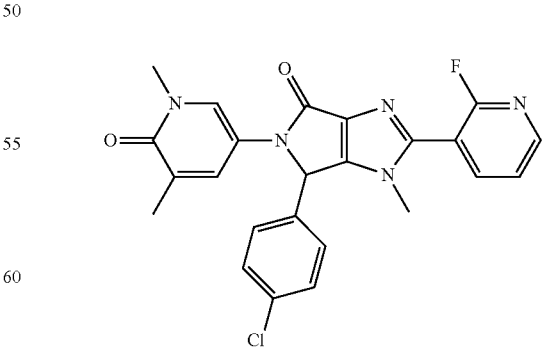

The title compound was prepared in analogy to the procedure described for Example 1 using 2-bromo-6-(4-chlorophenyl)-5-(1,5-dimethyl-6-oxo-1,6-dihydropyridin-3- yl)-1-methyl-5,6-dihydropyrrolo[3,4-d]imidazol-4(1H)-one (Step 32.3) and 2-fluoropyridine-3-boronic acid at 95° C. for 2 hr. The crude product was filtered through a PL-thiol SPE cartridge, washed with MeOH. The resulting filtrate was concentrated under reduced pressure and purified by preparative achiral SFC (column Silica, gradient isocratic 20%_total 30 min). t$_R$: 0.81 min (LC-MS 2); ESI-MS: 464.3 [M+H]$^+$ (LC-MS 2).

Step 32.1: ethyl 2-bromo-5(4-chlorophenyl)((1,5-dimethyl-6-oxo-1,6-dihydropyridin-3-yl)amino)methyl)-1-methyl-1H-imidazole-4-carboxylate

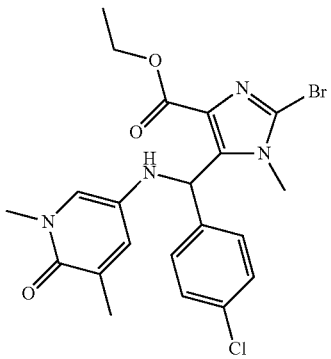 [SMILES: CCOC(=O)c1nc(Br)n(C)c1C(Nc1cc(C)c(=O)n(C)c1)c1ccc(Cl)cc1]

The title compound was prepared in analogy to the procedure described in Step 1.9 using ethyl 2-bromo-5-((4-chlorophenyl)(hydroxy)methyl)-1-methyl-1H-imidazole-4-carboxylate (Step 16.3) and 5-amino-1,3-dimethylpyridin-2(1H)-one (Step 4.3) at RT for 4 hr. t$_R$: 0.98 min (LC-MS 2); ESI-MS: 493.2/495.2 [M+H]$^+$ (LC-MS 2).

Step 32.2: 2-bromo-5 (4-chlorophenyl)((1,5-dimethyl-6-oxo-1,6-dihydropyridin-3-yl)amino)methyl)-1-methyl-1H-imidazole-4-carboxylic acid

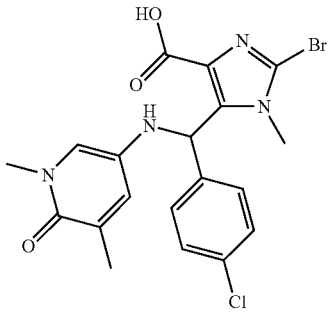 [SMILES: Cc1cc(NC(c2ccc(Cl)cc2)c2c(C(=O)O)nc(Br)n2C)cn(C)c1=O]

The title compound was prepared in analogy to the procedure described in Step 1.10 using ethyl 2-bromo-5-((4-chlorophenyl)((1,5-dimethyl-6-oxo-1,6-dihydropyridin-3-yl)amino)methyl)-1-methyl-1H-imidazole-4-carboxylate (Step 32.1) at RT for 2 hr. t$_R$: 0.80 min (LC-MS 2); ESI-MS: 465.1/467.1 [M+H]$^+$; ESI-MS: 463.1/465.2 [M−H]$^−$ (LC-MS 2).

Step 32.3: 2-bromo-6-(4-chlorophenyl)-5-(1,5-dimethyl-6-oxo-1,6-dihydropyridin-3-yl)-1-methyl-5,6-dihydropyrrolo[3,4-d]imidazol-4(1H)-one

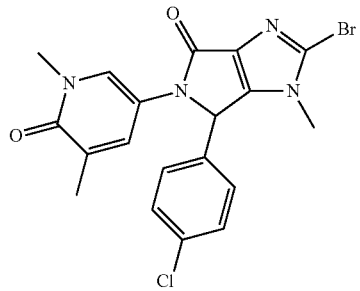 [SMILES: Cc1cc(N2C(=O)c3nc(Br)n(C)c3C2c2ccc(Cl)cc2)cn(C)c1=O]

The title compound was prepared in analogy to the procedure described in Step 1.11 using 2-bromo-5-((4-chlorophenyl)((1,5-dimethyl-6-oxo-1,6-dihydropyridin-3-yl)amino)methyl)-1-methyl-1H-imidazole-4-carboxylic acid (Step 32.2). The crude product was purified by silica gel column chromatography (CH$_2$Cl$_2$/MeOH 0-10% MeOH) to afford a grey solid. t$_R$: 0.81 min (LC-MS 2); ESI-MS: 403.2/405.1 [M+H]$^+$; ESI-MS: 401.3/403.2 [M−H]$^−$ (LC-MS 2).

EXAMPLE 33

1-(tert-butyl)-6-(4-chlorophenyl)-2-cyclopropyl-5-(1,5-dimethyl-6-oxo-1,6-dihydropyridin-3-yl)-5,6-dihydropyrrolo[3,4-d]imidazol-4(1H)-one

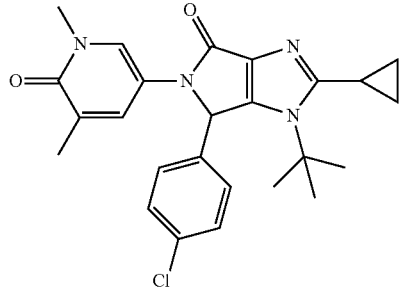 [SMILES: Cc1cc(N2C(=O)c3nc(C4CC4)n(C(C)(C)C)c3C2c2ccc(Cl)cc2)cn(C)c1=O]

The title compound was prepared in analogy to the procedure described for Example 13 using 2-bromo-1-(tert-butyl)-6-(4-chlorophenyl)-5-(1,5-dimethyl-6-oxo-1,6-dihydropyridin-3-yl)-5,6-dihydropyrrolo[3,4-d]imidazol-4(1H)-one (Step 33.6) at 125° C. for 8 hr. The crude product was purified by preparative achiral SFC (column 4-EP, gradient 14-19% over 6 min_total 11 min) to afford a white product. t$_R$: 0.96 min (LC-MS 2); ESI-MS: 451 [M+H]$^+$ (LC-MS 2).

Step 33.1: ethyl 1-tert-butyl-1H-imidazole-4-carboxylate

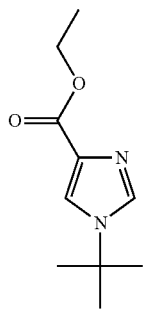

The title compound was prepared following the procedure described in the literature (*Organic Letters*, 2002, Vol. 4, No. 23, 4133-4134).

Step 33.2: ethyl 2-bromo-1-tert-butyl-1H-imidazole-4-carboxylate

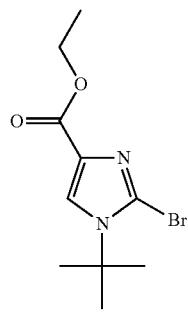

The title compound was prepared in analogy to the procedure described in Step 1.7 using ethyl 1-tert-butyl-1H-imidazole-4-carboxylate (Step 33.1) at RT overnight. The crude product was purified by silica gel column chromatography (hexane/EtOAc 0-50% EtOAc). $t_R$: 0.90 min (LC-MS 1); ESI-MS: 275/277 [M+H]$^+$ (LC-MS 1).

Step 33.3: ethyl 2-bromo-1-(tert-butyl)-5((4-chlorophenyl)(hydroxy)methyl)-1H-imidazole-4-carboxylate

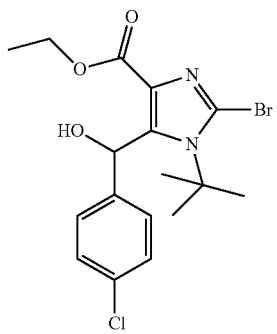

The title compound was prepared in analogy to the procedure described in Step 9.6 using ethyl 2-bromo-1-tert-butyl-1H-imidazole-4-carboxylate (Step 33.2) and 4-chlorobenzaldehyde. $t_R$: 1.21 min (LC-MS 2); ESI-MS: 415/417 [M+H]$^+$ (LC-MS 2).

Step 33.4: ethyl 2-bromo-1-(tert-butyl)-5-((4-chlorophenyl)((1,5-dimethyl-6-oxo-1,6-dihydropyridin-3-yl)amino)methyl)-1H-imidazole-4-carboxylate

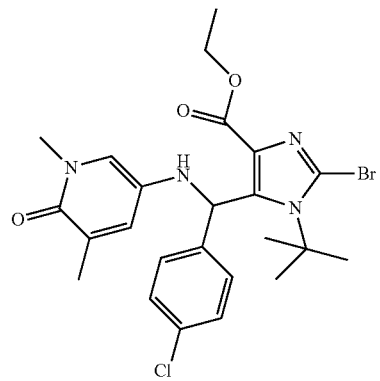 [SMILES: CCOC(=O)c1nc(Br)n(C(C)(C)C)c1C(Nc1cc(C)c(=O)n(C)c1)c1ccc(Cl)cc1]

The title compound was prepared in analogy to the procedure described in Step 1.9 using ethyl 2-bromo-1-(tert-butyl)-5-((4-chlorophenyl)(hydroxy)methyl)-1H-imidazole-4-carboxylate (Step 33.3) and 5-amino-1,3-dimethylpyridin-2(1H)-one (Step 4.3). The crude product was purified by silica gel column chromatography (CH$_2$Cl$_2$/MeOH 0-10% MeOH) to afford dark red solid. $t_R$: 1.11 min (LC-MS 2); ESI-MS: 535/537 [M+H]$^+$ (LC-MS 2).

Step 33.5: 2-bromo-1-(tert-butyl)-5-((4-chlorophenyl)((1,5-dimethyl-6-oxo-1,6-dihydropyridin-3-yl)amino)methyl)-1H-imidazole-4-carboxylic acid

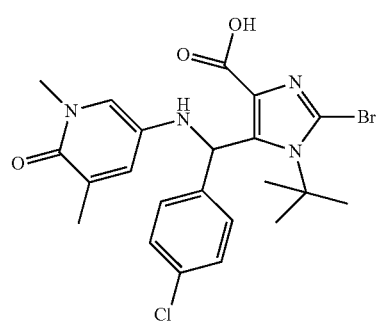 [SMILES: Cc1cc(NC(c2ccc(Cl)cc2)c2c(C(=O)O)nc(Br)n2C(C)(C)C)cn(C)c1=O]

The title compound was prepared in analogy to the procedure described in Step 9.8 using ethyl 2-bromo-1-(tert-butyl)-5-((4-chlorophenyl)((1,5-dimethyl-6-oxo-1,6-dihydropyridin-3-yl)amino)methyl)-1H-imidazole-4-carboxylate (Step 33.4). $t_R$: 0.98 min (LC-MS 2); ESI-MS: 489/491 [M+H−H$_2$O]$^+$ (LC-MS 2).

Step 33.6: 2-bromo-1-(tert-butyl)-6-(4-chlorophenyl)-5-(1,5-dimethyl-6-oxo-1,6-dihydropyridin-3-yl)-5,6-dihydropyrrolo[3,4-d]imidazol-4(1H)-one

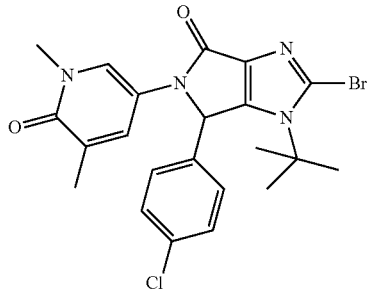 [SMILES: Cc1cc(N2C(=O)c3nc(Br)n(C(C)(C)C)c3C2c2ccc(Cl)cc2)cn(C)c1=O]

The title product was prepared in analogy to the procedure described in Step 1.11 using 2-bromo-1-(tert-butyl)-5 ((4-chlorophenyl)((1,5-dimethyl-6-oxo-1,6-dihydropyridin-3-yl)amino)methyl)-1H-imidazole-4-carboxylic acid (Step 33.5) at 0-5° C. for 45 min. The crude product was crystallized in Et$_2$O/sonication to afford pale yellow crystals. $t_R$: 0.98 min (LC-MS 2); ESI-MS: 489/491 [M+H]$^+$ (LC-MS 2).

EXAMPLE 34

6-(4-chlorophenyl)-2-(2,4-dimethoxypyrimidin-5-yl)-5-(3,7-dimethylbenzo[d]-isoxazol-5-yl)-1-isopropyl-5,6-dihydropyrrolo[3,4-d]imidazol-4(1H)-one

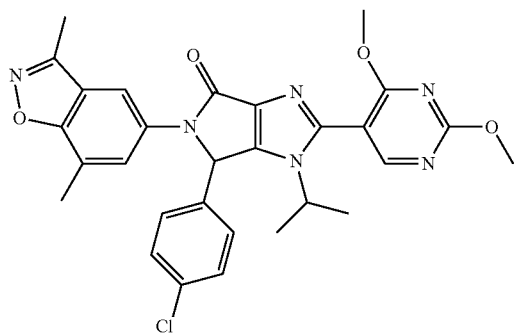 [SMILES: COc1ncc(-c2nc3c(n2C(C)C)C(c2ccc(Cl)cc2)N(c2cc(C)c4onc(C)c4c2)C3=O)c(OC)n1]

The title compound was prepared in analogy to the procedure described in Example 1 using 2-bromo-6-(4-chlorophenyl)-5-(3,7-dimethylbenzo[d]isoxazol-5-yl)-1-isopropyl-5,6-dihydropyrrolo-[3,4-d]imidazol-4(1H)-one (Step 34.9) and (2,4-dimethoxypyrimidin-5-yl)boronic acid in DMF at 100° C. for 1 hr. The reaction mixture was diluted with aq. NaH$_2$PO$_4$ solution and extracted with EtOAc. Combined extracts were dried over MgSO$_4$, filtered and concentrated under reduced pressure. The crude product was first purified by silica gel column chromatography (hexane/(CH$_2$Cl$_2$/MeOH 9:1) 10-100% (CH$_2$Cl$_2$/MeOH 9:1)) followed by preparative achiral SFC (column Silica, gradient 22-27% over 6 min_total 11 min) to afford a pale beige solid. $t_R$: 1.15 min (LC-MS 2); ESI-MS: 559/561 [M+H]$^+$ (LC-MS 2); TLC (EtOAc/MeOH) R$_f$=0.44; $^1$H NMR (400 MHz, DMSO-d$_6$) δ ppm 0.53 (d, J=6.7 Hz, 3 H) 1.43 (d, J=6.7 Hz, 3 H) 2.43 (s, 3 H) 2.52 (s, 3 H) 3.96 (s, 3 H) 4.00 (s, 3 H) 4.15 (m, 1 H) 6.81 (s, 1 H) 7.33-7.47 (m, 4 H) 7.66 (s, 1 H) 7.80 (d, J=1.5 Hz, 1 H) 8.51 (s, 1 H).

Step 34.1: 1-(2-hydroxy-3-methylphenyl)ethanone

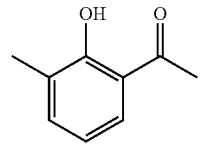

To a colorless solution of 3-methyl-salicylic acid (10 g, 65.7 mmol) in Et$_2$O (350 mL) under Ar and cooled down to 0° C. was added dropwise methyllithium 1.6M in Et$_2$O (123 mL, 197 mmol) over 30 min. The resulting mixture was stirred at this temperature for 30 min then allowed to warm up and stir overnight at RT. The reaction mixture was poured onto a cold 2N HCl and the product was extracted with EtOAc. Combined extracts were washed with 10% NaHCO$_3$ solution and brine, dried over MgSO$_4$, filtered and concentrated under reduced pressure to afford the title product (5.14 g, 32.5 mmol, 49% yield) as a pale yellow oil. $t_R$: 0.99 min (LC-MS 2); ESI-MS: no ionisation [M+H]$^+$ (LC-MS 2); TLC (hexane/EtOAc 3:1) R$_f$=0.55.

Step 34.2: (E)-1-(2-hydroxy-3-methylphenyl)ethanone oxime

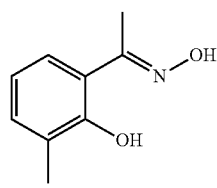

1-(2-Hydroxy-3-methylphenyl)ethanone (Step 34.1) (5.14 g, 32.5 mmol) was dissolved in MeOH (70 mL) and NaOAc (4.27 g, 52.0 mmol) and hydroxylamine hydrochloride (3.39 g, 48.8 mmol) were successively added. The resulting mixture was stirred at 60° C. for 3 hr. The reaction mixture was concentrated under reduced pressure, the residue was diluted with water and extracted with EtOAc. Combined extracts were washed with brine, dried over MgSO$_4$, filtered and concentrated under reduced pressure to afford the title product (5.5 g, 31.0 mmol, 95% yield) as a colorless solid. $t_R$: 0.93 min (LC-MS 2); ESI-MS: 166 [M+H]$^+$, ESI-MS: 164 [M−H]$^-$ (LC-MS 2); TLC (hexane/EtOAc 1:1) R$_f$=0.66.

Step 34.3: 1-(2-hydroxy-3-methylphenyl)ethanone O-acetyl oxime

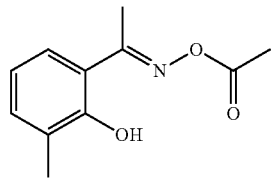

1-(2-Hydroxy-3-methylphenyl)ethanone oxime (Step 34.2) (5.5 g, 30 mmol) was added into Ac$_2$O (48.1 mL, 509 mmol) under Ar and the resulting mixture was stirred at RT for 1.5 hr. The reaction was concentrated to 10 mL volume under reduced pressure; the resulting suspension was diluted with cold water and stirred at RT until a fine precipitate was formed. The resulting solid was filtrated off, washed with water and dried to afford the title product (6.025 g, 28.8 mmol, 96% yield) as colorless solid. $t_R$: 1.08 min (LC-MS 2); ESI-MS: 208 [M+H]$^+$; TLC (hexane/EtOAc 1:1) $R_f$=0.60.

Step 34.4: 3,7-dimethylbenzo[d]isoxazole

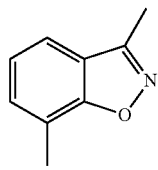

1-(2-Hydroxy-3-methylphenyl)ethanone O-acetyl oxime (Step 34.3) (6.0 g, 29.0 mmol) was dissolved in pyridine (60 mL) and the resulting mixture was heated at 130° C. for 40 hr, cooled down to RT and concentrated under reduced pressure. The crude product was purified by silica gel column chromatography (hexane/EtOAc 0-50% EtOAc) to afford the title product (3.62 g, 23.12 mmol, 80% yield) as pale yellow oil. $t_R$: 0.96 min (LC-MS 2); ESI-MS: 148 [M+H]$^+$; TLC (hexane/EtOAc 3:1) $R_f$=0.56.

Step 34.5: 3,7-dimethyl-5-nitrobenzo[d]isoxazole

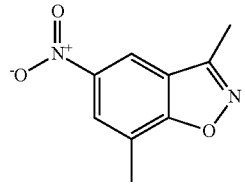

3,7-Dimethylbenzo[d]isoxazole (Step 34.4) (2 g, 12.77 mmol) was dissolved in H$_2$SO$_4$ (5 mL), cooled down and stirred at 0° C. HNO$_3$ (0.878 mL, 12.77 mmol) was slowly added and the resulting mixture was stirred at 0° C. for 1 hr. The reaction was diluted with water (60 mL) and extracted with CH$_2$Cl$_2$. Combined extracts were washed with NaHCO$_3$ solution and brine, dried over MgSO$_4$, filtered and concentrated. The resulting yellow solid was triturated with Et$_2$O, filtrated off, washed with Et$_2$O and dried to afford the title product (1.86 g, 9.29 mmol, 72.7% yield) as yellow solid. $t_R$: 0.98 min (LC-MS 2); ESI-MS: 193 [M+H]$^+$ (LC-MS 2).

Step 34.6: 3,7-dimethylbenzo[d]isoxazol-5-amine

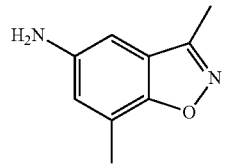

To a suspension of 3,7-dimethyl-5-nitrobenzo[d]isoxazole (Step 34.5) (50 mg, 0.260 mmol) in acetic acid (1.5 mL) was added dropwise a solution of SnCl$_2$.2H$_2$O (176 mg, 0.781 mmol) in HCl conc (0.316 mL, 10.41 mmol) and the resulting mixture was stirred at RT overnight. The reaction was poured onto cold 4N NaOH and extracted with EtOAc. Combined extracts were dried over MgSO$_4$, filtered and concentrated under reduced pressure. The crude product was purified by silica gel column chromatography (hexane/EtOAc 0-55%) to afford the title product (25 mg, 0.153 mmol, 58% yield) as beige solid. $t_R$: 0.57 min (LC-MS 2); ESI-MS: 163 [M+H]$^+$ (LC-MS 2); TLC (hexane/EtOAc 1:1) $R_f$=0.23.

Step 34.7: 2-bromo-5 ((4-chlorophenyl)((3,7-dimethylbenzo[d]isoxazol-5-yl)amino)methyl)-1-isopropyl-1H-imidazole-4-carboxylate

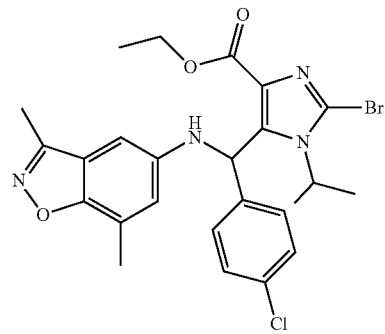 [SMILES: CCOC(=O)c1nc(Br)n(C(C)C)c1C(Nc1cc(C)c2onc(C)c2c1)c1ccc(Cl)cc1]

The title compound was prepared in analogy to the procedure described for Step 1.9 using ethyl 2-bromo-5-((4-chlorophenyl)(hydroxy)methyl)-1-isopropyl-1H-imidazole-4-carboxylate (Step 9.6) and 3,7-dimethylbenzo[d]isoxazol-5-amine (Step 34.6). The crude product was purified by silica gel column chromatography (hexane/EtOAc 20-100% EtOAc) to afford a pale yellow solid. $t_R$: 1.34 min (LC-MS 2); ESI-MS: 545/547 [M+H]$^+$ (LC-MS 2).

Step 34.8: 2-bromo-5 ((4-chlorophenyl)((3,7-dimethylbenzo[d]isoxazol-5-yl)amino)methyl)-1-isopropyl-1H-imidazole-4-carboxylic acid

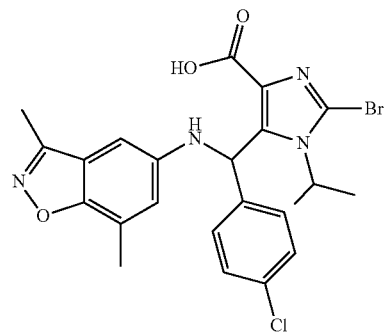 [SMILES: Cc1noc2c(C)cc(NC(c3ccc(Cl)cc3)c3c(C(=O)O)nc(Br)n3C(C)C)cc12]

To a solution of ethyl 2-bromo-5 ((4-chlorophenyl)((3,7-dimethylbenzo[d]isoxazol-5-yl)amino)-methyl)-1-isopropyl-1H-imidazole-4-carboxylate (Step 34.7) (1.0 g, 1.832 mmol) in MeOH (20 mL) cooled down to 0° C. was added 4N NaOH (6.87 mL, 27.5 mmol). The resulting mixture was stirred at RT for 2 hr at 45° C. The reaction mixture was cooled down to 0° C., acidified adding dropwise 4N HCl (7.5 mL) and MeOH was removed under reduced pressure. The resulting aq. layer was extracted with EtOAc. Combined extracts were washed with brine, dried over MgSO$_4$, filtered and concentrated under reduced pressure to afford the title product (920 mg, 1.741 mmol, 95% yield) as beige amorphous solid. $t_R$: 1.15 min (LC-MS 2); ESI-MS: 517/519 [M+H]$^+$; ESI-MS: 515/517 [M−H]$^−$ (LC-MS 2).

Step 34.9: 2-bromo-6-((4-chlorophenyl)-5-(3,7-dimethylbenzo[d]isoxazol-5-yl)-1-isopropyl-5,6-dihydropyrrolo[3,4-d]imidazol-4(1H)-one

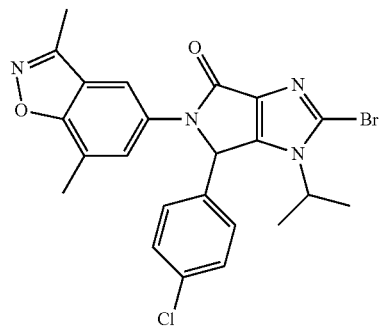 [SMILES: Cc1noc2c(C)cc(N3C(=O)c4nc(Br)n(C(C)C)c4C3c3ccc(Cl)cc3)cc12]

The title product was prepared in analogy to the procedure described in Step 1.11 using 2-bromo-5-((4-chlorophenyl)((3,7-dimethylbenzo[d]isoxazol-5-yl)amino)methyl)-1-isopropyl-1H-imidazole-4-carboxylic acid (Step 34.8). The crude product was crystallized in iPr$_2$O/sonication to afford a pale colorless solid. $t_R$: 1.17 min (LC-MS 2); ESI-MS: 499/501 [M+H]$^+$ (LC-MS 2); TLC (EtOAc) R$_f$=0.44.

EXAMPLE 35

6-(4-chlorophenyl)-5-(3,7-dimethylbenzo[d]isoxazol-5-yl)-1-isopropyl-2-(6-methoxypyridin-3-yl)-5,6-dihydropyrrolo[3,4-d]imidazol-4(1H)-one

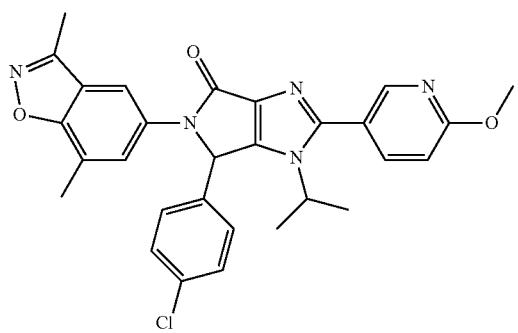 [SMILES: COc1ccc(-c2nc3c(n2C(C)C)C(c2ccc(Cl)cc2)N(c2cc(C)c4onc(C)c4c2)C3=O)cn1]

The title compound was prepared in analogy to the procedure described for Example 1 using 2-bromo-6-(4-chlorophenyl)-5-(3,7-dimethylbenzo[d]isoxazol-5-yl)-1-isopropyl-5,6-dihydropyrrolo-[3,4-d]imidazol-4(1H)-one (Step 34.9) and (6-methoxypyridin-3-yl)boronic acid at 100° C. for 1 hr. The crude product was first purified by silica gel column chromatography (hexane/(EtOAc/MeOH 9:1) 20-100% (EtOAc/MeOH 9:1) followed by preparative achiral SFC (column Silica, gradient isocratic 15% 16 min_total 20 min) to afford a white solid. $t_R$: 1.18 min (LC-MS 2); ESI-MS: 528/530 [M+H]$^+$ (LC-MS 2); TLC (EtOAc/MeOH 9:1) R$_f$=0.59; $^1$H NMR (400 MHz, DMSO-d$_6$) δ ppm 0.66 (d, J=6.7 Hz, 3 H) 1.47 (d, J=6.7 Hz, 4 H) 2.45 (s, 3 H) 2.52 (s, 3 H) 3.94 (s, 3 H) 4.41 (m, 1 H) 6.78 (m, 1 H) 6.99 (m, 1 H) 7.37-7.48 (m, 4 H) 7.67 (m, 1 H) 7.81 (m, 1 H) 7.92-7.98 (m, 1 H) 8.43 (m, 1 H).

EXAMPLE 36

6-(4-chlorophenyl)-5-(1,5-dimethyl-6-oxo-1,6-dihydropyridin-3-yl)-2-(5-fluoro-2-methoxypyridin-4-yl)-3-propyl-5,6-dihydropyrrolo[3,4-d]imidazol-4(3H)-one

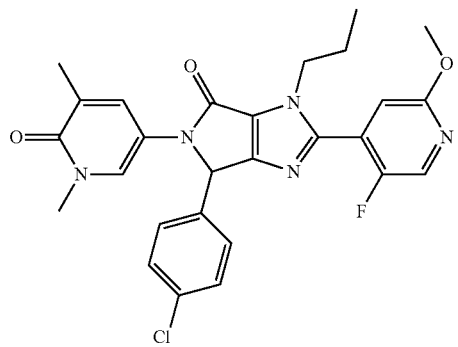 [SMILES: CCCn1c(-c2cc(OC)ncc2F)nc2c1C(=O)N(c1cc(C)c(=O)n(C)c1)C2c1ccc(Cl)cc1]

The title compound was prepared in analogy to the procedure described for Example 1 using 2-bromo-6-(4-chlorophenyl)-5-(1,5-dimethyl-6-oxo-1,6-dihydropyridin-3-yl)-3-propyl-5,6-dihydropyrrolo[3,4-d]imidazol-4(3H)-one (Step 36.8) and (5-fluoro-2-methoxypyridin-4-yl)boronic acid at 100° C. for 16 hr. The crude product was purified by silica gel column chromatography (hexane/(EtOAc/MeOH 9:1) 20-100% (EtOAc/MeOH 9:1) to afford a yellow solid. $t_R$: 1.05 min (LC-MS 2); ESI-MS: 522/524 [M+H]$^+$ (LC-MS 2); TLC (EtOAc/MeOH 9:1) R$_f$=0.42; $^1$H NMR (400 MHz, DMSO-d$_6$) δ ppm 0.75 (t, J=7.3 Hz, 3 H) 1.82-1.92 (m, 2 H) 1.96 (s, 3 H) 3.39 (s, 3 H) 3.90 (s, 3 H) 4.06 (t, J=7.1 Hz, 2 H) 6.22 (s, 1 H) 7.08 (d, J=4.6 Hz, 1 H) 7.29 (d, J=8.5 Hz, 2 H) 7.42 (d, J=8.4 Hz, 2 H) 7.46 (d, J=1.5 Hz, 1 H) 7.77 (d, J=2.6 Hz, 1 H) 8.40 (s, 1 H).

Step 36.1: dibutyl 1H-imidazole-4,5-dicarboxylate

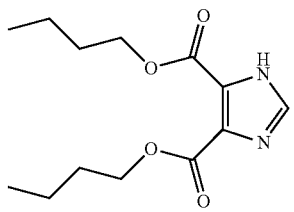 [SMILES: CCCCOC(=O)c1nc[nH]c1C(=O)OCCCC]

The title compound was prepared following the procedure described in the literature (J. Chem. Soc., Perkin Trans. 1, 1980, 495-505). $t_R$: 0.96 min (LC-MS 2); ESI-MS: 269 [M+H]$^+$; ESI-MS: 267.3 [M−H]$^−$ (LC-MS 2); TLC (EtOAc/heptane 1:1) R$_f$=0.12.

Step 36.2: dibutyl 2-bromo-1H-imidazole-4,5-dicarboxylate

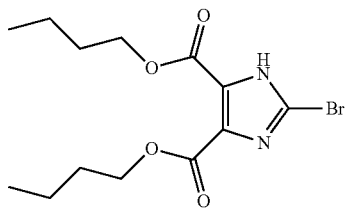 [SMILES: CCCCOC(=O)c1nc(Br)[nH]c1C(=O)OCCCC]

To a solution of dibutyl 1H-imidazole-4,5-dicarboxylate (Step 36.1) (20 g, 74.5 mmol) in $CH_2Cl_2$ (250 mL) and ACN (83 mL) were added successively $K_2CO_3$ (11.33 g, 82 mmol) then dropwise bromine (4.22 mL, 82 mmol). The resulting mixture was stirred 1 hr at RT. The reaction mixture was poured onto aq. $Na_2S_2O_3$ solution and extracted with $CH_2Cl_2$. Combined extracts were washed with brine, dried over $MgSO_4$, filtered and concentrated under reduced pressure to afford the title product (27.1 g, 74.1 mmol, 99% yield) as a yellow oil. $t_R$: 1.09 min (LC-MS 2); ESI-MS: 347/349 $[M+H]^+$; ESI-MS: 345/347 $[M-H]^-$ (LC-MS 2); TLC (EtOAc/heptane 1:1) $R_f$=0.39.

Step 36.3: dibutyl 2-bromo-1-propyl-1H-imidazole-4,5-dicarboxylate

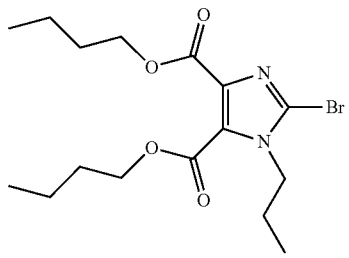 [SMILES: CCCCOC(=O)c1nc(Br)n(CCC)c1C(=O)OCCCC]

To a solution of dibutyl 2-bromo-1H-imidazole-4,5-dicarboxylate (Step 36.2) (14.2 g, 40.9 mmol) in DMF (100 mL) were added $K_2CO_3$ (9.61 g, 69.5 mmol) and 1-iodopropane (6.02 mL, 61.3 mmol). The resulting mixture was stirred at 80° C. for 1.5 hr. The reaction mixture was concentrated under reduced pressure. The residue was diluted with water and extracted with EtOAc. Combined extracts were washed with brine, dried over $MgSO_4$, filtered and concentrated under reduced pressure to afford the title product (14.93 g, 37.6 mmol, 92% yield) as yellow oil. $t_R$: 1.35 min (LC-MS 2); ESI-MS: 389/391 $[M+H]^+$ (LC-MS 2); TLC (hexane/EtOAc 3:1) $R_f$=0.38.

Step 36.4: butyl 2-bromo-4-formyl-1-propyl-1H-imidazole-5-carboxylate

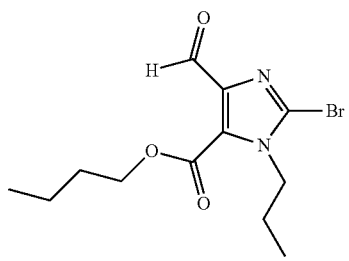 [SMILES: CCCCOC(=O)c1c(C=O)nc(Br)n1CCC]

To a solution of dibutyl 2-bromo-1-propyl-1H-imidazole-4,5-dicarboxylate (Step 36.3) (14.8 g, 37.3 mmol) in THF (150 mL) under Ar was added at −78° C. a 1M solution of DIBAL-H in THF (50.3 mL, 50.3 mmol) and the resulting mixture was stirred at this temperature for 1 hr. Additional 1M DIBAL-H solution in THF (20 mL) was added and the mixture was stirred for 0.5 hr at −50° C. to complete the reaction. The reaction mixture was poured onto a mixture of ice (400 g) and 4N HCl (100 mL) and let stir for 30 min. The aq. layer was extracted with EtOAc. Combined extracts were washed with brine, dried over $MgSO_4$, filtered and concentrated under reduced pressure. The crude product was purified by silica gel column chromatography (hexane/EtOAc 3:1) to afford the title product (7.78 g, 24.28 mmol, 65% yield) as pale yellow oil. $t_R$: 1.10 min (LC-MS 2); ESI-MS: 317/319 $[M+H]^+$ (LC-MS 2); TLC (EtOAc/hexane 1:1) $R_f$=0.47.

Step 36.5: butyl 2-bromo-4-((4-chlorophenyl)(hydroxy)methyl)-1-propyl-1H-imidazole-5-carboxylate

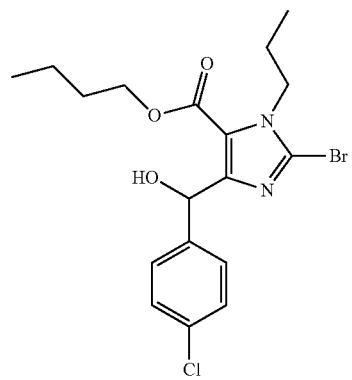 [SMILES: CCCCOC(=O)c1c(C(O)c2ccc(Cl)cc2)nc(Br)n1CCC]

To a solution of butyl 2-bromo-4-formyl-1-propyl-1H-imidazole-5-carboxylate (Step 36.4) (7.7 g, 24.28 mmol) in THF (100 mL) under Ar was added at −78° C. a 1M solution of ((4-chlorophenyl)-magnesium bromide in $Et_2O$ (34 mL, 34 mmol) and the resulting mixture was stirred for 1 hr at −78° C. The reaction mixture was poured onto aq. $NH_4Cl$ solution and the product was extracted with EtOAc. Combined extracts were washed with brine, dried over $MgSO_4$, filtered and concentrated under reduced pressure. The crude product was purified by silica gel column chromatography (hexane/EtOAc 5-50% EtOAc) to afford the title product (9.03 g, 20.59 mmol, 85% yield) as pale yellow resin. $t_R$: 1.33 min (LC-MS 2); ESI-MS: 429/431 $[M+H]^+$ (LC-MS 2); TLC (toluene/EtOAc 3:1) $R_f$=0.48.

Step 36.6: butyl 2-bromo-44((4-chlorophenyl)((1,5-dimethyl-6-oxo-1,6-dihydropyridin-3-yl)amino)methyl)-1-propyl-1H-imidazole-5-carboxylate

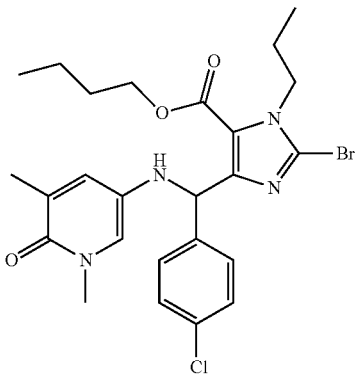 [SMILES: CCCCOC(=O)c1c(C(Nc2cc(C)c(=O)n(C)c2)c2ccc(Cl)cc2)nc(Br)n1CCC]

The title compound was prepared in analogy to the procedure described in Step 1.9 using butyl 2-bromo-4-(((4-chlorophenyl)(hydroxy)methyl)-1-propyl-1H-imidazole-5-carboxylate (Step 36.5) and 5-amino-1,3-dimethylpyridin-2 (1H)-one (Step 4.3). The crude product was purified by silica gel column chromatography (hexane/(EtOAc/MeOH 9:1) 15-100% (EtOAc/MeOH 9:1)) to afford a yellow solid. $t_R$: 1.30 min (LC-MS 2); ESI-MS: 549/531 [M+H]$^+$ (LC-MS 2); TLC (EtOAc/MeOH 9:1) $R_f$=0.41.

Step 36.7: 2-bromo-44((4-chlorophenyl)((1,5-dimethyl-6-oxo-1,6-dihydropyridin-3-yl)amino)-methyl)-1-propyl-1H-imidazole-5-carboxylic acid

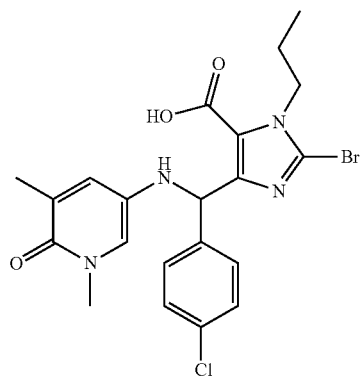 [SMILES: CCCn1c(Br)nc(C(Nc2cc(C)c(=O)n(C)c2)c2ccc(Cl)cc2)c1C(=O)O]

The title compound was prepared in analogy to the procedure described in Step 34.8 using butyl 2-bromo-4-(((4-chlorophenyl)((1,5-dimethyl-6-oxo-1,6-dihydropyridin-3-yl)amino)methyl)-1-propyl-1H-imidazole-5-carboxylate (Step 36.6) to afford a pale brown solid. $t_R$: 0.93 min (LC-MS 2); ESI-MS: 493/495 [M+H]$^+$; ESI-MS: 491/493 [M−H]$^−$ (LC-MS 2).

Step 36.8: 2-bromo-6-(4-chlorophenyl)-5-(1,5-dimethyl-6-oxo-1,6-dihydropyridin-3-yl)-3-propyl-5,6-dihydropyrrolo[3,4-d]imidazol-4(3H)-one

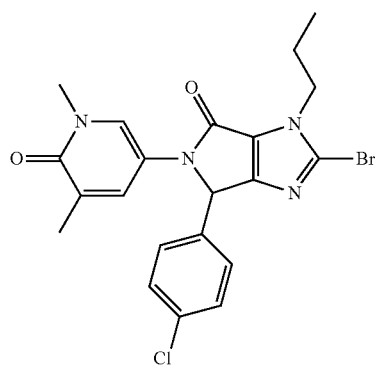 [SMILES: CCCn1c(Br)nc2c1C(=O)N(c1cc(C)c(=O)n(C)c1)C2c1ccc(Cl)cc1]

The title product was prepared in analogy to the procedure described in Step 1.11 using 2-bromo-4-((4-chlorophenyl)((1,5-dimethyl-6-oxo-1,6-dihydropyridin-3-yl)amino) methyl)-1-propyl-1H-imidazole-5-carboxylic acid (Step 36.7). The crude product was purified by silica gel column chromatography (hexane/(EtOAc/MeOH 9:1) 20-100% (EtOAc/MeOH 9:1)) to afford a pale greenish amorphous solid. $t_R$: 0.99 min (LC-MS 2); ESI-MS: 475/477 [M+H]$^+$ (LC-MS 2); TLC (EtOAc/MeOH 9:1) $R_f$=0.40.

EXAMPLE 37

5-(4-(4-chlorophenyl)-5-(1,5-dimethyl-6-oxo-1,6-dihydropyridin-3-yl)-6-oxo-1-propyl-1,4,5,6-tetrahydropyrrolo[3,4-d]imidazol-2-yl)nicotinonitrile

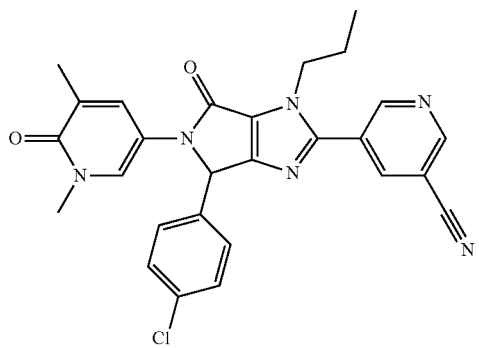 [SMILES: CCCn1c(-c2cncc(C#N)c2)nc2c1C(=O)N(c1cc(C)c(=O)n(C)c1)C2c1ccc(Cl)cc1]

The title compound was prepared in analogy to the procedure described for Example 1 using 2-bromo-6-((4-chlorophenyl)-5-(1,5-dimethyl-6-oxo-1,6-dihydropyridin-3-yl)-3-propyl-5,6-dihydropyrrolo[3,4-d]imidazol-4(3H)-one (Step 36.8) and (5-cyanopyridin-3-yl)boronic acid pinacolester at 100° C. for 5 hr. The crude product was purified by silica gel column chromatography (hexane/(EtOAc/MeOH 9:1) 20-100% (EtOAc/MeOH 9:1) to afford a beige amorphous solid. $t_R$: 0.92 min (LC-MS 2); ESI-MS: 499/501 [M+H]$^+$; ESI-MS: 497 [M−H]$^−$ (LC-MS 2); TLC (EtOAc/MeOH 9:1) $R_f$=0.16; $^1$H NMR (400 MHz, DMSO-$d_6$) δ ppm 0.79 (t, J=7.3 Hz, 3 H) 1.84-1.94 (m, 2 H) 1.96 (s, 3 H) 3.37-3.43 (m, 3 H) 4.26 (t, J=7.1 Hz, 2 H) 6.22 (s, 1 H) 7.30 (d, J=8.4 Hz, 2 H) 7.42 (d, J=8.4 Hz, 2 H) 7.47 (d, J=1.6 Hz, 1 H) 7.78 (d, J=2.7 Hz, 1 H) 8.65 (t, J=2.0 Hz, 1 H) 9.14 (d, J=2.2 Hz, 1 H) 9.16 (d, J=2.0 Hz, 1 H).

EXAMPLE 38

6-(4-chlorophenyl)-5-(1,5-dimethyl-6-oxo-1,6-dihydropyridin-3-yl)-3-ethyl-2-(6-methoxypyridin-3-yl)-5,6-dihydropyrrolo[3,4-d]imidazol-4(3H)-one

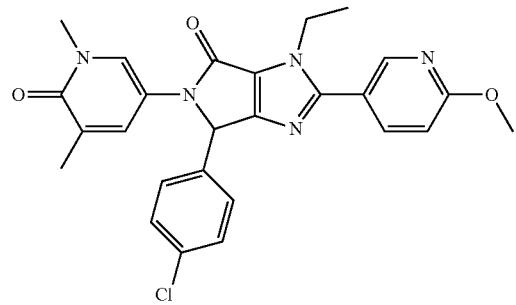 [SMILES: CCn1c(-c2ccc(OC)nc2)nc2c1C(=O)N(c1cc(C)c(=O)n(C)c1)C2c1ccc(Cl)cc1]

The title compound was prepared in analogy to the procedure described for Example 1 using 2-bromo-6-(4-chlorophenyl)-5-(1,5-dimethyl-6-oxo-1,6-dihydropyridin-3- yl)-3-ethyl-5,6-dihydropyrrolo[3,4-d]imidazol-4(3H)-one (Step 38.9) and (6-methoxypyridin-3-yl)boronic acid at 100° C. for 4 hr. The crude product was purified by silica gel column chromatography (hexane/EtOAc/MeOH 80:20:2 to 0:10:1) to afford a light yellow foam. $t_R$: 0.95 min (LC-MS 2); ESI-MS: 490/492 [M+H]$^+$ (LC-MS 2); TLC (CH$_2$Cl$_2$/MeOH 9:1) R$_f$=0.32; $^1$H NMR (400 MHz, CDCl$_3$) δ ppm 1.5 -1.59 (m, 3 H) 2.04 (s, 3 H) 3.41 (s, 3 H) 3.93 (s, 3 H) 4.22 (q, J=7.2 Hz, 2 H) 5.58 (s, 1 H) 6.79 (d, J=8.6 Hz, 1 H) 7.08 (d, J=8.6 Hz, 2 H) 7.17 (d, J=2.7 Hz, 1 H) 7.25 (d, J=8.6 Hz, 2 H) 7.76 (d, J=2.5 Hz, 1 H) 7.78 (d, J=2.5 Hz, 1 H) 8.33 (d, J=2.3 Hz, 1 H).

Step 38.1: dimethyl 2-bromo-1H-imidazole-4,5-dicarboxylate

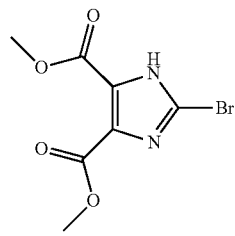

The title compound was prepared in analogy to the procedure described in Step 36.2 using methyl 1H-imidazole-4,5-dicarboxylate at RT for 2 hr. The reaction mixture was quenched with a minimum volume of aq. Na$_2$S$_2$O$_3$ solution and the yellow suspension was filtered and the filtrate was concentrated under reduced pressure. About 30-40% of the total amount of product was obtained. Most of the product had crystallized and required repeated dissolution with hot THF-MeOH 4:1 mixture (500 mL). The extraction from a saturated aq. phase was producing even less product. The individual extracted batches, probably containing some KBr salt, were combined and dried under reduced pressure. The residual salt was always checked after each treatment with THF-MeOH if still some product was present. It required 4 extraction cycles to remove the polar and poorly soluble product from the inorganic salts. TLC (CH$_2$Cl$_2$/MeOH 10:1) R$_f$=0.42.

Step 38.2: dimethyl 2-bromo-1-(4-methoxybenzyl)-1H-imidazole-4,5-dicarboxylate

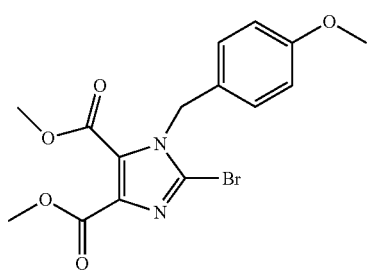

The title compound was prepared in analogy to the procedure described in Step 36.3 using dimethyl 2-bromo-1H-imidazole-4,5-dicarboxylate (Step 38.1) and 4-methoxybenzyl chloride at 50° C. for 14 hr. The reaction mixture was concentrated under reduced pressure. The residue was diluted with aq. 10% Na$_2$CO$_3$ solution and ice and extracted with EtOAc. Combined extracts were washed with brine, dried over MgSO$_4$, filtered and concentrated under reduced pressure to afford a yellow oil. $t_R$: 0.97 min (LC-MS 2); ESI-MS: 383/385 [M+H]$^+$ (LC-MS 2); TLC (EtOAc) R$_f$=0.75.

Step 38.3: methyl 2-bromo-4-formyl-1-(4-methoxybenzyl)-1H-imidazole-5-carboxylate

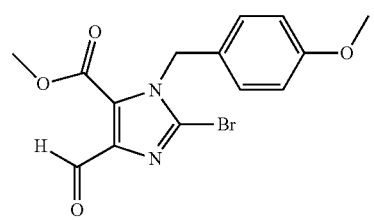

The title compound was prepared in analogy to the procedure described in Step 36.4 using dimethyl 2-bromo-1-(4-methoxybenzyl)-1H-imidazole-4,5-dicarboxylate (Step 38.2). After dissolution of the crude product in a small amount of EtOAc and Et$_2$O and subsequent seeding the product started to crystallize. The crystals were filtrated off and dried to afford light yellow crystals. $t_R$: 0.91 min (LC-MS 2); ESI-MS: 353/355 [M+H]$^+$ (LC-MS 2); TLC (hexane/EtOAc 1.1) R$_f$=0.27.

Step 38.4: methyl 2-bromo-4-formyl-1H-imidazole-5-carboxylate

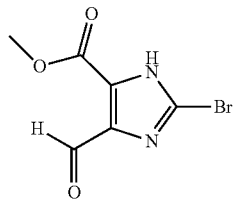

A solution of methyl 2-bromo-4-formyl-1-(4-methoxybenzyl)-1H-imidazole-5-carboxylate Step 38.3) (30.5 g, 85 mmol) in TFA (50 mL) was heated up and stirred at 70° C. for 30 min. The reaction mixture was concentrated under reduced pressure. The oily residue was evaporated twice with toluene (250 mL). The crude product was crystallized in hot toluene to afford the title product (15.9 g, 64.8 mmol, 77% yield) as light beige solid. $t_R$: 0.47 min (LC-MS 2); ESI-MS: 233/235 [M+H]$^+$; ESI-MS: 231/233 [M−H]$^-$ (LC-MS 2).

Step 38.5: methyl 2-bromo-1-ethyl-4-formyl-1H-imidazole-5-carboxylate

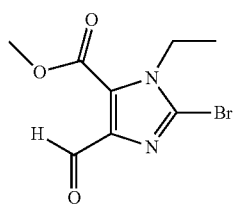

The title compound was prepared in analogy to the procedure described in Step 36.3 using methyl 2-bromo-4-formyl-1H-imidazole-5-carboxylate (Step 38.4) and ethyl iodide at 50° C. for 1 hr. The crude product was purified by silica gel column chromatography (hexane/EtOAc 30-100% EtOAc) to afford a white crystalline solid. $t_R$: 0.69 min (LC-MS 2); ESI-MS: 261/263 [M+H]$^+$ (LC-MS 2); TLC (EtOAc) $R_f$=0.23.

Step 38.6: methyl 2-bromo-4-((4-chlorophenyl)(hydroxy)methyl)-1-ethyl-1H-imidazole-5-carboxylate

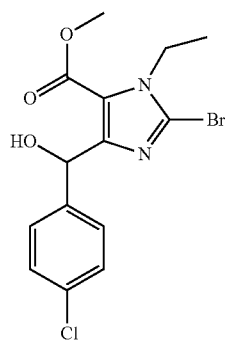

The title compound was prepared in analogy to the procedure described in Step 36.5 using methyl 2-bromo-1-ethyl-4-formyl-1H-imidazole-5-carboxylate (Step 38.5) (addition of the Grignard reagent and reaction were performed at 0° C. instead of −78° C.). The crude product was purified by silica gel column chromatography (hexane/EtOAc 10:1 to 3:1) to afford a colorless oil. $t_R$: 1.04 min (LC-MS 2); ESI-MS: 373/375 [M+H]$^+$ (LC-MS 2); TLC (hexane/EtOAc 1:1) $R_f$=0.32.

Step 38.7: methyl 2-bromo-4-((4-chlorophenyl)((1,5-dimethyl-6-oxo-1,6-dihydropyridin-3-yl)amino)methyl)-1-ethyl-1H-imidazole-5-carboxylate

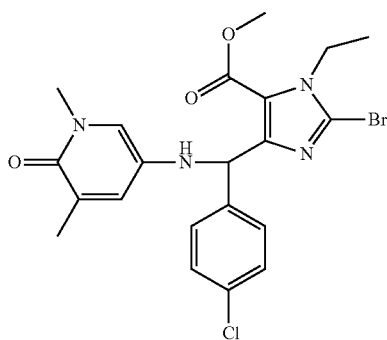 [SMILES: CCn1c(Br)nc(C(Nc2cc(C)c(=O)n(C)c2)c2ccc(Cl)cc2)c1C(=O)OC]

The title compound was prepared in analogy to the procedure described in Step 1.9 using methyl 2-bromo-4-((4-chlorophenyl)(hydroxy)methyl)-1-ethyl-1H-imidazole-5-carboxylate (Step 38.6) and 5-amino-1,3-dimethylpyridin-2(1H)-one (Step 4.3). The crude product was purified by silica gel column chromatography (hexane/EtOAc/MeOH 50:50:5 to 0:50:5) to afford a brown foam. $t_R$: 1.07 min (LC-MS 2); ESI-MS: 493/495 [M+H]$^+$ (LC-MS 2).

Step 38.8: 2-bromo-4-((4-chlorophenyl)((1,5-dimethyl-6-oxo-1,6-dihydropyridin-3-yl)amino)methyl)-1-ethyl-1H-imidazole-5-carboxylic acid

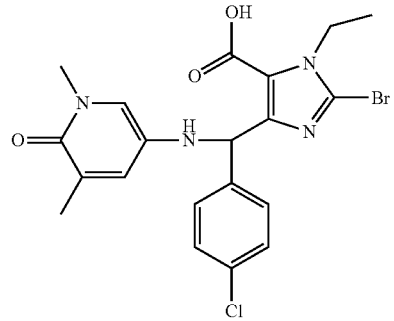 [SMILES: CCn1c(Br)nc(C(Nc2cc(C)c(=O)n(C)c2)c2ccc(Cl)cc2)c1C(=O)O]

The title compound was prepared in analogy to the procedure described in Step 34.8 using methyl 2-bromo-4-((4-chlorophenyl)((1,5-dimethyl-6-oxo-1,6-dihydropyridin-3-yl)amino)methyl)-1-ethyl-1H-imidazole-5-carboxylate (Step 38.7) to afford a brown foam. $t_R$: 0.88 min (LC-MS 2); ESI-MS: 479/481 [M+H]$^+$; ESI-MS: 477.0/479.1 [M−H]$^-$ (LC-MS 2).

Step 38.9: 2-bromo-6-(4-chlorophenyl)-5-(1,5-dimethyl-6-oxo-1,6-dihydropyridin-3-yl)-3-ethyl-5,6-dihydropyrrolo[3,4-d]imidazol-4(3H)-one

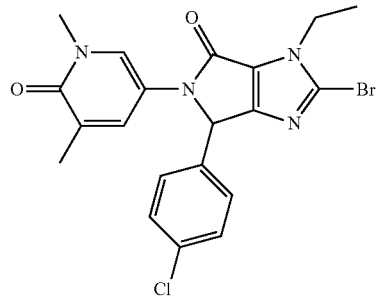 [SMILES: CCn1c(Br)nc2c1C(=O)N(c1cc(C)c(=O)n(C)c1)C2c1ccc(Cl)cc1]

The title product was prepared in analogy to the procedure described in Step 1.11 using 2-bromo-4-((4-chlorophenyl)((1,5-dimethyl-6-oxo-1,6-dihydropyridin-3-yl)amino)methyl)-1-ethyl-1H-imidazole-5-carboxylic acid (Step 38.8). The crude product was purified by silica gel column chromatography (hexane/EtOAc/MeOH 75:25:2 to 0:100:10) to afford a beige foam. $t_R$: 0.99 min (LC-MS 2); ESI-MS: 461/463 [M+H]$^+$ (LC-MS 2); TLC (EtOAc) $R_f$=0.08.

EXAMPLE 39

(R)-6-(4-chlorophenyl)-5-(1,5-dimethyl-6-oxo-1,6-dihydropyridin-3-yl)-3-ethyl-2-(6-methoxypyridin-3-yl)-5,6-dihydropyrrolo[3,4-d]imidazol-4(3H)-one

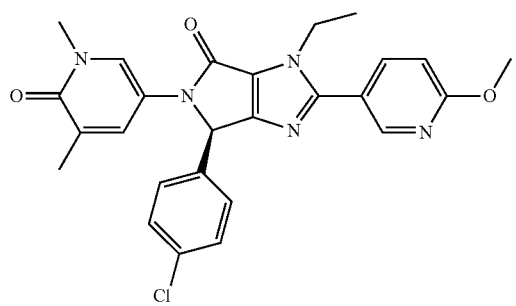 [SMILES: CCn1c(-c2ccc(OC)nc2)nc2c1C(=O)N(c1cc(C)c(=O)n(C)c1)[C@@H]2c1ccc(Cl)cc1]

The title compound (131 mg, 0.265 mmol, 46% yield) was obtained enantiomerically pure (98% ee) after chiral preparative chromatography (Chiralpak AD-H, 250×30 mm; mobile phase: scCO$_2$/EtOH 60:40 isocratic; flow rate: 120 mL/min; detection 290 nm) of the racemic mixture of 6-((4-chlorophenyl)-5-(1,5-dimethyl-6-oxo-1,6-dihydropyridin-3-yl)-3-ethyl-2-(6-methoxypyridin-3-yl)-5,6-dihydropyrrolo[3,4-d]imidazol-4(3H)-one (Example 38) (280 mg, 0.571 mmol). The second enantiomer, (S)-6-((4-chlorophenyl)-5-(1,5-dimethyl-6-oxo-1,6-dihydropyridin-3-yl)-3-ethyl-2-(6-methoxypyridin-3-yl)-5,6-dihydropyrrolo[3,4-d]imidazol-4(3H)-one (128 mg, 0.259 mmol, 45% yield), was obtained enantiomerically pure (>99.5% ee) via the same separation.

EXAMPLE 40

6-(4-chlorophenyl)-5-(1,5-dimethyl-6-oxo-1,6-dihydropyridin-3-yl)-3-ethyl-2-(2-methoxypyridin-3-yl)-5,6-dihydropyrrolo[3,4-d]imidazol-4(3H)-one

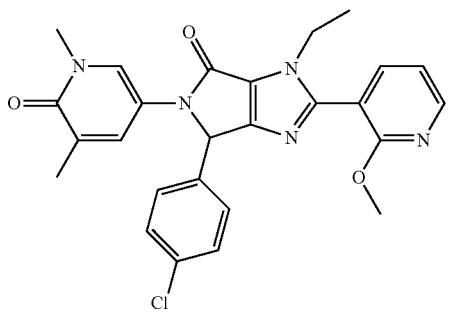 [SMILES: CCn1c(-c2cccnc2OC)nc2c1C(=O)N(c1cc(C)c(=O)n(C)c1)C2c1ccc(Cl)cc1]

The title compound was prepared in analogy to the procedure described for Example 1 using 2-bromo-6-((4-chlorophenyl)-5-(1,5-dimethyl-6-oxo-1,6-dihydropyridin-3-yl)-3-ethyl-5,6-dihydropyrrolo[3,4-d]imidazol-4(3H)-one (Step 38.9) and (2-methoxypyridin-3-yl)boronic acid at 100° C. for 2 hr. The crude product was purified by silica gel column chromatography (hexane/(EtOAc/MeOH 9:1) 20-100% (EtOAc/MeOH 9:1)) to afford a yellow foam. $t_R$: 0.93 min (LC-MS 2); ESI-MS: 490/492 [M+H]$^+$ (LC-MS 2); TLC (EtOAc/MeOH 9:1) R$_f$=0.24; $^1$H NMR (400 MHz, DMSO-d$_6$) δ ppm 1.46 (t, J=7.2 Hz, 3 H) 1.96 (s, 3 H) 3.39 (s, 3 H) 3.87-3.98 (m, 5 H) 6.16 (s, 1 H) 7.16 (dd, J=7.3, 5.0 Hz, 1 H) 7.31 (d, J=8.8 Hz, 2 H) 7.41 (d, J=8.8 Hz, 2 H) 7.47 (d, J=1.6 Hz, 1 H) 7.77 (d, J=2.7 Hz, 1 H) 7.86 (dd, J=7.4, 1.9 Hz, 1 H) 8.37 (dd, J=5.0, 1.9 Hz, 1 H).

EXAMPLE 41

(R)-6-(4-chlorophenyl)-5-(1,5-dimethyl-6-oxo-1,6-dihydropyridin-3-yl)-3-ethyl-2-(2-methoxypyridin-3-yl)-5,6-dihydropyrrolo[3,4-d]imidazol-4(3H)-one

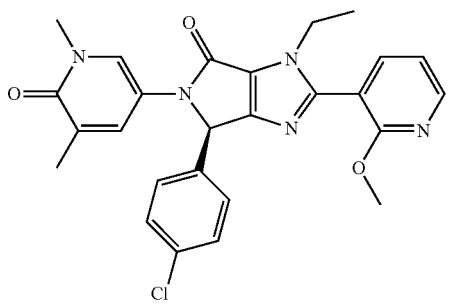 [SMILES: CCn1c(-c2cccnc2OC)nc2c1C(=O)N(c1cc(C)c(=O)n(C)c1)[C@@H]2c1ccc(Cl)cc1]

The title compound (145 mg, 0.293 mmol, 46% yield) was obtained enantomerically pure (>99% ee) after chiral preparative chromatography (Chiralpak IC 20 μm, 7.65× 37.5 cm; mobile phase: MeOH/EtOH 25:75 isocratic; flow rate: 80 mL/min; detection 220 nm and 254 nm) of the racemic mixture of 6-((4-chlorophenyl)-5-(1,5-dimethyl-6-oxo-1,6-dihydropyridin-3-yl)-3-ethyl-2-(2-methoxypyridin-3-yl)-5,6-dihydropyrrolo[3,4-d]imidazol-4(3H)-one (Example 40) (280 mg, 0.571 mmol). The second enantiomer (S)-6-((4-chlorophenyl)-5-(1,5-dimethyl-6-oxo-1,6-dihydropyridin-3-yl)-3-ethyl-2-(2-methoxypyridin-3-yl)-5,6-dihydropyrrolo[3,4-d]imidazol-4(3H)-one (160 mg, 0.323 mmol, 49% yield) was obtained enantiomerically pure (>99% ee) via the same separation.

EXAMPLE 42

6-(4-chlorophenyl)-5-(1,5-dimethyl-6-oxo-1,6-dihydropyridin-3-yl)-3-ethyl-2-(1-methyl-1H-pyrazol-5-yl)-5,6-dihydropyrrolo[3,4-d]imidazol-4(3H)-one

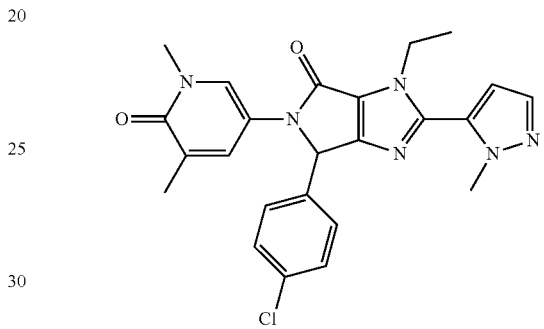

The title compound was prepared in analogy to the procedure described for Example 1 using 2-bromo-6-((4-chlorophenyl)-5-(1,5-dimethyl-6-oxo-1,6-di hydropyridin-3-yl)-3-ethyl-5,6-dihydropyrrolo[3,4-d]imidazol-4(3H)-one (Step 38.9) and (1-methyl-1H-pyrazol-5-yl)boronic acid at 100° C. for 2 hr. The crude product was first purified by silica gel column chromatography (hexane/(CH$_2$Cl$_2$/MeOH 19:1) 50-100% (CH$_2$Cl$_2$/MeOH 19:1)) followed by preparative achiral SFC (column Silica, gradient 20-25% over 6 min_total 11 min) to afford a yellow foam. $t_R$: 0.85 min (LC-MS 2); ESI-MS: 463/465 [M+H]$^+$ (LC-MS 2); TLC (CH$_2$Cl$_2$/MeOH 19:1) R$_f$=0.33; $^1$H NMR (400 MHz, DMSO-d$_6$) δ ppm 1.49 (t, J=7.2 Hz, 3 H) 1.96 (s, 3 H) 3.39 (s, 3 H) 3.90 (s, 3 H) 4.16-4.26 (m, 2 H) 6.20 (s, 1 H) 6.73 (d, J=2.1 Hz, 1H) 7.30 (d, J=8.4 Hz, 2 H) 7.41 (d, J=8.4 Hz, 2 H) 7.44 (m, 1 H) 7.63 (d, J=2.0 Hz, 1 H) 7.75 (d, J=2.7 Hz, 1 H).

EXAMPLE 43

6-(4-chlorophenyl)-1-cyclopropyl-5-(1,5-dimethyl-6-oxo-1,6-dihydropyridin-3-yl)-2-(thiazol-2-yl)-5,6-dihydropyrrolo[3,4-d]imidazol-4(1H)-one

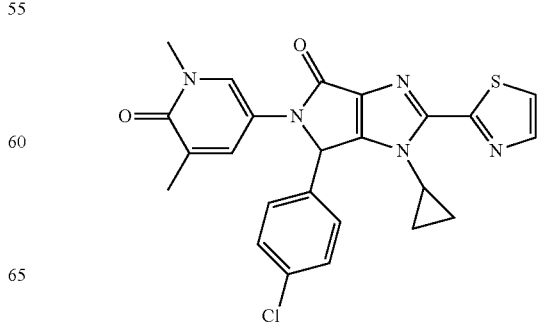

The title compound was prepared in analogy to the procedure described for Example 15 using 2-bromo-6-((4-chlorophenyl)-1-cyclopropyl-5-(1,5-dimethyl-6-oxo-1,6-dihydropyridin-3-yl)-5,6-dihydropyrrolo[3,4-d]imidazol-4(1H)-one (Step 43.6) and 2-tributylstannyl-thiazole. The crude product was first purified by silica gel column chromatography (CH$_2$Cl$_2$/MeOH 0-10% MeOH) followed by preparative achiral SFC (column PPU, gradient 20-25% over 6 min_total 11 min) to afford a white solid. t$_R$: 0.95 min (LC-MS 2); ESI-MS: 478 [M+H]$^+$ (LC-MS 2).

Step 43.1: ethyl 1-cyclopropyl-1H-imidazole-4-carboxylate

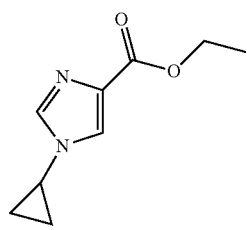

A MW vial was charged with cyclopropylamine (3.80 mL, 53.5 mmol) and (Z)-ethyl 3-(dimethylamino)-2-isocyanoacrylate (Step 1.5) (3 g, 17.84 mmol) in n-BuOH (8 mL). The MW vial was sealed and the resulting mixture was heated up and stirred overnight at 100° C. The reaction mixture was diluted with saturated aq. NaHCO$_3$ solution and EtOAc. The aq. layer was separated off and extracted with EtOAc. Combined extracts were dried over Na$_2$SO$_4$, filtered and concentrated under reduced pressure. The crude product was purified by silica gel column chromatography (heptane/EtOAc 20-100% EtOAc) to afford the title product (2.24 g, 68% yield) as orange oil. t$_R$: 0.63 min (LC-MS 2); ESI-MS: 181 [M+H]$^+$ (LC-MS 2); TLC (EtOAc) R$_f$=0.18.

Step 43.2: ethyl 2-bromo-1-cyclopropyl-1H-imidazole-4-carboxylate

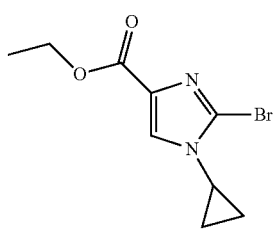

The title compound was prepared in analogy to the procedure described in Step 1.7 using ethyl 1-cyclopropyl-1H-imidazole-4-carboxylate (Step 43.1). The crude product was purified by silica gel chromatography (hexane/EtOAc 5-50% EtOAc) to afford a light yellow sticky oil. t$_R$: 0.82 min (LC-MS 2); ESI-MS: 259/261 [M+H]$^+$ (LC-MS 2); TLC (hexane/EtOAc 1:1) R$_f$=0.40.

Step 43.3: ethyl 2-bromo-5((4-chlorophenyl)(hydroxy)methyl)-1-cyclopropyl-1H-imidazole-4-carboxylate

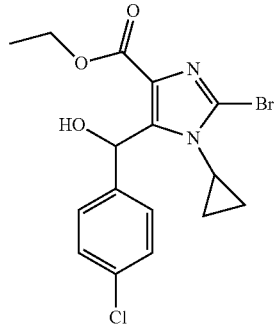 [SMILES: CCOC(=O)c1nc(Br)n(C2CC2)c1C(O)c1ccc(Cl)cc1]

The title compound was prepared in analogy to the procedure described in Step 9.6 using ethyl 2-bromo-1-cyclopropyl-1H-imidazole-4-carboxylate (Step 43.2) and 4-chlorobenzaldehyde. The crude product was purified by silica gel column chromatography (hexane/EtOAc 5-60% EtOAc) and crystallized in TBME to afford white crystals. t$_R$: 1.14 min (LC-MS 2); ESI-MS: 399/401 [M+H]$^+$ (LC-MS 2); TLC (hexane/EtOAc 1:1) R$_f$=0.41.

Step 43.4: ethyl 2-bromo-5 ((4-chlorophenyl)((1,5-dimethyl-6-oxo-1,6-dihydropyridin-3-yl)amino)methyl)-1-cyclopropyl-1H-imidazole-4-carboxylate

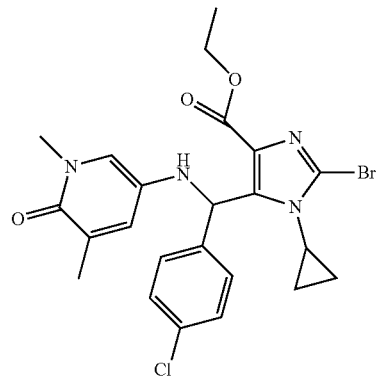 [SMILES: CCOC(=O)c1nc(Br)n(C2CC2)c1C(Nc1cc(C)c(=O)n(C)c1)c1ccc(Cl)cc1]

The title compound was prepared in analogy to the procedure described in Step 1.9 using ethyl 2-bromo-5-((4-chlorophenyl)(hydroxy)methyl)-1-cyclopropyl-1H-imidazole-4-carboxylate (Step 43.3) and 5-amino-1,3-dimethylpyridin-2(1H)-one (Step 4.3). t$_R$: 1.09 min (LC-MS 2); ESI-MS: 519/521 [M+H]$^+$ (LC-MS 2).

Step 43.5: 2-bromo-5 ((4-chlorophenyl)((1,5-dimethyl-6-oxo-1,6-dihydropyridin-3-yl)amino)methyl)-1-cyclopropyl-1H-imidazole-4-carboxylic acid

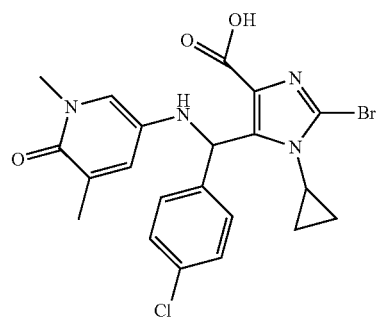 [SMILES: Cc1cc(NC(c2ccc(Cl)cc2)c2c(C(=O)O)nc(Br)n2C2CC2)cn(C)c1=O]

The title compound was prepared in analogy to the procedure described in Step 1.10 using ethyl 2-bromo-5-((4-chlorophenyl)((1,5-dimethyl-6-oxo-1,6-dihydropyridin-3-yl)amino)methyl)-1-cyclopropyl-1H-imidazole-4-carboxylate (Step 43.4). $t_R$: 0.85 min (LC-MS 2); ESI-MS: 491/493 [M+H]$^+$; ESI-MS: 489/491 [M−H]$^-$ (LC-MS 2).

Step 43.6: 2-bromo-6-(4-chlorophenyl)-1-cyclopropyl-5-(1,5-dimethyl-6-oxo-1,6-dihydropyridin-3-yl)-5,6-dihydropyrrolo[3,4-d]imidazol-4(1H)-one

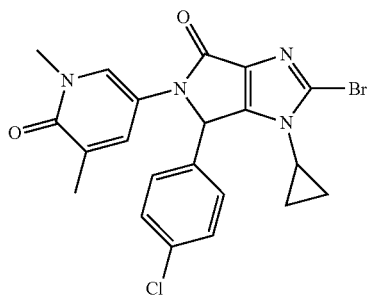 [SMILES: Cc1cc(N2C(=O)c3nc(Br)n(C4CC4)c3C2c2ccc(Cl)cc2)cn(C)c1=O]

The title product was prepared in analogy to the procedure described in Step 1.11 using 2-bromo-5-((4-chlorophenyl)((1,5-dimethyl-6-oxo-1,6-dihydropyridin-3-yl)amino)methyl)-1-cyclopropyl-1H-imidazole-4-carboxylic acid (Step 43.5) at 0-5° C. for 1 hr. The crude product was purified by silica gel column chromatography (EtOAc/EtOH 0-20% EtOH) and crystallized in TBME to afford beige crystals. $t_R$: 0.93 min (LC-MS 2); ESI-MS: 473/475 [M+H]$^+$; ESI-MS: 471/473 [M−H]$^-$ (LC-MS 2); TLC (EtOAc/EtOH 9:1) $R_f$=0.19.

EXAMPLE 44

6-(4-chlorophenyl)-5-(1,5-dimethyl-6-oxo-1,6-dihydropyridin-3-yl)-3-isopropyl-2-(2-methoxypyridin-3-yl)-5,6-dihydropyrrolo[3,4-d]imidazol-4(3H)-one

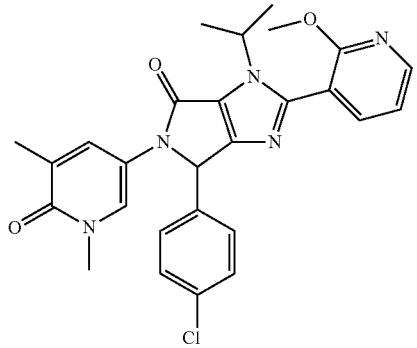 [SMILES: COc1ncccc1-c1nc2c(n1C(C)C)C(=O)N(c1cc(C)c(=O)n(C)c1)C2c1ccc(Cl)cc1]

The title compound was prepared in analogy to the procedure described for Example 2 6-(4-chlorophenyl)-5-(1,5-dimethyl-6-oxo-1,6-dihydropyridin-3-yl)-2-(2-methoxypyridin-3-yl)-5,6-dihydropyrrolo[3,4-d]imidazol-4(1H)-one (Step 44.1). The crude product was purified by preparative HPLC (gradient 35-55% CH$_3$CN in 16 min) followed by basic workup to afford a pale yellow solid. $t_R$: 1.00 min (LC-MS 2); ESI-MS: 504.3 [M+H]$^+$ (LC-MS 2).

Step 44.1: 6-(4-chlorophenyl)-5-(1,5-dimethyl-6-oxo-1,6-dihydropyridin-3-yl)-2-(2-methoxypyridin-3-yl)-5,6-dihydropyrrolo[3,4-d]imidazol-4(1H)-one

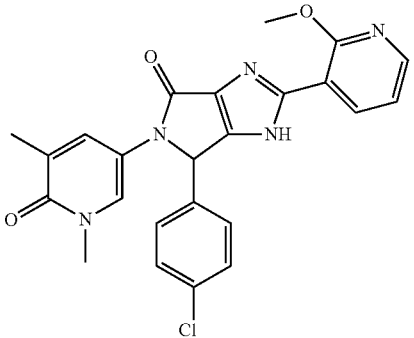 [SMILES: COc1ncccc1-c1nc2c([nH]1)C(c1ccc(Cl)cc1)N(c1cc(C)c(=O)n(C)c1)C2=O]

The title compound was prepared in analogy to the procedure described for Example 4 using 1-allyl-2-bromo-6-(4-chlorophenyl)-5-(1,5-dimethyl-6-oxo-1,6-dihydropyridin-3-yl)-5,6-dihydropyrrolo[3,4-d]imidazol-4(1H)-one (Step 4.6) and 2-methoxy-3-pyridinylboronic acid at 100° C. for 16 hr. After workup, the palladium was removed using a PL-thiol MP-resin and the resulting crude product was purified by silica gel column chromatography (EtOAc/MeOH 0-10% MeOH). $t_R$: 0.91 min (LC-MS 2); ESI-MS: 462.3 [M+H]$^+$; ESI-MS: 460.2 [M−H]$^-$ (LC-MS 2).

EXAMPLE 45

(R)-6-(4-chlorophenyl)-5-(1,5-dimethyl-6-oxo-1,6-dihydropyridin-3-yl)-3-isopropyl-2-(2-methoxypyridin-3-yl)-5,6-dihydropyrrolo[3,4-d]imidazol-4(3H)-one

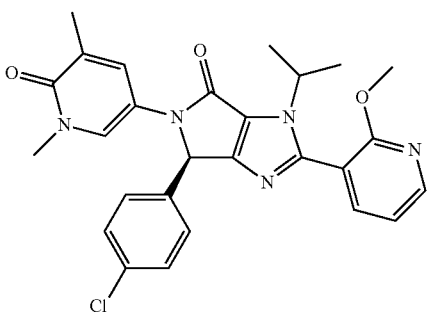 [SMILES: COc1ncccc1-c1nc2c(n1C(C)C)C(=O)N(c1cc(C)c(=O)n(C)c1)[C@@H]2c1ccc(Cl)cc1]

The title compound (7 mg, 0.013 mmol, 20.2% yield) was obtained enantiomerically pure (ee=87.8%) after chiral preparative chromatography (System: Thar Technologies Prep SFC200; column: Chiralpak AD-H, 250×50 mm; mobile phase: scCO$_2$/iPrOH/IPAm 50:50:0.5 isocratic; flow rate: 100 mL/min; detection 300 nm) of the racemic mixture of 6-((4-chlorophenyl)-5-(1,5-dimethyl-6-oxo-1,6-dihydropyridin-3-yl)-3-isopropyl-2-(2-methoxypyridin-3-yl)-5,6-dihydropyrrolo[3,4-d]imidazol-4(3H)-one (Example 44) (33 mg, 0.065 mmol). The second enantiomer (S)-6-((4-chlorophenyl)-5-(1,5-dimethyl-6-oxo-1,6-dihydropyridin-3-yl)-3-isopropyl-2-(2-methoxypyridin-3-yl)-5,6-dihydropyrrolo[3, 4-d]imidazol-4(3H)-one (10 mg, 0.019 mmol, 28.8% yield) was obtained enantiomerically pure (ee=95%) via the same separation.

EXAMPLE 46

6-(4-chlorophenyl)-2-cyclopropyl-5-(1,5-dimethyl-6-oxo-1,6-dihydropyridin-3-yl)-5,6-dihydropyrrolo[3,4-d]imidazol-4(3H)-one

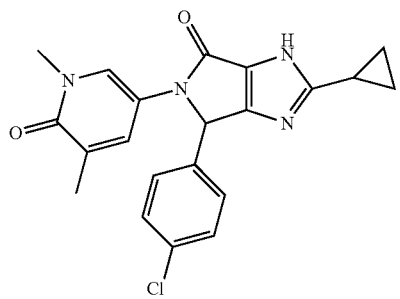 [SMILES: Cc1cc(N2C(=O)c3[nH]c(C4CC4)nc3C2c2ccc(Cl)cc2)cn(C)c1=O]

The title compound was prepared in analogy to the procedure described in Step 18.7 using 6-(4-chlorophenyl)-2-cyclopropyl-5-(1,5-dimethyl-6-oxo-1,6-dihydropyridin-3-yl)-3-(4-methoxybenzyl)-5,6-dihydropyrrolo[3,4-d]imidazol-4(3H)-one (Step 46.8). The crude product was purified by silica gel chromatography (EtOAc/MeOH 0.10% MeOH) to afford a yellowish solid. $t_R$: 0.76 min (LC-MS 2); ESI-MS: 395 [M+H]$^+$; ESI-MS: 393 [M−H]$^−$ (LC-MS 2).

Step 46.1: dibutyl 2-bromo-1-(4-methoxybenzyl)-1H-imidazole-4,5-dicarboxylate

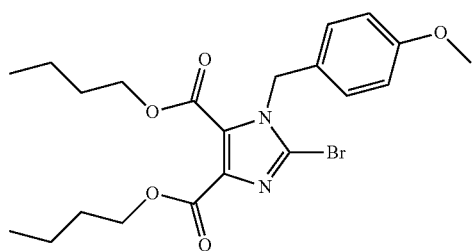 [SMILES: CCCCOC(=O)c1nc(Br)n(Cc2ccc(OC)cc2)c1C(=O)OCCCC]

The title compound was prepared in analogy to the procedure described in Step 38.2 using dibutyl 2-bromo-1H-imidazole-4,5-dicarboxylate (Step 36.2) at 50° C. for 8 hr. $t_R$: 1.37 min (LC-MS 2); ESI-MS: 467.2/469.2 [M+H]$^+$ (LC-MS 2).

Step 46.2: butyl-2-bromo-4-formyl-1-((4-methoxybenzyl)-1H-imidazole-5-carboxylate

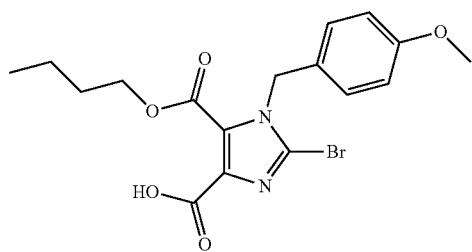 [SMILES: CCCCOC(=O)c1c(C(=O)O)nc(Br)n1Cc1ccc(OC)cc1]

The title compound was prepared in analogy to the procedure described in Step 38.3 using dibutyl 2-bromo-1-((4-methoxybenzyl)-1H-imidazole-4,5-dicarboxylate (Step 46.1). The crude product was purified by silica gel column chromatography (hexane/EtOAc 0-35% EtOAc) to afford a yellow oil. $t_R$: 1.16 min (LC-MS 2); ESI-MS: 395.2/397.1 [M+H]$^+$ (LC-MS 2).

Step 46.3: butyl-2-bromo-44(4-chlorophenyl)(hydroxy)methyl)-1-((4-methoxybenzyl)-1H-imidazole-5-carboxylate

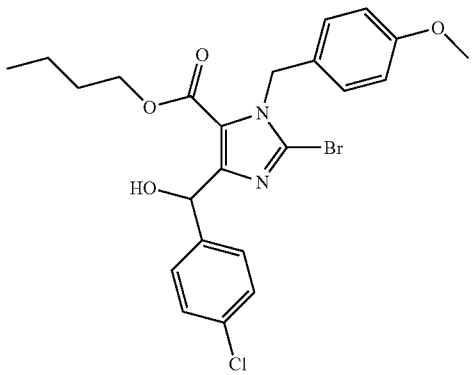 [SMILES: CCCCOC(=O)c1c(C(O)c2ccc(Cl)cc2)nc(Br)n1Cc1ccc(OC)cc1]

The title compound was prepared in analogy to the procedure described in Step 36.5 using butyl 2-bromo-4-formyl-1-(4-methoxybenzyl)-1H-imidazole-5-carboxylate (Step 46.2). The crude product was purified by silica gel chromatography (hexane/EtOAc 0-30% EtOAc) to afford a yellow oil. $t_R$: 1.34 min (LC-MS 2); ESI-MS: 507.2/509.2 [M+H]$^+$ (LC-MS 2).

Step 46.4: butyl-2-bromo-4-((4-chlorophenyl)((1,5-dimethyl-6-oxo-1,6-dihydropyridin-3-yl)amino)methyl)-1-((4-methoxybenzyl)-1H-imidazole-5-carboxylate

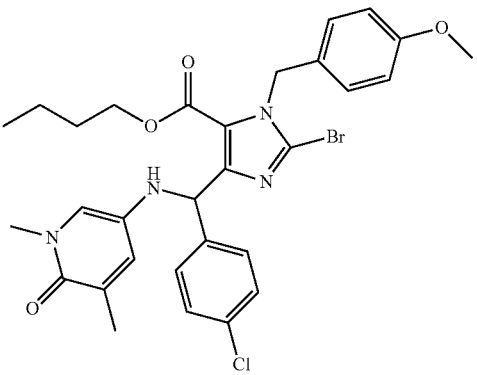 [SMILES: CCCCOC(=O)c1c(C(Nc2cc(C)c(=O)n(C)c2)c2ccc(Cl)cc2)nc(Br)n1Cc1ccc(OC)cc1]

The title compound was prepared in analogy to the procedure described in Step 1.9 using butyl 2-bromo-4-((4-chlorophenyl)(hydroxy)methyl)-1-((4-methoxybenzyl)-1H-imidazole-5-carboxylate (Step 46.3) and 5-amino-1,3-dimethylpyridin-2(1H)-one (Step 4.3). The crude product was purified by silica gel column chromatography (hexane/EtOAc 40-100% EtOAc, EtOAc/MeOH 0-10% MeOH) to afford a brownish foam. $t_R$: 1.32 min (LC-MS 2); ESI-MS: 627.3/629.2 [M+H]$^+$ (LC-MS 2).

Step 46.5: 2-bromo-4-((4-chlorophenyl)((1,5-dimethyl-6-oxo-1,6-dihydropyridin-3-yl)amino)methyl)-1-((4-methoxybenzyl)-1H-imidazole-5-carboxylic acid

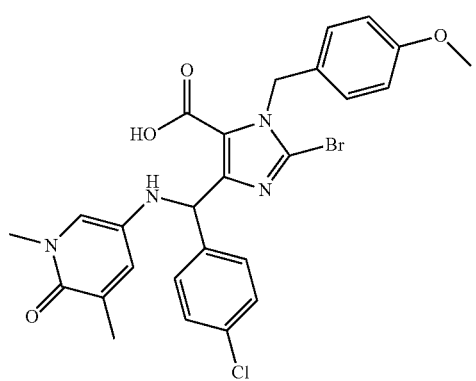

The title compound was prepared in analogy to the procedure described in Step 1.10 using butyl 2-bromo-4-((4-chlorophenyl)((1,5-dimethyl-6-oxo-1,6-dihydropyridin-3-yl)amino)methyl)-1-((4-methoxybenzyl)-1H-imidazole-5-carboxylate (Step 46.4). $t_R$: 0.99 min (LC-MS 2); ESI-MS: 571.2/573.1 [M+H]$^+$; ESI-MS: 569.1/571.0 [M–H]$^-$ (LC-MS 2).

Step 46.7: 2-bromo-6-((4-chlorophenyl)-5-(1,5-dimethyl-6-oxo-1,6-dihydropyridin-3-yl)-3-(4-methoxybenzyl)-5,6-dihydropyrrolo[3,4-d]imidazol-4(3H)-one

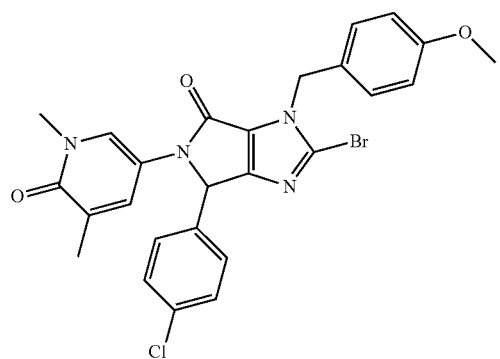 [SMILES: COc1ccc(Cn2c(Br)nc3c2C(=O)N(c2cc(C)c(=O)n(C)c2)C3c2ccc(Cl)cc2)cc1]

The title compound was prepared in analogy to the procedure described in Step 1.11 using 2-bromo-4-((4-chlorophenyl)((1,5-dimethyl-6-oxo-1,6-dihydropyridin-3-yl)amino)methyl)-1-(4-methoxybenzyl)-1H-imidazole-5-carboxylic acid (Step 46.5). $t_R$: 1.08 min (LC-MS 2); ESI-MS: 553.1/555.2 [M+H]$^+$; ESI-MS: 551.1/553.1 [M–H]$^-$ (LC-MS 2).

Step 46.8: 6-(4-chlorophenyl)-2-cyclopropyl-5-(1,5-dimethyl-6-oxo-1,6-dihydropyridin-3-yl)-3-(4-methoxybenzyl)-5,6-dihydropyrrolo[3,4-d]imidazol-4(3H)-one

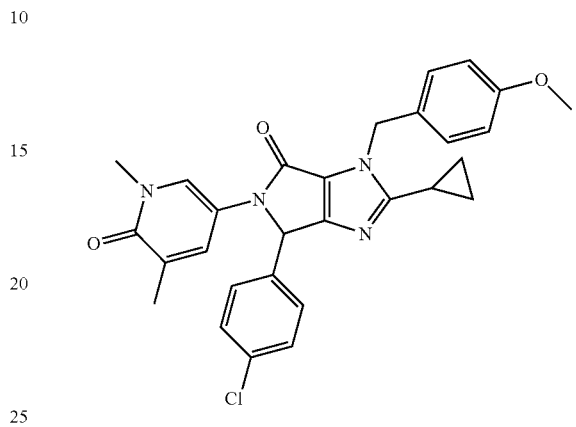

To a suspension of 2-bromo-6-(4-chlorophenyl)-5-(1,5-dimethyl-6-oxo-1,6-dihydropyridin-3-yl)-3-((4-methoxybenzyl)-5,6-dihydropyrrolo[3,4-d]imidazol-4(3H)-one (Step 46.7) (350 mg, 0.63 mmol) in toluene (5.6 mL) and water (0.63 mL) under Ar were added potassium cyclopropyltrifluoroborate (187 mg, 1.26 mmol), di(1-adamantyl)-n-butylphosphine (34 mg, 0.095 mmol), Pd(OAc)$_2$ (14.19 mg, 0.063 mmol) and Cs$_2$CO$_3$ (618 mg, 1.896 mmol). The reaction mixture was flushed with Ar, heated up and stirred at 110° C. for 16 hr. The reaction was diluted with water and EtOAc and both phases were separated. The aq. layer was extracted twice with EtOAc. Combined extracts were dried over Na$_2$SO$_4$, filtered and concentrated under reduced pressure. The crude product was purified by silica gel column chromatography (EtOAc/MeOH 0-10% MeOH) to afford the title product (203 mg, 0.37 mmol, 59.3% yield) as yellowish resin. $t_R$: 1.04 min (LC-MS 2); ESI-MS: 515/517 [M+H]$^+$; ESI-MS: 513/515 [M–H]$^-$ (LC-MS 2).

EXAMPLE 47

R-6-(4-chlorophenyl)-2-cyclopropyl-5-(1,5-dimethyl-6-oxo-1,6-dihydropyridin-3-yl)-5,6-dihydropyrrolo[3,4-d]imidazol-4(3H)-one

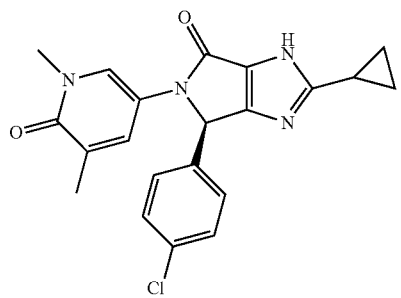 [SMILES: Cc1cc(N2C(=O)c3[nH]c(C4CC4)nc3[C@H]2c2ccc(Cl)cc2)cn(C)c1=O]

The title compound (16 mg, 0.040 mmol, 29.3% yield) was obtained enantiomerically pure (ee=98.8%) after chiral preparative chromatography (System: Sepiatec Prep SFC 100; column: Chiralpak IC, 250×30 mm; mobile phase: scCO$_2$/MeOH 75:25 isocratic; flow rate: 130 mL/min; detection 270 nm). t$_R$: 0.76 min (LC-MS 2); ESI-MS: 395 [M+H]$^+$; ESI-MS: 393 [M−H]$^−$ (LC-MS 2). of the racemic mixture of 6-(4-chlorophenyl)-2-cyclopropyl-5-(1,5-dimethyl-6-oxo-1,6-dihydropyridin-3-yl)-5,6-dihydropyrrolo[3,4-d]imidazol-4(3H)-one (Example 46) (54 mg, 0.137 mmol). The second enantiomer (S)-6-((4-chlorophenyl)-2-cyclopropyl-5-(1,5-dimethyl-6-oxo-1,6-dihydropyridin-3-yl)-5,6-dihydropyrrolo[3,4-d]imidazol-4(3H)-one (18 mg) was obtained enantiomerically pure (ee>=99.0%) via the same separation.

EXAMPLE 48

(R)-6-(4-chlorophenyl)-2-(2,5-dihydrofuran-3-yl)-5-(3,8-dimethyl-[1,2,4]triazolo[4,3-a]pyridin-6-yl)-1-isopropyl-5,6-dihydropyrrolo[3,4-d]imidazol-4(1H)-one

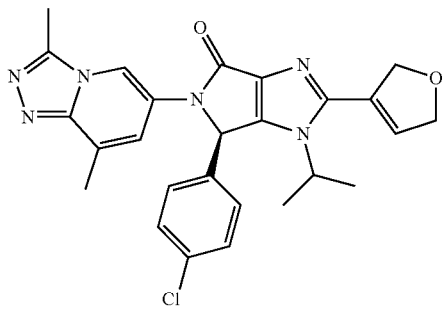 [SMILES: Cc1cc(N2C(=O)c3nc(C4=CCOC4)n(C(C)C)c3[C@H]2c2ccc(Cl)cc2)cn2c(C)nnc12]

The title compound (29 mg, 0.059 mmol, 43% yield) was obtained enantiomerically pure (99.5% ee) after chiral preparative chromatography (Chiralpak IA 5 µm, 250×20 mm; mobile phase: heptane/CH$_2$Cl$_2$/MeOH 65:25:10 isocratic; flow rate: 10 mL/min; detection 245 nm) of the racemic mixture of 6-((4-chlorophenyl)-2-(2,5-dihydrofuran-3-yl)-5-(3,8-di methyl-[1,2,4]triazolo[4,3-a]pyridin-6-yl)-1-isopropyl-5,6-dihydropyrrolo[3,4-d]imidazol-4(1H)-one (Example 11) (68 mg, 0.139 mmol). The second enantiomer (S)-6-((4-chlorophenyl)-2-(2,5-di hydrofuran-3-yl)-5-(3,8-dimethyl-[1,2,4]triazolo[4,3-a]pyridin-6-yl)-1-isopropyl-5,6-dihydropyrrolo[3,4-d]imidazol-4(1H)-one (30 mg, 0.060 mmol, 43% yield) was obtained enantiomerically pure (>99.5% ee) via the same separation (as 1$^{st}$ eluting component).

EXAMPLE 49

6-(4-Chlorophenyl)-5-(3,8-dimethyl-[1,2,4]triazolo[4,3-a]pyridin-6-yl)-1-isopropyl-2-(1,2,3,6-tetrahydropyridin-4-yl)-5,6-dihydropyrrolo[3,4-d]imidazol-4(1H)-one

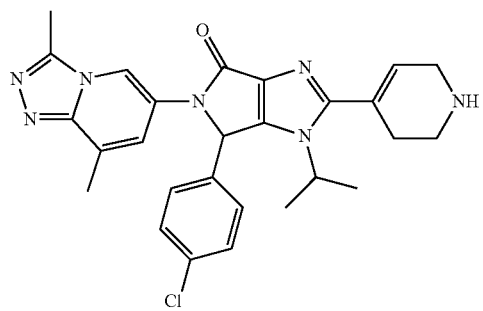 [SMILES: Cc1cc(N2C(=O)c3nc(C4=CCNCC4)n(C(C)C)c3C2c2ccc(Cl)cc2)cn2c(C)nnc12]

An ice-cooled solution of tert-butyl 4-{6-((4-chlorophenyl)-5-(3,8-dimethyl-[1,2,4]triazolo[4,3-a]pyridin-6-yl)-1-isopropyl-4-oxo-1,4,5,6-tetrahydropyrrolo[3,4-d]imidazol-2-yl}-5,6-dihydropyridine-1(2H)-carboxylate (30 mg; 0.050 mmol) (Step 49.1) in CH$_2$Cl$_2$ (1 mL) was treated with TFA (0.15 mL). After 1½ h the reaction mixture was poured into a sat. solution of NaHCO$_3$ and extracted with 3 portions of CH$_2$Cl$_2$. The extracts were washed with brine, dried (Na$_2$SO$_4$), filtered and concentrated under reduced pressure to give the title compound. t$_R$: 0.61 min (LC-MS 2); ESI-MS: 502/504 [M+H]$^+$ (LC-MS 2). $^1$H NMR (400 MHz, DMSO-d$_6$) δ ppm 0.62 (d, J=6.8 Hz, 3 H) 1.46 (d, J=6.8 Hz, 3 H) 2.27 (m, 1 H) 2.43 (s, 3 H) 2.5 (m, 1 H) 2.64 (s, 3 H) 2.94 (m, 2 H) 3.40 (m, 2 H) 4.60 (m, 1 H) 6.03 (m, 1 H) 6.69 (s, 1H) 7.40 (m, 5H) 8.39 (s, 1 H).

Step 49.1: tert-Butyl 4-{6-(4-chlorophenyl)-5-(3,8-dimethyl-[1,2,4]triazolo[4,3-a]pyridin-6-yl)-1-isopropyl-4-oxo-1,4,5,6-tetrahydropyrrolo[3,4-d]imidazol-2-yl}-5,6-dihydropyridine-1(2H)-carboxylate

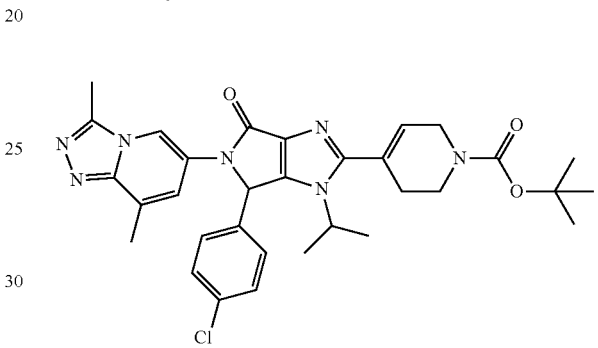

The title compound was prepared using an analogous procedure to that described in Example 1 using 2-bromo-6-(4-chlorophenyl)-5-(3,8-dimethyl-[1,2,4]triazolo[4,3-a]pyridin-6-yl)-1-isopropyl-5,6-dihydropyrrolo[3,4-d]imidazol-4(1H)-one (Step 9.9) and tert-butyl 4-(4,4,5,5-tetramethyl-1,3,2-dioxaborolan-2-yl)-5,6-dihydropyridine-1(2H)-carboxylate at 90° C. for 9½ hr. The crude product was purified by silica gel column chromatography (CH$_2$Cl$_2$/MeOH 0-15% MeOH). t$_R$: 1.07 min (LC-MS 2); ESI-MS: 602/604 [M+H]$^+$ (LC-MS 2); TLC (CH$_2$Cl$_2$/MeOH 9:1) R$_f$=0.19.

EXAMPLE 50

6-(4-Chlorophenyl)-5-(3,8-dimethyl-[1,2,4]triazolo[4,3-a]pyridin-6-yl)-1-isopropyl-2-(1-methyl-1,2,3,6-tetrahydropyridin-4-yl)-5,6-dihydropyrrolo[3,4-d]imidazol-4(1H)-one

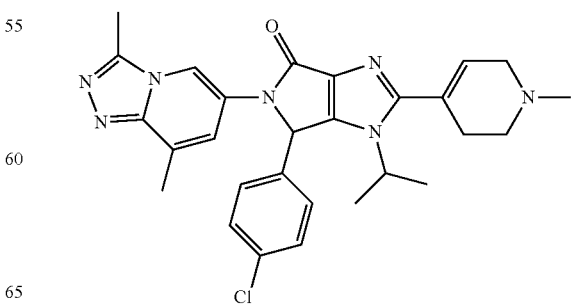

The title compound was prepared using an analogous procedure to that described in Example 1 using 2-bromo-6-(4-chlorophenyl)-5-(3,8-dimethyl-[1,2,4]triazolo[4,3-a]pyridin-6-yl)-1-isopropyl-5,6-dihydropyrrolo[3,4-d]imidazol-4(1H)-one (Step 9.9) and 1-methyl-4-(4,4,5,5-tetramethyl-1,3,2-dioxaborolan-2-yl)-1,2,3,6-tetrahydropyridine at 90° C. for 14 hr. The crude product was purified by preparative HPLC (gradient 5-100% CH$_3$CN in 20 min), followed by basic workup. t$_R$: 0.62 min (LC-MS 2); ESI-MS: 516/518 [M+H]$^+$ (LC-MS 2); $^1$H NMR (400 MHz, DMSO-d$_6$) δ ppm 0.62 (d, J=6.8 Hz, 3 H) 1.46 (d, J=6.8 Hz, 3 H) 2.30 (s, 3 H) 2.38 (m, 1 H) 2.45 (s, 3 H) 2.6 (m, 3 H) 2.65 (s, 3 H) 3.00 (m, 1 H) 3.09 (m, 1 H) 4.60 (m, 1 H) 6.00 (m, 1 H) 6.70 (s, 1H) 7.40 (m, 1H) 7.41 (m, 4H) 8.40 (s, 1 H).

EXAMPLE 51

6-(4-Chlorophenyl)-5-(3,8-dimethyl-[1,2,4]triazolo[4,3-a]pyridin-6-yl)-1-isopropyl-2-(2,2,6,6-tetramethyl-1,2,3,6-tetrahydropyridin-4-yl)-5,6-dihydropyrrolo[3,4-d]imidazol-4(1H)-one

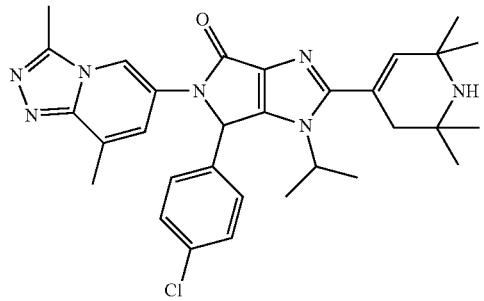 [SMILES: Cc1cc(N2C(=O)c3nc(C4=CC(C)(C)NC(C)(C)C4)n(C(C)C)c3C2c2ccc(Cl)cc2)cn2c(C)nnc12]

The title compound was prepared using an analogous procedure to that described in Example 1 using 2-bromo-6-((4-chlorophenyl)-5-(3,8-dimethyl-[1,2,4]triazolo[4,3-a]pyridin-6-yl)-1-isopropyl-5,6-dihydropyrrolo[3,4-d]imidazol-4(1H)-one (Step 9.9) and 2,2,6,6-tetramethyl-4-(4,4,5,5-tetramethyl-1,3,2-dioxaborolan-2-yl)-1,2,3,6-tetrahydropyridine at 90° C. for 22 hr. The crude product was purified by preparative HPLC (gradient 20-55% CH$_3$CN in 30 min), followed by basic workup. t$_R$: 0.68 min (LC-MS 2); ESI-MS: 558/560 [M+H]$^+$ (LC-MS 2); $^1$H NMR (400 MHz, DMSO-d$_6$) δ ppm 0.64 (d, J=6.8 Hz, 3 H) 1.14, 1.15 (2 s, 6 H) 1.20 (sb, 6 H) 1.47 (d, J=6.9 Hz, 3 H) 2.10 (d, J=16.5 Hz, 1 H) 2.27 (d, J=16.4 Hz, 1 H) 2.45 (s, 3 H) 2.66 (s, 3 H) 4.56 (m, 1 H) 5.95 (s, 1 H) 6.71 (s, 1H) 7.42 (m, 5H) 8.40 (s, 1 H).

EXAMPLE 52

6-(4-chlorophenyl)-1-isopropyl-5-(8-methoxy-3-methyl-[1,2,4]triazolo[4,3-a]pyridin-6-yl)-2-(6-methoxypyridin-3-yl)-5,6-dihydropyrrolo[3,4-d]imidazol-4(1H)-one

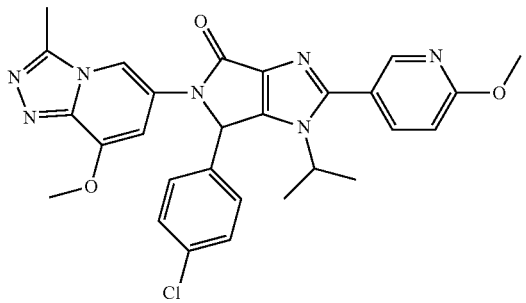 [SMILES: COc1ccc(-c2nc3c(n2C(C)C)C(c2ccc(Cl)cc2)N(c2cc(OC)c4nnc(C)n4c2)C3=O)cn1]

The compound was prepared in analogy to the procedure described for Example 1 using 2-bromo-6-(4-chlorophenyl)-1-isopropyl-5-(8-methoxy-3-methyl-[1,2,4]triazolo[4,3-a]pyridin-6-yl)-5,6-dihydropyrrolo[3,4-d]imidazol-4(1H)-one (Step 17.7) at 85° C. for 3 hr. The reaction mixture was concentrated in vacuo and the residue diluted with CH$_2$Cl$_2$ and water. The aq. layer was separated off and extracted with CH$_2$Cl$_2$. Combined extracts were dried over Na$_2$SO$_4$, filtered and concentrated under reduced pressure. Crystallization from MeOH gave the title compound. t$_R$: 0.94 min (LC-MS 2); ESI-MS: 544 [M+H]$^+$ (LC-MS 2).

EXAMPLE 53

6-(4-chlorophenyl)-2-(3,6-dihydro-2H-pyran-4-yl)-1-isopropyl-5-(8-methoxy-3-methyl-[1,2,4]triazolo[4,3-a]pyridin-6-yl)-5,6-dihydropyrrolo[3,4-d]imidazol-4(1H)-one

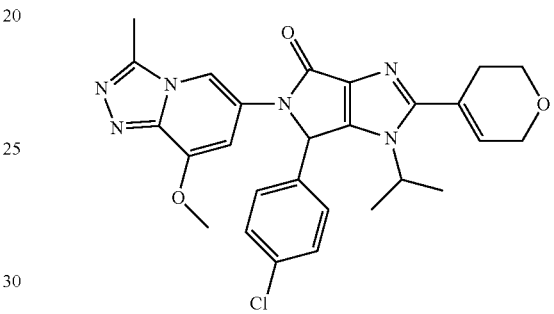

The title compound was prepared in analogy to the procedure described for Example 13 using 2-bromo-6-(4-chlorophenyl)-1-isopropyl-5-(8-methoxy-3-methyl-[1,2,4]triazolo[4,3-a]pyridin-6-yl)-5,6-dihydropyrrolo[3,4-d]imidazol-4(1H)-one (Step 17.7) and potassium 3,6-dihydro-2H-pyran-4-trifluoroborate under heating at 115° C. for 3 hr. The reaction mixture was concentrated in vacuo and the residue diluted with CH$_2$Cl$_2$ and water. The aq. layer was separated off and extracted with CH$_2$Cl$_2$. Combined extracts were dried over Na$_2$SO$_4$, filtered and concentrated under reduced pressure. The crude product was purified by preparative HPLC (gradient 5-100% CH$_3$CN in 20 min), followed by basic workup to afford the desired product as white solid. t$_R$: 0.86 min (LC-MS 2); ESI-MS: 519 [M+H]$^+$ (LC-MS 2).

EXAMPLE 54

6-(4-chlorophenyl)-2-(2,4-dimethoxypyrimidin-5-yl)-5-(8-methoxy-3-methyl-[1,2,4]triazolo[4,3-a]pyridin-6-yl)-1-methyl-5,6-dihydropyrrolo[3,4-d]imidazol-4(1H)-one

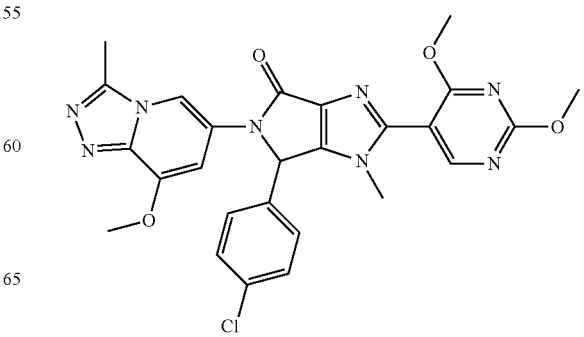

The compound was prepared in analogy to the procedure described for Example 1 using 2-bromo-6-(4-chlorophenyl)-1-methyl-5-(8-methoxy-3-methyl-[1,2,4]triazolo[4,3-a]pyridin-6-yl)-5,6-dihydropyrrolo[3,4-d]imidazol-4(1H)-one (Step 54.3) and 2,4-dimethoxypyrimidine-5-boronic acid at 85° C. for 2 hr. The reaction mixture was concentrated in vacuo and the residue diluted with CH$_2$Cl$_2$ and water. The aq. layer was separated off and extracted with CH$_2$Cl$_2$. Combined extracts were dried over Na$_2$SO$_4$, filtered and concentrated under reduced pressure. The crude product was purified by preparative achiral SFC (column Diol/grad 22-27%; 11 min). t$_R$: 0.82 min (LC-MS 2); ESI-MS: 547 [M+H]$^+$ (LC-MS 2).

Step 54.1: ethyl 2-bromo-5 ((4-chlorophenyl)((8-methoxy-3-methyl-[1,2,4]triazolo[4,3-a]pyridin-6-yl)amino)methyl)-1-methyl-1H-imidazole-4-carboxylate

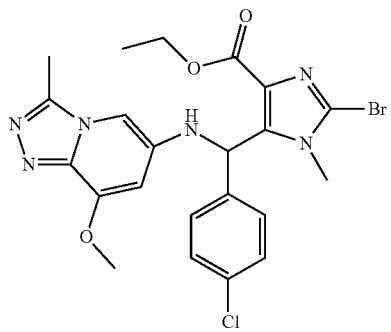 [SMILES: CCOC(=O)c1nc(Br)n(C)c1C(Nc1cc(OC)c2nnc(C)n2c1)c1ccc(Cl)cc1]

The title compound was prepared in analogy to the procedure described for Step 1.9 using ethyl 2-bromo-5-((4-chlorophenyl)(hydroxy)methyl)-1-methyl-1H-imidazole-4-carboxylate (Step 16.3) and 8-methoxy-3-methyl-[1,2,4]triazolo[4,3-a]pyridin-6-amine (Step 17.4). The crude product was purified by silica gel column chromatography (CH$_2$Cl$_2$/EtOH 1-80% EtOH) to afford the title compound. t$_R$: 0.97 min (LC-MS 2); ESI-MS: 533/535 [M+H]$^+$ (LC-MS 2).

Step 54.2: 2-bromo-5 ((4-chlorophenyl)((8-methoxy-3-methyl-[1,2,4]triazolo[4,3-a]pyridin-6-yl)amino)methyl)-1-methyl-1H-imidazole-4-carboxylic acid

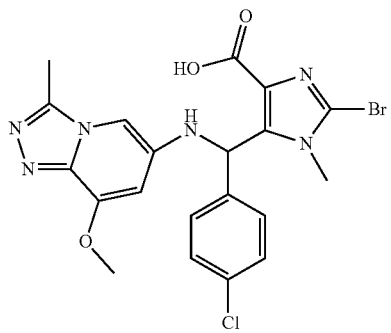 [SMILES: COc1cc(NC(c2ccc(Cl)cc2)c2c(C(=O)O)nc(Br)n2C)cn2c(C)nnc12]

The title compound was prepared in analogy to the procedure described in Step 1.10 using ethyl 2-bromo-5- ((4-chlorophenyl)((8-methoxy-3-methyl-[1,2,4]triazolo[4,3-a]pyridin-6-yl)amino)methyl)-1-methyl-1H-imidazole-4-carboxylate at 40° C. The reaction mixture was acidified with 4 N HCl and then concentrated. The residue was stirred in CH$_2$Cl$_2$/MeOH 5:1. The suspension was filtered and the filtrate concentrated. t$_R$: 0.81 min (LC-MS 2); ESI-MS: 505/507 [M+H]$^+$; ESI-MS: 504/505 [M–H]$^-$ (LC-MS 2).

Step 54.3: 2-bromo-6-(4-chlorophenyl)-5-(8-methoxy-3-methyl-[1,2,4]triazolo[4,3-a]pyridin-6-yl)-1-methyl-5,6-dihydropyrrolo[3,4-d]imidazol-4(1H)-one

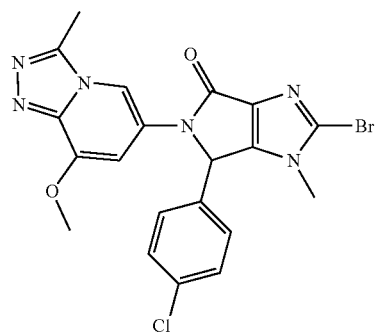 [SMILES: COc1cc(N2C(=O)c3nc(Br)n(C)c3C2c2ccc(Cl)cc2)cn2c(C)nnc12]

The title compound was prepared in analogy to the procedure described in Step 1.11 using 2-bromo-5-((4-chlorophenyl)((8-methoxy-3-methyl-[1,2,4]triazolo[4,3-a]pyridin-6-yl)amino)methyl)-1-methyl-1H-imidazole-4-carboxylic acid. The reaction mixture was diluted with CH$_2$Cl$_2$ and aq. NaHCO$_3$. The aq. layer was separated off and extracted with CH$_2$Cl$_2$. Combined extracts were washed with brine and dried over Na$_2$SO$_4$, filtered and concentrated under reduced pressure. The crude product was purified by silica gel column chromatography (CH$_2$Cl$_2$/EtOH 1-80% EtOH) to afford the title product. t$_R$: 0.81 min (LC-MS 2); ESI-MS: 487/489 [M+H]$^+$ (LC-MS 2).

EXAMPLE 55

6-(4-chlorophenyl)-5-(8-methoxy-3-methyl-[1,2,4]triazolo[4,3-a]pyridin-6-yl)-2-(6-methoxypyridin-3-yl)-1-methyl-5,6-dihydropyrrolo[3,4-d]imidazol-4(1H)-one

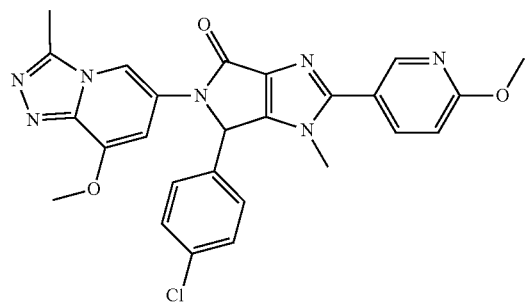 [SMILES: COc1ccc(-c2nc3c(n2C)C(c2ccc(Cl)cc2)N(c2cc(OC)c4nnc(C)n4c2)C3=O)cn1]

The compound was prepared in analogy to the procedure described for Example 1 using 2-bromo-6-(4-chlorophenyl)-1-methyl-5-(8-methoxy-3-methyl-[1,2,4]triazolo[4,3-a]

pyridin-6-yl)-5,6-dihydropyrrolo[3,4-d]imidazol-4(1H)-one (Step 54.3) and 2-methoxypyridine-5-boronic acid at 85° C. for 3 hr. The reaction mixture was concentrated in vacuo and the residue diluted with CH$_2$Cl$_2$ and water. The aq. layer was separated off and extracted with CH$_2$Cl$_2$. Combined extracts were dried over Na$_2$SO$_4$, filtered and concentrated under reduced pressure. The crude product was purified by preparative achiral SFC (column Diol/grad 22-27%; 11 min). t$_R$: 0.85 min (LC-MS 2); ESI-MS: 516 [M+H]$^+$ (LC-MS 2).

EXAMPLE 56

6-(4-chlorophenyl)-2-cyclopropyl-5-(8-methoxy-3-methyl-[1,2,4]triazolo[4,3-a]pyridin-6-yl)-1-methyl-5,6-dihydropyrrolo[3,4-d]imidazol-4(1H)-one

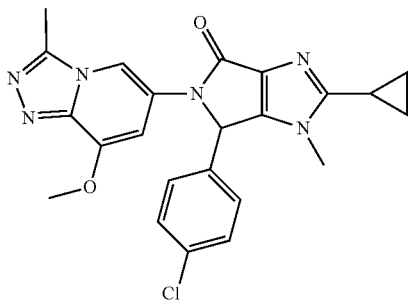 [SMILES: COc1cc(N2C(=O)c3nc(C4CC4)n(C)c3C2c2ccc(Cl)cc2)cn2c(C)nnc12]

The title compound was prepared in analogy to the procedure described for Example 13 using 2-bromo-6-(4-chlorophenyl)-1-methyl-5-(8-methoxy-3-methyl-[1,2,4]triazolo[4,3-a]pyridin-6-yl)-5,6-dihydropyrrolo[3,4-d]imidazol-4(1H)-one (Step 54.3) and potassium cyclopropyltrifluoroborate under heating at 115° C. for 4 hr. The reaction mixture was diluted with CH$_2$Cl$_2$ and aq. NaHCO$_3$. The aq. layer was separated off and extracted with CH$_2$Cl$_2$. Combined extracts were washed with brine and dried over Na$_2$SO$_4$, filtered and concentrated under reduced pressure. The crude product was purified by preparative achiral SFC (column Silica/isocratic 20%; total 24 min). t$_R$: 0.90 min (LC-MS 2); ESI-MS: 449 [M+H]$^+$ (LC-MS 2).

EXAMPLE 57

6-(4-chlorophenyl)-2-cyclopropyl-5-(3,8-dimethyl-[1,2,4]triazolo[4,3-a]pyridin-6-yl)-1-methyl-5,6-dihydropyrrolo[3,4-d]imidazol-4(1H)-one

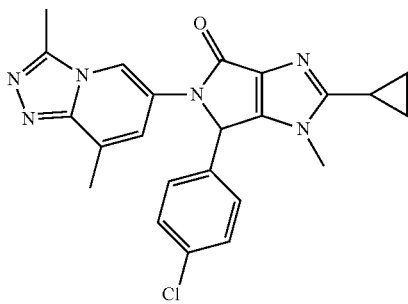 [SMILES: Cc1cc(N2C(=O)c3nc(C4CC4)n(C)c3C2c2ccc(Cl)cc2)cn2c(C)nnc12]

The title compound was prepared in analogy to the procedure described for Example 13 using 2-bromo-6-(4-chlorophenyl)-5-(3,8-dimethyl-[1,2,4]triazolo[4,3-a]pyridin-6-yl)-1-methyl-5,6-dihydropyrrolo[3,4-d]imidazol-4 (1H)-one (Step 16.6) and potassium cyclopropyltrifluoroborate under heating at 115° C. for 16 hr. The reaction mixture was diluted with CH$_2$Cl$_2$ and aq. NaHCO$_3$. The aq. layer was separated off and extracted with CH$_2$Cl$_2$. Combined extracts were washed with brine and dried over Na$_2$SO$_4$, filtered and concentrated under reduced pressure. The crude product was purified by preparative achiral SFC (column 2-EP/grad 18-23%; 11 min). t$_R$: 0.85 min (LC-MS 2); ESI-MS: 433 [M+H]$^+$ (LC-MS 2); $^1$H NMR (400 MHz, DMSO-d$_6$) δ 8.35 (s, 1H), 7.40 (s, 4H), 7.32 (m, 1H), 6.58 (s, 1H), 3.45 (s, 3H), 2.63 (s, 3H), 2.45 (s, 3H), 2.06 (m, 1H), 0.99 (m, 4H).

EXAMPLE 58

6-(4-chlorophenyl)-5-(3,8-dimethyl-[1,2,4]triazolo[4,3-a]pyridin-6-yl)-1-isopropyl-2-methyl-5,6-dihydropyrrolo[3,4-d]imidazol-4(1H)-one

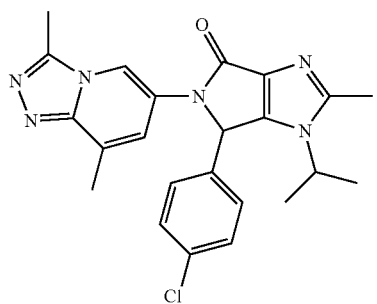 [SMILES: Cc1cc(N2C(=O)c3nc(C)n(C(C)C)c3C2c2ccc(Cl)cc2)cn2c(C)nnc12]

The compound was prepared in analogy to the procedure described for Example 1 using 2-bromo-6-(4-chlorophenyl)-5-(3,8-dimethyl-[1,2,4]triazolo[4,3-a]pyridin-6-yl)-1-isopropyl-5,6-dihydropyrrolo[3,4-d]imidazol-4(1H)-one (Step 9.9) and trimethylboroxine at 90° C. for 2 hr. The reaction mixture was concentrated in vacuo and the residue diluted with CH$_2$Cl$_2$ and water. The aq. layer was separated off and extracted with CH$_2$Cl$_2$. Combined extracts were dried over Na$_2$SO$_4$, filtered and concentrated under reduced pressure. The crude product was purified by silica gel column chromatography (CH$_2$Cl$_2$/EtOH 3-20% EtOH) to afford the title compound. t$_R$: 0.82 min (LC-MS 2); ESI-MS: 435 [M+H]$^+$ (LC-MS 2); $^1$H NMR (600 MHz, DMSO-d$_6$) δ 8.38 (s, 1H), 7.39 (m, 5H), 6.65 (s, 1H), 4.46 (m, 1H), 2.65 (s, 3H), 2.46 (s, 3H), 2.44 (s, 3H), 1.42 (d, 3H), 0.65 (d, 3H).

EXAMPLE 59

(R)-6-(4-chlorophenyl)-5-(3,8-dimethyl-[1,2,4]triazolo[4,3-a]pyridin-6-yl)-1-isopropyl-2-methyl-5,6-dihydropyrrolo[3,4-d]imidazol-4(1H)-one

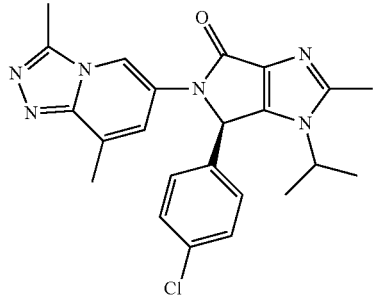 [SMILES: Cc1cc(N2C(=O)c3nc(C)n(C(C)C)c3[C@H]2c2ccc(Cl)cc2)cn2c(C)nnc12]

The title compound (52 mg) was obtained enantiomerically pure (>99% ee) after chiral preparative chromatography (Chiralpak AD-H, 250×30 mm; mobile phase: CO$_2$/(iPrOH+0.1% NH$_3$) 0-40%; flow rate: 50 mL/min; detection 220 nm) of the racemic mixture of 6-(4-chlorophenyl)-5-(3,8-dimethyl-[1,2,4]triazolo[4,3-a]pyridin-6-yl)-1-isopropyl-2-methyl-5,6-dihydropyrrolo[3,4-d]imidazol-4(1H)-one (Example 58; 110 mg). The second enantiomer (S)-6-((4-chlorophenyl)-5-(3,8-dimethyl-[1,2,4]triazolo[4,3-a]pyridin-6-yl)-1-isopropyl-2-methyl-5,6-dihydropyrrolo[3,4-d]imidazol-4(1H)-one (51 mg) was obtained enantiomerically pure (>99% ee) via the same separation.

EXAMPLE 60

6-(4-chlorophenyl)-2-(3,6-dihydro-2H-pyran-4-yl)-1-isopropyl-5-((4-methoxy-1-methyl-1H-benzo[d][1,2,3]triazol-6-yl)-5,6-dihydropyrrolo[3,4-d]imidazol-4(1H)-one

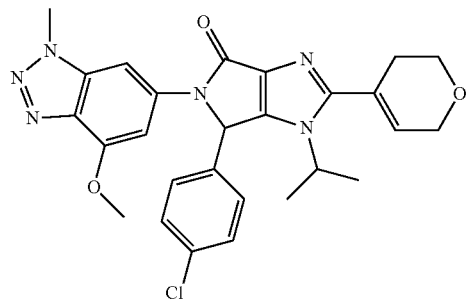 [SMILES: COc1cc(N2C(=O)c3nc(C4=CCOCC4)n(C(C)C)c3C2c2ccc(Cl)cc2)cc2c1nnn2C]

The title compound was prepared in analogy to the procedure described for Example 1 using 2-bromo-6-(4-chlorophenyl)-1-isopropyl-5-((4-methoxy-1-methyl-1H-benzo[d][1,2,3]triazol-6-yl)-5,6-dihydropyrrolo[3,4-d]imidazol-4(1H)-one (Step 60.7) and 3,6-dihydro-2H-pyran-4-boronic acid pinacolester under heating at 85° C. for 2 hr. The reaction mixture was concentrated in vacuo and the residue diluted with CH$_2$Cl$_2$ and aq. NaHCO$_3$. The aq. layer was separated off and extracted with CH$_2$Cl$_2$. Combined extracts were dried over Na$_2$SO$_4$, filtered and concentrated under reduced pressure. The crude product was purified by preparative HPLC (gradient 5-100% CH$_3$CN in 20 min), followed by basic workup. $t_R$: 0.97 min (LC-MS 2); ESI-MS: 519 [M+H]$^+$ (LC-MS 2).

Step 60.1:
5-bromo-3-methoxy-N-methyl-2-nitroaniline

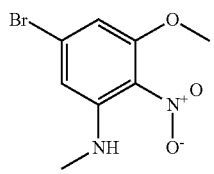

A mixture of 5-bromo-1-fluoro-3-methoxy-2-nitrobenzene (CAS: 1137869-91-0, 5.5 g, 22 mmol) and a solution of methyl amine in THF (2 M; 44 ml) was slowly heated up to 75° C. After 2 h at 75° C., the reaction mixture was cooled down to rt. The solid was filtered off and discarded. Concentration of the filtrate gave the title compound. $t_R$: 1.07 min (LC-MS 2); ESI-MS: 261/263 [M+H]$^+$ (LC-MS 2).

Step 60.2:
5-bromo-3-methoxy-N1-methylbenzene-1,2-diamine

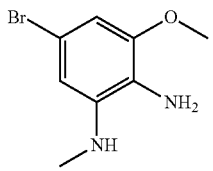

A mixture of 5-bromo-3-methoxy-N-methyl-2-nitroaniline (8.8 g, 33 mmol) and Raney nickel (1 g) in MeOH/THF 1:1 (0.4 L) was hydrogenated. The catalyst was filtered off and the filtrate concentrated, yielding the title compound. $t_R$: 0.90 min (LC-MS 2); ESI-MS: 231/233 [M+H]$^+$ (LC-MS 2).

Step 60.3: 6-bromo-4-methoxy-1-methyl-1H-benzo[d][1,2,3]triazole

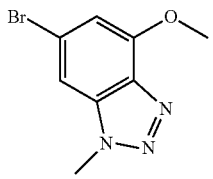

A mixture of 5-bromo-3-methoxy-N1-methylbenzene-1,2-diamine (7.7 g, 33 mmol) and conc. HCl (42 mL) was cooled in an ice bath. Then a solution of NaNO$_2$ (2.56 g, 37 mmol) in H$_2$O (25 mL) was added during 15 min. The suspension was stirred for 15 min at 0° C. and 30 min at rt. The reaction mixture was diluted with EtOAc (100 mL), H$_2$O (50 mL) and brine (100 mL). The aq. layer was separted off and extracted with EtOAc. Combined extracts were dried over Na$_2$SO$_4$, filtered and concentrated under reduced pressure. The crude product was purified by silica gel column chromatography (hexane/EtOAc 3-40% EtOAc) to afford the title compound. $t_R$: 0.86 min (LC-MS 2); ESI-MS: 242/244 [M+H]$^+$ (LC-MS 2).

Step 60.4: 4-methoxy-1-methyl-1H-benzo[d][1,2,3]triazol-6-amine

A mixture of 6-bromo-4-methoxy-1-methyl-1H-benzo[d][1,2,3]triazole (0.80 g, 3.3 mmol), 2-di-tert-butylphosphino-2'-(N,N-dimethyl-amino) biphenyl (56 mg, 0.165 mmol), Pd$_2$(dba)$_3$.HCCl$_3$ (34 mg, 0.033 mmol), sodium tert-butoxide (0.445 g, 4.63 mmol) and NH$_3$ (0.5 M in dioxane, 33 mL, 16.5 mmol) was distributed on two micro wave tubes. The mixtures were heated for 30 min at 120° C. in a micro wave device and then cooled down to rt. Additional amounts of 2-di-tert-butylphosphino-2'-(N,N-dimethyl-amino) biphenyl (56 mg, 0.165 mmol) and Pd$_2$(dba)$_3$.HCCl$_3$ (34 mg, 0.033 mmol) were added. Heating for additional 30 min at 120° C. under micro wave irradiation led to complete conversion of the 6-bromo-4-methoxy-1-methyl-1H-benzo[d][1,2,3]triazole. The cold reaction mixture was filtered and the filtrate concentrated in vacuo. Stirring of the residue in a mixture of CH$_2$Cl$_2$ (10 mL) and hexane (10 mL) led to crystalline product. $t_R$: 0.44 min (LC-MS 2); ESI-MS: 179 [M+H]$^+$ (LC-MS 2); $^1$H NMR (600 MHz, DMSO-d$_6$) δ 6.18 (d, 1H), 6.10 (d, 1H), 5.62 (s, 2H), 4.01 (s, 3H), 3.91 (s, 3H).

Step 60.5: ethyl 2-bromo-5-((4-chlorophenyl)(((4-methoxy-1-methyl-1H-benzo[d][1,2,3]triazol-6-yl)amino)methyl)-1-isopropyl-1H-imidazole-4-carboxylate

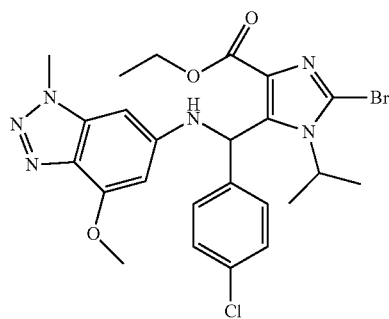 [SMILES: CCOC(=O)c1nc(Br)n(C(C)C)c1C(Nc1cc(OC)c2nnn(C)c2c1)c1ccc(Cl)cc1]

The title compound was prepared in analogy to the procedure described for Step 1.9 using ethyl 2-bromo-5-((4-chlorophenyl)(hydroxy)methyl)-1-isopropyl-1H-imidazole-4-carboxylate (Step 9.6) and 4-methoxy-1-methyl-1H-benzo[d][1,2,3]triazol-6-amine. The reaction mixture was diluted with CH$_2$Cl$_2$ and aq. NaHCO$_3$. The aq. layer was separated off and extracted with CH$_2$Cl$_2$. Combined extracts were dried over Na$_2$SO$_4$, filtered and concentrated under reduced pressure. The crude product was purified by silica gel column chromatography (hexane/EtOAc 50-75% EtOAc) to afford the title compound. $t_R$: 1.18 min (LC-MS 2); ESI-MS: 561/563 [M+H]$^+$ (LC-MS 2).

Step 60.6: 2-bromo-5-((4-chlorophenyl)(((4-methoxy-1-methyl-1H-benzo[d][1,2,3]triazol-6-yl)amino)methyl)-1-isopropyl-1H-imidazole-4-carboxylic acid

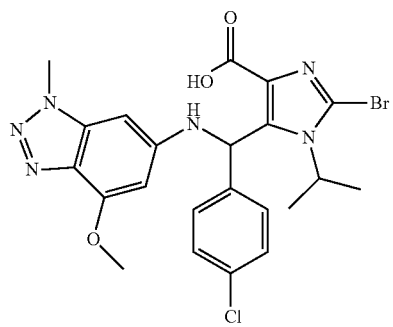 [SMILES: COc1cc(NC(c2ccc(Cl)cc2)c2c(C(=O)O)nc(Br)n2C(C)C)cc2c1nnn2C]

The title compound was prepared in analogy to the procedure described in Step 1.10 using ethyl 2-bromo-5-((4-chlorophenyl)(((4-methoxy-1-methyl-1H-benzo[d][1,2,3]triazol-6-yl)amino)methyl)-1-isopropyl-1H-imidazole-4-carboxylate at 40 to 60° C. Neutralization of the cold reaction mixture with 4 N HCl led to a precipitation of the product. Filtration and washing with water gave the title compound. $t_R$: 0.99 min (LC-MS 2); ESI-MS: 533/535 [M+H]$^+$ (LC-MS 2).

Step 60.7: 2-bromo-6-(4-chlorophenyl)-1-isopropyl-5-((4-methoxy-1-methyl-1H-benzo[d][1,2,3]triazol-6-yl)-5,6-dihydropyrrolo[3,4-d]imidazol-4(1H)-one

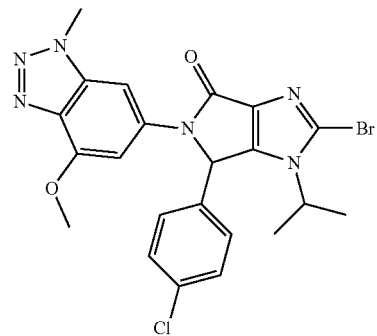 [SMILES: COc1cc(N2C(=O)c3nc(Br)n(C(C)C)c3C2c2ccc(Cl)cc2)cc2c1nnn2C]

The title compound was prepared in analogy to the procedure described in Step 1.11 using 2-bromo-5-((4-chlorophenyl)((4-methoxy-1-methyl-1H-benzo[d][1,2,3]triazol-6-yl)amino)methyl)-1-isopropyl-1H-imidazole-4-carboxylic acid. The resulting suspension was filtered and the solid product washed with CH$_2$Cl$_2$. More product could be isolated from the filtrate by extraction (CH$_2$Cl$_2$, aq. NaHCO$_3$). $t_R$: 1.03 min (LC-MS 2); ESI-MS: 515/517 [M+H]$^+$ (LC-MS 2).

EXAMPLE 61

(R)-6-(4-chlorophenyl)-2-(3,6-dihydro-2H-pyran-4-yl)-1-isopropyl-5-((4-methoxy-1-methyl-1H-benzo[d][1,2,3]triazol-6-yl)-5,6-dihydropyrrolo[3,4-d]imidazol-4(1H)-one

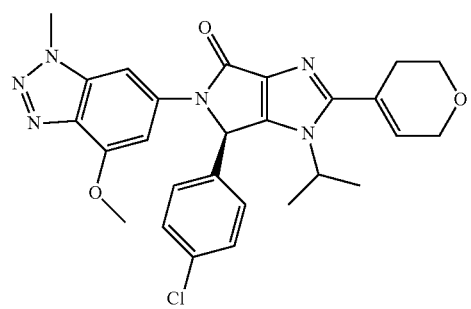 [SMILES: COc1cc(N2C(=O)c3nc(C4=CCOCC4)n(C(C)C)c3[C@H]2c2ccc(Cl)cc2)cc2c1nnn2C]

The title compound (74 mg) was obtained enantiomerically pure (>99% ee) after chiral preparative chromatography (Chiralpak AD-H, 250×4.6 mm; mobile phase: CO$_2$/(MeOH+0.05% Et$_2$NH) 0-50%; flow rate: 2 mL/min; detection 220 nm) of the racemic mixture of 6-(4-chlorophenyl)-2-(3,6-dihydro-2H-pyran-4-yl)-1-isopropyl-5-((4-methoxy-1-methyl-1H-benzo[d][1,2,3]triazol-6-yl)-5,6-dihydropyrrolo[3,4-d]imidazol-4(1H)-one (Example 60; 175 mg). The second enantiomer (S)-6-((4-chlorophenyl)-2-(3,6-dihydro-2H-pyran-4-yl)-1-isopropyl-5-(4-methoxy-1-methyl-1H-benzo[d][1,2,3]triazol-6-yl)-5,6-dihydropyrrolo[3,4-d]imidazol-4(1H)-one (61 mg) was obtained enantiomerically pure (>99% ee) via the same separation.

EXAMPLE 62

6-(4-chlorophenyl)-1-isopropyl-5-((4-methoxy-1-methyl-1H-benzo[d][1,2,3]triazol-6-yl)-2-(1-methyl-1,2,5,6-tetrahydropyridin-3-yl)-5,6-dihydropyrrolo[3,4-d]imidazol-4(1H)-one

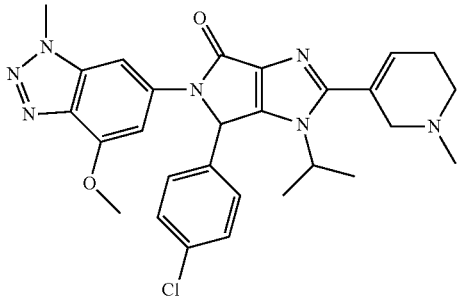 [SMILES: COc1cc(N2C(=O)c3nc(C4=CCCN(C)C4)n(C(C)C)c3C2c2ccc(Cl)cc2)cc2c1nnn2C]

The title compound was prepared in analogy to the procedure described for Example 1 using 2-bromo-6-(4-chlorophenyl)-1-isopropyl-5-((4-methoxy-1-methyl-1H-benzo[d][1,2,3]triazol-6-yl)-5,6-dihydropyrrolo[3,4-d]imidazol-4(1H)-one (Step 60.7) and 1-methyl-5-(4,4,5,5-tetramethyl-1,3,2-dioxaborolat-2-yl)-1,2,3,6-tetrahydropyridine under heating at 85° C. for 7 hr. The reaction mixture was diluted with CH$_2$Cl$_2$ and H$_2$O. The aq. layer was separated off and extracted with CH$_2$Cl$_2$. Combined extracts were dried over Na$_2$SO$_4$, filtered and concentrated under reduced pressure. The crude product was purified by preparative HPLC (gradient 5-100% CH$_3$CN in 20 min), followed by basic workup. t$_R$: 0.75 min (LC-MS 2); ESI-MS: 532 [M+H]$^+$ (LC-MS 2).

EXAMPLE 63

6-(4-chlorophenyl)-1-isopropyl-5-((4-methoxy-1-methyl-1H-benzo[d][1,2,3]triazol-6-yl)-2-methyl-5,6-dihydropyrrolo[3,4-d]imidazol-4(1H)-one

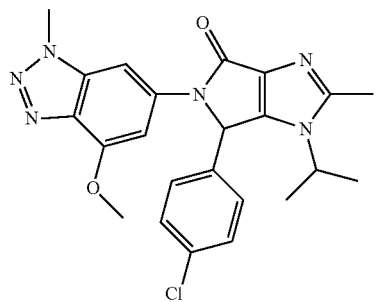 [SMILES: COc1cc(N2C(=O)c3nc(C)n(C(C)C)c3C2c2ccc(Cl)cc2)cc2c1nnn2C]

The title compound was prepared in analogy to the procedure described for Example 1 using 2-bromo-6-(4-chlorophenyl)-1-isopropyl-5-((4-methoxy-1-methyl-1H-benzo[d][1,2,3]triazol-6-yl)-5,6-dihydropyrrolo[3,4-d]imidazol-4(1H)-one (Step 60.7) and trimethylboroxine at 85° C. for 1½ hr. The reaction mixture was diluted with CH$_2$Cl$_2$ and H$_2$O. The aq. layer was separated off and extracted with CH$_2$Cl$_2$. Combined extracts were dried over Na$_2$SO$_4$, filtered and concentrated under reduced pressure. The crude product was purified by preparative HPLC (gradient 5-100% CH$_3$CN in 20 min), followed by basic workup. t$_R$: 0.93 min (LC-MS 2); ESI-MS: 451 [M+H]$^+$ (LC-MS 2); $^1$H NMR (600 MHz, DMSO-d$_6$) δ 7.55 (d, 1H), 7.37 (m, 4H), 7.11 (d, 1H), 6.79 (s, 1H), 4.46 (m, 1H), 4.19 (s, 3H), 4.00 (s, 3H), 2.46 (s, 3H), 1.45 (d, 3H), 0.63 (d, 3H).

EXAMPLE 64

6-(4-chlorophenyl)-1-isopropyl-5-((4-methoxy-1-methyl-1H-benzo[d][1,2,3]triazol-6-yl)-2-(tetrahydro-2H-pyran-4-yl)-5,6-dihydropyrrolo[3,4-d]imidazol-4(1H)-one

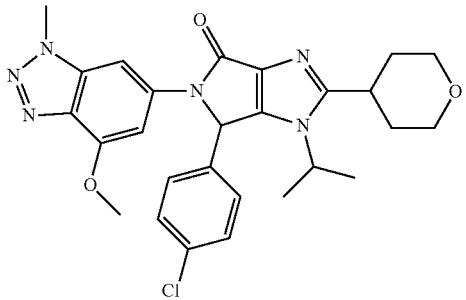

6-((4-Chlorophenyl)-2-(3,6-dihydro-2H-pyran-4-yl)-1-isopropyl-5-((4-methoxy-1-methyl-1H-benzo[d][1,2,3]triazol-6-yl)-5,6-dihydropyrrolo[3,4-d]imidazol-4(1H)-one (Ex. 60; 88 mg, 0.17 mmol) in MeOH (5 mL) was hydrogenated in presence of Pd(OH)$_2$ (20 mg) during 35 h. The catalyst was filtered off and the filtrate concentrated. The crude product was purified by preparative HPLC (gradient 5-100% CH$_3$CN in 20 min), followed by basic workup. t$_R$: 0.95 min (LC-MS 2); ESI-MS: 521 [M+H]$^+$ (LC-MS 2).

EXAMPLE 65 methyl 4-(6-(4-chlorophenyl)-5-(3,8-dimethyl-[1,2,4]triazolo[4,3-a]pyridin-6-yl)-1-isopropyl-4-oxo-1,4,5,6-tetrahydropyrrolo[3,4-d]imidazol-2-yl)-5,6-dihydropyridine-1(2H)-carboxylate

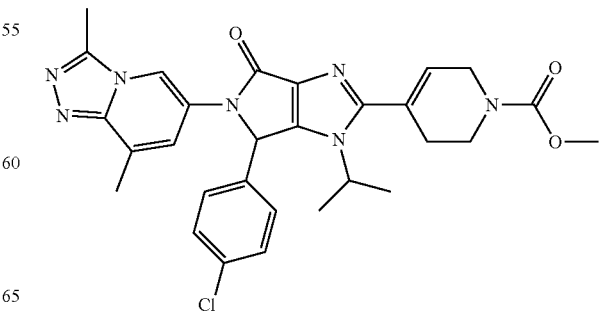

An ice-cooled solution of 6-(4-chlorophenyl)-5-(3,8-dimethyl-[1,2,4]triazolo[4,3-a]pyridin-6-yl)-1-isopropyl-2-(1,2,3,6-tetrahydropyridin-4-yl)-5,6-dihydropyrrolo[3,4-d]imidazol-4(1H)-one (50 mg; 0.10 mmol) (Ex. 49) in CH$_2$Cl$_2$ (5 mL) and pyridine (1 mL) was treated with methyl chloroformate (24 μL, 0.3 mmol). After 1½ h the reaction mixture was poured into a solution of NaHCO$_3$ and extracted with 3 portions of CH$_2$Cl$_2$. The extracts were washed with brine, dried (Na$_2$SO$_4$), filtered and concentrated under reduced pressure. The crude product was purified by silica gel column chromatography (CH$_2$Cl$_2$/EtOH 0-15% EtOH) to afford the title compound. t$_R$: 0.89 min (LC-MS 2); ESI-MS: 560 [M+H]$^+$ (LC-MS 2).

EXAMPLE 66

2-(1-acetyl-1,2,3,6-tetrahydropyridin-4-yl)-6-((4-chlorophenyl)-5-(3,8-dimethyl-[1,2,4]triazolo[4,3-a]pyridin-6-yl)-1-isopropyl-5,6-dihydropyrrolo[3,4-d]imidazol-4(1H)-one

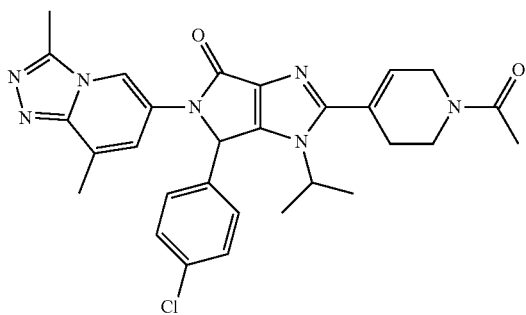 [SMILES: CC(=O)N1CC=C(c2nc3c(n2C(C)C)C(c2ccc(Cl)cc2)N(c2cc(C)c4nnc(C)n4c2)C3=O)CC1]

An ice-cooled solution of 6-((4-chlorophenyl)-5-(3,8-dimethyl-[1,2,4]triazolo[4,3-a]pyridin-6-yl)-1-isopropyl-2-(1,2,3,6-tetrahydropyridin-4-yl)-5,6-dihydropyrrolo[3,4-d]imidazol-4(1H)-one (50 mg; 0.10 mmol) (Ex. 49) in CH$_2$Cl$_2$ (5 mL) and pyridine (1 mL) was treated with acetic anhydride (14 μL, 0.15 mmol). After 1½ h the reaction mixture was poured into a solution of NaHCO$_3$ and extracted with 3 portions of CH$_2$Cl$_2$. The extracts were washed with brine, dried (Na$_2$SO$_4$), filtered and concentrated under reduced pressure. The crude product was purified by preparative HPLC (gradient 5-100% CH$_3$CN in 20 min), followed by basic workup. t$_R$: 0.78 min (LC-MS 2); ESI-MS: 544 [M+H]$^+$ (LC-MS 2).

EXAMPLE 67

6-(4-chlorophenyl)-5-(3,8-dimethyl-[1,2,4]triazolo[4,3-a]pyridin-6-yl)-1-isopropyl-2-(1-(methylsulfonyl)-1,2,3,6-tetrahydropyridin-4-yl)-5,6-dihydropyrrolo[3,4-d]imidazol-4(1H)-one

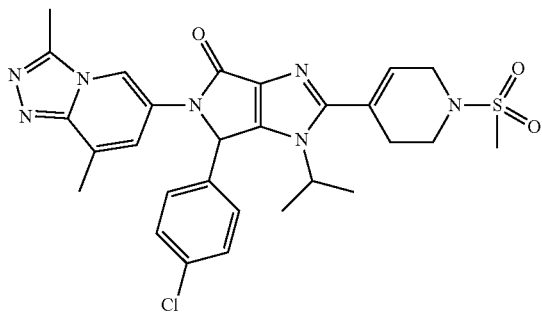 [SMILES: Cc1cc(N2C(=O)c3nc(C4=CCN(S(C)(=O)=O)CC4)n(C(C)C)c3C2c2ccc(Cl)cc2)cn2c(C)nnc12]

An ice-cooled solution of 6-((4-chlorophenyl)-5-(3,8-dimethyl-[1,2,4]triazolo[4,3-a]pyridin-6-yl)-1-isopropyl-2-(1,2,3,6-tetrahydropyridin-4-yl)-5,6-dihydropyrrolo[3,4-d]imidazol-4(1H)-one (50 mg; 0.10 mmol) (Ex. 49) in CH$_2$Cl$_2$ (5 mL) and pyridine (1 mL) was treated with 3 portions of methansulfonic anhydride (each time 26.8 mg, 0.15 mmol). After 30 h the reaction mixture was poured into a solution of NaHCO$_3$ and extracted with 3 portions of CH$_2$Cl$_2$. The extracts were washed with brine, dried (Na$_2$SO$_4$), filtered and concentrated under reduced pressure. The crude product was purified by preparative HPLC (gradient 5-100% CH$_3$CN in 20 min), followed by basic workup. t$_R$: 0.91 min (LC-MS 2); ESI-MS: 580 [M+H]$^+$ (LC-MS 2).

EXAMPLE 68

6-(4-chlorophenyl)-5-(3,8-dimethyl-[1,2,4]triazolo[4,3-a]pyridin-6-yl)-2-(1-ethyl-1,2,3,6-tetrahydropyridin-4-yl)-1-isopropyl-5,6-dihydropyrrolo[3,4-d]imidazol-4(1H)-one

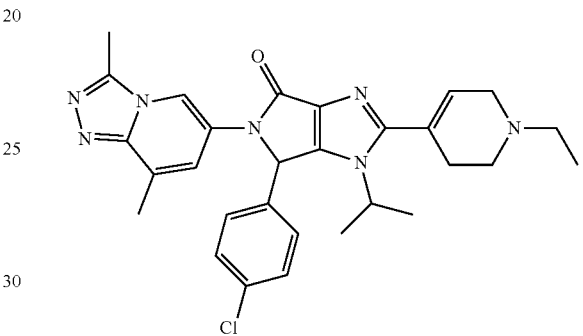

A solution of 6-((4-chlorophenyl)-5-(3,8-dimethyl-[1,2,4]triazolo[4,3-a]pyridin-6-yl)-1-isopropyl-2-(1,2,3,6-tetrahydropyridin-4-yl)-5,6-dihydropyrrolo[3,4-d]imidazol-4(1H)-one (82 mg; 0.16 mmol) (Ex. 49) in CH$_2$Cl$_2$ (2 mL) was treated with sodium triacetoxyborohydride (105 mg, 0.5 mmol) and acetic acid (28 μL, 0.5 mmol). After 5 min acetaldehyde (14 μL, 0.25 mmol) was added portion wise during 30 min. After 4 h at rt, more sodium triacetoxyborohydride (27 mg), acetaldehyde (3.5 μL) and acetic acid (7 μL) were added. Stirring was continued for 16 h. Then the reaction mixture was poured into a solution of NaHCO$_3$ and extracted with 3 portions of CH$_2$Cl$_2$. The extracts were washed with brine, dried (Na$_2$SO$_4$), filtered and concentrated under reduced pressure. The crude product was purified by preparative HPLC (gradient 5-100% CH$_3$CN in 20 min), followed by basic workup. t$_R$: 0.64 min (LC-MS 2); ESI-MS: 530 [M+H]$^+$ (LC-MS 2).

EXAMPLE 69 isobutyl 4-(6-(4-chlorophenyl)-5-(3,8-dimethyl-[1,2,4]triazolo[4,3-a]pyridin-6-yl)-1-isopropyl-4-oxo-1,4,5,6-tetrahydropyrrolo[3,4-d]imidazol-2-yl)-5,6-dihydropyridine-1(2H)-carboxylate

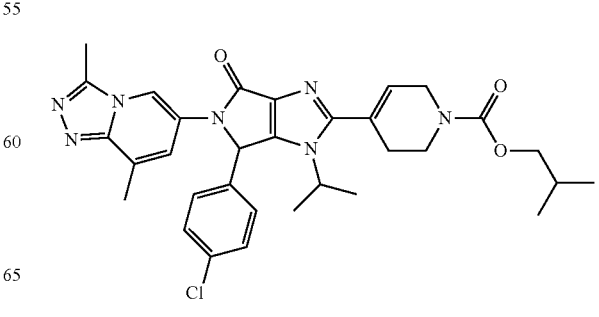

An ice-cooled solution of 6-(4-chlorophenyl)-5-(3,8-dimethyl-[1,2,4]triazolo[4,3-a]pyridin-6-yl)-1-isopropyl-2-(1,2,3,6-tetrahydropyridin-4-yl)-5,6-dihydropyrrolo[3,4-d]imidazol-4(1H)-one (50 mg; 0.10 mmol) (Ex. 49) in CH$_2$Cl$_2$ (5 mL) and pyridine (1 mL) was treated with isobutyl chloroformate (20 µL, 0.15 mmol). After 1½ h the reaction mixture was poured into a solution of NaHCO$_3$ and extracted with 3 portions of CH$_2$Cl$_2$. The extracts were washed with brine, dried (Na$_2$SO$_4$), filtered and concentrated under reduced pressure. The crude product was purified by preparative achiral SFC (column NH2/grad 22-27%; 11 min). $t_R$: 1.11 min (LC-MS 2); ESI-MS: 602 [M+H]$^+$ (LC-MS 2).

EXAMPLE 70 ethyl 4-(6-(4-chlorophenyl)-5-(3,8-dimethyl-[1,2,4]triazolo[4,3-a]pyridin-6-yl)-1-isopropyl-4-oxo-1,4,5,6-tetrahydropyrrolo[3,4-d]imidazol-2-yl)-5,6-dihydropyridine-1(2H)-carboxylate

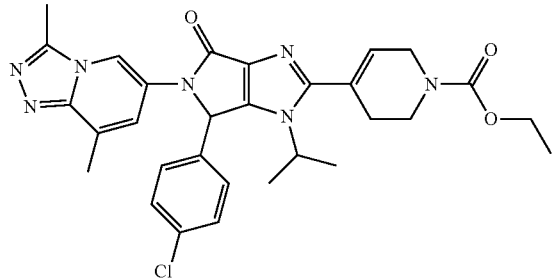 [SMILES: CCOC(=O)N1CC=C(c2nc3c(n2C(C)C)C(c2ccc(Cl)cc2)N(c2cc(C)c4nnc(C)n4c2)C3=O)CC1]

An ice-cooled solution of 6-(4-chlorophenyl)-5-(3,8-dimethyl-[1,2,4]triazolo[4,3-a]pyridin-6-yl)-1-isopropyl-2-(1,2,3,6-tetrahydropyridin-4-yl)-5,6-dihydropyrrolo[3,4-d]imidazol-4(1H)-one (60 mg; 0.12 mmol) (Ex. 49) in CH$_2$Cl$_2$ (5 mL) and pyridine (1 mL) was treated with ethyl chloroformate (17 µL, 0.18 mmol). After 1½ h the reaction mixture was poured into a solution of NaHCO$_3$ and extracted with 3 portions of CH$_2$Cl$_2$. The extracts were washed with brine, dried (Na$_2$SO$_4$), filtered and concentrated under reduced pressure. The crude product was purified by preparative HPLC (gradient 5-100% CH$_3$CN in 20 min), followed by basic workup. $t_R$: 0.96 min (LC-MS 2); ESI-MS: 574 [M+H]$^+$ (LC-MS 2).

EXAMPLE 71 isopropyl 4-(6-(4-chlorophenyl)-5-(3,8-dimethyl-[1,2,4]triazolo[4,3-a]pyridin-6-yl)-1-isopropyl-4-oxo-1,4,5,6-tetrahydropyrrolo[3,4-d]imidazol-2-yl)-5,6-dihydropyridine-1(2H)-carboxylate

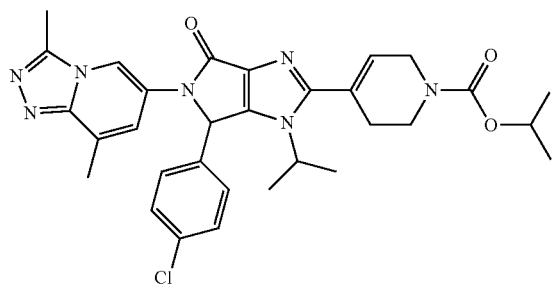 [SMILES: Cc1cc(N2C(=O)c3nc(C4=CCN(C(=O)OC(C)C)CC4)n(C(C)C)c3C2c2ccc(Cl)cc2)cn2c(C)nnc12]

An ice-cooled solution of 6-(4-chlorophenyl)-5-(3,8-dimethyl-[1,2,4]triazolo[4,3-a]pyridin-6-yl)-1-isopropyl-2-(1,2,3,6-tetrahydropyridin-4-yl)-5,6-dihydropyrrolo[3,4-d]imidazol-4(1H)-one (50 mg; 0.10 mmol) (Ex. 49) in CH$_2$Cl$_2$ (5 mL) and pyridine (1 mL) was treated with isopropyl chloroformate (1 M in toluene; 0.15 mL, 0.15 mmol). After 1½ h the reaction mixture was poured into a solution of NaHCO$_3$ and extracted with 3 portions of CH$_2$Cl$_2$. The extracts were washed with brine, dried (Na$_2$SO$_4$), filtered and concentrated under reduced pressure. The crude product was purified by preparative achiral SFC (column Diol/grad 18-23%; 11 min). $t_R$: 1.02 min (LC-MS 2); ESI-MS: 588 [M+H]$^+$ (LC-MS 2).

EXAMPLE 72

N-(tert-butyl)-4-(6-(4-chlorophenyl)-5-(3,8-dimethyl-[1,2,4]triazolo[4,3-a]pyridin-6-yl)-1-isopropyl-4-oxo-1,4,5,6-tetrahydropyrrolo[3,4-d]imidazol-2-yl)-5,6-dihydropyridine-1(2H)-carboxamide

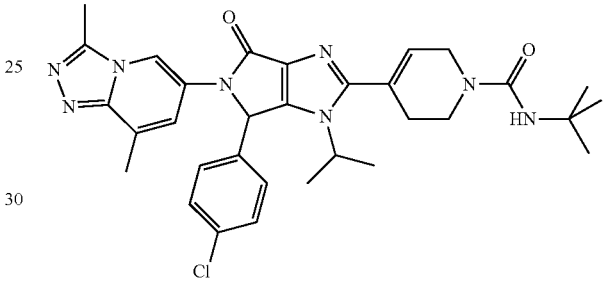

An ice-cooled solution of 6-(4-chlorophenyl)-5-(3,8-dimethyl-[1,2,4]triazolo[4,3-a]pyridin-6-yl)-1-isopropyl-2-(1,2,3,6-tetrahydropyridin-4-yl)-5,6-dihydropyrrolo[3,4-d]imidazol-4(1H)-one (50 mg; 0.10 mmol) (Ex. 49) in CH$_2$Cl$_2$ (2 mL) was treated with tert-butylisocyanate (18 µL, 0.15 mmol). After 2½ h at rt the reaction mixture was concentrated under reduced pressure. The crude product was purified by preparative achiral SFC (column 2-EP/grad 16-21%; 11 min). $t_R$: 0.99 min (LC-MS 2); ESI-MS: 601 [M+H]$^+$ (LC-MS 2).

EXAMPLE 73

6-(4-chlorophenyl)-1-isopropyl-5-((4-methoxy-1-methyl-1H-benzo[d][1,2,3]triazol-6-yl)-2-(1-methyl-1,2,3,6-tetrahydropyridin-4-yl)-5,6-dihydropyrrolo[3,4-d]imidazol-4(1H)-one

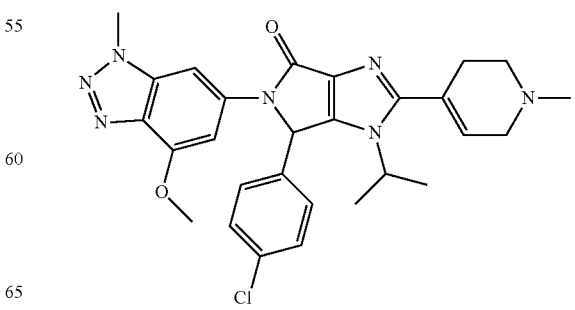

The title compound was prepared in analogy to the procedure described for Example 1 using 2-bromo-6-(4-chlorophenyl)-1-isopropyl-5-((4-methoxy-1-methyl-1H-benzo[d][1,2,3]triazol-6-yl)-5,6-dihydropyrrolo[3,4-d]imidazol-4(1H)-one (Step 60.7) and 1-methyl-1,2,3,6,-tetrahydropyridin-4-boronic acid pinacolester under heating at 85° C. for 4 hr. The reaction mixture was concentrated in vacuo and the residue diluted with $CH_2Cl_2$ and aq. $NaHCO_3$. The aq. layer was separated off and extracted with $CH_2Cl_2$. Combined extracts were dried over $Na_2SO_4$, filtered and concentrated under reduced pressure. The crude product was purified by silica gel column chromatography [$CH_2Cl_2$/(EtOH+5% $NH_3$) 2-25% (EtOH+5% $NH_3$)] to afford the title compound. $t_R$: 0.73 min (LC-MS 2); ESI-MS: 532 [M+H]$^+$ (LC-MS 2).

EXAMPLE 74

6-(4-chlorophenyl)-1-isopropyl-5-(4-methoxy-1-methyl-1H-benzo[d][1,2,3]triazol-6-yl)-2-(2-methoxypyridin-3-yl)-5,6-dihydropyrrolo[3,4-d]imidazol-4(1H)-one

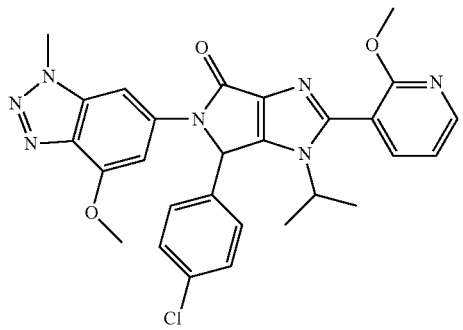 [SMILES: COc1ncccc1-c1nc2c(n1C(C)C)C(c1ccc(Cl)cc1)N(c1cc(OC)c3nnn(C)c3c1)C2=O]

The title compound was prepared in analogy to the procedure described for Example 1 using 2-bromo-6-(4-chlorophenyl)-1-isopropyl-5-(4-methoxy-1-methyl-1H-benzo[d][1,2,3]triazol-6-yl)-5,6-dihydropyrrolo[3,4-d]imidazol-4(1H)-one (Step 60.7) and 2-methoxy-3-pyridineboronic acid pinacolester under heating at 85° C. for 4 hr. The reaction mixture was concentrated in vacuo and the residue diluted with $CH_2Cl_2$ and $H_2O$. The aq. layer was separated off and extracted with $CH_2Cl_2$. Combined extracts were dried over $Na_2SO_4$, filtered and concentrated under reduced pressure. The crude product was purified by silica gel column chromatography [TBME/($CH_2Cl_2$+10% EtOH) 5-48% (EtOH+10% EtOH)] to afford the title compound. $t_R$: 1.05 min (LC-MS 2); ESI-MS: 544 [M+H]$^+$ (LC-MS 2).

EXAMPLE 75

6-(4-chlorophenyl)-5-(3,8-dimethyl-[1,2,4]triazolo[4,3-a]pyridin-6-yl)-1-isopropyl-2-(Piperidin-4-yl)-5,6-dihydropyrrolo[3,4-d]imidazol-4(1H)-one

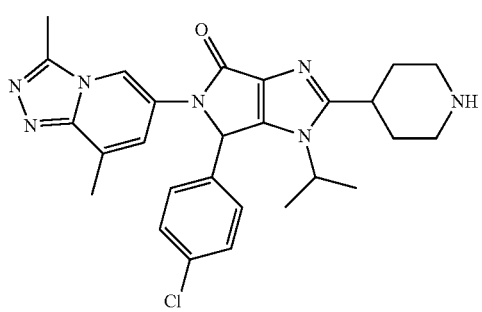 [SMILES: Cc1cc(N2C(=O)c3nc(C4CCNCC4)n(C(C)C)c3C2c2ccc(Cl)cc2)cn2c(C)nnc12]

Hydrogenation of 6-(4-chlorophenyl)-5-(3,8-dimethyl-[1,2,4]triazolo[4,3-a]pyridin-6-yl)-1-isopropyl-2-(1,2,3,6-tetrahydropyridin-4-yl)-5,6-dihydropyrrolo[3,4-d]imidazol-4(1H)-one (116 mg; 0.23 mmol) (Ex. 49) in EtOH (20 mL) in presence of Pd(OH)$_2$ (0.17 g, 20%) as described in Ex. 64 gave the title compound. $t_R$: 0.77 min (LC-MS 2); ESI-MS: 504 [M+H]$^+$ (LC-MS 2).

EXAMPLE 76 methyl 4-(6-(4-chlorophenyl)-5-(3,8-dimethyl-[1,2,4]triazolo[4,3-a]pyridin-6-yl)-1-isopropyl-4-oxo-1,4,5,6-tetrahydropyrrolo[3,4-d]imidazol-2-yl)piperidine-1-carboxylate

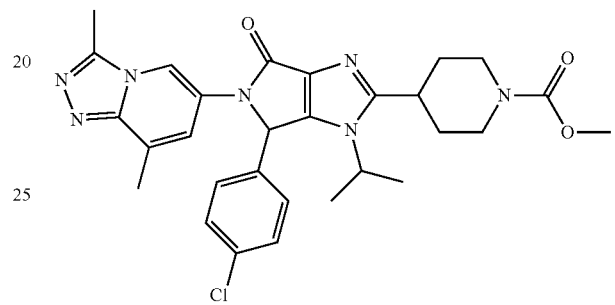

An ice-cooled solution of 6-(4-chlorophenyl)-5-(3,8-dimethyl-[1,2,4]triazolo[4,3-a]pyridin-6-yl)-1-isopropyl-2-(piperidin-4-yl)-5,6-dihydropyrrolo[3,4-d]imidazol-4(1H)-one (98 mg; 0.113 mmol) (Ex. 75) in $CH_2Cl_2$ (6 mL) and pyridine (1.2 mL) was treated with 2 portions of methyl chloroformate (each time 13 µL, 0.17 mmol). After 4 h the reaction mixture was poured into a solution of $NaHCO_3$ and extracted with 3 portions of $CH_2Cl_2$. The extracts were washed with brine, dried ($Na_2SO_4$), filtered and concentrated under reduced pressure. The crude product was purified by preparative HPLC (gradient 5-100% $CH_3CN$ in 20 min), followed by basic workup. $t_R$: 0.91 min (LC-MS 2); ESI-MS: 562 [M+H]$^+$ (LC-MS 2).

EXAMPLE 77

6-(4-chlorophenyl)-5-(1,4-dimethyl-1H-benzo[d][1,2,3]triazol-6-yl)-1-isopropyl-2-(2-methoxypyridin-3-yl)-5,6-dihydropyrrolo[3,4-d]imidazol-4(1H)-one

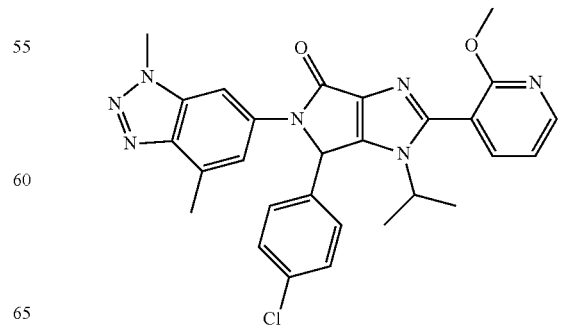

The title compound was prepared in analogy to the procedure described for Example 1 using 2-bromo-6-(4-chlorophenyl)-5-(1,4-dimethyl-1H-benzo[d][1,2,3]triazol-6-yl)-1-isopropyl-5,6-dihydropyrrolo[3,4-d]imidazol-4(1H)-one (Step 77.3) and 2-methoxy-3-pyridineboronic acid pinacolester under heating at 90° C. for 2½ hr. The reaction mixture was diluted with EtOAc and a solution of NaHCO$_3$. The aq. layer was separated off and extracted with EtOAc. Combined extracts were washed with brine, dried over Na$_2$SO$_4$, filtered and concentrated under reduced pressure. The crude product was purified by preparative HPLC (gradient 5-100% CH$_3$CN in 20 min), followed by basic workup. t$_R$: 1.09 min (LC-MS 2); ESI-MS: 528 [M+H]$^+$ (LC-MS 2).

Step 77.1: ethyl 2-bromo-5-((4-chlorophenyl)(0,4-dimethyl-1H-benzo[d][1,2,3]triazol-6-yl)amino)methyl)-1-isopropyl-1H-imidazole-4-carboxylate

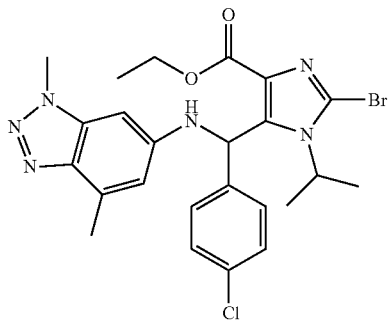 [SMILES: CCOC(=O)c1nc(Br)n(C(C)C)c1C(Nc1cc(C)c2nnn(C)c2c1)c1ccc(Cl)cc1]

The title compound was prepared in analogy to the procedure described for Step 1.9 using ethyl 2-bromo-5-((4-chlorophenyl)(hydroxy)methyl)-1-isopropyl-1H-imidazole-4-carboxylate (Step 9.6) and 1,4-dimethyl-1H-benzo[d][1,2,3]triazol-6-amine (Step 1.4). The reaction mixture was diluted with CH$_2$Cl$_2$ and cold 1 N HCl. The aq. layer was separated off and extracted with CH$_2$Cl$_2$. The organic layers were washed with aq. NaHCO$_3$, dried over Na$_2$SO$_4$, filtered and concentrated under reduced pressure. The crude product was used as such for the next step. t$_R$: 1.20 min (LC-MS 2); ESI-MS: 545/547 [M+H]$^+$ (LC-MS 2).

Step 77.2: 2-bromo-5-((4-chlorophenyl)((1,4-dimethyl-1H-benzo[d][1,2,3]triazol-6-yl)amino)methyl)-1-isopropyl-1H-imidazole-4-carboxylic acid

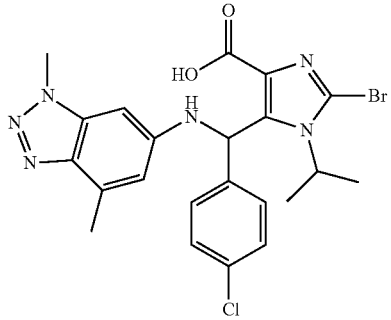 [SMILES: Cc1cc(NC(c2ccc(Cl)cc2)c2c(C(=O)O)nc(Br)n2C(C)C)cc2c1nnn2C]

The title compound was prepared in analogy to the procedure described in Step 1.10 using ethyl 2-bromo-5-((4-chlorophenyl)((1,4-dimethyl-1H-benzo[d][1,2,3]triazol-6-yl)amino)methyl)-1-isopropyl-1H-imidazole-4-carboxylate. The reaction mixture was acidified with 4 N HCl and then concentrated. The residue was stirred in CH$_2$Cl$_2$/MeOH 5:1. The suspension was filtered and the filtrate concentrated. t$_R$: 0.88 min (LC-MS 2); ESI-MS: 517/519 [M+H]$^+$.

Step 77.3: 2-bromo-6-(4-chlorophenyl)-5-(1,4-dimethyl-1H-benzo[d][1,2,3]triazol-6-yl)-1-isopropyl-5,6-dihydropyrrolo[3,4-d]imidazol-4(1H)-one

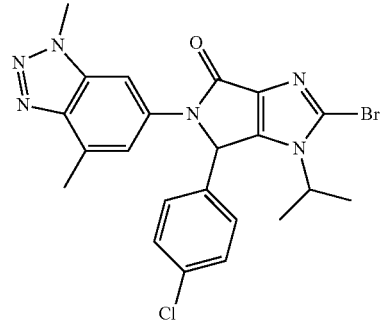 [SMILES: Cc1cc(N2C(=O)c3nc(Br)n(C(C)C)c3C2c2ccc(Cl)cc2)cc2c1nnn2C]

The title compound was prepared in analogy to the procedure described in Step 1.11 using 2-bromo-5-(((4-chlorophenyl)((1,4-dimethyl-1H-benzo[d][1,2,3]triazol-6-yl)amino)methyl)-1-isopropyl-1H-imidazole-4-carboxylic acid. The reaction mixture was diluted with CH$_2$Cl$_2$ and aq. NaHCO$_3$. The aq. layer was separated off and extracted with CH$_2$Cl$_2$. Combined extracts were washed with brine and dried over Na$_2$SO$_4$, filtered and concentrated under reduced pressure. Crystallisation from MeOH gave the title compound. More product could be isolated from the filtrate by silica gel column chromatography (CH$_2$Cl$_2$/EtOH 0-10% EtOH). t$_R$: 1.04 min (LC-MS 2); ESI-MS: 499/501 [M+H]$^+$ (LC-MS 2).

EXAMPLE 78

6-(4-chlorophenyl)-5-(1,4-dimethyl-1H-benzo[d][1,2,3]triazol-6-yl)-1-isopropyl-2-(1-methyl-1,2,3,6-tetrahydropyridin-4-yl)-5,6-dihydropyrrolo[3,4-d]imidazol-4(1H)-one

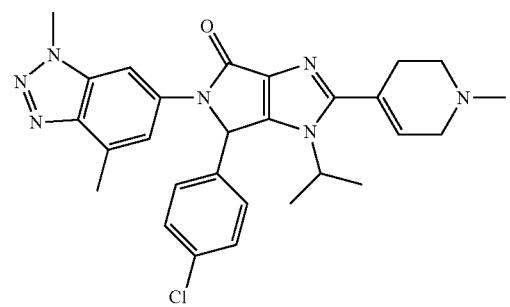 [SMILES: Cc1cc(N2C(=O)c3nc(C4=CCN(C)CC4)n(C(C)C)c3C2c2ccc(Cl)cc2)cc2c1nnn2C]

The title compound was prepared in analogy to the procedure described for Example 1 using 2-bromo-6-(4-chlorophenyl)-5-(1,4-dimethyl-1H-benzo[d][1,2,3]triazol-6-yl)-1-isopropyl-5,6-dihydropyrrolo[3,4-d]imidazol-4(1H)-one (Step 77.3) and 1-methyl-1,2,3,6- tetrahydropyridine-4 boronic acid pinacolester under heating at 90° C. for 4 hr. The reaction mixture was diluted with EtOAc and a solution of NaHCO₃. The aq. layer was separated off and extracted with EtOAc. Combined extracts were washed with brine, dried over Na₂SO₄, filtered and concentrated under reduced pressure. The crude product was purified by preparative HPLC (gradient 5-100% CH₃CN in 20 min), followed by basic workup. $t_R$: 0.89 min (LC-MS 2); ESI-MS: 516 [M+H]⁺ (LC-MS 2).

EXAMPLE 79

6-(4-chlorophenyl)-2-(3,6-dihydro-2H-pyran-4-yl)-5-(1,4-dimethyl-1H-benzo[d][1,2,3]triazol-6-yl)-1-isopropyl-5,6-dihydropyrrolo[3,4-d]imidazol-4(1H)-one

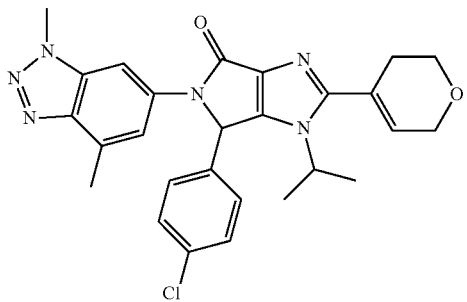 [SMILES: Cc1cc(N2C(=O)c3nc(C4=CCOCC4)n(C(C)C)c3C2c2ccc(Cl)cc2)cc2c1nnn2C]

The title compound was prepared in analogy to the procedure described for Example 1 using 2-bromo-6-(4-chlorophenyl)-5-(1,4-dimethyl-1H-benzo[d][1,2,3]triazol-6-yl)-1-isopropyl-5,6-dihydropyrrolo[3,4-d]imidazol-4(1H)-one (Step 77.3) and 3,6-dihydro-2H-pyran-4-boronic acid pinacolester under heating at 90° C. for 2½ hr. The reaction mixture was diluted with EtOAc and a solution of NaHCO₃. The aq. layer was separated off and extracted with EtOAc. Combined extracts were washed with brine, dried over Na₂SO₄, filtered and concentrated under reduced pressure. The crude product was purified by silica gel column chromatography (EtOAc/MeOH 0-10% MeOH) to afford the title compound. $t_R$: 1.00 min (LC-MS 2); ESI-MS: 503 [M+H]⁺ (LC-MS 2); ¹H NMR (600 MHz, DMSO-d₆) δ 7.81 (m, 1H), 7.51 (m, 1H), 7.44 (mb, 2H), 7.38 (d, 2H), 6.80 (s, 1H), 6.11 (m, 1H), 4.64 (m, 1H), 4.26 (m, 2H), 4.24 (s, 3H); 3.88 (m, 1H), 3.79 (m, 1H), 2.63 (m, 1H), 2.61 (s, 3H), 2.40 (m, 1H), 1.50 (d, 3H), 0.62 (d, 3H).

EXAMPLE 80

6-(4-chlorophenyl)-5-(1,4-dimethyl-1H-benzo[d][1,2,3]triazol-6-yl)-1-isopropyl-2-(tetrahydro-2H-pyran-4-yl)-5,6-dihydropyrrolo[3,4-d]imidazol-4(1H)-one

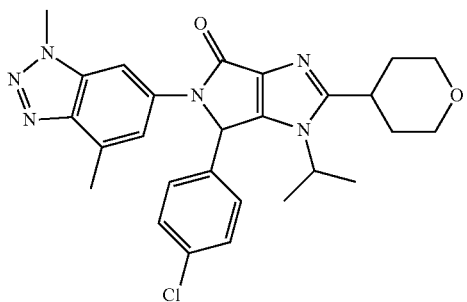 [SMILES: Cc1cc(N2C(=O)c3nc(C4CCOCC4)n(C(C)C)c3C2c2ccc(Cl)cc2)cc2c1nnn2C]

Hydrogenation of 6-(4-chlorophenyl)-2-(3,6-dihydro-2H-pyran-4-yl)-5-(1,4-dimethyl-1H-benzo[d][1,2,3]triazol-6-yl)-1-isopropyl-5,6-dihydropyrrolo[3,4-d]imidazol-4(1H)-one (66 mg; 0.13 mmol) (Ex. 79) in EtOH (10 mL) in presence of Pd(OH)₂ (0.02 g, 20%) as described in Ex. 64 and purification by preparative achiral SFC (column 2-EP/grad 18-23%; 11 min) gave the title compound. $t_R$: 0.99 min (LC-MS 2); ESI-MS: 505 [M+H]⁺ (LC-MS 2); ¹H NMR (600 MHz, DMSO-d₆) δ 7.78 (m, 1H), 7.49 (m, 1H), 7.41 (br. s, 2H), 7.37 (d, 2H), 6.75 (s, 1H), 4.62 (m, 1H), 4.23 (s, 3H), 3.94 (m, 2H), 3.49 (m, 2H), 3.16 (m, 1H), 2.60 (s, 3H), 1.90 (m, 1H), 1.79 (m, 3H), 1.48 (d, 3H), 0.59 (d, 3H).

EXAMPLE 81

(R)-6-(4-chlorophenyl)-2-(3,6-dihydro-2H-pyran-4-yl)-5-(1,4-dimethyl-1H-benzo[d][1,2,3]triazol-6-yl)-1-isopropyl-5,6-dihydropyrrolo[3,4-d]imidazol-4(1H)-one

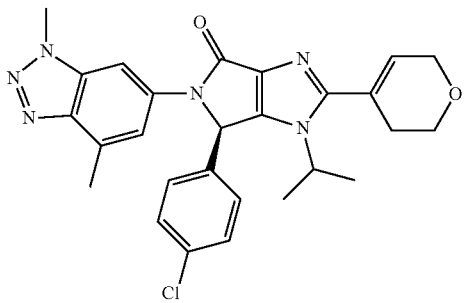 [SMILES: Cc1cc(N2C(=O)c3nc(C4=CCOCC4)n(C(C)C)c3[C@H]2c2ccc(Cl)cc2)cc2c1nnn2C]

The title compound (42 mg) was obtained enantiomerically pure (>99% ee) after chiral preparative chromatography (Chiralcel OD-H, 250×20 mm; mobile phase: heptane/EtOH 1:1; flow rate: 10 mL/min; detection 220 nm) of the racemic mixture of 6-((4-chlorophenyl)-2-(3,6-dihydro-2H-pyran-4-yl)-5-(1,4-dimethyl-1H-benzo[d][1,2,3]triazol-6-yl)-1-isopropyl-5,6-dihydropyrrolo[3,4-d]imidazol-4(1H)-one (Example 79; 100 mg). The second enantiomer (S)-6-(4-chlorophenyl)-2-(3,6-dihydro-2H-pyran-4-yl)-5-(1,4-dimethyl-1H-benzo[d][1,2,3]triazol-6-yl)-1-isopropyl-5,6-dihydropyrrolo[3,4-d]imidazol-4(1H)-one (43 mg) was obtained enantiomerically pure (>99% ee) via the same separation.

EXAMPLE 82

(R)-6-(4-chlorophenyl)-5-(1,4-dimethyl-1H-benzo[d][1,2,3]triazol-6-yl)-1-isopropyl-2-(tetrahydro-2H-pyran-4-yl)-5,6-dihydropyrrolo[3,4-d]imidazol-4(1H)-one

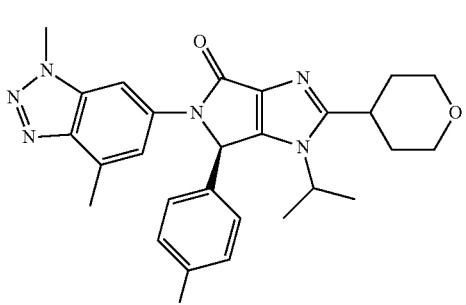

The title compound (65 mg) was obtained enantiomerically pure (>99% ee) after chiral preparative chromatography (Chiralpak AD-3, 250×4.6 mm; mobile phase: $CO_2$/(MeOH+0.05% $Et_2NH$) 0-40%; flow rate: 2.4 mL/min; detection 220 nm) of the racemic mixture of 6-(4-chlorophenyl)-5-(1,4-dimethyl-1H-benzo[d][1,2,3]triazol-6-yl)-1-isopropyl-2-(tetrahydro-2H-pyran-4-yl)-5,6-dihydropyrrolo[3,4-d]imidazol-4(1H)-one (Example 80; 132 mg). The second enantiomer (S)-6-((4-chlorophenyl)-5-(1,4-dimethyl-1H-benzo[d][1,2,3]triazol-6-yl)-1-isopropyl-2-(tetrahydro-2H-pyran-4-yl)-5,6-dihydropyrrolo[3,4-d]imidazol-4(1H)-one (57 mg) was obtained enantiomerically pure (>99% ee) via the same separation.

EXAMPLE 83

6-(4-chlorophenyl)-5-(1,4-dimethyl-1H-benzo[d][1,2,3]triazol-6-yl)-1-isopropyl-2-(6-methoxypyridin-3-yl)-5,6-dihydropyrrolo[3,4-d]imidazol-4(1H)-one

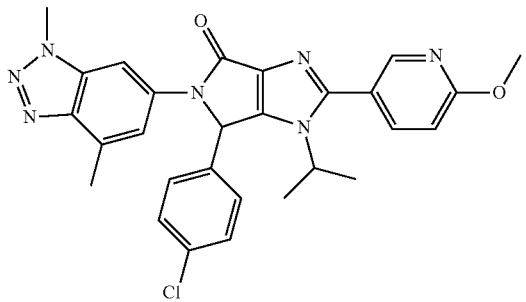 [SMILES: COc1ccc(-c2nc3c(n2C(C)C)C(c2ccc(Cl)cc2)N(c2cc(C)c4nnn(C)c4c2)C3=O)cn1]

The title compound was prepared in analogy to the procedure described for Example 1 using 2-bromo-6-(4-chlorophenyl)-5-(1,4-dimethyl-1H-benzo[d][1,2,3]triazol-6-yl)-1-isopropyl-5,6-dihydropyrrolo[3,4-d]imidazol-4(1H)-one (Step 77.3) and 2-methoxy-5-pyridineboronic acid pinacolester under heating at 90° C. for 2½ hr. The reaction mixture was diluted with EtOAc and a solution of $NaHCO_3$. The aq. layer was separated off and extracted with EtOAc. Combined extracts were washed with brine, dried over $Na_2SO_4$, filtered and concentrated under reduced pressure. The crude product was purified by preparative HPLC (gradient 5-100% $CH_3CN$ in 20 min), followed by basic workup. $t_R$: 1.08 min (LC-MS 2); ESI-MS: 528 $[M+H]^+$ (LC-MS 2).

EXAMPLE 84

(R)-6-(4-chlorophenyl)-2-(3,6-dihydro-2H-pyran-4-yl)-5-(3,8-dimethyl-[1,2,4]triazolo[4,3-a]pyridin-6-yl)-1-isopropyl-5,6-dihydropyrrolo[3,4-d]imidazol-4(1H)-one

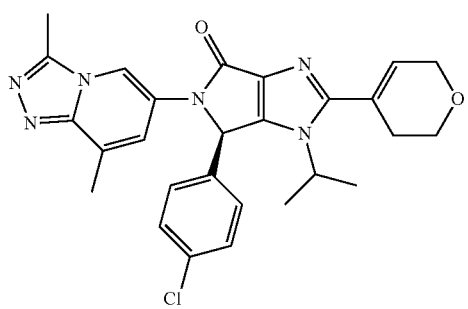 [SMILES: Cc1cc(N2C(=O)c3nc(C4=CCOCC4)n(C(C)C)c3[C@H]2c2ccc(Cl)cc2)cn2c(C)nnc12]

The title compound (45 mg) was obtained enantiomerically pure (>99% ee) after chiral preparative chromatography (Chiralpak AD-H, 250×4.6 mm; mobile phase: heptane/EtOH 6:4; flow rate: 1 mL/min; detection 210 nm) of the racemic mixture of 6-((4-chlorophenyl)-2-(3,6-dihydro-2H-pyran-4-yl)-5-(3,8-dimethyl-[1,2,4]triazolo[4,3-a]pyridin-6-yl)-1-isopropyl-5,6-dihydropyrrolo[3,4-d]imidazol-4(1H)-one (Example 14; 100 mg). The second enantiomer (S)-6-((4-chlorophenyl)-2-(3,6-dihydro-2H-pyran-4-yl)-5-(3,8-dimethyl-[1,2,4]triazolo[4,3-a]pyridin-6-yl)-1-isopropyl-5,6-dihydropyrrolo[3,4-d]imidazol-4(1H)-one (42 mg) was obtained enantiomerically pure (>99% ee) via the same separation.

EXAMPLE 85

(R)-6-(4-chlorophenyl)-5-(3,8-dimethyl-[1,2,4]triazolo[4,3-a]pyridin-6-yl)-1-isopropyl-2-(1-methyl-1,2,5,6-tetrahydropyridin-3-yl)-5,6-dihydropyrrolo[3,4-d]imidazol-4(1H-one

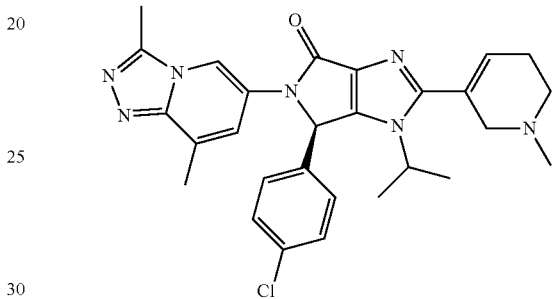

The title compound (66 mg) was obtained enantiomerically pure (>99% ee) after chiral preparative chromatography (Chiralpak AD-H, 250×4.6 mm; mobile phase: $CO_2$/(iPrOH+0.05% $Et_2NH$) 0-50%; flow rate: 2 mL/min; detection 220 nm) of the racemic mixture of 6-(4-chlorophenyl)-5-(3,8-dimethyl-[1,2,4]triazolo[4,3-a]pyridin-6-yl)-1-isopropyl-2-(1-methyl-1,2,5,6-tetrahydropyridin-3-yl)-5,6-dihydropyrrolo[3,4-d]imidazol-4(1H)-one (Example 12; 151 mg). The second enantiomer (S)-6-((4-chlorophenyl)-5-(3,8-dimethyl-[1,2,4]triazolo[4,3-a]pyridin-6-yl)-1-isopropyl-2-(1-methyl-1,2,5,6-tetrahydropyridin-3-yl)-5,6-dihydropyrrolo[3,4-d]imidazol-4(1H)-one (66 mg) was obtained enantiomerically pure (>99% ee) via the same separation.

EXAMPLE 86

6-(4-chlorophenyl)-5-(3,8-dimethyl-[1,2,4]triazolo[4,3-a]pyridin-6-yl)-1-isopropyl-2-(tetrahydro-2H-pyran-4-yl)-5,6-dihydropyrrolo[3,4-d]imidazol-4(1H)-one

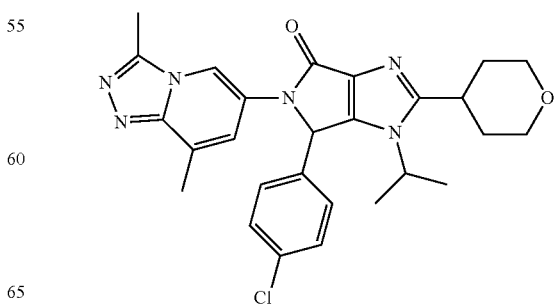

Hydrogenation of 6-(4-chlorophenyl)-2-(3,6-dihydro-2H-pyran-4-yl)-5-(3,8-dimethyl-[1,2,4]triazolo[4,3-a]pyridin-6-yl)-1-isopropyl-5,6-dihydropyrrolo[3,4-d]imidazol-4(1H)-one (Example 14; 50 mg) in EtOH (4 mL) in presence of Pd(OH)$_2$ (0.03 g, 20%) as described in Ex. 64 and purification by preparative achiral SFC (column 2-EP/grad 15-20%; 11 min) gave the title compound. $t_R$: 0.87 min (LC-MS 2); ESI-MS: 505 [M+H]$^+$ (LC-MS 2); $^1$H NMR (600 MHz, DMSO-d$_6$) δ 7.78 (s, 1H), 7.49 (s, 1H), 7.41 (br. s, 2H), 7.37 (d, 2H), 6.75 (s, 1H), 4.62 (m, 1H), 4.23 (s, 3H), 3.94 (m, 2H), 3.48 (m, 2H), 3.15 (m, 1H), 2.60 (s, 3H), 1.90 (m, 1H), 1.79 (m, 3H), 1.48 (d, 3H), 0.59 (d, 3H).

EXAMPLE 87

(R)-6-(4-chlorophenyl)-5-(3,8-dimethyl-[1,2,4]triazolo[4,3-a]pyridin-6-yl)-1-isopropyl-2-(tetrahydro-2H-pyran-4-yl)-5,6-dihydropyrrolo[3,4-d]imidazol-4(1H)-one

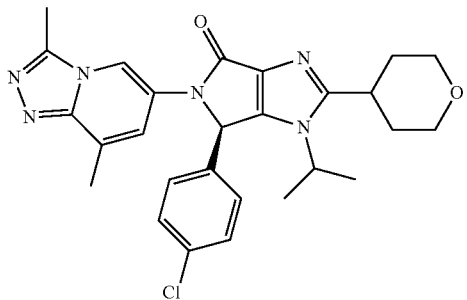 [SMILES: Cc1cc(N2C(=O)c3nc(C4CCOCC4)n(C(C)C)c3[C@H]2c2ccc(Cl)cc2)cn2c(C)nnc12]

The title compound (25 mg) was obtained enantiomerically pure (>99% ee) after chiral preparative chromatography (Chiralcel OD-H, 250×4.6 mm; mobile phase: heptane/EtOH 1:1; flow rate: 1 mL/min; detection 220 nm) of the racemic mixture of 6-((4-chlorophenyl)-5-(3,8-dimethyl-[1,2,4]triazolo[4,3-a]pyridin-6-yl)-1-isopropyl-2-(tetrahydro-2H-pyran-4-yl)-5,6-dihydropyrrolo[3,4-d]imidazol-4(1H)-one (Example 86; 58 mg). The second enantiomer (S)-6-(4-chlorophenyl)-5-(3,8-dimethyl-[1,2,4]triazolo[4,3-a]pyridin-6-yl)-1-isopropyl-2-(tetrahydro-2H-pyran-4-yl)-5,6-dihydropyrrolo[3,4-d]imidazol-4(1H)-one (26 mg) was obtained enantiomerically pure (>99% ee) via the same separation.

EXAMPLE 88

6-(4-chlorophenyl)-2-(3,6-dihydro-2H-pyran-4-yl)-5-(3-(fluoromethyl)-8-methyl-[1,2,4]triazolo[4,3-a]pyridin-6-yl)-1-isopropyl-5,6-dihydropyrrolo[3,4-d]imidazol-4(1H)-one

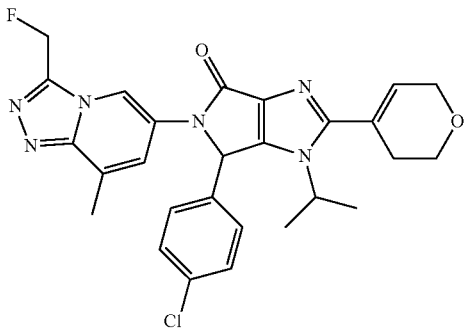 [SMILES: Cc1cc(N2C(=O)c3nc(C4=CCOCC4)n(C(C)C)c3C2c2ccc(Cl)cc2)cn2c(CF)nnc12]

The title compound was prepared in analogy to the procedure described for Example 1 using 2-bromo-6-(4-chlorophenyl)-5-(3-(fluoromethyl)-8-methyl-[1,2,4]triazolo[4,3-a]pyridin-6-yl)-1-isopropyl-5,6-dihydropyrrolo[3,4-d]imidazol-4(1H)-one (Step 88.8) and 3,6-dihydro-2H-pyran-4-boronic acid pinacolester under heating at 90° C. for 5½ hr. The reaction mixture was diluted with EtOAc and a solution of NaHCO$_3$. The aq. layer was separated off and extracted with EtOAc. Combined extracts were washed with brine, dried over Na$_2$SO$_4$, filtered and concentrated under reduced pressure. The crude product was purified by preparative HPLC (gradient 5-100% CH$_3$CN in 20 min), followed by basic workup. $t_R$: 1.00 min (LC-MS 2); ESI-MS: 521 [M+H]$^+$ (LC-MS 2); $^1$H NMR (600 MHz, DMSO-d$_6$) δ 8.71 (s, 1H), 7.63 (s, 1H), 7.41 (m, 4H), 6.76 (s, 1H), 6.12 (m, 1H), 5.94 (ddd, 2H), 4.65 (hept, 1H), 4.26 (m, 2H), 3.88 (m, 1H), 3.80 (m, 1H), 2.62 (m, 1H), 2.51 (s, 3H), 2.40 (m, 1H), 1.48 (d, 3H), 0.64 (d, 3H).

Step 88.1: 2-hydrazinyl-3-methyl-5-nitropyridine

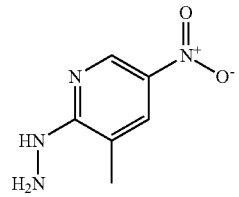

Hydrazine hydrate (12.7 mL, 0.26 mol) was added to a solution of 2-chloro-3-methyl-5-nitropyridine (15 g, 87 mmol) in EtOH (150 ml). This solution was stirred for 2 hr at 60° C. Cooling in an ice bath led to crystalline product, which was filtered off and washed with H$_2$O and Et$_2$O. $t_R$: 0.42 min (LC-MS 2); ESI-MS: 169 [M+H]$^+$ (LC-MS 2)

Step 88.2: 2-fluoroacetic anhydride

N,N'-Dicyclohexylcarbodiimide (14.5 g, 70.5 mmol) was added to a solution of 2-fluoroacetic acid (5 g, 64 mmol) in THF (64 ml). This suspension was stirred for 2 h at rt. The precipitate was filtered off and the filtrate used directly for Step 88.3.

Step 88.3: 2-fluoro-N'-(3-methyl-5-nitropyridin-2-yl)acetohydrazide

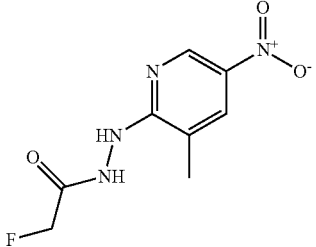 [SMILES: Cc1cc([N+](=O)[O-])cnc1NNC(=O)CF]

2-Hydrazinyl-3-methyl-5-nitropyridine (5 g, 29.7 mmol) was added to a solution of 2-fluoroacetic anhydride in THF (65.4 ml, =32 mmol). The reaction mixture was stirred for 10 min and then partially concentrated. Dilution of the residue with H$_2$O (0.25 L) led to precipitation of the product, which was filtered off and washed with H$_2$O and a small amount of Et$_2$O. t$_R$: 0.49 min (LC-MS 2); ESI-MS: 229 [M+H]$^+$ (LC-MS 2); contains 40% 1,3-dicyclohexylurea.

Step 88.4: 3-(fluoromethyl)-8-methyl-6-nitro-[1,2,4]triazolo[4,3-a]pyridine

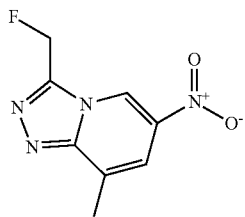

To a solution of 2-fluoro-N'-(3-methyl-5-nitropyridin-2-yl)acetohydrazide (9.1 g, 23.9 mmol) in acetonitrile (150 mL) was added DIPEA (3.13 mL, 18 mmol), followed by dropwise addition of POCl$_3$ (3.35 mL, 35.9 mmol). The reaction mixture was stirred for 1 h at rt and 16 h at 70° C., cooled to rt and concentrated, then poured into a small amount of warm water and stirred for 30 min. After neutralization with NaHCO$_3$ (10 g, pH 4), the product was extracted with 3 portions of EtOAc/MeOH 9:1. The organic layers were washed with brine, dried with MgSO$_4$ and concentrated. Purification by silica gel column chromatography [hexane/(EtOAc/MeOH 9:1) 10-100% (EtOAc/MeOH 9:1)] gave the title compound. t$_R$: 0.59 min (LC-MS 2); ESI-MS: 211 [M+H]$^+$ (LC-MS 2).

Step 88.5: 3-(fluoromethyl)-8-methyl-[1,2,4]triazolo[4,3-a]pyridin-6-amine

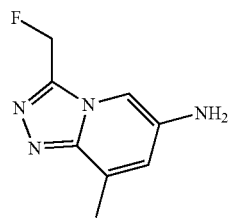

A mixture of 3-(fluoromethyl)-8-methyl-6-nitro-[1,2,4]triazolo[4,3-a]pyridine (4.3 g, 20.46 mmol) and Pd/C 10% (1.3 g) in MeOH (50 mL) was hydrogenated at 55° C. during 6 h. The catalyst was filtered off and the filtrate concentrated. Purification by silica gel column chromatography [hexane/(EtOAc/MeOH 9:1) 50-100% (EtOAc/MeOH 9:1)] gave the title compound. t$_R$: 0.40 min (LC-MS 2); ESI-MS: 181 [M+H]$^+$ (LC-MS 2); $^1$H NMR (400 MHz, DMSO-d$_6$) δ 7.48 (s, 1H), 6.89 (s, 1H), 5.86 (d, J=49 Hz, 2H), 5.26 (s, 2H), 2.49 (s, 3H).

Step 88.6: ethyl 2-bromo-5-((4-chlorophenyl)((3-(fluoromethyl)-8-methyl-[1,2,4]triazolo[4,3-a]pyridin-6-yl)amino)methyl)-1-isopropyl-1H-imidazole-4-carboxylate

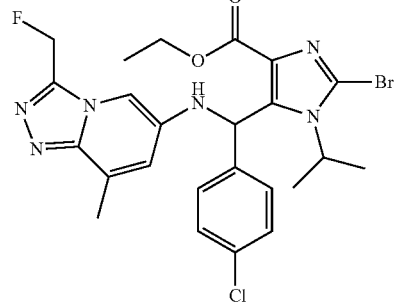

The title compound was prepared in analogy to the procedure described for Step 1.9 using ethyl 2-bromo-5-((4-chlorophenyl)(hydroxy)methyl)-1-isopropyl-1H-imidazole-4-carboxylate (Step 9.6) and 3-(fluoromethyl)-8-methyl-[1,2,4]triazolo[4,3-a]pyridin-6-amine. t$_R$: 1.12 min (LC-MS 2); ESI-MS: 563/565 [M+H]$^+$ (LC-MS 2).

Step 88.7: 2-bromo-5-((4-chlorophenyl)((3-(fluoromethyl)-8-methyl-[1,2,4]triazolo[4,3-a]pyridin-6-yl)amino)methyl)-1-isopropyl-1H-imidazole-4-carboxylic acid

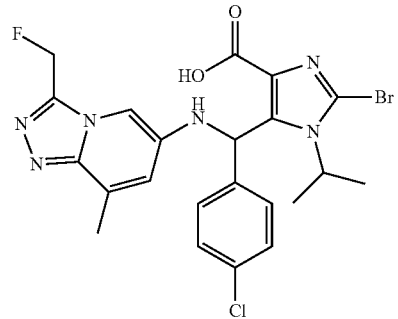 [SMILES: Cc1cc(NC(c2ccc(Cl)cc2)c2c(C(=O)O)nc(Br)n2C(C)C)cn2c(CF)nnc12]

The title compound was prepared in analogy to the procedure described in Step 1.10 using ethyl 2-bromo-5-((4-chlorophenyl)((3-(fluoromethyl)-8-methyl-[1,2,4]triazolo[4,3-a]pyridin-6-yl)amino)methyl)-1-isopropyl-1H-imidazole-4-carboxylate. The reaction mixture was acidified with 4 N HCl and then partially concentrated. Dilution with water led to crystalline product which was filtered off. t$_R$: 0.94 min (LC-MS 2); ESI-MS: 535/537 [M+H]$^+$ (LC-MS 2).

Step 88.8: 2-bromo-6-(4-chlorophenyl)-5-(3-(fluoromethyl)-8-methyl-[1,2,4]triazolo[4,3-a]pyridin-6-yl)-1-isopropyl-5,6-dihydropyrrolo[3,4-d]imidazol-4(1H)-one

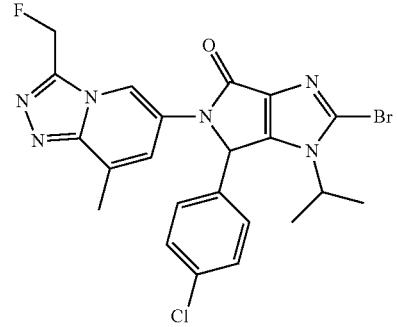 [SMILES: Cc1cc(N2C(=O)c3nc(Br)n(C(C)C)c3C2c2ccc(Cl)cc2)cn2c(CF)nnc12]

The title compound was prepared in analogy to the procedure described in Step 1.11 using 2-bromo-5-((4-chlorophenyl)((3-(fluoromethyl)-8-methyl-[1,2,4]triazolo[4,3-a]pyridin-6-yl)amino)methyl)-1-isopropyl-1H-imidazole-4-carboxylic acid. The reaction mixture was diluted with $CH_2Cl_2$ and a solution of $NaHCO_3$. The aq. layer was separated off and extracted with $CH_2Cl_2$. Combined extracts were washed with brine, dried over $Na_2SO_4$, filtered and concentrated under reduced pressure. Crystallization from MeOH afforded the desired product. More product could be obtained by silica gel column chromatography ($CH_2Cl_2$/MeOH 0-10% MeOH). $t_R$: 0.97 min (LC-MS 2); ESI-MS: 517/519 [M+H]$^+$ (LC-MS 2).

EXAMPLE 89

6-(4-chlorophenyl)-5-(3-(fluoromethyl)-8-methyl-[1,2,4]triazolo[4,3-a]pyridin-6-yl)-1-isopropyl-2-(2-methoxypyridin-3-yl)-5,6-dihydropyrrolo[3,4-d]imidazol-4(1H)-one

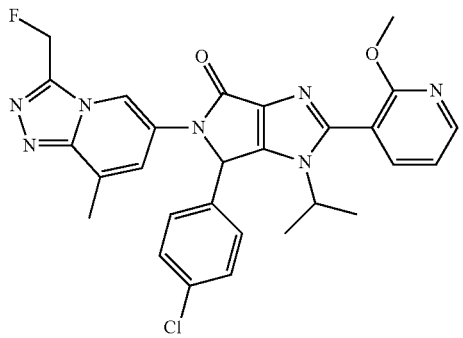 [SMILES: COc1ncccc1-c1nc2c(n1C(C)C)C(c1ccc(Cl)cc1)N(c1cc(C)c3nnc(CF)n3c1)C2=O]

The title compound was prepared in analogy to the procedure described for Example 1 using 2-bromo-6-(4-chlorophenyl)-5-(3-(fluoromethyl)-8-methyl-[1,2,4]triazolo[4,3-a]pyridin-6-yl)-1-isopropyl-5,6-dihydropyrrolo[3,4-d]imidazol-4(1H)-one (Step 88.8) and 2-methoxy-3-pyridineboronic acid under heating at 90° C. for 2 hr. The reaction mixture was diluted with EtOAc and a solution of $NaHCO_3$. The aq. layer was separated off and extracted with EtOAc. Combined extracts were washed with brine, dried over $Na_2SO_4$, filtered and concentrated under reduced pressure. The crude product was purified by preparative HPLC (gradient 5-100% $CH_3CN$ in 20 min), followed by basic workup. $t_R$: 0.99 min (LC-MS 2); ESI-MS: 546 [M+H]$^+$ (LC-MS 2).

EXAMPLE 90

6-(4-chlorophenyl)-5-(3-(fluoromethyl)-8-methyl-[1,2,4]triazolo[4,3-a]pyridin-6-yl)-1-isopropyl-2-(2,2,6,6-tetramethyl-1,2,3,6-tetrahydropyridin-4-yl)-5,6-dihydropyrrolo[3,4-d]imidazol-4(1H)-one

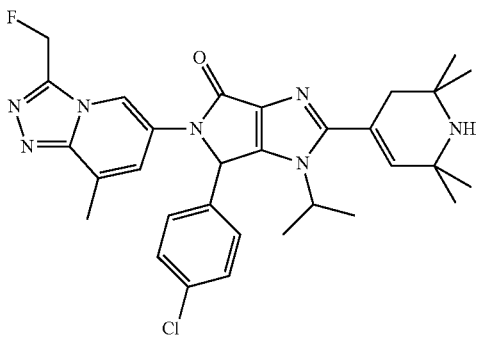 [SMILES: Cc1cc(N2C(=O)c3nc(C4=CC(C)(C)NC(C)(C)C4)n(C(C)C)c3C2c2ccc(Cl)cc2)cn2c(CF)nnc12]

The title compound was prepared in analogy to the procedure described for Example 1 using 2-bromo-6-(4-chlorophenyl)-5-(3-(fluoromethyl)-8-methyl-[1,2,4]triazolo[4,3-a]pyridin-6-yl)-1-isopropyl-5,6-dihydropyrrolo[3,4-d]imidazol-4(1H)-one (Step 88.8) and 2,2,6,6-tetramethyl-1,2,3,6-tetrahydro-4-pyridineboronic acid pinacol ester under heating at 90° C. for 4½ hr. The reaction mixture was diluted with EtOAc and a solution of $NaHCO_3$. The aq. layer was separated off and extracted with EtOAc. Combined extracts were washed with brine, dried over $Na_2SO_4$, filtered and concentrated under reduced pressure. The crude product was purified by preparative HPLC (gradient 5-100% $CH_3CN$ in 20 min), followed by basic workup. $t_R$: 0.86 min (LC-MS 2); ESI-MS: 576 [M+H]$^+$ (LC-MS 2).

EXAMPLE 91

6-(4-chlorophenyl)-5-(3-(fluoromethyl)-8-methyl-[1,2,4]triazolo[4,3-a]pyridin-6-yl)-1-isopropyl-2-(1-methyl-1,2,5,6-tetrahydropyridin-3-yl)-5,6-dihydropyrrolo[3,4-d]imidazol-4(1H-one

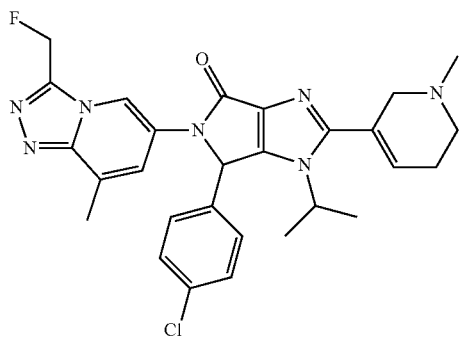 [SMILES: Cc1cc(N2C(=O)c3nc(C4=CCCN(C)C4)n(C(C)C)c3C2c2ccc(Cl)cc2)cn2c(CF)nnc12]

The title compound was prepared in analogy to the procedure described for Example 1 using 2-bromo-6-(4-chlorophenyl)-5-(3-(fluoromethyl)-8-methyl-[1,2,4]triazolo[4,3-a]pyridin-6-yl)-1-isopropyl-5,6-dihydropyrrolo[3,4-d]imidazol-4(1H)-one (Step 88.8) and 1-methyl-5-(4,4,4,5-tetramethyl-1,3,2-dioxaborolan-2-yl)-1,2,3,6-tetrahydropyridine under heating at 90° C. for 4 hr. The reaction mixture was diluted with EtOAc and a solution of $NaHCO_3$. The aq. layer was separated off and extracted with EtOAc. Combined extracts were washed with brine, dried over $Na_2SO_4$, filtered and concentrated under reduced pressure. The crude product was purified by preparative achiral SFC (column PPU/grad 30-35%; 11 min). $t_R$: 0.68 min (LC-MS 2); ESI-MS: 534 [M+H]$^+$ (LC-MS 2).

EXAMPLE 92

6-(4-chlorophenyl)-2-(2,5-dihydrofuran-3-yl)-5-(3-(fluoromethyl)-8-methyl-[1,2,4]triazolo[4,3-a]pyridin-6-yl)-1-isopropyl-5,6-dihydropyrrolo[3,4-d]imidazol-4(1H)-one

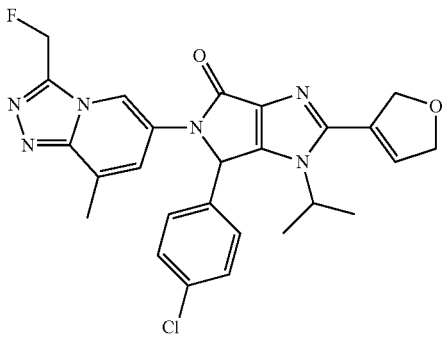 [SMILES: Cc1cc(N2C(=O)c3nc(C4=CCOC4)n(C(C)C)c3C2c2ccc(Cl)cc2)cn2c(CF)nnc12]

The title compound was prepared in analogy to the procedure described for Example 1 using 2-bromo-6-(4-chlorophenyl)-5-(3-(fluoromethyl)-8-methyl-[1,2,4]triazolo[4,3-a]pyridin-6-yl)-1-isopropyl-5,6-dihydropyrrolo[3,4-d]imidazol-4(1H)-one (Step 88.8) and 2-(2,5-dihydrofuran-3-yl)-4,4,5,5-tetramethyl-1,3,2-dioxaborolane under heating at 90° C. for 1 hr. The reaction mixture was diluted with EtOAc and a solution of NaHCO₃. The aq. layer was separated off and extracted with EtOAc. Combined extracts were washed with brine, dried over Na₂SO₄, filtered and concentrated under reduced pressure. The crude product was purified by preparative achiral SFC (column 4-EP/grad 20-25%; 11 min). $t_R$: 0.91 min (LC-MS 2); ESI-MS: 507 [M+H]⁺ (LC-MS 2).

EXAMPLE 93

6-(4-chlorophenyl)-2-(3,6-dihydro-2H-pyran-4-yl)-5-(1,4-dimethyl-1H-benzo[d][1,2,3]triazol-6-yl)-1-(oxetan-3-yl)-5,6-dihydropyrrolo[3,4-d]imidazol-4(1H)-one

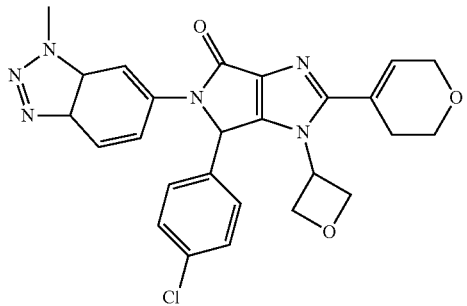 [SMILES: CN1N=NC2C=CC(N3C(=O)c4nc(C5=CCOCC5)n(C5COC5)c4C3c3ccc(Cl)cc3)=CC21]

The title compound was prepared in analogy to the procedure described for Example 1 using 2-bromo-6-((4-chlorophenyl)-5-(1,4-dimethyl-1H-benzo[d][1,2,3]triazol-6-yl)-1-(oxetan-3-yl)-5,6-dihydropyrrolo[3,4-d]imidazol-4(1H)-one (Step 93.6) and 3,6-dihydro-2H-pyran-4-boronic acid pinacolester under heating at 90° C. for 1½ hr. The reaction mixture was diluted with EtOAc and a solution of NaHCO₃. The aq. layer was separated off and extracted with EtOAc. Combined extracts were washed with brine, dried over Na₂SO₄, filtered and concentrated under reduced pressure. The crude product was purified by preparative achiral SFC (column PPU/grad 21-26%; 11 min). $t_R$: 0.89 min (LC-MS 2). $t_R$: 1.00 min (LC-MS 2); ESI-MS: 517 [M+H]⁺ (LC-MS 2); ¹H NMR (600 MHz, DMSO-d₆) δ 7.81 (s, 1H), 7.51 (s, 1H), 7.44 (d, 2H), 7.35 (d, 2H), 7.00 (s, 1H), 5.96 (s, 1H), 5.55 (m, 1H), 4.98 (t, 1H), 4.86 (t, 1H), 4.54 (t, 1H), 4.26 (m, 1H), 4.24 (s, 3H), 4.19 (m, 1H), 3.96 (t, 1H), 3.89 (m, 1H), 3.74 (m, 1H), 2.67 (m, 1H), 2.62 (s, 3H), 2.36 (m, 1H).

Step 93.1: ethyl 1-(oxetan-3-yl)-1H-imidazole-4-carboxylate

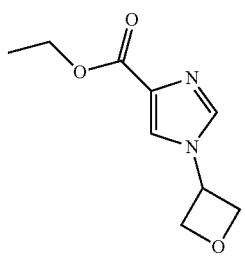

A stirred mixture of (Z)-ethyl 3-(dimethylamino)-2-isocyanoacrylate (Step 1.5) (4.8 g, 28.5 mmol) and 3-oxetamine (6.5 g, 86 mmol) in n-BuOH (3 mL) was heated at 70° C. during 16 hr. The reaction mixture was concentrated under reduced pressure and the residue purified by silica gel column chromatography (CH₂Cl₂/MeOH 0-10% MeOH). $t_R$: 0.45 min (LC-MS 1); ESI-MS: 179 [M+H]⁺ (LC-MS 1).

Step 93.2: ethyl 2-bromo-1-(oxetan-3-yl)-1H-imidazole-4-carboxylate

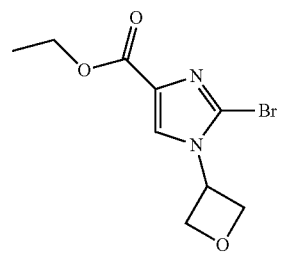

A mixture of ethyl 1-(oxetan-3-yl)-1H-imidazole-4-carboxylate (1.10 g, 4.49 mmol), K₃PO₄ (1.43 g, 6.73 mmol) and NBS (1.00 g, 5.6 mmol) in THF (27 mL) was stirred for 16 hr at rt. To drive the reaction to completion another portion of NBS (0.56 g) was added and stirring continued for 16 hr. The suspension was filtered and the filtrate concentrated. The residue was dissolved in EtOAc and a solution of NaHCO₃. The aq. layer was separated off and extracted with EtOAc. Combined extracts were washed with brine, dried over Na₂SO₄, filtered and concentrated. The crude product was purified by preparative HPLC (gradient 5-100% CH₃CN in 20 min), followed by basic workup. $t_R$: 0.58 min (LC-MS 2) $t_R$: 0.97 min (LC-MS 2); ESI-MS: 255/257 [M+H]⁺ (LC-MS 2).

Step 93.3: ethyl 2-bromo-5((4-chlorophenyl)(hydroxy)methyl)-1-(oxetan-3-yl)-1H-imidazole-4-carboxylate

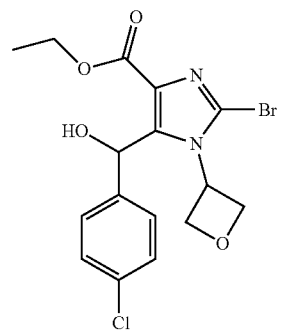 [SMILES: CCOC(=O)c1nc(Br)n(C2COC2)c1C(O)c1ccc(Cl)cc1]

The title compound was prepared in analogy to the procedure described for Step 9.6 using ethyl 2-bromo-1-(oxetan-3-yl)-1H-imidazole-4-carboxylate. Crystallization from iPr₂O gave the title compound. More product could be isolated from the filtrate by preparative achiral SFC (column 4-EP/grad 11-16%; 11 min). $t_R$: 0.89 min (LC-MS 2) $t_R$: 0.97 min (LC-MS 2); ESI-MS: 415/417 [M+H]⁺ (LC-MS 2).

Step 93.4: ethyl 2-bromo-5-((4-chlorophenyl)((1,4-dimethyl-1H-benzo[d][1,2,3]triazol-6-yl)amino)methyl)-1-(oxetan-3-yl)-1H-imidazole-4-carboxylate

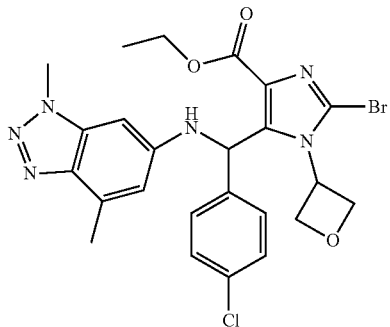 [SMILES: CCOC(=O)c1nc(Br)n(C2COC2)c1C(Nc1cc(C)c2nnn(C)c2c1)c1ccc(Cl)cc1]

The title compound was prepared in analogy to the procedure described for Step 1.9 using ethyl 2-bromo-5-((4-chlorophenyl)(hydroxy)methyl)-1-(oxetan-3-yl)-1H-imidazole-4-carboxylate and 1,4-dimethyl-1H-benzo[d][1,2,3]triazol-6-amine (Step 1.4). The reaction mixture was diluted with CH$_2$Cl$_2$ and cold 1 N HCl. The aq. layer was separated off and extracted with CH$_2$Cl$_2$. The organic layers were washed with aq. NaHCO$_3$, dried over Na$_2$SO$_4$, filtered and concentrated under reduced pressure. The crude product was used as such for the next step. t$_R$: 1.10 min (LC-MS 2); ESI-MS: 559/561 [M+H]$^+$ (LC-MS 2).

Step 93.5: 2-bromo-5-((4-chlorophenyl)(0,4-dimethyl-1H-benzo[d][1,2,3]triazol-6-yl)amino)methyl)-1-(oxetan-3-yl)-1H-imidazole-4-carboxylic acid

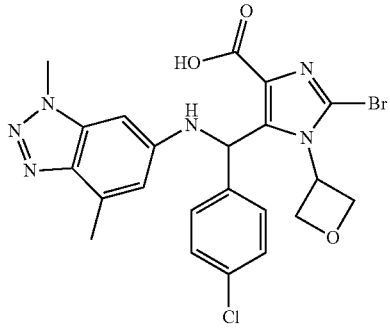 [SMILES: Cc1cc(NC(c2ccc(Cl)cc2)c2c(C(=O)O)nc(Br)n2C2COC2)cc2c1nnn2C]

The title compound was prepared in analogy to the procedure described in Step 1.10 using ethyl 2-bromo-5-((4-chlorophenyl)((1,4-dimethyl-1H-benzo[d][1,2,3]triazol-6-yl)amino)methyl)-1-(oxetan-3-yl)-1H-imidazole-4-carboxylate. The reaction mixture was acidified with 4 N HCl and then concentrated. The residue was stirred in CH$_2$Cl$_2$/MeOH 5:1. The suspension was filtered and the filtrate concentrated. t$_R$: 0.90 min (LC-MS 2); ESI-MS: 531/533 [M+H]$^+$.

Step 93.6: 2-bromo-6-(4-chlorophenyl)-5-(1,4-dimethyl-1H-benzo[d][1,2,3]triazol-6-yl)-1-(oxetan-3-yl)-5,6-dihydropyrrolo[3,4-d]imidazol-4(1H)-one

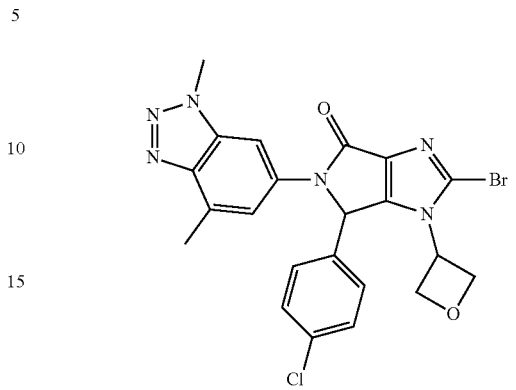

The title compound was prepared in analogy to the procedure described in Step 1.11 using 2-bromo-5-((4-chlorophenyl)((1,4-dimethyl-1H-benzo[d][1,2,3]triazol-6-yl)amino)methyl)-1-(oxetan-3-yl)-1H-imidazole-4-carboxylic acid. The reaction mixture was diluted with CH$_2$Cl$_2$ and aq. NaHCO$_3$. The aq. layer was separated off and extracted with CH$_2$Cl$_2$. Combined extracts were washed with brine and dried over Na$_2$SO$_4$, filtered and concentrated under reduced pressure. Crystallisation from MeOH gave the title compound. t$_R$: 0.95 min (LC-MS 2); ESI-MS: 413/515 [M+H]$^+$ (LC-MS 2).

EXAMPLE 94

6-(4-chlorophenyl)-5-(1,4-dimethyl-1H-benzo[d][1,2,3]triazol-6-yl)-2-methyl-1-(oxetan-3-yl)-5,6-dihydropyrrolo[3,4-d]imidazol-4(1H)-one

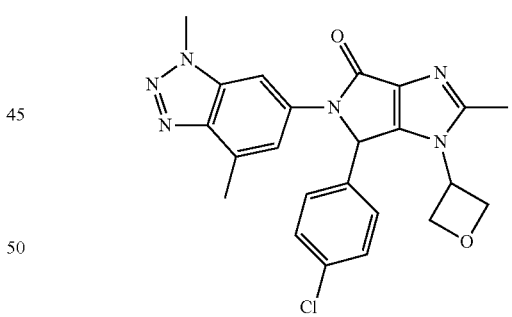

The title compound was prepared in analogy to the procedure described for Example 1 using 2-bromo-6-(4-chlorophenyl)-5-(1,4-dimethyl-1H-benzo[d][1,2,3]triazol-6-yl)-1-(oxetan-3-yl)-5,6-dihydropyrrolo[3,4-d]imidazol-4(1H)-one (Step 93.6) and trimethylboroxine under heating at 90° C. for 3 hr. The reaction mixture was diluted with EtOAc and a solution of NaHCO$_3$. The aq. layer was separated off and extracted with EtOAc. Combined extracts were washed with brine, dried over Na$_2$SO$_4$, filtered and concentrated under reduced pressure. The crude product was purified by preparative HPLC (gradient 5-100% CH$_3$CN in 20 min), followed by basic workup. t$_R$: 0.89 min (LC-MS 2). t$_R$: 0.83 min (LC-MS 2); ESI-MS: 449 [M+H]$^+$ (LC-MS 2).

EXAMPLE 95

6(4-chlorophenyl)-2-cyclopropyl-5-(1,4-dimethyl-1H-benzo[d][1,2,3]triazol-6-yl)-1-(oxetan-3-yl)-5,6-dihydropyrrolo[3,4-d]imidazol-4(1H)-one

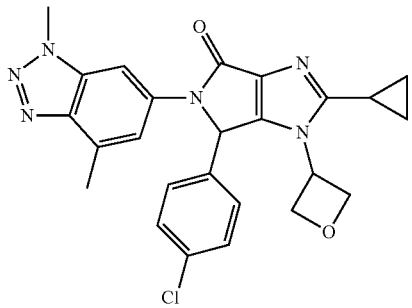 [SMILES: Cc1cc(N2C(=O)c3nc(C4CC4)n(C4COC4)c3C2c2ccc(Cl)cc2)cc2c1nnn2C]

The title compound was prepared in analogy to the procedure described for Example 13 using 2-bromo-6-(4-chlorophenyl)-5-(1,4-dimethyl-1H-benzo[d][1,2,3]triazol-6-yl)-1-(oxetan-3-yl)-5,6-dihydropyrrolo[3,4-d]imidazol-4 (1H)-one (Step 93.6) and potassium cyclopropyltrifluoroborate under heating at 115° C. for 6 hr. The reaction mixture was diluted with EtOAc and a solution of NaHCO$_3$. The aq. layer was separated off and extracted with EtOAc. Combined extracts were washed with brine, dried over Na$_2$SO$_4$, filtered and concentrated under reduced pressure. The crude product was purified by preparative achiral SFC (column PPU/grad 22-27%; 11 min). t$_R$: 0.89 min (LC-MS 2). t$_R$: 0.91 min (LC-MS 2); ESI-MS: 475 [M+H]$^+$ (LC-MS 2).

EXAMPLE 96

6-(4-chlorophenyl)-5-(1,4-dimethyl-1H-benzo[d][1,2,3]triazol-6-yl)-2-(1-methyl-1,2,3,6-tetrahydropyridin-4-yl)-1-(oxetan-3-yl)-5,6-dihydropyrrolo[3,4-d]imidazol-4(1H)-one

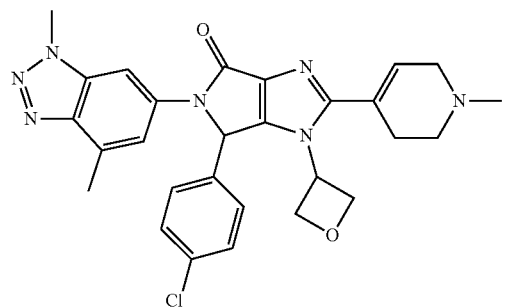 [SMILES: Cc1cc(N2C(=O)c3nc(C4=CCN(C)CC4)n(C4COC4)c3C2c2ccc(Cl)cc2)cc2c1nnn2C]

The title compound was prepared in analogy to the procedure described for Example 1 using 2-bromo-6-(4-chlorophenyl)-5-(1,4-dimethyl-1H-benzo[d][1,2,3]triazol-6-yl)-1-(oxetan-3-yl)-5,6-dihydropyrrolo[3,4-d]imidazol-4 (1H)-one (Step 93.6) and 1-methyl-1,2,3,6-tetrahydropyridine-4-boronic acid pinacol ester under heating at 90° C. for 1½ hr. The reaction mixture was diluted with EtOAc and a solution of NaHCO$_3$. The aq. layer was separated off and extracted with EtOAc. Combined extracts were washed with brine, dried over Na$_2$SO$_4$, filtered and concentrated under reduced pressure. The crude product was purified by preparative achiral SFC (column 2-EP/grad 22-27%; 11 min). t$_R$: 0.89 min (LC-MS 2). t$_R$: 0.89 min (LC-MS 2). t$_R$: 0.67 min (LC-MS 2); ESI-MS: 530 [M+H]$^+$ (LC-MS 2).

EXAMPLE 97

6-(4-chlorophenyl)-1-isopropyl-5-((4-methoxy-1-methyl-1H-benzo[d][1,2,3]triazol-6-yl)-2-(1-methylpiperidin-4-yl)-5,6-dihydropyrrolo[3,4-d]imidazol-4(1H)-one

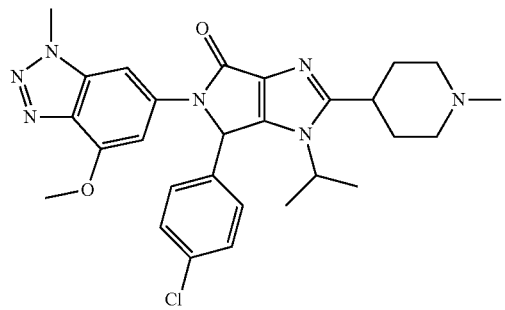 [SMILES: COc1cc(N2C(=O)c3nc(C4CCN(C)CC4)n(C(C)C)c3C2c2ccc(Cl)cc2)cc2c1nnn2C]

Hydrogenation of 6-(4-chlorophenyl)-1-isopropyl-5-((4-methoxy-1-methyl-1H-benzo[d][1,2,3]triazol-6-yl)-2-(1-methyl-1,2,3,6-tetrahydropyridin-4-yl)-5,6-dihydropyrrolo [3,4-d]imidazol-4(1H)-one (30 mg; 0.056 mmol) (Ex. 73) in EtOH (5 mL) in presence of Pt (0.14 g) during 116 hr, filtration, extensive washing of the residue with CH$_2$Cl$_2$/MeOH 4:1, concentration of the filtrate and purification by preparative HPLC (gradient 5-100% CH$_3$CN in 20 min), followed by basic workup gave the title compound. t$_R$: 0.73 min (LC-MS 2); ESI-MS: 534 [M+H]$^+$ (LC-MS 2).

EXAMPLE 98

6-(4-chlorophenyl)-5-(3,8-dimethyl-[1,2,4]triazolo[4,3-a]pyridin-6-yl)-1-isopropyl-2-(1-methylpiperidin-4-yl)-5,6-dihydropyrrolo[3,4-d]imidazol-4(1H)-one

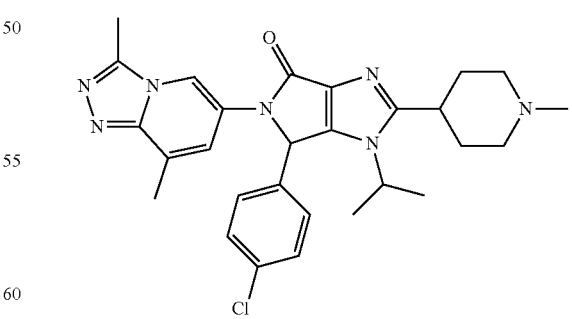

Hydrogenation 6-(4-chlorophenyl)-5-(3,8-dimethyl-[1,2,4]triazolo[4,3-a]pyridin-6-yl)-1-isopropyl-2-(1-methyl-1,2,3,6-tetrahydropyridin-4-yl)-5,6-dihydropyrrolo[3,4-d]imidazol-4(1H)-one (Example 50; 114 mg) in EtOH (4 mL) in presence of Pd(OH)$_2$ (0.06 g, 20%) as described in Ex. 64 and purification by preparative HPLC (gradient 5-100% CH₃CN in 20 min), followed by basic workup gave the title compound. $t_R$: 0.65 min (LC-MS 2); ESI-MS: 518 [M+H]⁺ (LC-MS 2).

EXAMPLE 99

6-(4-chlorophenyl)-5-(1,4-dimethyl-1H-benzo[d][1, 2,3]triazol-6-yl)-1-isopropyl-2-(tetrahydrofuran-3-yl)-5,6-dihydropyrrolo[3,4-d]imidazol-4(1H)-one

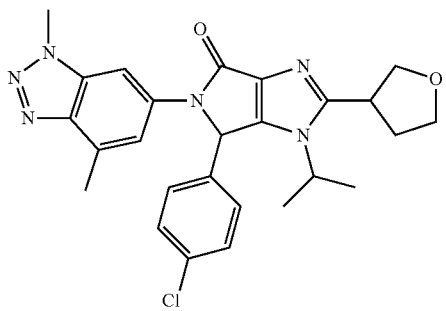 [SMILES: Cc1cc(N2C(=O)c3nc(C4CCOC4)n(C(C)C)c3C2c2ccc(Cl)cc2)cc2c1nnn2C]

The title compound was prepared in analogy to the procedure described in Step 1.11 using 5-((4-chlorophenyl)((1,4-dimethyl-1H-benzo[d][1,2,3]triazol-6-yl)amino)methyl)-1-isopropyl-2-(tetrahydrofuran-3-yl)-1H-imidazole-4-carboxylic acid (Step 99.5). The reaction mixture was diluted with CH₂Cl₂ and aq. NaHCO₃. The aq. layer was separated off and extracted with CH₂Cl₂. Combined extracts were washed with brine and dried over Na₂SO₄, filtered and concentrated under reduced pressure. Purification by preparative HPLC (gradient 5-100% CH₃CN in 20 min), followed by basic workup gave the title compound as a mixture of diastereomers. $t_R$: 0.98/0.99 min (LC-MS 2); ESI-MS: 491 [M+H]⁺ (LC-MS 2).

Step 99.1: ethyl 2-(4,5-dihydrofuran-3-yl)-1-isopropyl-1H-imidazole-4-carboxylate

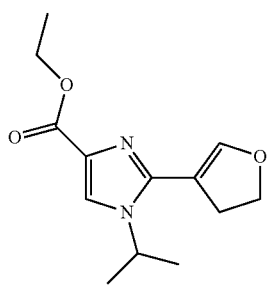 [SMILES: CCOC(=O)c1cn(C(C)C)c(C2=COCC2)n1]

The title compound was prepared in analogy to the procedure described for Example 1 using ethyl 2-bromo-1-isopropyl-1H-imidazole-4-carboxylate (Step 9.5) and 4,5-dihydrofuran-3-boronic acidpinacole ester under heating at 90° C. for 1½ hr. The reaction mixture was concentrated and the residue dissolved in EtOAc and H₂O. The aq. layer was separated off and extracted with EtOAc. Combined extracts were dried over Na₂SO₄, filtered and concentrated under reduced pressure. The crude product was purified by silica gel column chromatography (CH₂Cl₂/EtOAc 5-40% EtOAc). $t_R$: 0.77 min (LC-MS 2); ESI-MS: 251 [M+H]⁺.

Step 99.2: ethyl 1-isopropyl-2-(tetrahydrofuran-3-yl)-1H-imidazole-4-carboxylate

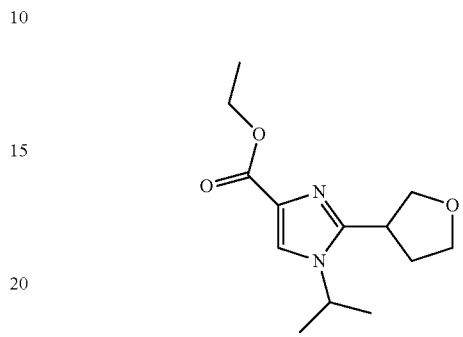

Hydrogenation of ethyl 2-(4,5-dihydrofuran-3-yl)-1-isopropyl-1H-imidazole-4-carboxylate (810 mg, 3.24 mmol) in EtOH (20 mL) in presence of Pd/C 10% (0.2 g) during 19 hr, filtration and concentration of the filtrate gave the title compound. $t_R$: 0.74 min (LC-MS 2); ESI-MS: 253 [M+H]⁺; ¹H NMR (600 MHz, DMSO-d₆) δ 7.97 (s, 1H), 4.50 (m, 1H), 4.21 (m, 2H), 4.05 (m, 1H), 3.88 (m, 1H), 3.77 (m, 2H), 3.60 (m, 1H), 2.25 (m, 1H), 2.13 (m, 1H), 1.38 (m, 6H), 1.26 (m, 3H).

Step 99.3: ethyl 5 ((4-chlorophenyl)(hydroxy)methyl)-1-isopropyl-2-(tetrahydrofuran-3-yl)-1H-imidazole-4-carboxylate

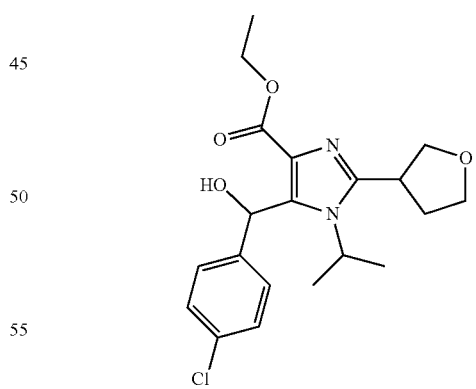

The title compound was prepared in analogy to the procedure described for Step 9.6 using ethyl 1-isopropyl-2-(tetrahydrofuran-3-yl)-1H-imidazole-4-carboxylate. Crystallization from CH₂Cl₂ gave the title compound as a mixture of diastereomers. Additional product could be obtained by silica gel column chromatography (CH₂Cl₂/TBME 20-100% TBME). $t_R$: 1.07/1.09 min (LC-MS 2) $t_R$: 0.97 min (LC-MS 2); ESI-MS: 393 [M+H]⁺.

Step 99.4: ethyl 5((4-chlorophenyl)(1,4-dimethyl-1H-benzo[d][1,2,3]triazol-6-yl)amino)methyl)-1-isopropyl-2-(tetrahydrofuran-3-yl)-1H-imidazole-4-carboxylate

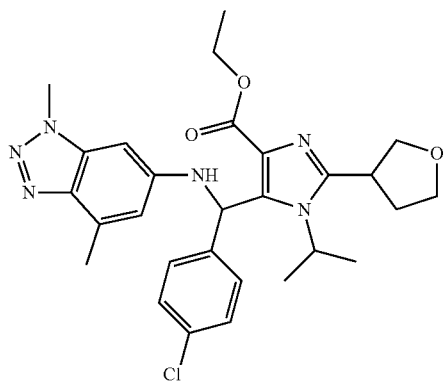 [SMILES: CCOC(=O)c1nc(C2CCOC2)n(C(C)C)c1C(Nc1cc(C)c2nnn(C)c2c1)c1ccc(Cl)cc1]

Ethyl 5-((4-chlorophenyl)(hydroxy)methyl)-1-isopropyl-2-(tetrahydrofuran-3-yl)-1H-imidazole-4-carboxylate (576 mg, 1.47 mmol) was dissolved in CH$_2$Cl$_2$ (7.5 mL) under Ar, TEA (1.016 mL, 7.33 mmol) was added and the resulting mixture was cooled down to −5° C. Methanesulfonic anhydride (511 mg, 2.93 mmol) was added portionwise and the reaction mixture was stirred for 30 min. The reaction was cooled down to −78° C., 1,4-dimethyl-1H-benzo[d][1,2,3]triazol-6-amine (Step 1.4) (262 mg, 1.61 mmol) was added. The mixture was allowed to warm up slowly to rt and was then diluted with CH$_2$Cl$_2$ and aq. NaHCO$_3$. The aq. layer was separated off and extracted with CH$_2$Cl$_2$. Combined extracts were washed with brine and dried over Na$_2$SO$_4$, filtered and concentrated under reduced pressure. Purification by preparative HPLC (gradient 5-100% CH$_3$CN in 20 min), followed by basic workup gave the title compound as a mixture of diastereomers. t$_R$: 1.10/1.11 min (LC-MS 2); ESI-MS: 537 [M+H]$^+$.

Step 99.5: 5 ((4-chlorophenyl)(0,4-dimethyl-1H-benzo[d][1,2,3]triazol-6-yl)amino)methyl)-1-isopropyl-2-(tetrahydrofuran-3-yl)-1H-imidazole-4-carboxylic acid

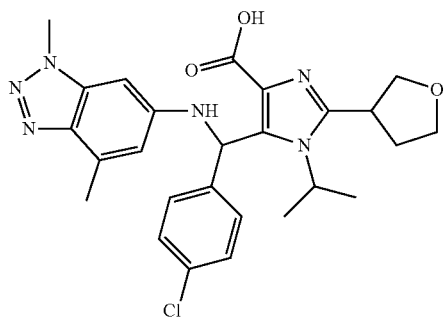 [SMILES: Cc1cc(NC(c2ccc(Cl)cc2)c2c(C(=O)O)nc(C3CCOC3)n2C(C)C)cc2c1nnn2C]

The title compound was prepared in analogy to the procedure described in Step 1.10 using ethyl 5-((4-chlorophenyl)((1,4-dimethyl-1H-benzo[d][1,2,3]triazol-6-yl)amino)methyl)-1-isopropyl-2-(tetrahydrofuran-3-yl)-1H-imidazole-4-carboxylate at 45° C. The reaction mixture was acidified with 4 N HCl and then concentrated. The residue was stirred in CH$_2$Cl$_2$/MeOH 5:1. The suspension was filtered and the filtrate concentrated. t$_R$: 0.91 min (LC-MS 2); ESI-MS: 509 [M+H]$^+$.

EXAMPLE 100

6-(4-chlorophenyl)-2-(3,6-dihydro-2H-pyran-4-yl)-5-(3,8-dimethyl-[1,2,4]triazolo[4,3-b]pyridazin-6-yl)-1-isopropyl-5,6-dihydropyrrolo[3,4-d]imidazol-4(1H)-one

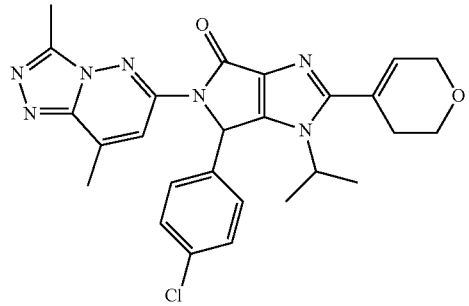 [SMILES: Cc1cc(N2C(=O)c3nc(C4=CCOCC4)n(C(C)C)c3C2c2ccc(Cl)cc2)nn2c(C)nnc12]

6-(4-Chlorophenyl)-2-(3,6-dihydro-2H-pyran-4-yl)-1-isopropyl-5,6-dihydropyrrolo[3,4-d]imidazol-4(1H)-one (Step 100.5) (50 mg, 0.14 mmol) was dissolved in dioxane (2.5 mL). 6-Chloro-3,8-dimethyl-[1,2,4]triazolo[4,3-b]pyridazine (Step 18.2) (38.3 mg, 0.21 mmol), Pd$_2$(dba)$_3$ (25.6 mg, 0.028 mmol), XantPhos (32.3 mg, 0.056 mmol) and Cs$_2$CO$_3$ (91 mg, 0.28 mmol) were added and the resulting mixture was heated up and stirred at 100° C. for 8 hr. The reaction mixture was diluted with dioxane (3 mL) and filtered. The filtrate was concentrated. Purification by silica gel column chromatography [CH$_2$Cl$_2$/(CH$_2$Cl$_2$/EtOH 9:1) 5-80% (CH$_2$Cl$_2$/EtOH 9:1)] and finally crystallization from CH$_3$CN gave the title product (41 mg, 58% yield). t$_R$: 0.96 min (LC-MS 2); ESI-MS: 504 [M+H]$^+$ (LC-MS 2); $^1$H NMR (600 MHz, DMSO-d$_6$) δ 8.17 (s, 1H), 7.54 (br. s, 2H), 7.45 (d, 2H), 6.69 (s, 1H), 6.14 (m, 1H), 4.62 (m, 1H), 4.25 (m, 2H), 3.87 (m, 1H), 3.80 (m, 1H), 2.68 (s, 3H), 2.62 (m, 1H), 2.57 (s, 3H), 2.40 (m, 1H), 1.47 (d, 3H), 0.60 (d, 3H).

Step 100.1: ethyl 5-(azido(4-chlorophenyl)methyl)-2-bromo-1-isopropyl-1H-imidazole-4-carboxylate Ethyl 2-bromo-5-((4-chlorophenyl)(hydroxy)methyl)-1-isopropyl-1H-imidazole-4-carboxylate (Step 9.6) (8.03 g, 20 mmol) was dissolved in CH$_2$Cl$_2$ (150 mL), TEA (13.9 mL, 100 mmol) was added and the resulting mixture was cooled down to −5° C. After portionwise addition of methanesulfonic anhydride (6.97 g, 40 mmol), the reaction mixture was stirred for 30 min. Then tetrabutylammonium azide (11.34 g, 40 mmol) was added. The mixture was allowed to warm up to rt. After 16 h it was diluted with CH$_2$Cl$_2$ and H$_2$O. The aq. layer was separated off and extracted with CH$_2$Cl$_2$. Combined extracts were washed with brine and dried over Na$_2$SO$_4$, filtered and concentrated under reduced pressure. Purification by silica gel column chromatography (hexane/TBME 5-30% TBME) gave the title product (7.6 g, 89% yield). t$_R$: 1.34 min (LC-MS 2); ESI-MS: 426/428 [M+H]$^+$ (LC-MS 2).

Step 100.2: ethyl 5-(azido(4-chlorophenyl)methyl)-2-(3,6-dihydro-2H-pyran-4-yl)-1-isopropyl-1H-imidazole-4-carboxylate

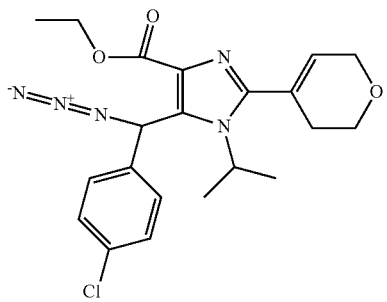

The title compound was prepared in analogy to the procedure described for Example 1 using ethyl 5-(azido(4-chlorophenyl)methyl)-2-bromo-1-isopropyl-1H-imidazole-4-carboxylate and 3,6-dihydro-2H-pyran-4-boronic acid pinacol ester under heating at 90° C. for 23 hr. The reaction mixture was diluted with EtOAc and H$_2$O. The aq. layer was separated off and extracted with EtOAc. Combined extracts were dried over Na$_2$SO$_4$, filtered and concentrated under reduced pressure. The crude product was purified by silica gel column chromatography (hexane/EtOAc 10-20% EtOAc). t$_R$: 1.24 min (LC-MS 2); ESI-MS: 430 [M+H]$^+$.

Step 100.3: ethyl 5-(amino(4-chlorophenyl)methyl)-2-(3,6-dihydro-2H-pyran-4-yl)-1-isopropyl-1H-imidazole-4-carboxylate

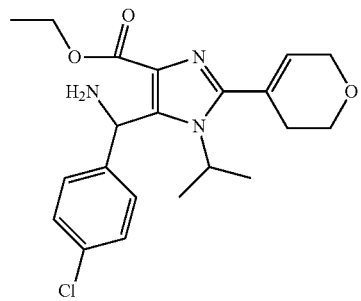 [SMILES: CCOC(=O)c1nc(C2=CCOCC2)n(C(C)C)c1C(N)c1ccc(Cl)cc1]

Hydrogenation of ethyl 5-(azido(4-chlorophenyl)methyl)-2-(3,6-dihydro-2H-pyran-4-yl)-1-isopropyl-1H-imidazole-4-carboxylate (757 mg, 1.74 mmol) in EtOH (10 mL) in presence of Raney nickel (0.1 g), filtration and concentration of the filtrate gave the title compound. t$_R$: 0.73 min (LC-MS 2); ESI-MS: 404 [M+H]$^+$ (LC-MS 2).

Step 100.4: 5-(amino(4-chlorophenyl)methyl)-2-(3,6-dihydro-2H-pyran-4-yl)-1-isopropyl-1H-imidazole-4-carboxylic acid

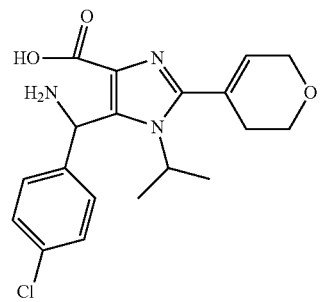 [SMILES: CC(C)n1c(C2=CCOCC2)nc(C(=O)O)c1C(N)c1ccc(Cl)cc1]

The title compound was prepared in analogy to the procedure described in Step 1.10 using ethyl 5-(amino(4-chlorophenyl)methyl)-2-(3,6-dihydro-2H-pyran-4-yl)-1-isopropyl-1H-imidazole-4-carboxylate at 50° C. The reaction mixture was acidified with 4 N HCl and then partially concentrated. Filtration gave the title compound. t$_R$: 0.56 min (LC-MS 2); ESI-MS: 376 [M+H]$^+$ (LC-MS 2).

Step 100.5: 6-(4-chlorophenyl)-2-(3,6-dihydro-2H-pyran-4-yl)-1-isopropyl-5,6-dihydropyrrolo[3,4-d]imidazol-4(1H)-one

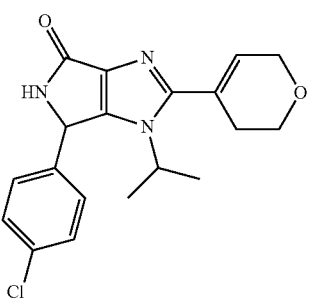 [SMILES: CC(C)n1c(C2=CCOCC2)nc2c1C(c1ccc(Cl)cc1)NC2=O]

The title compound was prepared in analogy to the procedure described in Step 1.11 using 5-(amino(4-chlorophenyl)methyl)-2-(3,6-dihydro-2H-pyran-4-yl)-1-isopropyl-1H-imidazole-4-carboxylic acid. The reaction mixture was diluted with CH$_2$Cl$_2$ and aq. NaHCO$_3$. The aq. layer was separated off and extracted with CH$_2$Cl$_2$. Combined extracts were washed with brine and dried over Na$_2$SO$_4$, filtered and concentrated under reduced pressure. Crystallization from iPr$_2$O gave the title compound. t$_R$: 0.84 min (LC-MS 2); ESI-MS: 358 [M+H]$^+$ (LC-MS 2).

EXAMPLE 101

6-(4-chlorophenyl)-5-(3,8-dimethyl-[1,2,4]triazolo[4,3-b]pyridazin-6-yl)-1-isopropyl-2-(tetrahydro-2H-pyran-4-yl)-5,6-dihydropyrrolo[3,4-d]imidazol-4(1H)-one

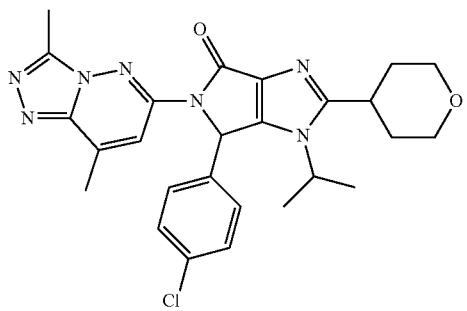 [SMILES: Cc1cc(N2C(=O)c3nc(C4CCOCC4)n(C(C)C)c3C2c2ccc(Cl)cc2)nn2c(C)nnc12]

6-(4-Chlorophenyl)-1-isopropyl-2-(tetrahydro-2H-pyran-4-yl)-5,6-dihydropyrrolo[3,4-d]imidazol-4(1H)-one (Step 101.1) (149 mg, 0.414 mmol) was dissolved in dioxane (7 mL). 6-Chloro-3,8-dimethyl-[1,2,4]triazolo[4,3-b]pyridazine (Step 18.2) (113 mg, 0.62 mmol), Pd$_2$(dba)$_3$ (76 mg, 0.083 mmol), XantPhos (96 mg, 0.166 mmol) and Cs$_2$CO$_3$ (270 mg, 0.83 mmol) were added and the resulting mixture was heated up and stirred at 100° C. for 8 hr. The reaction mixture was diluted with dioxane (8 mL) and filtered. The filtrate was concentrated. Purification by silica gel column chromatography [CH$_2$Cl$_2$/(CH$_2$Cl$_2$/EtOH 9:1) 5-80% (CH$_2$Cl$_2$/EtOH 9:1)] and finally by preparative HPLC (gradient 5-100% CH$_3$CN in 20 min), followed by basic workup gave the title product (45 mg, 21% yield). $t_R$: 0.94 min (LC-MS 2); ESI-MS: 506 [M+H]$^+$ (LC-MS 2).

Step 101.1: 6-(4-chlorophenyl)-1-isopropyl-2-(tetrahydro-2H-pyran-4-yl)-5,6-dihydropyrrolo[3,4-d]imidazol-4(1H)-one

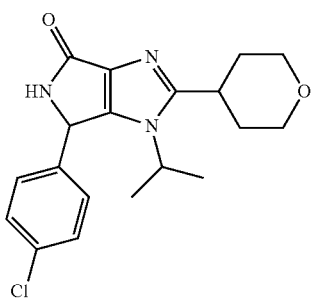 [SMILES: CC(C)n1c(C2CCOCC2)nc2c1C(c1ccc(Cl)cc1)NC2=O]

Hydrogenation of 6-(4-chlorophenyl)-2-(3,6-dihydro-2H-pyran-4-yl)-1-isopropyl-5,6-dihydropyrrolo[3,4-d]imidazol-4(1H)-one (Step 100.5) (128 mg, 0.286 mmol) in EtOH (8 mL) in presence of Raney nickel (0.035 g) during 40 h, filtration and concentration of the filtrate gave the title compound. $t_R$: 0.84 min (LC-MS 2); ESI-MS: 360 [M+H]$^+$ (LC-MS 2).

EXAMPLE 102

(R)-6-(4-chlorophenyl)-5-(3,8-dimethyl-[1,2,4]triazolo[4,3-b]pyridazin-6-yl)-1-isopropyl-2-(tetrahydro-2H-pyran-4-yl)-5,6-dihydropyrrolo[3,4-d]imidazol-4(1H)-one

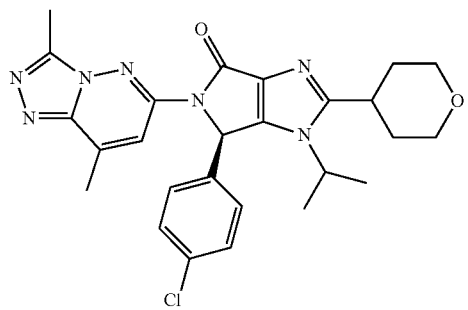 [SMILES: Cc1cc(N2C(=O)c3nc(C4CCOCC4)n(C(C)C)c3[C@H]2c2ccc(Cl)cc2)nn2c(C)nnc12]

The title compound (48 mg) was obtained enantiomerically pure (>99% ee) after chiral preparative chromatography (Chiralpak AD-H, 250×4.6 mm; mobile phase: heptane/EtOH/MeOH 85:7.5:7.5; flow rate: 1 mL/min; detection 220 nm) of the racemic mixture of 6-(4-chlorophenyl)-5-(3,8-dimethyl-[1,2,4]triazolo[4,3-b]pyridazin-6-yl)-1-isopropyl-2-(tetrahydro-2H-pyran-4-yl)-5,6-dihydropyrrolo[3,4-d]imidazol-4(1H)-one (Example 101; 112 mg). The second enantiomer (S)-6-((4-chlorophenyl)-5-(3,8-dimethyl-[1,2,4]triazolo[4,3-b]pyridazin-6-yl)-1-isopropyl-2-(tetrahydro-2H-pyran-4-yl)-5,6-dihydropyrrolo[3,4-d]imidazol-4(1H)-one (56 mg) was obtained enantiomerically pure (>99% ee) via the same separation.

EXAMPLE 103

(R)-6-(4-chlorophenyl)-2-(3,6-dihydro-2H-pyran-4-yl)-5-(3,8-dimethyl-[1,2,4]triazolo[4,3-b]pyridazin-6-yl)-1-isopropyl-5,6-dihydropyrrolo[3,4-d]imidazol-4(1H)-one

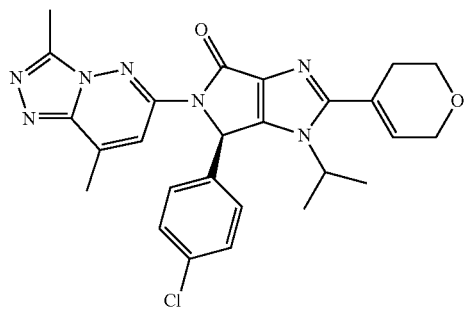 [SMILES: Cc1cc(N2C(=O)c3nc(C4=CCOCC4)n(C(C)C)c3[C@H]2c2ccc(Cl)cc2)nn2c(C)nnc12]

The title compound (43 mg) was obtained enantiomerically pure (>99% ee) after chiral preparative chromatography (Chiralpak AD-H, 250×4.6 mm; mobile phase: heptane/EtOH/MeOH 50:25:25; flow rate: 1 mL/min; detection 220 nm) of the racemic mixture of 6-(4-chlorophenyl)-2-(3,6-dihydro-2H-pyran-4-yl)-5-(3,8-dimethyl-[1,2,4]triazolo[4,3-b]pyridazin-6-yl)-1-isopropyl-5,6-dihydropyrrolo[3,4-d]imidazol-4(1H)-one (Example 100; 90 mg). The second enantiomer (S)-6-(4-chlorophenyl)-2-(3,6-dihydro-2H- pyran-4-yl)-5-(3,8-dimethyl-[1,2,4]triazolo[4,3-b]pyridazin-6-yl)-1-isopropyl-5,6-dihydropyrrolo[3,4-d]imidazol-4(1H)-one (45 mg) was obtained enantiomerically pure (>99% ee) via the same separation.

EXAMPLE 104

6-(4-chlorophenyl)-5-(3,8-dimethyl-[1,2,4]triazolo[4,3-a]pyridin-6-yl)-1-isopropyl-2-(1-neopentylpiperidin-4-yl)-5,6-dihydropyrrolo[3,4-d]imidazol-4(1H)-one

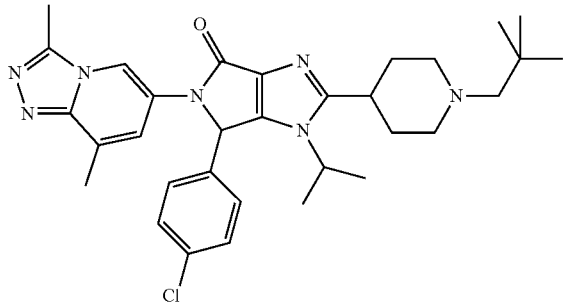 [SMILES: Cc1cc(N2C(=O)c3nc(C4CCN(CC(C)(C)C)CC4)n(C(C)C)c3C2c2ccc(Cl)cc2)cn2c(C)nnc12]

6-(4-Chlorophenyl)-5-(3,8-dimethyl-[1,2,4]triazolo[4,3-a]pyridin-6-yl)-1-isopropyl-2-(piperidin-4-yl)-5,6-dihydropyrrolo[3,4-d]imidazol-4(1H)-one (Example 75) (50 mg, 0.1 mmol) was dissolved in $CH_2Cl_2$ (1.5 ml). Sodiumtriacetoxyborohydride (63 mg, 0.30 mmol) and HOAc (17 µL, 0.30 mmol) were added, followed after 5 min by pivaldehyde (14 µL, 0.125 mmol). After 2½ hr, more pivaldehyde (14 µL) was added and stirring continued for 16 hr. Then other portions of sodiumtriacetoxyborohydride (63 mg), HOAc (17 µL) and pivaldehyde (14 µL) were added and stirring continued. This add-ons were repeated until complete conversion of 6-((4-chlorophenyl)-5-(3,8-dimethyl-[1,2,4]triazolo[4,3-a]pyridin-6-yl)-1-isopropyl-2-(piperidin-4-yl)-5,6-dihydropyrrolo[3,4-d]imidazol-4(1H)-one was observed. The reaction mixture was diluted with $CH_2Cl_2$ and aq. $NaHCO_3$. The aq. layer was separated off and extracted with $CH_2Cl_2$. Combined extracts were washed with brine and dried over $Na_2SO_4$, filtered and concentrated under reduced pressure. Purification by preparative HPLC (gradient 5-100% $CH_3CN$ in 20 min), followed by basic workup gave the title product. $t_R$: 0.75 min (LC-MS 2); ESI-MS: 574 [M+H]$^+$ (LC-MS 2).

EXAMPLE 105

6-(4-chlorophenyl)-5-(1,4-dimethyl-1H-benzo[d][1,2,3]triazol-6-yl)-1-(oxetan-3-yl)-2-(tetrahydro-2H-pyran-4-yl)-5,6-dihydropyrrolo[3,4-d]imidazol-4(1H)-one

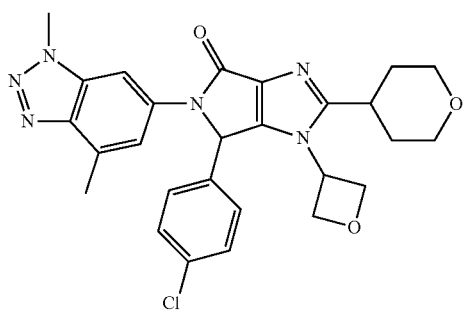 [SMILES: Cc1cc(N2C(=O)c3nc(C4CCOCC4)n(C4COC4)c3C2c2ccc(Cl)cc2)cc2c1nnn2C]

Hydrogenation 6-(4-chlorophenyl)-2-(3,6-dihydro-2H-pyran-4-yl)-5-(1,4-dimethyl-1H-benzo[d][1,2,3]triazol-6-yl)-1-(oxetan-3-yl)-5,6-dihydropyrrolo[3,4-d]imidazol-4(1H)-one (Example 93; 45 mg) in EtOH (10 mL) in presence of Pd(OH)$_2$ (23 mg, 20%) as described in Ex. 64 and purification by preparative HPLC (gradient 5-100% $CH_3CN$ in 20 min), followed by basic workup gave the title compound. $t_R$: 0.87 min (LC-MS 2); ESI-MS: 519 [M+H]$^+$ (LC-MS 2); $^1$H NMR (600 MHz, DMSO-d$_6$) δ 7.80 (s, 1H), 7.50 (s, 1H), 7.47 (d, 2H), 7.34 (d, 2H), 7.03 (s, 1H), 5.69 (m, 1H), 5.12 (t, 1H), 4.93 (t, 1H), 4.49 (t, 1H), 4.23 (s, 3H), 3.95 (m, 2H), 3.44 (m, 3H), 3.11 (m, 1H), 2.61 (s, 3H), 1.86 (m, 3H), 1.66 (m, 1H).

EXAMPLE 106

6-(4-chlorophenyl)-5-(1,4-dimethyl-1H-benzo[d][1,2,3]triazol-6-yl)-1-isopropyl-5,6-dihydropyrrolo[3,4-d]imidazol-4(1H)-one

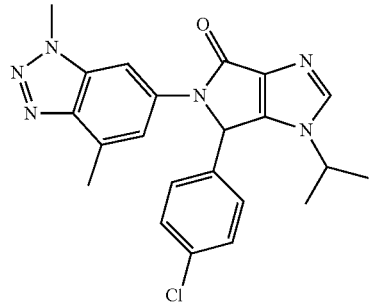 [SMILES: Cc1cc(N2C(=O)c3ncn(C(C)C)c3C2c2ccc(Cl)cc2)cc2c1nnn2C]

During the reaction of 2-bromo-6-(4-chlorophenyl)-5-(1,4-dimethyl-1H-benzo[d][1,2,3]triazol-6-yl)-1-isopropyl-5,6-dihydropyrrolo[3,4-d]imidazol-4(1H)-one (Step 77.3) with trimethylboroxine as described in Example 1, small amounts of the reduction product 6-((4-chlorophenyl)-5-(1,4-dimethyl-1H-benzo[d][1,2,3]triazol-6-yl)-1-isopropyl-5,6-dihydropyrrolo[3,4-d]imidazol-4(1H)-one were formed.

Separation by preparative HPLC (gradient 5-100% $CH_3CN$ in 20 min), followed by basic workup yielded the title compound. $t_R$: 0.89 min (LC-MS 2). $t_R$: 0.92 min (LC-MS 2); ESI-MS: 421 [M+H]$^+$ (LC-MS 2).

EXAMPLE 107

(R)-6-(4-chlorophenyl)-2-cyclopropyl-5-(3,8-dimethyl-[1,2,4]triazolo[4,3-a]pyridin-6-yl)-1-isopropyl-5,6-dihydropyrrolo[3,4-d]imidazol-4(1H)-one

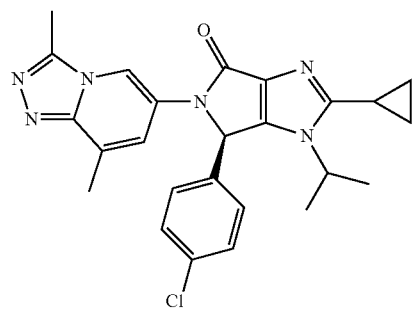 [SMILES: Cc1cc(N2C(=O)c3nc(C4CC4)n(C(C)C)c3[C@H]2c2ccc(Cl)cc2)cn2c(C)nnc12]

The title compound (74 mg) was obtained enantiomerically pure 97% ee) after chiral preparative chromatography (Chiralpak AD-H, 250×4.6 mm; mobile phase: heptane/iPrOH 60:40; flow rate: 1 mL/min; detection 220 nm) of the racemic mixture of 6-((4-chlorophenyl)-2-cyclopropyl-5-(3,8-dimethyl-[1,2,4]triazolo[4,3-a]pyridin-6-yl)-1-isopropyl-5,6-dihydropyrrolo[3,4-d]imidazol-4(1H)-one (Example 13; 158 mg). The second enantiomer (S)-6-((4-chlorophenyl)-2-cyclopropyl-5-(3,8-dimethyl-[1,2,4]triazolo[4,3-a]pyridin-6-yl)-1-isopropyl-5,6-dihydropyrrolo[3,4-d]imidazol-4 (1H)-one (79 mg) was obtained enantiomerically pure (>99% ee) via the same separation.

EXAMPLE 108

(R)-6-(4-chlorophenyl)-1-isopropyl-5-((4-methoxy-1-methyl-1H-benzo[d][1,2,3]triazol-6-yl)-2-(tetrahydro-2H-pyran-4-yl)-5,6-dihydropyrrolo[3,4-d]imidazol-4(1H)-one

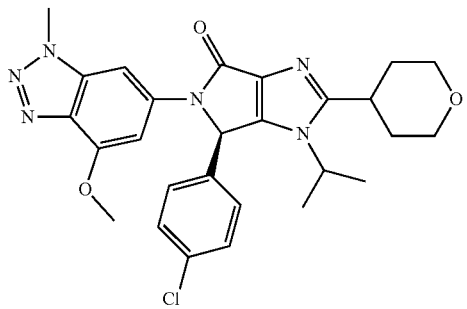 [SMILES: COc1cc(N2C(=O)c3nc(C4CCOCC4)n(C(C)C)c3[C@H]2c2ccc(Cl)cc2)cc2c1nnn2C]

The title compound (16 mg) was obtained enantiomerically pure (>99% ee) after chiral preparative chromatography (Chiralcel OD-H, 250×4.6 mm; mobile phase: heptane/EtOH 60:40; flow rate: 1 mL/min; detection 220 nm) of the racemic mixture of 6-((4-chlorophenyl)-1-isopropyl-5-(4-methoxy-1-methyl-1H-benzo[d][1,2,3]triazol-6-yl)-2-(tetrahydro-2H-pyran-4-yl)-5,6-dihydropyrrolo[3,4-d]imidazol-4 (1H)-one (Example 64; 37 mg). The second enantiomer (S)-6-((4-chlorophenyl)-1-isopropyl-5-((4-methoxy-1-methyl-1H-benzo[d][1,2,3]triazol-6-yl)-2-(tetrahydro-2H-pyran-4-yl)-5,6-dihydropyrrolo[3,4-d]imidazol-4(1H)-one (15 mg) was obtained enantiomerically pure (>99% ee) via the same separation.

EXAMPLE 109

(R)-6-(4-chlorophenyl)-5-(3,7-dimethyl-3H-benzo[d][1,2,3]triazol-5-yl)-1-isopropyl-2-methyl-5,6-dihydropyrrolo[3,4-d]imidazol-4(1H)-one

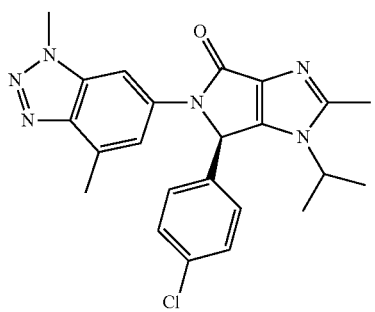 [SMILES: Cc1cc(N2C(=O)c3nc(C)n(C(C)C)c3[C@H]2c2ccc(Cl)cc2)cc2c1nnn2C]

The title compound (57 mg) was obtained enantiomerically pure (>99% ee) after chiral preparative chromatography (Chiralcel OD-3, 150×4.6 mm; mobile phase: CO$_2$/(EtOH+0.05% Et$_2$NH) 0-50%; flow rate: 1 mL/min; detection 220 nm) of the racemic mixture of 6-(4-chlorophenyl)-5-(3,7-dimethyl-3H-benzo[d][1,2,3]triazol-5-yl)-1-isopropyl-2-methyl-5,6-dihydropyrrolo[3,4-d]imidazol-4(1H)-one (Example 2; 125 mg). The second enantiomer (S)-6-(4-chlorophenyl)-5-(3,7-dimethyl-3H-benzo[d][1,2,3]triazol-5-yl)-1-isopropyl-2-methyl-5,6-dihydropyrrolo[3,4-d]imidazol-4(1H)-one (42 mg) was obtained enantiomerically pure (>99% ee) via the same separation.

EXAMPLE 110

(R)-6-(4-chlorophenyl)-5-(3,8-dimethyl-[1,2,4]triazolo[4,3-b]pyridazin-6-yl)-1-isopropyl-2-methyl-5,6-dihydropyrrolo[3,4-d]imidazol-4(1H)-one

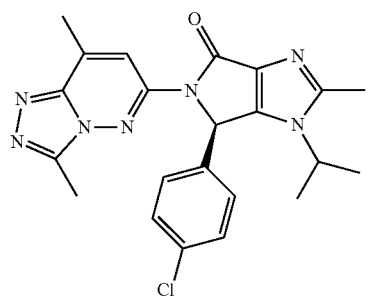 [SMILES: Cc1cc(N2C(=O)c3nc(C)n(C(C)C)c3[C@H]2c2ccc(Cl)cc2)nn2c(C)nnc12]

The title compound (37 mg) was obtained enantiomerically pure (>99% ee) after chiral preparative chromatography (Chiralpak AD-H, 250×4.6 mm; mobile phase: heptane/EtOH 65:35; flow rate: 1 mL/min; detection 220 nm) of the racemic mixture of 6-((4-chlorophenyl)-5-(3,8-dimethyl-[1,2,4]triazolo[4,3-b]pyridazin-6-yl)-1-isopropyl-2-methyl-5,6-dihydropyrrolo[3,4-d]imidazol-4(1H)-one (Example 18; 78 mg). The second enantiomer (S)-6-((4-chlorophenyl)-5-(3,8-dimethyl-[1,2,4]triazolo[4,3-b]pyridazin-6-yl)-1-isopropyl-2-methyl-5,6-dihydropyrrolo[3,4-d]imidazol-4(1H)-one (35 mg) was obtained enantiomerically pure (>99% ee) via the same separation.

EXAMPLE 111

(R)-6-(4-chlorophenyl)-1-isopropyl-5-((4-methoxy-1-methyl-1H-benzo[d][1,2,3]triazol-6-yl)-2-(2-methoxypyridin-3-yl)-5,6-dihydropyrrolo[3,4-d]imidazol-4(1H-one

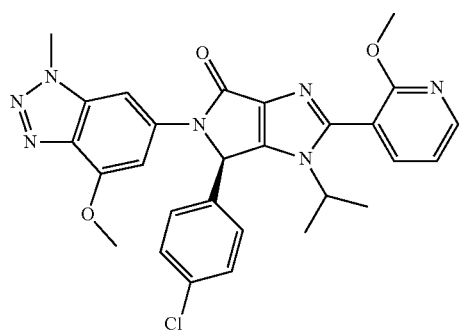 [SMILES: COc1ncccc1-c1nc2c(n1C(C)C)[C@@H](c1ccc(Cl)cc1)N(c1cc(OC)c3nnn(C)c3c1)C2=O]

The title compound (30 mg) was obtained enantiomerically pure (>99% ee) after chiral preparative chromatography (Chiralpak AD-H, 250×4.6 mm; mobile phase: heptane/EtOH/MeOH 6:2:2; flow rate: 1 mL/min; detection 220 nm) of the racemic mixture of 6-(4-chlorophenyl)-1-isopropyl-5-(4-methoxy-1-methyl-1H-benzo[d][1,2,3]triazol-6-yl)-2-(2-methoxypyridin-3-yl)-5,6-dihydropyrrolo[3,4-d]imidazol-4(1H)-one (Example 74; 71 mg). The second enantiomer (S)-6-(4-chlorophenyl)-1-isopropyl-5-(4-methoxy-1-methyl-1H-benzo[d][1,2,3]triazol-6-yl)-2-(2-methoxypyridin-3-yl)-5,6-dihydropyrrolo[3,4-d]imidazol-4(1H)-one (32 mg) was obtained enantiomerically pure (>99% ee) via the same separation.

EXAMPLE 112

(R)-6-(4-chlorophenyl)-5-(1,4-dimethyl-1H-benzo[d][1,2,3]triazol-6-yl)-1-isopropyl-2-(2-methoxypyridin-3-yl)-5,6-dihydropyrrolo[3,4-d]imidazol-4(1H)-one

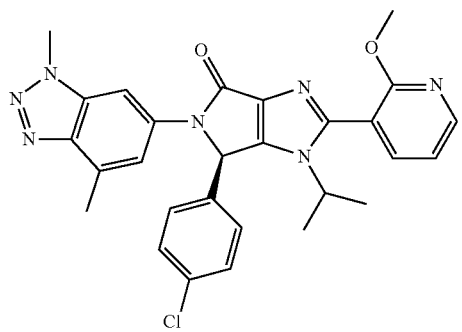 [SMILES: COc1ncccc1-c1nc2c(n1C(C)C)[C@@H](c1ccc(Cl)cc1)N(c1cc(C)c3nnn(C)c3c1)C2=O]

The title compound (46 mg) was obtained enantiomerically pure (>99% ee) after chiral preparative chromatography (Chiralpak 1A, 250×4.6 mm; mobile phase: heptane/EtOH/MeOH 70:15:15; flow rate: 1 mL/min; detection 210 nm) of the racemic mixture of 6-((4-chlorophenyl)-5-(1,4-dimethyl-1H-benzo[d][1,2,3]triazol-6-yl)-1-isopropyl-2-(2-methoxypyridin-3-yl)-5,6-dihydropyrrolo[3,4-d]imidazol-4(1H)-one (Example 77; 105 mg). The second enantiomer (S)-6-((4-chlorophenyl)-5-(1,4-dimethyl-1H-benzo[d][1,2,3]triazol-6-yl)-1-isopropyl-2-(2-methoxypyridin-3-yl)-5,6-dihydropyrrolo[3,4-d]imidazol-4(1H)-one (46 mg) was obtained enantiomerically pure (>99% ee) via the same separation.

EXAMPLE 113

6-(4-chlorophenyl)-1-isopropyl-5-(4-methoxy-1-methyl-1H-benzo[d][1,2,3]triazol-6-yl)-2-(6-methoxypyridin-3-yl)-5,6-dihydropyrrolo[3,4-d]imidazol-4(1H)-one

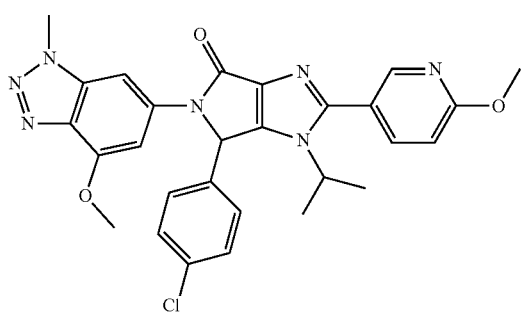 [SMILES: COc1ccc(-c2nc3c(n2C(C)C)C(c2ccc(Cl)cc2)N(c2cc(OC)c4nnn(C)c4c2)C3=O)cn1]

The title compound was prepared in analogy to the procedure described for Example 1 using 2-bromo-6-(4-chlorophenyl)-1-isopropyl-5-(4-methoxy-1-methyl-1H-benzo[d][1,2,3]triazol-6-yl)-5,6-dihydropyrrolo[3,4-d]imidazol-4(1H)-one (Step 60.7) and 2-methoxy-5-pyridineboronic acid under heating at 85° C. for 4 hr. The reaction mixture was concentrated in vacuo and the residue diluted with $CH_2Cl_2$ and $H_2O$. The aq. layer was separated off and extracted with $CH_2Cl_2$. Combined extracts were dried over $Na_2SO_4$, filtered and concentrated under reduced pressure. The crude product was purified by silica gel column chromatography [TBME/($CH_2Cl_2$+10% EtOH) 5-48% (EtOH+10% EtOH)] to afford the title compound. $t_R$: 1.07 min (LC-MS 2); ESI-MS: 544 [M+H]$^+$ (LC-MS 2).

EXAMPLE 114

(R)-6-(4-chlorophenyl)-1-isopropyl-5-(4-methoxy-1-methyl-1H-benzo[d][1,2,3]triazol-6-yl)-2-(6-methoxypyridin-3-yl)-5,6-dihydropyrrolo[3,4-d]imidazol-4(1H)-one

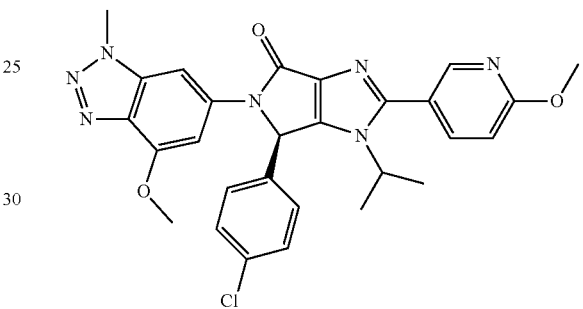

The title compound (27 mg) was obtained enantiomerically pure (>99% ee) after chiral preparative chromatography (Chiralpak IB-H, 250×4.6 mm; mobile phase: heptane/EtOH/MeOH 50:25:25; flow rate: 1 mL/min; detection 220 nm) of the racemic mixture of 6-(4-chlorophenyl)-1-isopropyl-5-(4-methoxy-1-methyl-1H-benzo[d][1,2,3]triazol-6-yl)-2-(6-methoxypyridin-3-yl)-5,6-dihydropyrrolo[3,4-d]imidazol-4(1H)-one (Example 113; 70 mg). The second enantiomer (S)-6-(4-chlorophenyl)-1-isopropyl-5-(4-methoxy-1-methyl-1H-benzo[d][1,2,3]triazol-6-yl)-2-(6-methoxypyridin-3-yl)-5,6-dihydropyrrolo[3,4-d]imidazol-4(1H)-one (32 mg) was obtained enantiomerically pure (>99% ee) via the same separation.

EXAMPLE 115

6-(4-chlorophenyl)-3-cyclopropyl-5-(3,8-dimethyl-[1,2,4]triazolo[4,3-a]pyridin-6-yl)-2-methyl-5,6-dihydropyrrolo[3,4-d]imidazol-4(3H)-one

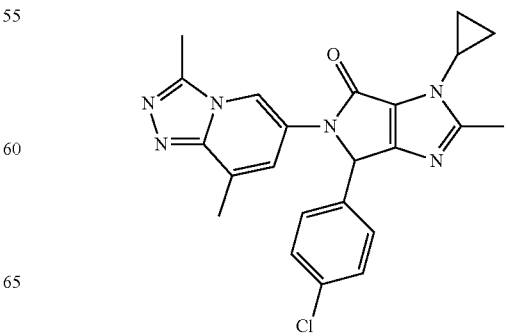

The title compound was prepared in analogy to the procedure described for Example 1 using 2-bromo-6-(4-chlorophenyl)-3-cyclopropyl-5-(3,8-dimethyl-[1,2,4]triazolo[4,3-a]pyridin-6-yl)-5,6-dihydropyrrolo[3,4-d]imidazol-4(3H)-one (Step 115.9) and trimethylboroxine under heating at 85° C. for 1½ hr. The reaction mixture was diluted with CH$_2$Cl$_2$ and a solution of NaHCO$_3$. The aq. layer was separated off and extracted with CH$_2$Cl$_2$. Combined extracts were washed with brine, dried over Na$_2$SO$_4$, filtered and concentrated under reduced pressure. The crude product was purified by preparative HPLC (gradient 5-100% CH$_3$CN in 20 min), followed by basic workup. t$_R$: 0.89 min (LC-MS 2). t$_R$: 0.82 min (LC-MS 2); ESI-MS: 433 [M+H]$^+$ (LC-MS 2); $^1$H NMR (600 MHz, DMSO-d$_6$) δ 8.43 (s, 1H), 7.40 (m, 1H), 7.35 (d, 2H), 7.32 (d, 2H), 6.37 (s, 1H), 3.47 (m, 1H), 2.63 (s, 3H), 2.49 (s, 3H), 2.45 (s, 3H), 1.25 (m, 2H), 1.11 (m, 2H).

Step 115.1: diethyl 2-(N-cyclopropylformamido)-3-hydroxymaleate

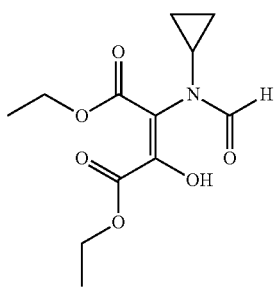 [SMILES: CCOC(=O)/C(O)=C(\C(=O)OCC)N(C=O)C1CC1]

Diethyl oxalate (7.47 g, 51.1 mmol) was added to a solution of NaOEt (21% in EtOH; 19.08 mL, 51.1 mmol) in Et$_2$O (40 mL). A solution of ethyl 2-(N-cyclopropylformamido)acetate (8.75 g, 51.1 mmol) in Et$_2$O (20 mL) was added and the mixture was stirred for 17 h at rt. The reaction mixture was added to a mixture of ice (70 g) and NaCl (10 g). After filtration the aq. layer was separated from the filtrate and washed with Et$_2$O (30 mL). The organic layer was washed with H$_2$O (20 mL) and discarded. The combined aq. layers containing the title compound were used as such in Step 115.2.

Step 115.2: diethyl 1-cyclopropyl-2-thioxo-2,3-dihydro-1H-imidazole-4,5-dicarboxylate

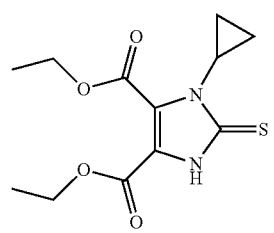 [SMILES: CCOC(=O)c1[nH]c(=S)n(C2CC2)c1C(=O)OCC]

To the combined aq. layers from Step 115.1 containing diethyl 2-(N-cyclopropylformamido)-3-hydroxymaleate, potassium thiocyanate (8.78 g, 88 mmol), conc. HCl (11.5 mL; 0.14 mol) and EtOH (20 mL) were added. The solution was stirred for 8 hr at 60° C. and then cooled down to rt. The resulting suspension was filtered and the title compound washed with a small amount of H$_2$O/EtOH (8.89 g, 56%). t$_R$: 0.84 min (LC-MS 2); ESI-MS: 285 [M+H]$^+$ (LC-MS 2).

Step 115.3: diethyl 1-cyclopropyl-1H-imidazole-4,5-dicarboxylate

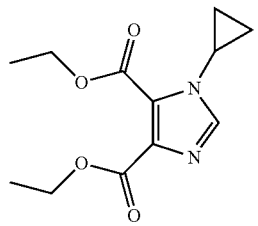 [SMILES: CCOC(=O)c1ncn(C2CC2)c1C(=O)OCC]

Diethyl 1-cyclopropyl-2-thioxo-2,3-dihydro-1H-imidazole-4,5-dicarboxylate (10.56 g, 33.4 mmol) was dissolved in acetic acid (165 mL). A solution of H$_2$O$_2$ (30% in H$_2$O; 13.66 mL, 134 mmol) was added dropwise, while the temperature was kept below 55° C. by adequate cooling of the reaction mixture. After 90 min the mixture was concentrated under reduced pressure. The residue was dissolved in EtOAc (150 mL) and cooled in an ice bath. A diluted aq. solution of Na$_2$CO$_3$ was added (pH 8-9). The aq. layer was separated off and extracted with EtOAc. Combined extracts were washed with H$_2$O and brine, dried over Na$_2$SO$_4$, filtered and concentrated under reduced pressure to yield the title compound (8.19 g, 97%). t$_R$: 0.79 min (LC-MS 2); ESI-MS: 253 [M+H]$^+$ (LC-MS 2); $^1$H NMR (600 MHz, DMSO-d$_6$) δ 7.94 (s, 1H), 4.33 (q, 2H), 4.23 (q, 2H), 3.55 (m, 1H), 1.31 (t, 3H), 1.25 (t, 3H), 1.00 (m, 4H).

Step 115.4: diethyl 2-bromo-1-cyclopropyl-1H-imidazole-4,5-dicarboxylate

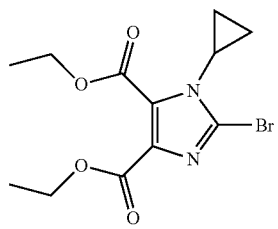 [SMILES: CCOC(=O)c1nc(Br)n(C2CC2)c1C(=O)OCC]

Diethyl 1-cyclopropyl-1H-imidazole-4,5-dicarboxylate (8.19 g, 32.5 mmol) was dissolved in CCl$_4$ (120 mL). NBS (8.09 g, 45.5 mmol) and azo-bis-(isobutyronitrile) (533 mg, 3.25 mmol) were added. The mixture was stirred for 10 hr at 80° C. and cooled to rt. The suspension was filtered and the filtrate washed twice with H$_2$O (50 mL). The aq. layers were extracted with CH$_2$Cl$_2$ (30 mL). Combined extracts were dried over Na$_2$SO$_4$, filtered and concentrated under reduced pressure to give the title compound (11.35 g). t$_R$: 0.95 min (LC-MS 2); ESI-MS: 331/333 [M+H]$^+$ (LC-MS 2).

Step 115.5: ethyl 2-bromo-1-cyclopropyl-4-formyl-1H-imidazole-5-carboxylate

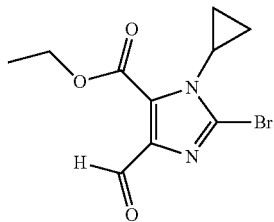 [SMILES: CCOC(=O)c1c(C=O)nc(Br)n1C1CC1]

The title compound was prepared in analogy to the procedure described in Step 36.4 using diethyl 2-bromo-1-cyclopropyl-1H-imidazole-4,5-dicarboxylate by reduction with DIBAL-H at −65° C. and was obtained after aq. work-up. $t_R$: 0.82 min (LC-MS 2); ESI-MS: 287/289 [M+H]$^+$ (LC-MS 2).

Step 115.6: ethyl 2-bromo-4((4-chlorophenyl)(hydroxy)methyl)-1-cyclopropyl-1H-imidazole-5-carboxylate

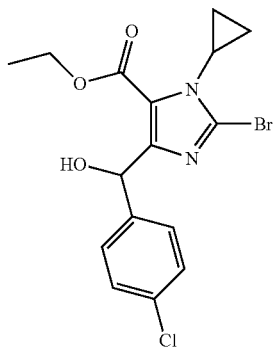 [SMILES: CCOC(=O)c1c(C(O)c2ccc(Cl)cc2)nc(Br)n1C1CC1]

The title compound was prepared in analogy to the procedure described in Step 36.5 using ethyl 2-bromo-1-cyclopropyl-4-formyl-1H-imidazole-5-carboxylate. Purification by silica gel column chromatography (CH$_2$Cl$_2$/TBME 0-7% TBME) gave the product. $t_R$: 1.12 min (LC-MS 2); ESI-MS: 399/401 [M+H]$^+$.

Step 115.7: ethyl 2-bromo-4((4-chlorophenyl)((3,8-dimethyl-[1,2,4]triazolo[4,3-a]pyridin-6-yl)amino)methyl)-1-cyclopropyl-1H-imidazole-5-carboxylate

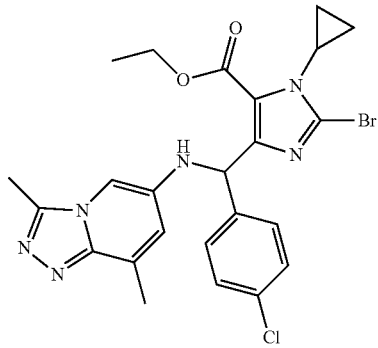 [SMILES: CCOC(=O)c1c(C(Nc2cc(C)c3nnc(C)n3c2)c2ccc(Cl)cc2)nc(Br)n1C1CC1]

Ethyl 2-bromo-4((4-chlorophenyl)(hydroxy)methyl)-1-cyclopropyl-1H-imidazole-5-carboxylate (874 mg, 2.19 mmol) was dissolved in CH$_2$Cl$_2$ (50 mL), TEA (1.82 mL, 13.1 mmol) was added and the resulting mixture was cooled down to −78° C. A solution of methanesulfonic anhydride (762 mg, 4.37 mmol) in CH$_2$Cl$_2$ (10 mL) was added and the reaction mixture was stirred for 50 min. After addition of 3,8-dimethyl-[1,2,4]triazolo[4,3-a]pyridin-6-amine (Step 9.3) (532 mg, 3.28 mmol) the reaction mixture was allowed to warm up slowly to RT. The reaction mixture was washed with H$_2$O. The aq. layer was extracted with 3 portions of EtOAc. The organic layers were washed with H$_2$O and brine, dried over Na$_2$SO$_4$, filtered and concentrated under reduced pressure. Purification by silica gel column chromatography (EtOAc/EtOH 0-100% EtOH) gave the product. $t_R$: 1.12 min (LC-MS 2); ESI-MS: 543/545 [M+H]$^+$.

Step 115.8: 2-bromo-44((4-chlorophenyl)((3,8-dimethyl-[1,2,4]triazolo[4,3-a]pyridin-6-yl)amino)methyl)-1-cyclopropyl-1H-imidazole-5-carboxylic acid

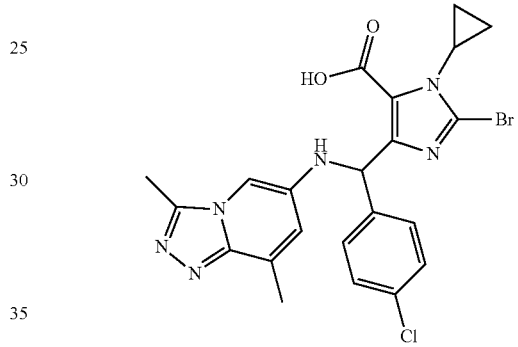

The title compound was prepared in analogy to the procedure described in Step 1.10 using ethyl 2-bromo-44((4-chlorophenyl)((3,8-dimethyl-[1,2,4]triazolo[4,3-a]pyridin-6-yl)amino)methyl)-1-cyclopropyl-1H-imidazole-5-carboxylate in MeOH/H$_2$O. The reaction mixture was acidified with 4 N HCl and then concentrated. The residue was stirred in CH$_2$Cl$_2$/MeOH 4:1. The suspension was filtered and the filtrate concentrated. $t_R$: 0.84 min (LC-MS 2); ESI-MS: 515/517 [M+H]$^+$ (LC-MS 2).

Step 115.9: 2-bromo-6-(4-chlorophenyl)-3-cyclopropyl-5-(3,8-dimethyl-[1,2,4]triazolo[4,3-a]pyridin-6-yl)-5,6-dihydropyrrolo[3,4-d]imidazol-4(3H)-one

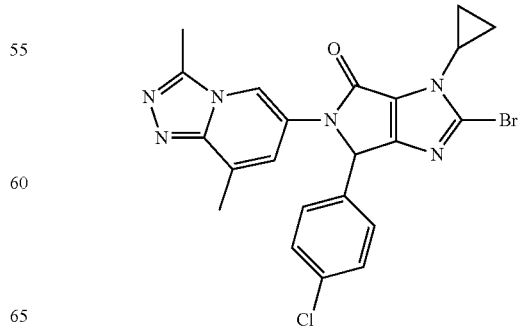

The title compound was prepared in analogy to the procedure described in Step 1.11 using 2-bromo-4-((4-chlorophenyl)((3,8-dimethyl-[1,2,4]triazolo[4,3-a]pyridin-6-yl)amino)methyl)-1-cyclopropyl-1H-imidazole-5-carboxylic acid. The reaction mixture was concentrated. Purification by preparative HPLC (gradient 5-100% CH$_3$CN in 20 min), followed by basic workup gave the title product. t$_R$: 0.95 min (LC-MS 2); ESI-MS: 497/499 [M+H]$^+$ (LC-MS 2).

EXAMPLE 116

6-(4-chlorophenyl)-2-(3,6-dihydro-2H-pyran-4-yl)-5-(3,8-dimethyl-[1,2,4]triazolo[4,3-a]pyridin-6-yl)-5,6-dihydropyrrolo[3,4-d]imidazol-4(1H)-one

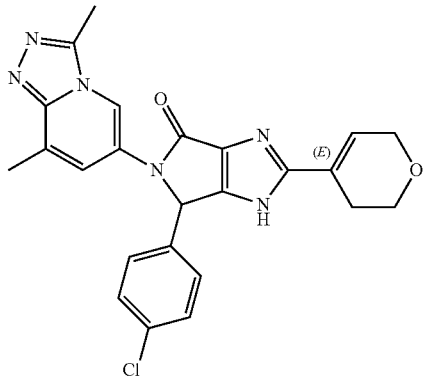 [SMILES: Cc1cc(N2C(=O)c3nc(C4=CCOCC4)[nH]c3C2c2ccc(Cl)cc2)cn2c(C)nnc12]

Step 116.1: Ethyl 1-allyl-2-bromo-5 ((4-chlorophenyl)((3,8-dimethyl-[1,2,4]triazolo[4,3-a]pyridin-6-yl)amino)methyl)-1H-imidazole-4-carboxylate The title compound was prepared in analogy to the procedure described in Step 1.9 using ethyl 1-allyl-2-bromo-5-((4-chlorophenyl)(hydroxy)methyl)-1H-imidazole-4-carboxylate (Step 1.8) and 3,8-dimethyl-[1,2,4]triazolo[4,3-a]pyridin-6-amine (Step 9.3) as starting materials. The crude product was purified by flash chromatography (Isco RediSep 80 g column, CH$_2$Cl$_2$/MeOH; gradient 0-15% MeOH). t$_R$: 1.03 min (LC-MS 2); ESI-MS: 544 [M+H]$^+$ (LC-MS 2).

Step 116.2: 1-allyl-2-bromo-5 ((4-chlorophenyl)((3,8-dimethyl-[1,2,4]triazolo[4,3-a]pyridin-6-yl)amino)methyl)-1H-imidazole-4-carboxylic acid The title compound was prepared in analogy to the procedure described in Step 1.10 using ethyl 1-allyl-2-bromo-5 ((4-chlorophenyl)((3,8-dimethyl-[1,2,4]triazolo[4,3-a]pyridin-6-yl)amino)methyl)-1H-imidazole-4-carboxylate (Step 116.1) as starting material. t$_R$: 0.84 min (LC-MS 2); ESI-MS: 517.1 [M+H]$^+$/513.1 [M−H]$^−$ (LC-MS 2).

Step 116.3: 1-allyl-2-bromo-6-(4-chlorophenyl)-5-(3,8-dimethyl-[1,2,4]triazolo[4,3-a]pyridin-6-yl)-5,6-dihydropyrrolo[3,4-d]imidazol-4(1H)-one The title compound was prepared in analogy to the procedure described in Step 1.11 using ethyl 1-allyl-2-bromo-5 (4-chlorophenyl)((3,8-dimethyl-[1,2,4]triazolo[4,3-a]pyridin-6-yl)amino)methyl)-1H-imidazole-4-carboxylic acid (Step 116.2) as starting material. t$_R$: 0.89 min (LC-MS 2); ESI-MS: 499.1 [M+H]$^+$/497.1 [M−H]$^−$ (LC-MS 2).

Step 116.4: 6-(4-chlorophenyl)-2-(3,6-dihydro-2H-pyran-4-yl)-5-(3,8-dimethyl-[1,2,4]triazolo[4,3-a]pyridin-6-yl)-5,6-dihydropyrrolo[3,4-d]imidazol-4(1H)-one The title compound was prepared in analogy to the procedure described in Example 13 using 1-allyl-2-bromo-6-(4-chlorophenyl)-5-(3,8-dimethyl-[1,2,4]triazolo[4,3-a]pyridin-6-yl)-5,6-dihydropyrrolo[3,4-d]imidazol-4(1H)-one (Step 116.3) and 3,6-dihydro-2H-pyran-4-boronic acid pinacol ester as starting materials. The crude product was purified by preparative HPLC (column: Waters SunFire C18, 30×100×5 mm; solvent A water/0.1% TFA; solvent B acetonitrile; gradient 25-45% B in 16 min) t$_R$: 0.75 min (LC-MS 2); ESI-MS: 461.1 [M+H]$^+$/459.1 [M−H]$^−$ (LC-MS 2).

EXAMPLE 117

6-(4-chlorophenyl)-5-(3,8-dimethyl-[1,2,4]triazolo[4,3-a]pyridin-6-yl)-2-(6-methoxypyridin-3-yl)-5,6-dihydropyrrolo[3,4-d]imidazol-4(1H)-one

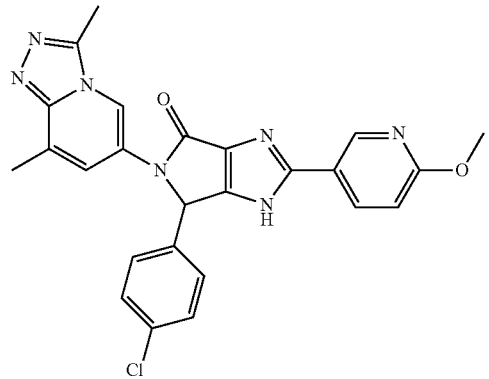

The title compound was prepared in analogy to the procedure described in Example 13 using 1-allyl-2-bromo-6-(4-chlorophenyl)-5-(3,8-dimethyl-[1,2,4]triazolo[4,3-a]pyridin-6-yl)-5,6-dihydropyrrolo[3,4-d]imidazol-4(1H)-one (Step 116.3) and 2-methoxy-5-pyridineboronic acid as starting materials. The crude product was purified by preparative HPLC (column: Waters SunFire C18, 30×100×5 µm; solvent A: water/0.1% TFA; solvent B: acetonitrile; gradient 25-45% B in 16 min) to give the title compound as white solid. t$_R$: 0.84 min (LC-MS 2); ESI-MS: 461.1 [M+H]$^+$/459.1 [M−H]$^−$ (LC-MS 2).

EXAMPLE 118

(R)-6-(4-chlorophenyl)-5-(3,7-dimethyl-3H-benzo[d][1,2,3]triazol-5-yl)-3-isopropyl-2-methyl-5,6-dihydropyrrolo[3,4-d]imidazol-4(3H)-one

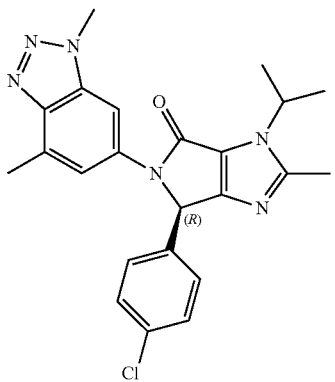

The title compound (21 mg, 38% yield) was obtained enantiomerically pure (>99% ee) after chiral preparative chromatography (system: Thar SFC200 preparative SFC; column: Chiralpak IA, 30×250 mm; mobile phase: scCO$_2$/iPrOH+5% CH$_2$Cl$_2$ 75:25; flow: 200 g/min; temperature: 38° C.; detection UV: 300 nm) of the racemic mixture of 6-((4-chlorophenyl)-5-(3,7-dimethyl-3H-benzo[d][1,2,3]triazol-5-yl)-3-isopropyl-2-methyl-5,6-dihydropyrrolo[3,4-d]imidazol-4(3H)-one (Example 3).

(R)-6-(4-chlorophenyl)-5-(3,7-dimethyl-3H-benzo[d][1,2,3]triazol-5-yl)-3-isopropyl-2-methyl-5,6-dihydropyrrolo[3,4-d]imidazol-4(3H)-one. t$_R$: 3.54 min (system: Thar analytical SFC system; column: Chiralpak IA, 4.6×250 mm; mobile phase: scCO$_2$/iPrOH 75:25; flow: 4.0 mL/min; temperature: 35° C.; detection UV: 220 nm).

(S)-6-(4-chlorophenyl)-5-(3,7-dimethyl-3H-benzo[d][1,2,3]triazol-5-yl)-3-isopropyl-2-methyl-5,6-dihydropyrrolo[3,4-d]imidazol-4(3H)-one. t$_R$: 5.24 min (system: Thar analytical SFC system; column: Chiralpak IA, 4.6×250 mm; mobile phase: scCO$_2$/iPrOH 75:25; flow: 4.0 mL/min; temperature: 35° C.; detection UV: 220 nm).

EXAMPLE 119

6-(4-chlorophenyl)-5-(3,7-dimethyl-3H-benzo[d][1,2,3]triazol-5-yl)-3-ethyl-2-methyl-5,6-dihydropyrrolo[3,4-d]imidazol-4(3H)-one

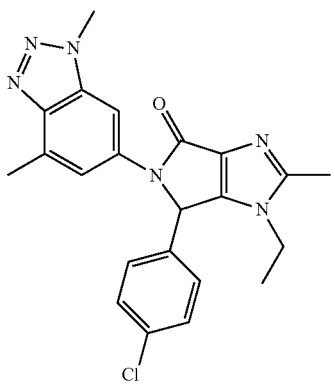

The title compound was prepared in analogy to the procedure described in Example 2 using 6-(4-chlorophenyl)-5-(3,7-dimethyl-3H-benzo[d][1,2,3]triazol-5-yl)-2-methyl-5,6-dihydropyrrolo[3,4-d]imidazol-4(1H)-one (Example 1) and 1-iodo ethan as starting materials. Purification of the crude material by preparative HPLC (column: Waters SunFire C18, 30×100×5 µm; solvent A: water/0.1% TFA; solvent B: acetonitrile; gradient 25-45% B in 16 min) afforded 40 mg of 6-(4-chlorophenyl)-5-(3,7-dimethyl-3H-benzo[d][1,2,3]triazol-5-yl)-3-ethyl-2-methyl-5,6-dihydropyrrolo[3,4-d]imidazol-4(3H)-one, (Example 121) and 34 mg of the title compound. t$_R$: 0.90 min (LC-MS 2); ESI-MS: 421.1 [M+H]$^+$ (LC-MS 2).

EXAMPLE 120

(R)-6-(4-chlorophenyl)-5-(3,7-dimethyl-3H-benzo[d][1,2,3]triazol-5-yl)-1-ethyl-2-methyl-5,6-dihydropyrrolo[3,4-d]imidazol-4(1H)-one

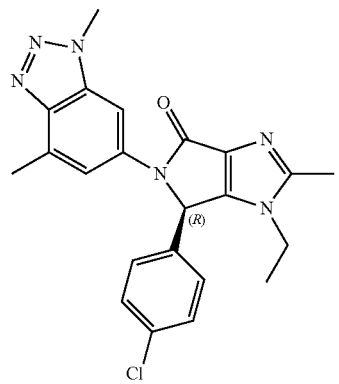

The title compound (8 mg, 26% yield) was obtained enantiomerically pure (>99% ee) after chiral preparative chromatography (system: Gilson 215 prep; column: Chiralcel OD-H, 20×250 mm; mobile phase: heptane/EtOH/MeOH 50:25:25; flow: 12 mL/min; temperature: 38° C.; detection UV: 220 nm) of the racemic mixture of 6-((4-chlorophenyl)-5-(3,7-dimethyl-3H-benzo[d][1,2,3]triazol-5-yl)-1-ethyl-2-methyl-5,6-dihydropyrrolo[3,4-d]imidazol-4(1H)-one (Example 119).

(R)-6-((4-chlorophenyl)-5-(3,7-dimethyl-3H-benzo[d][1,2,3]triazol-5-yl)-1-ethyl-2-methyl-5,6-dihydropyrrolo[3,4-d]imidazol-4(1H)-one. t$_R$: 8.48 min (analytical system: Shimadzu LC 20AT; column: Chiralcel OD-H, 4.6×250 mm; mobile phase: heptane/EtOH/MeOH 50:25:25; flow: 1.0 mL/min; temperature: 35° C.; detection UV: 220 nm).

(S)-6-(4-chlorophenyl)-5-(3,7-dimethyl-3H-benzo[d][1,2,3]triazol-5-yl)-3-ethyl-2-methyl-5,6-dihydropyrrolo[3,4-d]imidazol-4(3H)-one. t$_R$: 4.38 min (system: Shimadzu LC 20AT; column: Chiralcel OD-H, 4.6×250 mm; mobile phase: heptane/EtOH/MeOH 50:25:25; flow: 1.0 mL/min; temperature: 35° C.; detection UV: 220 nm).

EXAMPLE 121

6-(4-chlorophenyl)-5-(3,7-dimethyl-3H-benzo[d][1,2,3]triazol-5-yl)-3-ethyl-2-methyl-5,6-dihydropyrrolo[3,4-d]imidazol-4(3H)-one

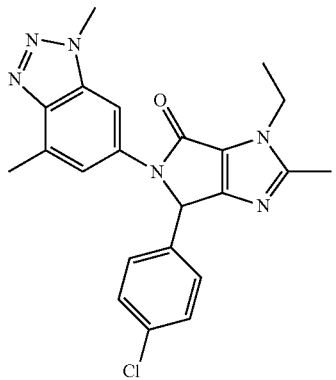

The preparation of the title compound is described in Example 119. $t_R$: 0.94 min (LC-MS 2); ESI-MS: 421.1 [M+H]$^+$ (LC-MS 2).

EXAMPLE 122

(R)-6-(4-chlorophenyl)-5-(3,7-dimethyl-3H-benzo[d][1,2,3]triazol-5-yl)-3-ethyl-2-methyl-5,6-dihydropyrrolo[3,4-d]imidazol-4(3H)-one

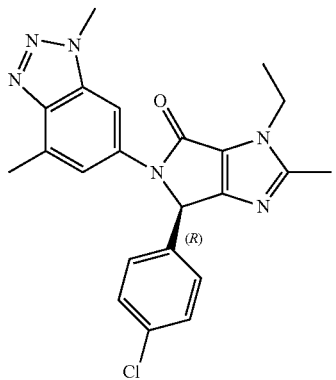

The title compound (13 mg, 38% yield) was obtained enantiomerically pure (>99% ee) after chiral preparative chromatography (system: Gilson 215 prep; column: Chiralpak AD-H, 20×250 mm; mobile phase: EtOH/MeOH 50:50; flow: 12 mL/min; temperature: 38° C.; detection UV: 220 nm) of the racemic mixture of 6-((4-chlorophenyl)-5-(3,7-dimethyl-3H-benzo[d][1,2,3]triazol-5-yl)-3-ethyl-2-methyl-5,6-dihydropyrrolo[3,4-d]imidazol-4(3H)-one (Example 121).

(R)-6-(4-chlorophenyl)-5-(3,7-dimethyl-3H-benzo[d][1,2,3]triazol-5-yl)-3-ethyl-2-methyl-5,6-dihydropyrrolo[3,4-d]imidazol-4(3H)-one. $t_R$: 9.63 min (analytical system: Shimadzu LC 20AT; column: Chiralpak AD-H, 4.6×250 mm; mobile phase: EtOH/MeOH 50:50; flow: 1.0 mL/min; temperature: 35° C.; detection UV: 220 nm).

(S)-6-(4-chlorophenyl)-5-(3,7-dimethyl-3H-benzo[d][1,2,3]triazol-5-yl)-3-ethyl-2-methyl-5,6-dihydropyrrolo[3,4-d]imidazol-4(3H)-one. $t_R$: 5.18 min (analytical system: Shimadzu LC 20AT; column: Chiralpak AD-H, 4.6×250 mm; mobile phase: EtOH/MeOH 50:50; flow: 1.0 mL/min; temperature: 35° C.; detection UV: 220 nm).

EXAMPLE 123

6-(4-chlorophenyl)-5-(3,8-dimethyl-[1,2,4]triazolo[4,3-a]pyridin-6-yl)-2-(2-methoxypyridin-3-yl)-5,6-dihydropyrrolo[3,4-d]imidazol-4(1H)-one

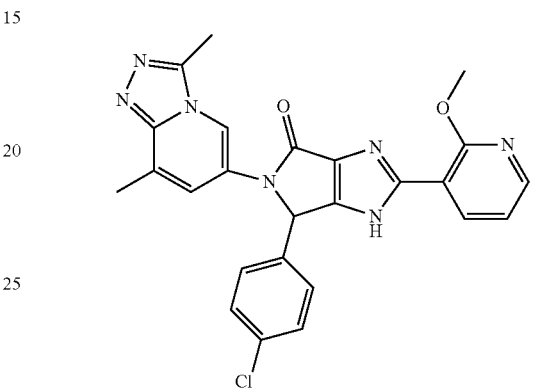

The title compound was prepared in analogy to the procedure described in Example 1 using 1-allyl-2-bromo-6-(4-chlorophenyl)-5-(3,8-dimethyl-[1,2,4]triazolo[4,3-a]pyridin-6-yl)-5,6-dihydropyrrolo[3,4-d]imidazol-4(1H)-one (Step 116.3) and 2-methoxypyridine-3-boronic acid as starting materials. The crude product was purified by flash chromatography (ISCO-flashmaster system; column: 40 g. solvent A: dichloromethan; solvent B: MeOH; gradient (% B): 0% for 10 min, 0-10% for 30 min, 10% for 10 min; flow 50 mL/min. $t_R$: 0.9 min (LC-MS 2); ESI-MS: 486.4 [M+H]$^+$/484.4 [M−H]$^−$ (LC-MS 2).

EXAMPLE 124

6-(4-chlorophenyl)-2-(2,4-dimethoxypyrimidin-5-yl)-5-(3,8-dimethyl-[1,2,4]triazolo[4,3-a]pyridin-6-yl)-5,6-dihydropyrrolo[3,4-d]imidazol-4(1H)-one

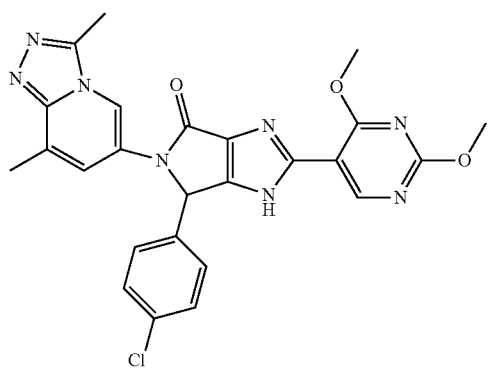

The title compound was prepared in analogy to the procedure described in Example 1 using 1-allyl-2-bromo-6-

(4-chlorophenyl)-5-(3,8-dimethyl-[1,2,4]triazolo[4,3-a]
pyridin-6-yl)-5,6-dihydropyrrolo[3,4-d]imidazol-4(1H)-one
(Step 116.3) and 2,4-dimethoxypyrimidine-5-boronic acid
as starting materials. Purification of the crude material by
preparative HPLC (column: Waters SunFire C18, 30×100×5
µm; solvent A: water/0.1% TFA; solvent B: acetonitrile;
gradient 25-45% B in 16 min) afforded the title compound
as a white powder. $t_R$: 0.85 min (LC-MS 2); ESI-MS: 517.3
[M+H]$^+$/515.2 [M−H]$^−$ (LC-MS 2).

EXAMPLE 125

6-(4-chlorophenyl)-5-(8-methoxy-3-methyl-[1,2,4]
triazolo[4,3-a]pyridin-6-yl)-2-(6-methoxypyridin-3-
yl)-5,6-dihydropyrrolo[3,4-d]imidazol-4(1H)-one

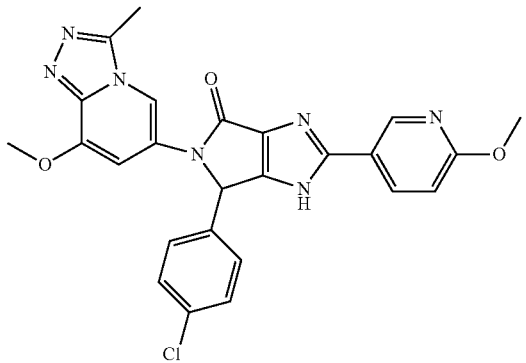

The title compound was prepared in analogy to the
procedure described in Example 1 using 1-allyl-2-bromo-6-
(4-chlorophenyl)-5-(8-methoxy-3-methyl-[1,2,4]triazolo[4,
3-a]pyridin-6-yl)-5,6-dihydropyrrolo[3,4-d]imidazol-4
(1H)-one (Step 125.3) and 2-methoxy-5-pyridine boronic
acid as starting materials. The crude product was purified by
flash chromatography (ISCO-flashmaster system; column:
40 g, solvent A: dichloromethan; solvent B: MeOH; gradient
(% B): 0% to 100% in 45 min; flow 50 mL/min. $t_R$: 0.83 min
(LC-MS 2); ESI-MS: 502.0 [M+H]$^+$/500.1 [M−H]$^−$ (LC-MS
2).

Step 125.1: ethy-1-allyl 2-bromo-5 ((4-chlorophe-
nyl)((8-methoxy-3-methyl-[1,2,4]triazolo[4,3-a]pyri-
din-6-yl)amino)methyl-1-H-imidazole-4-carboxylate The title compound was prepared in analogy to the
procedure described in Step 1.9 using ethyl 1-allyl-2-bromo-
5-((4-chlorophenyl)(hydroxy)methyl)-1H-imidazole-4-car-
boxylate (Step 1.8) and 8-methoxy-3-methyl-[1,2,4]triazolo
[4,3-a]pyridin-6-amine (step 17.4) as starting materials. The
crude product was purified by flash chromatography (Isco
RediSep 80 g column, CH$_2$Cl$_2$/MeOH; gradient 0-10%
MeOH). $t_R$: 1.01 min (LC-MS 2); ESI-MS: 561.2 [M+H]$^+$/
559.2 [M−H]$^−$ (LC-MS 2).

Step 125.2: 1-allyl 2-bromo-5 ((4-chlorophenyl)((8-
methoxy-3-methyl-[1,2,4]triazolo[4,3-a]pyridin-6-
yl)amino)methyl-1-H-imidazole-4-carboxylic acid The title compound was prepared in analogy to the
procedure described in Step 1.10 using ethy-1-allyl
2-bromo-5 ((4-chlorophenyl)((8-methoxy-3-methyl-[1,2,4]
triazolo[4,3-a]pyridin-6-yl)amino)methyl-1-H-imidazole-4-
carboxylate (Step 125.1) as starting material. $t_R$: 0.85 min
(LC-MS 2); ESI-MS: 533.1 [M+H]$^+$/531.1 [M−H]$^−$ (LC-MS
2).

Step 125.3: 1-allyl-2-bromo-6-((4-chlorophenyl)-5-
(8-methoxy-3-methyl-[1,2,4]triazolo[4,3-a]pyridin-
6-yl)-5,6-dihydropyrrolo[3,4-d]imidazol-4(1H)-one The title compound was prepared in analogy to the
procedure described in Step 1.11 using 1-allyl 2-bromo-5
((4-chlorophenyl)((8-methoxy-3-methyl-[1,2,4]triazolo[4,
3-a]pyridin-6-yl)amino)methyl-1-H-imidazole-4-carboxylic
acid (Step 125.2) as starting material. $t_R$: 0.88 min (LC-MS
2); ESI-MS: 515.1 [M+H]$^+$/513.1 [M−H]$^−$ (LC-MS 2).

EXAMPLE 126

(R)-6-(4-chlorophenyl)-5-(8-methoxy-3-methyl-[1,2,
4]triazolo[4,3-a]pyridin-6-yl)-2-(6-methoxypyridin-
3-yl)-5,6-dihydropyrrolo[3,4-d]imidazol-4(1H)-one

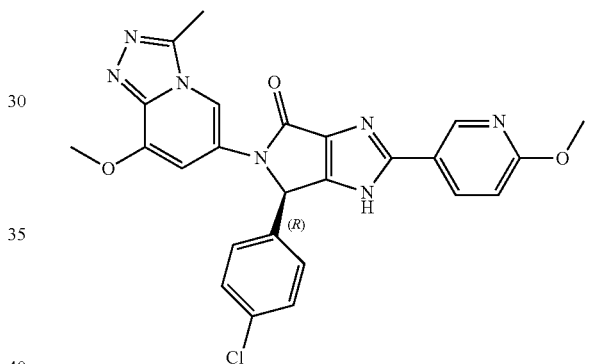

The title compound (44 mg, 26% yield) was obtained
enantiomerically pure (>99% ee) after chiral preparative
chromatography (system: Gilson PLC2020; column: Chiral-
cel OD-H, 20×250 mm; mobile phase: Heptane/EtOH
80:20; flow: 10 mL/min; temperature: 38° C.; detection UV:
220 nm) of the racemic mixture of 6-((4-chlorophenyl)-5-
(8-methoxy-3-methyl-[1,2,4]triazolo[4,3-a]pyridin-6-yl)-2-
(6-methoxypyridin-3-yl)-5,6-dihydropyrrolo[3,4-d]imida-
zol-4(1H)-one (Example 125).

(R)-6-(4-chlorophenyl)-5-(8-methoxy-3-methyl-[1,2,4]
triazolo[4,3-a]pyridin-6-yl)-2-(6-methoxypyridin-3-yl)-5,6-
dihydropyrrolo[3,4-d]imidazol-4(1H)-one. $t_R$: 14.76 min
(analytical system: Shimadzu LC 20AT; column: Chiralcel
OD-H, 4.6×250 mm; mobile phase: EtOH/MeOH 50:50;
flow: 1.0 mL/min; temperature: 35° C.; detection UV: 220
nm).

(S)-6-(4-chlorophenyl)-5-(8-methoxy-3-methyl-[1,2,4]
triazolo[4,3-a]pyridin-6-yl)-2-(6-methoxypyridin-3-yl)-5,6-
dihydropyrrolo[3,4-d]imidazol-4(1H)-one. $t_R$: 18.17 min
(analytical system: Shimadzu LC 20AT; column: Chiralcel
OD-H, 4.6×250 mm; mobile phase: EtOH/MeOH 50:50;
flow: 1.0 mL/min; temperature: 35° C.; detection UV: 220
nm).

EXAMPLE 127

6-(4-chlorophenyl)-2-(2,4-dimethoxypyrimidin-5-yl)-5-(8-methoxy-3-methyl-[1,2,4]triazolo[4,3-a]pyridin-6-yl)-5,6-dihydropyrrolo[3,4-d]imidazol-4(1H)-one

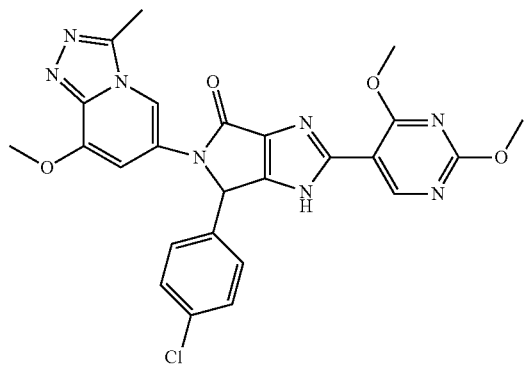

The title compound was prepared in analogy to the procedure described in Example 1 using 1-allyl-2-bromo-6-(4-chlorophenyl)-5-(8-methoxy-3-methyl-[1,2,4]triazolo[4,3-a]pyridin-6-yl)-5,6-dihydropyrrolo[3,4-d]imidazol-4(1H)-one (Step 125.3) and 2,4-dimethoxy-pyrimidine-5-boronic acid as starting materials. The crude product was purified by flash chromatography (ISCO-flashmaster system; column: 40 g, solvent A: dichloromethan; solvent B: MeOH; gradient (% B): 0% to 100% in 45 min; Flow 50 mL/min. $t_R$: 0.84 min (LC-MS 2); ESI-MS: 533.2 [M+H]$^+$/531.2 [M−H]$^-$ (LC-MS 2).

EXAMPLE 128

(R)-6-(4-chlorophenyl)-2-(2,4-dimethoxypyrimidin-5-yl)-5-(8-methoxy-3-methyl-[1,2,4]triazolo[4,3-a]pyridin-6-yl)-5,6-dihydropyrrolo[3,4-d]imidazol-4(1H)-one

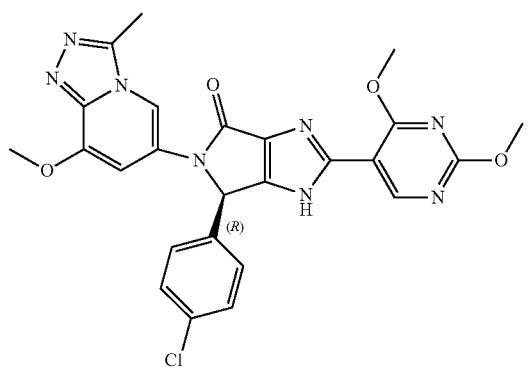

The title compound (22 mg, 44% yield) was obtained enantiomerically pure (>99% ee) after chiral preparative chromatography (system: Thar SFC200; column: Chiralpak AD-H, 20×250 mm; mobile phase: scCO$_2$/MeOH 60:40; flow: 10 mL/min; temperature: 38° C.; detection UV: 220 nm) of the racemic mixture of 6-(4-chlorophenyl)-2-(2,4-dimethoxypyrimidin-5-yl)-5-(8-methoxy-3-methyl-[1,2,4]triazolo[4,3-a]pyridin-6-yl)-5,6-dihydropyrrolo[3,4-d]imidazol-4(1H)-one (Example 127).

(R)-6-(4-chlorophenyl)-2-(2,4-dimethoxypyrimidin-5-yl)-5-(8-methoxy-3-methyl-[1,2,4]triazolo[4,3-a]pyridin-6-yl)-5,6-dihydropyrrolo[3,4-d]imidazol-4(1H)-one. $t_R$: 2.86 min (analytical system: system: Thar/Waters SFC Investigator MS (ZQ); column: Chiralpak AD-H, 4.6×250 mm; mobile phase: scCO$_2$/MeOH 60:40; flow: 1.0 mL/min; temperature: 35° C.; detection UV: 220 nm).

(S)-6-(4-chlorophenyl)-2-(2,4-dimethoxypyrimidin-5-yl)-5-(8-methoxy-3-methyl-[1,2,4]triazolo[4,3-a]pyridin-6-yl)-5,6-dihydropyrrolo[3,4-d]imidazol-4(1H)-one. $t_R$: 7.17 min (analytical system: system: Thar/Waters SFC Investigator MS (ZQ); column: Chiralpak AD-H, 4.6×250 mm; mobile phase: scCO$_2$/MeOH 60:40; flow: 1.0 mL/min; temperature: 35° C.; detection UV: 220 nm).

EXAMPLE 129

(R)-6-(4-chlorophenyl)-5-(3,8-dimethyl-[1,2,4]triazolo[4,3-a]pyridin-6-yl)-2-(6-methoxypyridin-3-yl)-5,6-dihydropyrrolo[3,4-d]imidazol-4(1H)-one

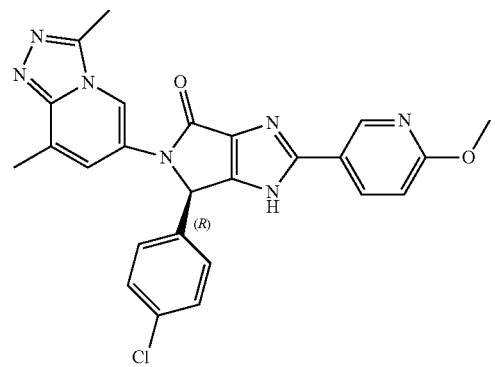

The title compound (20 mg, 40% yield) was obtained enantiomerically pure (>99% ee) after chiral preparative chromatography chromatography (system: Thar SFC200; column: Chiralpak AD-H, 20×250 mm; mobile phase: scCO$_2$/isopropylalcohol 60:40; flow: 140 g/min; temperature: 38° C.; detection UV: 220 nm) of the racemic mixture of 6-((4-chlorophenyl)-5-(3,8-dimethyl-[1,2,4]triazolo[4,3-a]pyridin-6-yl)-2-(6-methoxypyridin-3-yl)-5,6-dihydropyrrolo[3,4-d]imidazol-4(1H)-one (Example 117).

(R)-6-(4-chlorophenyl)-5-(3,8-dimethyl-[1,2,4]triazolo[4,3-a]pyridin-6-yl)-2-(6-methoxypyridin-3-yl)-5,6-dihydropyrrolo[3,4-d]imidazol-4(1H)-one. $t_R$: 3.34 min (analytical system: system: Thar/Waters SFC Investigator MS (ZQ); column: Chiralpak AD-H, 4.6×250 mm; mobile phase: scCO$_2$/isopropylalcohol 60:40; flow: 4.0 mL/min; temperature: 35° C.; detection UV: 220 nm).

(S)-6-((4-chlorophenyl)-5-(3,8-dimethyl-[1,2,4]triazolo[4,3-a]pyridin-6-yl)-2-(6-methoxypyridin-3-yl)-5,6-dihydropyrrolo[3,4-d]imidazol-4(1H)-one. $t_R$: 5.89 min (analytical system: Thar/Waters SFC Investigator MS (ZQ); column: Chiralpak AD-H, 4.6×250 mm; mobile phase: scCO$_2$/isopropylalcohol 60:40; flow: 4.0 mL/min; temperature: 35° C.; detection UV: 220 nm).

EXAMPLE 130

6-(4-chlorophenyl)-5-(1,5-dimethyl-6-oxo-1,6-dihydropyridin-3-yl)-1-methyl-2-morpholino-5,6-dihydropyrrolo[3,4-d]imidazol-4(1H)-one

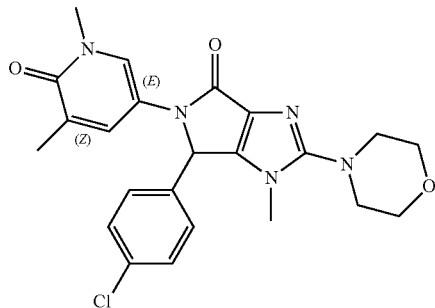 [SMILES: Cc1cc(N2C(=O)c3nc(N4CCOCC4)n(C)c3C2c2ccc(Cl)cc2)cn(C)c1=O]

To a solution of 2-bromo-5-(5-chloro-1-methyl-6-oxo-1,6-dihydropyridin-3-yl)-6-((4-chlorophenyl)-1-methyl-5,6-dihydropyrrolo[3,4-d]imidazol-4(1H)-one (50 mg, 0.112 mmol; Step 130.3) in DMSO (3 mL) was added morpholine (195 mg, 2.23 mmol) and cesium fluoride (25.4 mg, 0.17 mmol). The reaction vessel was sealed and heated to 120° C. for 6 h. It was then allowed to cool to ambient temperature and diluted with EtOAc and water. The organic layer was separated, dried and concentrated to give the crude product which was purified by SFC chromatography (Thar 100; column: PFP, 25 cm, Ø 3 cm, 5 μm, 60 Å; gradient: 19% B for 1 min, 19-24% B in 6 min, 24-50% B in 1 min, 50% B for 1 min, 50%-19% B in 1 min, 19% B for 0.5 min; A: scCO$_2$, B: MeOH; flow: 100 mL/min) to afford the title compound. $t_R$: 0.78 min (LC-MS 2); ESI-MS: 454.2 [M+H]. $^1$H NMR (400 MHz, MeOH-d4) δ ppm 2.04 (s, 3 H) 3.10-3.15 (m, 4 H) 3.32 (s, 3 H) 3.49 (s, 3 H) 3.76-3.84 (m, 4 H) 6.04 (s, 1 H) 7.24 (d, J=8.59 Hz, 2 H); (7.34-7.41 (m, 3 H); 7.54 (s, 1H).

Step 130.1: methyl 2-bromo-5-(((5-chloro-1-methyl-6-oxo-1,6-dihydropyridin-3-yl)amino)(4-chlorophenyl)methyl)-1-methyl-1H-imidazole-4-carboxylate The title compound was prepared in analogy to the procedure described in Step 1.9 using ethyl 2-bromo-5-((4-chlorophenyl)(hydroxy)methyl)-1-methyl-1H-imidazole-4-carboxylate (Step 16.3) and 5-amino-1,3-dimethylpyridin-2(1H)-one (Step 4.3) as starting materials. The crude product was purified by flash chromatography (Isco RediSep 80 g column, CH$_2$Cl$_2$/MeOH; gradient 0-2% MeOH). $t_R$: 0.94 min (LC-MS 2); ESI-MS: 502.0 [M+H]$^+$ (LC-MS 2).

Step 130.2: 2-bromo-5-(((5-chloro-1-methyl-6-oxo-1,6-dihydropyridin-3-yl)amino)(4-chlorophenyl)methyl)-1-methyl-1H-imidazole-4-carboxylic acid The title compound was prepared in analogy to the procedure described in Step 1.10 using methyl 2-bromo-5-(((5-chloro-1-methyl-6-oxo-1,6-dihydropyridin-3-yl)amino)(4-chlorophenyl)methyl)-1-methyl-1H-imidazole-4-carboxylate yl)amino)methyl-1-H-imidazole-4-carboxylate (Step 130.1) as starting material. $t_R$: 0.80 min (LC-MS 2); ESI-MS: 486.9 [M+H]$^+$/484.9 [M–H]$^-$ (LC-MS 2).

Step 130.3: 2-bromo-5-(5-chloro-1-methyl-6-oxo-1,6-dihydropyridin-3-yl)-6-((4-chlorophenyl)-1-methyl-5,6-dihydropyrrolo[3,4-d]imidazol-4(1H)-one The title compound was prepared in analogy to the procedure described in Step 1.11 using 2-bromo-5-((5-chloro-1-methyl-6-oxo-1,6-dihydropyridin-3-yl)amino)((4-chlorophenyl)methyl)-1-methyl-1H-imidazole-4-carboxylic acid (Step 130.2) as starting material. $t_R$: 0.83 min (LC-MS 2); ESI-MS: 471.1 [M+H]$^+$/469.01 [M–H]$^-$ (LC-MS 2).

EXAMPLE 131

6-(4-chlorophenyl)-5-(3-(difluoromethyl)-8-methyl-[1,2,4]triazolo[4,3-a]pyridin-6-yl)-1-isopropyl-2-methyl-5,6-dihydropyrrolo[3,4-d]imidazol-4(1H)-one

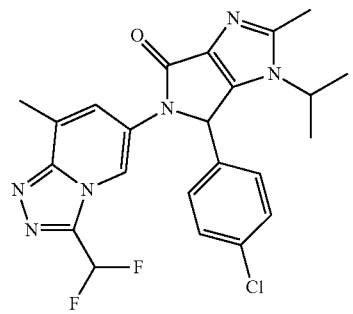 [SMILES: Cc1cc(N2C(=O)c3nc(C)n(C(C)C)c3C2c2ccc(Cl)cc2)cn2c(C(F)F)nnc12]

The title compound was prepared in analogy to the procedure described for Example 1 using 2-bromo-6-((4-chlorophenyl)-5-(3-(difluoromethyl)-8-methyl-[1,2,4]triazolo[4,3-a]pyridin-6-yl)-1-isopropyl-5,6-dihydropyrrolo[3,4-d]imidazol-4(1H)-one (Step 131.6) as a starting material. Purification of the crude material by preparative HPLC (column: Waters SunFire C18, 30×100×5 μm; solvent A: water/0.1% TFA; solvent B: acetonitrile; gradient 25-45% B in 16 min) afforded the title compound as a white solid. $t_R$: 0.91 min (LC-MS 2); ESI-MS: 471.3 [M+H]$^+$ (LC-MS 2).

Step 131.1: 2-hydrazinyl-3-methyl-5-nitropyridine

At ambient temperature 2-chloro-3-methyl-5-nitropyridine (250 g, 1449 mmol) and ethanol (2.8 L) were placed in a reaction vessel to give a yellow suspension. Hydrazine hydrate (352 mL, 7243 mmol) was added via dropping funnel. The reaction mixture changed to a dark red solution. The internal temperature raised slowly up to 50° C. after 1 hour. The reaction was allowed to stir for an additional hour and then cooled in a dry ice/acetone bath to 10° C. and stirred for 30 min. The resulting suspension was filtered and washed twice with ice water (200 ml) and twice with MTBE (200 ml). The yellow filter cake was dried at 50° C. for 5 hours under vacuum to give the title compound as a yellow powder.

Step 131.2: 3-(difluoromethyl)-8-methyl-6-nitro-[1,2,4]triazolo[4,3-a]pyridine

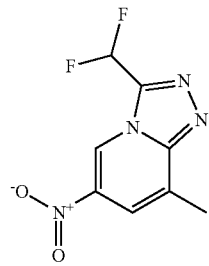

To a solution of 2-hydrazinyl-3-methyl-5-nitropyridine (2 g, 11.9 mmol) in THF (50 mL) was added a solution of 2,2-difluoroacetic anhydride (1.68 mL, 13.08 mmol) in THF (2 mL) at 0° C. over a period of 0.5 h. The reaction mixture was stirred for 0.5 h at 0° C. and the initially formed 2,2-difluoro-N'-(3-methyl-5-nitropyridin-2-yl)acetohydrazide was subsequently heated for 4 h at 140° C. in the MW. The reaction mixture was concentrated and the crude product was purified by silica gel column chromatography (hexane/CH$_2$Cl$_2$/MeOH 90:10:1 to 50:50:5) to provide the title product (2.31 g, 85% yield) as a brown solid. t$_R$: 0.68 min (LC-MS 1); ESI-MS: 229 [M+H]$^+$ (LC-MS 1); R$_f$=0.48 (hexane/EtOAc/MeOH 50:50:5); $^1$H NMR (400 MHz, DMSO-d$_6$) δ ppm 2.69 (s, 3 H) 7.77 (t, J=56.7 Hz, 1 H) 8.09 (s, 1 H) 9.60 (s, 1 H).

Step 131.3: 3-(difluoromethyl)-8-methyl-[1,2,4]triazolo[4,3-a]pyridin-6-amine

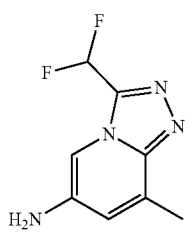

A solution of 3-(difluoromethyl)-8-methyl-6-nitro-[1,2,4]triazolo[4,3-a]pyridine (3.3 g, 10.12 mmol) in MeOH (30 mL) was hydrogenated over 10% Pd/C (0.86 g) for 3 h at 50° C. and 1000 mbar H$_2$. The reaction mixture was filtered over Celite and the filtrate was concentrated. The crude product was purified by silica gel column chromatography (hexane/CH$_2$Cl$_2$/MeOH 100:100:5 to 0:100:5 containing 0.2% NEt$_3$) to provide the title product (1.05 g, 49% yield) as a white solid. t$_R$: 0.46 min (LC-MS 1); ESI-MS: 199 [M+H]$^+$ (LC-MS 1); R$_f$=0.35 (CH$_2$Cl$_2$/MeOH 19:1); $^1$H NMR (400 MHz, DMSO-d$_6$) δ ppm 2.52 (s, 3H) 5.41 (s, 2 H) 6.95 (s, 1 H) 7.61 (t, J=53.9 Hz, 1 H) 7.56 (s, 1 H).

Step 131.4: ethyl 2-bromo-5 ((4-chlorophenyl)((3-(difluoromethyl)-8-methyl-[1,2,4]triazolo[4,3-a]pyridin-6-yl)amino)methyl)-1-isopropyl-1H-imidazole-4-carboxylate The title compound was prepared in analogy to the procedure described for Step 1.9 using ethyl 2-bromo-5-((4-chlorophenyl)(hydroxy)methyl)-1-isopropyl-1H-imidazole-4-carboxylate (Step 9.6) and 3-(difluoromethyl)-8-methyl-[1,2,4]triazolo[4,3-a]pyridin-6-amine (Step 131.3). t$_R$: 1.14 min (LC-MS 2); ESI-MS: 583.1 [M+H]$^+$ (LC-MS 2).

Step 131.5: 2-bromo-5 ((4-chlorophenyl)((3-(difluoromethyl)-8-methyl-[1,2,4]triazolo[4,3-a]pyridin-6-yl)amino)methyl)-1-isopropyl-1H-imidazole-4-carboxylic acid The title compound was prepared in analogy to the procedure described in Step 1.10 using ethyl 2-bromo-5 ((4-chlorophenyl)((3-(difluoromethyl)-8-methyl-[1,2,4]triazolo[4,3-a]pyridin-6-yl)amino)methyl)-1H-imidazole-4-carboxylate (Step 131.4). The crude product was diluted with CH$_2$Cl$_2$/MeOH 5:1 and sonicated. The resulting solid was filtered off, washed with CH$_2$Cl$_2$/MeOH 5:1 and the combined filtrates were concentrated under reduced pressure to afford the desired product. t$_R$: 0.96 min (LC-MS 2); ESI-MS: 555.2 [M+H]$^+$/551.1[M–H]$^-$ (LC-MS 2).

Step 131.6: 2-bromo-6-(4-chlorophenyl)-5-(3-(difluoromethyl)-8-methyl-[1,2,4]triazolo[4,3-a]pyridin-6-yl)-1-isopropyl-5,6-dihydropyrrolo[3,4-d]imidazol-4(1H)-one The title compound was prepared in analogy to the procedure described in Step 1.11 using 2-bromo-5-((4-chlorophenyl)((3-(difluoromethyl)-8-methyl-[1,2,4]triazolo[4,3-a]pyridin-6-yl)amino)methyl)-1-isopropyl-1H-imidazole-4-carboxylic acid (Step 131.5). Tituration of the crude product with diethylether afforded the title compound as beige solid. t$_R$: 1.02 min (LC-MS 2); ESI-MS: 537.2 [M+H]$^+$ (LC-MS 2).

EXAMPLE 132

6-(4-chlorophenyl)-5-(3-(difluoromethyl)-8-methyl-[1,2,4]triazolo[4,3-a]pyridin-6-yl)-1-isopropyl-2-(2-methoxypyridin-3-yl)-5,6-dihydropyrrolo[3,4-d]imidazol-4(1H)-one

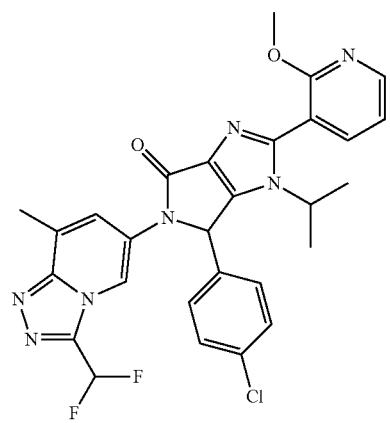 [SMILES: COc1ncccc1-c1nc2c(n1C(C)C)C(c1ccc(Cl)cc1)N(c1cc(C)c3nnc(C(F)F)n3c1)C2=O]

The title compound was prepared in analogy to the procedure described for Example 1 using 2-bromo-6-(4-chlorophenyl)-5-(3-(difluoromethyl)-8-methyl-[1,2,4]triazolo[4,3-a]pyridin-6-yl)-1-isopropyl-5,6-dihydropyrrolo[3,4-d]imidazol-4(1H)-one (Step 131.6) and 2-methoxy-3- pyridineboronic acid as a starting materials. Purification of the crude material by preparative HPLC (column: Waters SunFire C18, 30×100×5 μm; solvent A: water/0.1% TFA; solvent B: acetonitrile; gradient 40-60% B in 16 min) afforded the title compound as a white solid. $t_R$: 1.06 min (LC-MS 2); ESI-MS: 564.3 [M+H]$^+$ (LC-MS 2). $^1$H NMR (400 MHz, DMSO-d6) δ ppm 0.53 (d, J=6.72 Hz, 3 H) 1.43 (d, J=6.72 Hz, 3 H) 2.56 (s, 3 H) 3.90 (s, 3 H) 4.09 (quin, J=6.76 Hz, 1 H) 6.90 (s, 1 H) 7.16-7.24 (m, 1 H) 7.41-7.46 (m, 2 H) 7.50 (d, J=7.58 Hz, 2 H) 7.73 (d, J=5.38 Hz, 2 H) 7.93 (dd, J=7.27, 1.90 Hz, 1 H) 8.39 (dd, J=5.01, 1.83 Hz, 1 H) 8.70 (s, 1 H).

EXAMPLE 133

6-(4-chlorophenyl)-5-(3,7-dimethyl-3H-benzo[d][1,2,3]triazol-5-yl)-2-(2-methoxypyridin-3-yl)-5,6-dihydropyrrolo[3,4-d]imidazol-4(1H)-one

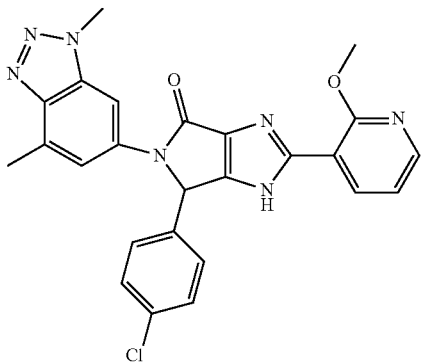 [SMILES: COc1ncccc1-c1nc2c([nH]1)C(c1ccc(Cl)cc1)N(c1cc(C)c3nnn(C)c3c1)C2=O]

The title compound was prepared in analogy to the procedure described for Example 1 using: 1-allyl-2-bromo-6-(4-chlorophenyl)-5-(3,7-dimethyl-3H-benzo[d][1,2,3]triazol-5-yl)-5,6-dihydropyrrolo[3,4-d]imidazol-4(1H)-one (Step 1.11) and 2-methoxy-3-pyridineboronic acid as a starting materials. Purification of the crude material by preparative HPLC (column: Waters SunFire C18, 30×100×5 μm; solvent A: water/0.1% TFA; solvent B: acetonitrile; gradient 40-60% B in 16 min) afforded the title compound as a beige solid. $t_R$: 1.06 min (LC-MS 2); ESI-MS: 486.3 [M+H]$^+$/484.2 [M−H]$^-$. (LC-MS 2).

EXAMPLE 134

6-(4-chlorophenyl)-2-(3,6-dihydro-2H-pyran-4-yl)-5-(1,5-dimethyl-6-oxo-1,6-dihydropyridin-3-yl)-5,6-dihydropyrrolo[3,4-d]imidazol-4(1H)-one

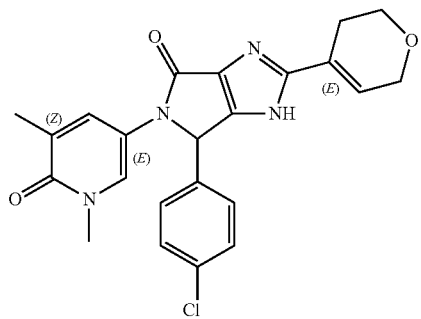 [SMILES: Cc1cc(N2C(=O)c3nc(C4=CCOCC4)[nH]c3C2c2ccc(Cl)cc2)cn(C)c1=O]

The title compound was prepared in analogy to the procedure described for Example 1 using: 1-allyl-2-bromo-6-(4-chlorophenyl)-5-(1,5-dimethyl-6-oxo-1,6-dihydropyridin-3-yl)-5,6-dihydropyrrolo[3,4-d]imidazol-4(1H)-one (Step 4.6) and 3,6-dihydro-2H-pyran-4-boronic acid pinacol ester as a starting materials. Purification of the crude material by preparative HPLC (column: Waters SunFire C18, 30×100×5 μm; solvent A: water/0.1% TFA; solvent B: acetonitrile; gradient 20-40% B in 16 min) afforded the title compound as a beige solid. $t_R$: 0.77 min (LC-MS 2); ESI-MS: 437.3 [M+H]$^+$/435.2 [M−H]$^-$ (LC-MS 2).

EXAMPLE 135

6-(4-chlorophenyl)-5-(1,5-dimethyl-6-oxo-1,6-dihydropyridin-3-yl)-2-(1-methyl-1,2,3,6-tetrahydropyridin-4-yl)-5,6-dihydropyrrolo[3,4-d]imidazol-4(1H)-one

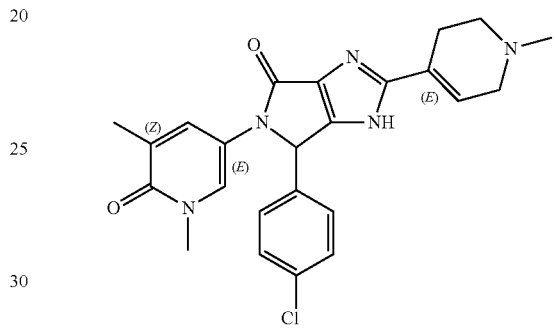

The title compound was prepared in analogy to the procedure described for Example 1 using: 1-allyl-2-bromo-6-(4-chlorophenyl)-5-(1,5-dimethyl-6-oxo-1,6-dihydropyridin-3-yl)-5,6-dihydropyrrolo[3,4-d]imidazol-4(1H)-one (Step 4.6) and 1-methyl-1,2,3,6-tetrahydropyridine-4-boronic acid pinacol ester as a starting materials. Purification of the crude material by preparative HPLC (column: Waters SunFire C18, 30×100×5 μm; solvent A: water/0.1% TFA; solvent B: acetonitrile; gradient 10-30% B in 16 min) afforded the title compound as a beige solid. $t_R$: 0.57 min (LC-MS 2); ESI-MS: 450.3 [M+H]$^+$/448.3 [M−H]$^-$ (LC-MS 2).

EXAMPLE 136

6-(4-chlorophenyl)-5-(3,8-dimethyl-[1,2,4]triazolo[4,3-a]pyridin-6-yl)-2-(2-methoxy-4-(trifluoromethyl)phenyl)-5,6-dihydropyrrolo[3,4-d]imidazol-4(1H)-one

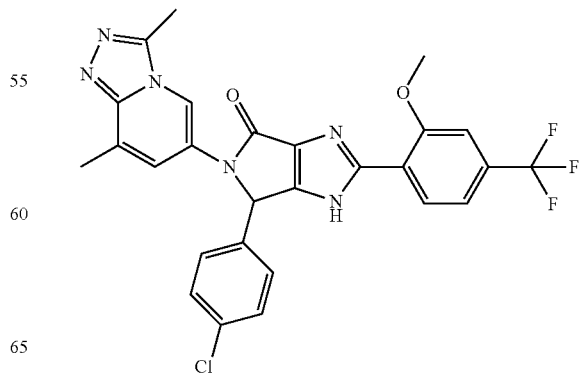

The title compound was prepared in analogy to the procedure described for Example 1 using 1-allyl-2-bromo-6-(4-chlorophenyl)-5-(3,8-dimethyl-[1,2,4]triazolo[4,3-a]pyridin-6-yl)-5,6-dihydropyrrolo[3,4-d]imidazol-4(1H)-one (Step 116.3) and 2-methoxy-4-trifluoromethylphenylboronic acid as a starting materials. Purification of the crude material by SFC chromatography (Thar 100; column: PFP, 25 cm, Ø 3 cm, 5 μm, 60 Å; gradient: 18% B for 1 min, 18-23% B in 6 min, 23-50% B in 1 min, 50% B for 1 min, 50%-18% B in 1 min, 18% B for 0.5 min; A: scCO$_2$, B: MeOH; flow: 100 mL/min) to afford the title compound. $t_R$: 1.11 min (LC-MS 2); ESI-MS: 553.2 [M+H]$^+$/551.2 [M−H]$^-$ (LC-MS 2).

EXAMPLE 137

6-(4-chlorophenyl)-5-(3,8-dimethyl-[1,2,4]triazolo[4,3-a]pyridin-6-yl)-2-((4-fluoro-2-methoxyphenyl)-5,6-dihydropyrrolo[3,4-d]imidazol-4(1H)-one

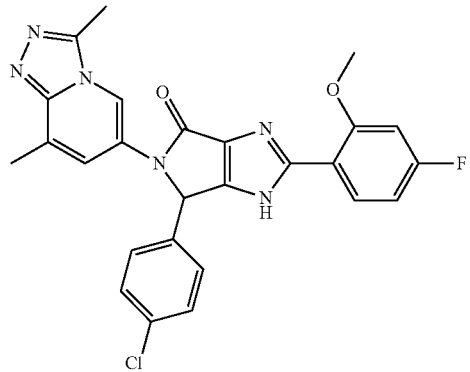 [SMILES: COc1cc(F)ccc1-c1nc2c([nH]1)C(c1ccc(Cl)cc1)N(c1cc(C)c3nnc(C)n3c1)C2=O]

The title compound was prepared in analogy to the procedure described for Example 1 using 1-allyl-2-bromo-6-(4-chlorophenyl)-5-(3,8-dimethyl-[1,2,4]triazolo[4,3-a]pyridin-6-yl)-5,6-dihydropyrrolo[3,4-d]imidazol-4(1H)-one (Step 116.3) and 4-fluoro-2-methoxyphenyl boronic acid as a starting materials. Purification of the crude material by SFC chromatography (Thar 100; column: PFP, 25 cm, Ø 3 cm, 5 μm, 60 Å; gradient: 19% B for 1 min, 19-24% B in 6 min, 24-50% B in 1 min, 50% B for 1 min, 50%-19% B in 1 min, 19% B for 0.5 min; A: scCO$_2$, B: MeOH; flow: 100 mL/min) to afford the title compound. $t_R$: 0.99 min (LC-MS 2); ESI-MS: 503.2 [M+H]$^+$/501.2 [M−H]$^-$ (LC-MS 2).

EXAMPLE 138

6-(4-chlorophenyl)-5-(3,7-dimethyl-3H-[1,2,3]triazolo[4,5-b]pyridin-5-yl)-1-isopropyl-2-(6-methoxypyridin-3-yl)-5,6-dihydropyrrolo[3,4-d]imidazol-4(1H)-one

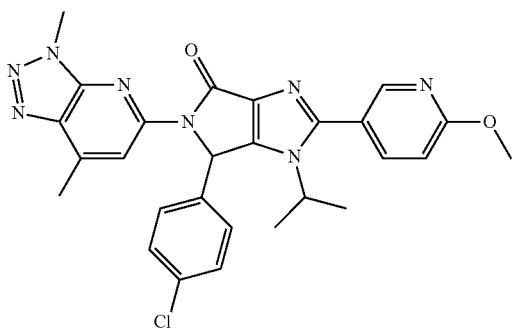 [SMILES: COc1ccc(-c2nc3c(n2C(C)C)C(c2ccc(Cl)cc2)N(c2cc(C)c4nnn(C)c4n2)C3=O)cn1]

The title compound was prepared in analogy to the procedure described for Example 1 using 2-bromo-6-(4-chlorophenyl)-5-(3,7-dimethyl-3H-[1,2,3]triazolo[4,5-b]pyridin-5-yl)-1-isopropyl-5,6-dihydropyrrolo[3,4-d]imidazol-4(1H)-one (Step 138.8) and 2-methoxy-5-pyridineboronic acid. Tituration of the crude material with MeOH afforded the title compound as a beige solid. $t_R$: 1.18 min (LC-MS 2); ESI-MS: 529.4 [M+H]$^+$.

Step 138.1: 2,6-dichloro-4-methyl-3-nitropyridine 2,6-Dichloro-4-methylpyridine (1 g, 6.17 mmol) was added to TFAA (5 mL) at 0° C. and nitric acid (0.58 mL, 12.9 mmol) was added drop-wise to this suspension while all solids dissolved.

The reaction was allowed to stir at rt for 18 hrs. It was then added slowly to a chilled solution of sodium metabisulfite (1.173 g in 8 ml of water). After 2 hrs of standing at rt, it was neutralized to pH 7 with 8N NaOH. The aqueous solution was extracted twice with DCM and the combined organic extracts were washed with brine, dried (Na$_2$SO$_4$) and concentrated to afford a white solid. $t_R$: 1.07 min (LC-MS 2); ESI-MS: no ionisation (LC-MS 2). $^1$H NMR (400 MHz, DMSO-d6) δ ppm 2.39 (s, 3 H) 7.90 (s, 1 H).

Step 138.2: 6-chloro-N,4-dimethyl-3-nitropyridin-2-amine 2,6-Dichloro-4-methyl-3-nitropyridine (Step 31.1; 1.17 g, 5.68 mmol) was added at rt to a 2M solution of methylamine in THF and allowed to stir for 30 min. The reaction mixture was then diluted with EtOAc/water, extracted twice with EtOAc and the combined organic extracts were washed with brine, dried (Na$_2$SO$_4$) and concentrated. The crude product was purified by flash chromatography (ISCO combi flash; EtOAc/hexanes: 1:4, SiO$_2$) to afford the title compound as a yellow solid. $t_R$: 1.08 min (LC-MS 2); ESI-MS: 202.0 [M+H]$^+$; $^1$H NMR (400 MHz, DMSO-d6) δ ppm 2.39 (s, 3 H) 2.90 (d, J=4.65 Hz, 3 H) 6.73 (s, 1 H) 7.95 (d, J=3.91 Hz, 1 H).

Step 138.3: 6-chloro-N-2,4-dimethylpyridine-2,3-diamine

6-Chloro-N,4-dimethyl-3-nitropyridin-2-amine (Step 31.2; 1 g, 4.96 mmol) was added to aqueous ammonium chloride solution (21 mL) and iron powder (1.4 g, 24.80 mmol). The reaction mixture was heated to 85° C. and stirred for 30 min. It was then filtered through celite and the filter cake washed with EtOH. The EtOH was evaporated. The resulting aqueous phase was extracted three times with DCM and the combined organic extracts were washed with brine, dried (Na$_2$SO$_4$) and concentrated. The remaining crude product was purified by chromatography (EtOAc/hexanes 1:1, SiO$_2$) to afford the title compound as a yellow oil. $t_R$: 0.74 min (LC-MS 2); ESI-MS: 172.0 [M+H]$^+$; $^1$H NMR (400 MHz, DMSO-d6) δ ppm 1.98 (s, 3 H) 2.77 (d, J=4.69 Hz, 3 H) 4.46 (s, 2 H) 5.91 (d, J=4.30 Hz, 1 H) 6.28 (s, 1 H).

Step 138.4: 5-chloro-3,7-dimethyl-3H-[1,2,3]triazolo[4,5-b]pyridine

The title compound was prepared in analogy to the procedure described for Step 1.3 except using 6-chloro-N-2,4-dimethylpyridine-2,3-diamine (Step 138.3) as a starting material. The crude product was purified by flash chromatography (EtOAc/hexanes 1:4, SiO$_2$) to afford the title compound as a white solid. $t_R$: 0.78 min (LC-MS 2); ESI-MS: 183.0 (LC-MS 2). $^1$H NMR (400 MHz, DMSO-d6) δ ppm 2.72 (t, J=0.98 Hz, 3 H) 4.18-4.30 (m, 3 H) 7.43 (t, J=0.78 Hz, 1 H).

Step 138.5: 3,7-dimethyl-3H-[1,2,3]triazolo[4,5-b]pyridin-5-amine

5-Chloro-3,7-dimethyl-3H-[1,2,3]triazolo[4,5-b]pyridine (Step 138.4; 500 mg, 2.20 mmol) was introduced in a MW vial and aqueous ammonia solution (25% wt; 13 mL) was added: the vial was capped and submitted to MW irradiation at 120° C. for 6 h. It was allowed to cool to rt and the precipitated reaction product isolated by filtration, washed with cold diethyl ether and ried to give the title compound as a white solid. $t_R$: 0.43 min (LC-MS 2); ESI-MS: 164.1 [M+H]$^+$ (LC-MS 2).

Step 138.6: ethyl 2-bromo-5-((4-chlorophenyl)((3,7-dimethyl-3H-[1,2,3]triazolo[4,5-b]pyridin-5-yl)amino)methyl)-1-isopropyl-1H-imidazole-4-carboxylate Ethyl 2-bromo-5-((4-chlorophenyl)(hydroxy)methyl)-1-isopropyl-1H-imidazole-4-carboxylate) (Step 9.6; 2.5 g, 6.22 mmol) was dissolved in DCM (65 mL). TEA (4.34 mL, 31.10 mmol) was added and the reaction mixture cooled to 5° C. Methanesulfonic anhydride (2.71 g, 15.56 mmol) was added and the reaction allowed to stir for 30 min at rt. It was recooled to 5° C. followed by addition of 3,7-dimethyl-3H-[1,2,3]triazolo[4,5-b]pyridin-5-amine (Step 138.5; 1.06 g, 6.54 mmol), the cooling bath was removed and the reaction mixture allowed to stir for 72 h. It was then diluted with DCM, and the organic layer washed with 1M HCl solution and sat. NaHCO$_3$, dried and concentrated. The remaining crude material was purified by flash chromatography (ISCO flashmaster, 40 g column; DCM/MeOH; gradient 0-10% MeOH) to afford the title compound as a yellow oil (1.13 g, 31% yield). $t_R$: 1.23 min (LC-MS 2); ESI-MS: 546.2/549.1 [M+H]$^+$ (LC-MS 2).

Step 138.7: 2-bromo-54(4-chlorophenyl)((3,7-dimethyl-3H-[1,2,3]triazolo[4,5-b]pyridin-5-yl)amino)methyl)-1-isopropyl-1H-imidazole-4-carboxylic acid The title compound was prepared in analogy to the procedure described in Step 1.10 using Ethyl-2-bromo-5-((4-chlorophenyl)((3,7-dimethyl-3H-[1,2,3]triazolo[4,5-b]pyridin-5-yl)amino)methyl)-1-isopropyl-1H-imidazole-4-carboxylate (1.13 g, 2.06 mmol) (Step 138.6) as a starting material to afford the title compound as a yellow solid. $t_R$: 1.05 min (LC-MS 2); ESI-MS: 518.2/520.2 [M+H]$^+$ (LC-MS 2); 516.2/518.1 [M–H] (LC-MS2).

Step 138.8: 2-bromo-6-(4-chlorophenyl)-5-(3,7-dimethyl-3H-[1,2,3]triazolo[4,5-b]pyridin-5-yl)-1-isopropyl-5,6-dihydropyrrolo[3,4-d]imidazol-4(1H)-one The title compound was prepared in analogy to the procedure described in Step 1.11 using 2-bromo-5-((4-chlorophenyl)((3,7-dimethyl-3H-[1,2,3]triazolo[4,5-b]pyridin-5-yl)amino)methyl)-1-isopropyl-1H-imidazole-4-carboxylic acid (Step 138.7) as starting material. $t_R$: 1.18 min (LC-MS 2); ESI-MS: 502.2 [M+H]$^+$/500.2 [M–H]$^-$ (LC-MS 2).

EXAMPLE 139

6-(4-chlorophenyl)-5-(3-(difluoromethyl)-8-methyl-[1,2,4]triazolo[4,3-a]pyridin-6-yl)-2-methyl-5,6-dihydropyrrolo[3,4-d]imidazol-4(1H)-one

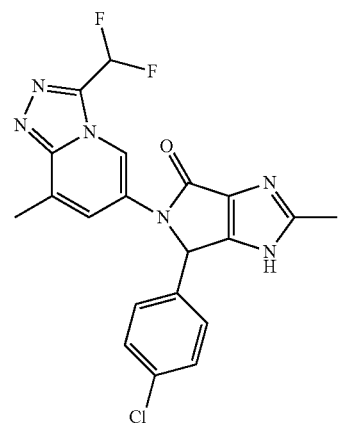

The title compound was prepared in analogy to the procedure described for Example 1 using 1-allyl-2-bromo-6-(4-chlorophenyl)-5-(3-(difluoromethyl)-8-methyl-[1,2,4]triazolo[4,3-a]pyridin-6-yl)-5,6-dihydropyrrolo[3,4-d]imidazol-4(1H)-one (Step 139.3) and trimethoxy boroxin as starting materials. Purification of the crude material by SFC chromatography (Thar 100; column: PFP, 25 cm, Ø 3 cm, 5 μm, 60 Å; gradient: 15% B for 1 min, 15-20% B in 6 min, 20-50% B in 1 min, 50% B for 1 min, 50%-15% B in 1 min, 15% B for 0.5 min; A: scCO$_2$, B: MeOH; flow: 100 mL/min) afforded the title compound. $t_R$: 0.79 min (LC-MS 2); ESI-MS: 429.2 [M+H]$^+$/427.2 [M–H]$^-$ (LC-MS 2).

Step 139.1: ethyl 1-allyl-2-bromo-5-((4-chlorophenyl)((3-(difluoromethyl)-8-methyl-[1,2,4]triazolo[4,3-a]pyridin-6-yl)amino)methyl)-1H-imidazole-4-carboxylate The title compound was prepared in analogy to the procedure described in Step 1.9 using ethyl 1-allyl-2-bromo-5-((4-chlorophenyl)(hydroxy)methyl)-1H-imidazole-4-carboxylate (Step 1.8) and 3-(difluoromethyl)-8-methyl-[1,2,4]triazolo[4,3-a]pyridin-6-amine (Step 131.3). The crude product was purified by silica gel column chromatography (CH$_2$Cl$_2$/MeOH 0-10% MeOH) to afford the title product as a yellow solid. $t_R$: 1.11 min (LC-MS 2); ESI-MS: 581.2 [M+H]$^+$ (LC-MS 2).

Step 139.2: 1-allyl-2-bromo-54(4-chlorophenyl)((3-(difluoromethyl)-8-methyl-[1,2,4]triazolo[4,3-a]pyridin-6-yl)amino)methyl)-1H-imidazole-4-carboxylic acid The title compound was prepared in analogy to the procedure described in Step 1.10 using ethyl 1-allyl-2-bromo-54(4-chlorophenyl)((3-(difluoromethyl)-8-methyl-

[1,2,4]triazolo[4,3-a]pyridin-6-yl)amino)methyl)-1H-imidazole-4-carboxylate (Step 139.1). $t_R$: 0.93 min (LC-MS 2); ESI-MS: 355.1 [M+H]$^+$; ESI-MS: 353.0 [M−H]$^-$ (LC-MS 2).

Step 139.3: 1-allyl-2-bromo-6-(4-chlorophenyl)-5-(3-(difluoromethyl)-8-methyl-[1,2,4]triazolo[4,3-a]pyridin-6-yl)-5,6-dihydropyrrolo[3,4-d]imidazol-4(1H)-one The title compound was prepared in analogy to the procedure described in Step 1.11 using 1-allyl-2-bromo-54 (4-chlorophenyl)((3-(difluoromethyl)-8-methyl-[1,2,4]triazolo[4,3-a]pyridin-6-yl)amino)methyl)-1H-imidazole-4-carboxylic acid (Step 139.2). $t_R$: 1.03 min (LC-MS 2); ESI-MS: 535.2 [M+H]$^+$/531.1 [M−H]$^-$ (LC-MS 2).

EXAMPLE 140

6-(4-chlorophenyl)-5-(3-(difluoromethyl)-8-methyl-[1,2,4]triazolo[4,3-a]pyridin-6-yl)-2-(2-methoxypyridin-3-yl)-5,6-dihydropyrrolo[3,4-d]imidazol-4(1H)-one

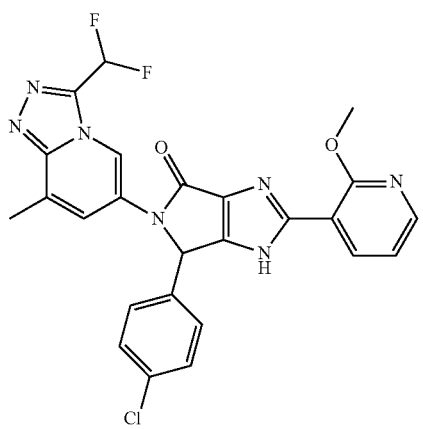 [SMILES: COc1ncccc1-c1nc2c([nH]1)C(c1ccc(Cl)cc1)N(c1cc(C)c3nnc(C(F)F)n3c1)C2=O]

The title compound was prepared in analogy to the procedure described for Example 1 using 1-allyl-2-bromo-6-(4-chlorophenyl)-5-(3-(difluoromethyl)-8-methyl-[1,2,4]triazolo[4,3-a]pyridin-6-yl)-5,6-dihydropyrrolo[3,4-d]imidazol-4(1H)-one (Step 139.3) and 2-methoxy-3-pyridine boronic acid as starting materials. Purification of the crude material by SFC chromatography (Thar 100; column: PFP, 25 cm, Ø 3 cm, 5 μm, 60 Å; gradient: 14% B for 1 min, 14-19% B in 6 min, 19-50% B in 1 min, 50% B for 1 min, 50%-14% B in 1 min, 14% B for 0.5 min; A: scCO$_2$, B: MeOH; flow: 100 mL/min) afforded the title compound. $t_R$: 1.04 min (LC-MS 2); ESI-MS: 522.2 [M+H]$^+$/520.2 [M−H]$^-$ (LC-MS 2).

EXAMPLE 141

6-(4-chlorophenyl)-5-(3-(difluoromethyl)-8-methyl-[1,2,4]triazolo[4,3-a]pyridin-6-yl)-2-(6-methoxypyridin-3-yl)-5,6-dihydropyrrolo[3,4-d]imidazol-4(1H)-one

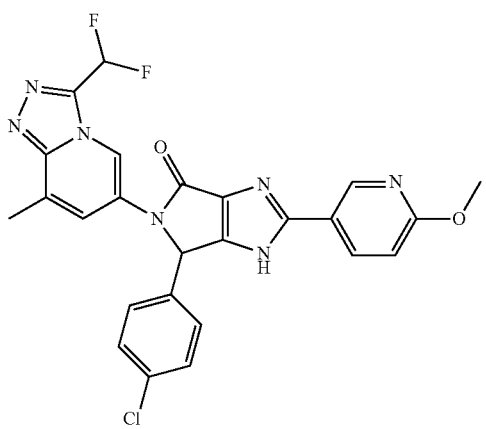

The title compound was prepared in analogy to the procedure described for Example 1 using 1-allyl-2-bromo-6-(4-chlorophenyl)-5-(3-(difluoromethyl)-8-methyl-[1,2,4]triazolo[4,3-a]pyridin-6-yl)-5,6-dihydropyrrolo[3,4-d]imidazol-4(1H)-one (Step 139.3) and 2-methoxy-5-pyridine boronic acid as starting materials. Purification of the crude material by SFC chromatography (Thar 100; column: PFP, 25 cm, Ø 3 cm, 5 μm, 60 Å; gradient: 19% B for 1 min, 19-24% B in 6 min, 24-50% B in 1 min, 50% B for 1 min, 50%-19% B in 1 min, 19% B for 0.5 min; A: scCO$_2$, B: MeOH; flow: 100 mL/min) afforded the title compound. $t_R$: 0.98 min (LC-MS 2); ESI-MS: 522.2 [M+H]$^+$/520.2 [M−H]$^-$ (LC-MS 2).

EXAMPLE 142

(R)-6-(4-chlorophenyl)-5-(3,8-dimethyl-[1,2,4]triazolo[4,3-a]pyridin-6-yl)-2-(2-methoxypyridin-3-yl)-5,6-dihydropyrrolo[3,4-d]imidazol-4(1H)-one

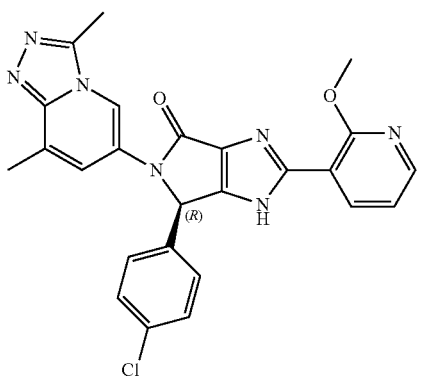

The title compound (20 mg, 39% yield) was obtained enantiomerically pure (>99% ee) after chiral preparative chromatography (system: Gilson PLC2020; column: Chiralcel OD-H, 20×250 mm; mobile phase: Heptane/EtOH/MeOH 70:15:15; flow: 10 mL/min; temperature: 38° C.; detection UV: 220 nm) of the racemic mixture of 6-(4-chlorophenyl)-5-(3,8-dimethyl-[1,2,4]triazolo[4,3-a]pyridin-6-yl)-2-(2-methoxypyridin-3-yl)-5,6-dihydropyrrolo[3,4-d]imidazol-4(1H)-one (Example 123).

(R)-6-(4-chlorophenyl)-5-(3,8-dimethyl-[1,2,4]triazolo[4,3-a]pyridin-6-yl)-2-(2-methoxypyridin-3-yl)-5,6-dihydropyrrolo[3,4-d]imidazol-4(1H)-one. $t_R$: 7.29 min (analytical system: Agilent HPLC system; column: Chiralcel OD-H, 4.6×250 mm; mobile phase: Heptane/EtOH/MeOH 60:20:20; flow: 1.0 mL/min; temperature: 35° C.; detection UV: 220 nm).

(S)-6-(4-chlorophenyl)-5-(3,8-dimethyl-[1,2,4]triazolo[4,3-a]pyridin-6-yl)-2-(2-methoxypyridin-3-yl)-5,6-dihydropyrrolo[3,4-d]imidazol-4(1H)-one. $t_R$: 5.62 min (analytical system: Agilent HPLC system; column: Chiralcel OD-H, 4.6×250 mm; mobile phase: Heptane/EtOH/MeOH 60:20:20; flow: 1.0 mL/min; temperature: 35° C.; detection UV: 220 nm).

EXAMPLE 143

6-(4-chlorophenyl)-5-(3-(difluoromethyl)-8-methyl-[1,2,4]triazolo[4,3-a]pyridin-6-yl)-2-(2,4-dimethoxypyrimidin-5-yl)-1-isopropyl-5,6-dihydropyrrolo[3,4-d]imidazol-4(1H)-one

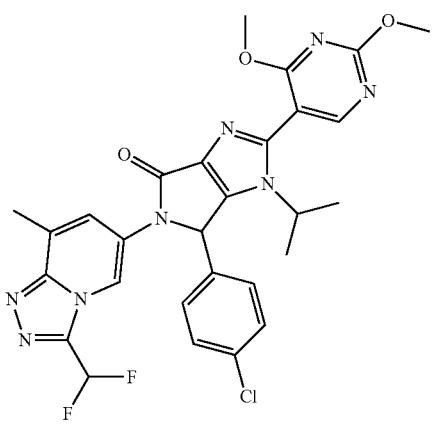 [SMILES: COc1ncc(-c2nc3c(n2C(C)C)C(c2ccc(Cl)cc2)N(c2cc(C)c4nnc(C(F)F)n4c2)C3=O)c(OC)n1]

The title compound was prepared in analogy to the procedure described for Example 1 using 2-bromo-6-(4-chlorophenyl)-5-(3-(difluoromethyl)-8-methyl-[1,2,4]triazolo[4,3-a]pyridin-6-yl)-1-isopropyl-5,6-dihydropyrrolo[3,4-d]imidazol-4(1H)-one (Step 131.6) and 2,4-dimethoxy-5-pyrimidinyl boronic acid as starting materials. Purification of the crude material by flash chromatography (ISCO system; 40 g column SiO$_2$; solvent A: hexanes; solvent B: EtOAc; gradient (% B): 20% for 3 min, 20-50% for 15 min, 50% for 20 min, 50-100% for 15 min, 100% for 35 min; flow 40 mL/min afforded the title compound as a white powder. $t_R$: 1.03 min (LC-MS 2); ESI-MS: 595.3 [M+H]$^+$/593.2 [M−H]$^−$ (LC-MS 2). $^1$H NMR (400 MHz, DMSO-d6) δ ppm 0.54 (d, J=6.60 Hz, 3 H) 1.42 (d, J=6.72 Hz, 3 H) 2.55 (s, 3 H) 3.96 (s, 3 H) 4.00 (s, 3 H) 4.16 (quin, J=6.66 Hz, 1 H) 6.90 (s, 1 H) 7.38-7.55 (m, 4 H) 7.56-7.89 (m, 2 H) 8.51 (s, 1 H) 8.69 (s, 1 H).

EXAMPLE 144

6-(4-chlorophenyl)-5-(3-(difluoromethyl)-8-methyl-[1,2,4]triazolo[4,3-a]pyridin-6-yl)-1-isopropyl-2-(2-methoxy-4-(trifluoromethyl)phenyl)-5,6-dihydropyrrolo[3,4-d]imidazol-4(1H)-one

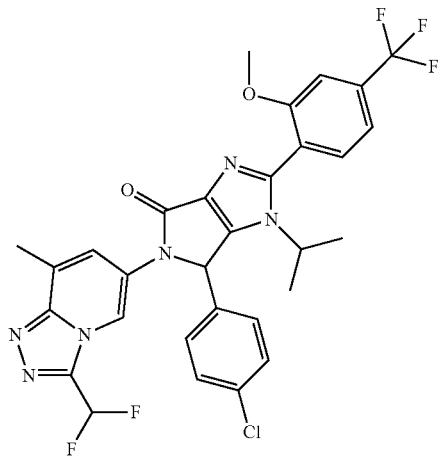 [SMILES: COc1cc(C(F)(F)F)ccc1-c1nc2c(n1C(C)C)C(c1ccc(Cl)cc1)N(c1cc(C)c3nnc(C(F)F)n3c1)C2=O]

The title compound was prepared in analogy to the procedure described for Example 1 using 2-bromo-6-(4-chlorophenyl)-5-(3-(difluoromethyl)-8-methyl-[1,2,4]triazolo[4,3-a]pyridin-6-yl)-1-isopropyl-5,6-dihydropyrrolo[3,4-d]imidazol-4(1H)-one (Step 131.6) and 2-methoxy-4-trifluoromethylphenylboronic acid as starting materials. Purification of the crude material by flash chromatography (ISCO system; 40 g column SiO$_2$; solvent A: hexanes; solvent B: EtOAc; gradient (% B): 0% for 5 min, 0-50% for 15 min, 50% for 10 min, 50-100% for 30 min; flow 40 mL/min followed by preparative HPLC. Column: Waters Sunfire C18, 5 um, 30×100 mm; solvent A: water+0.1% TFA; solvent B: acetonitrile+0.1% TFA; gradient (% B): 50-70% in 16 minutes; flow 50 ml/min afforded the title compound as a white powder. $t_R$: 1.21 min (LC-MS 2); ESI-MS: 631.3 [M+H]$^+$/629.3 [M−H]$^−$ (LC-MS 2). $^1$H NMR (400 MHz, DMSO-d6) ε ppm ppm 0.51 (d, J=6.11 Hz, 3 H) 1.42 (d, J=6.72 Hz, 3 H) 2.56 (s, 3 H) 3.90 (s, 3H) 4.07 (dt, J=13.51, 6.69 Hz, 1 H) 6.91 (s, 1 H) 7.41-7.53 (m, 6 H) 7.57-7.88 (m, 3 H) 8.70 (s, 1 H).

EXAMPLE 145

6-(4-chlorophenyl)-2-cyclopropyl-5-(3-(difluoromethyl)-8-methyl-[1,2,4]triazolo[4,3-a]pyridin-6-yl)-1-isopropyl-5,6-dihydropyrrolo[3,4-d]imidazol-4(1H)-one

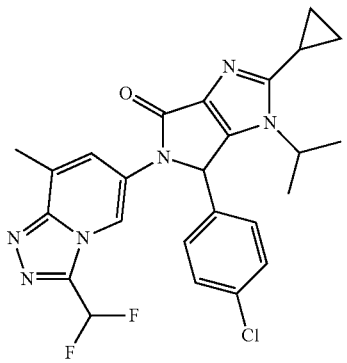 [SMILES: Cc1cc(N2C(=O)c3nc(C4CC4)n(C(C)C)c3C2c2ccc(Cl)cc2)cn2c(C(F)F)nnc12]

The title compound was prepared in analogy to the procedure described for Example 13 using 2-bromo-6-(4-chlorophenyl)-5-(3-(difluoromethyl)-8-methyl-[1,2,4]triazolo[4,3-a]pyridin-6-yl)-1-isopropyl-5,6-dihydropyrrolo[3,4-d]imidazol-4(1H)-one (Step 131.6) as starting material and di-(1-adamantyl)-n-butylphosphine in the place of Ruphos ligand. Purification of the crude material by flash chromatography (ISCO system; 40 g column SiO$_2$; solvent A: hexanes; solvent B: EtOAc; gradient (% B): 50% for 10 min, 50-100% for 40 min, 100% for 20 min; flow 40 mL/min followed by tituration with diethyl ether afforded the title compound as a white powder. t$_R$: 1.04 min (LC-MS 2); ESI-MS: 497.4 [M+H]$^+$.

EXAMPLE 146

(R)-6-(4-chlorophenyl)-5-(3-(difluoromethyl)-8-methyl-[1,2,4]triazolo[4,3-a]pyridin-6-yl)-1-isopropyl-2-methyl-5,6-dihydropyrrolo[3,4-d]imidazol-4(1H)-one

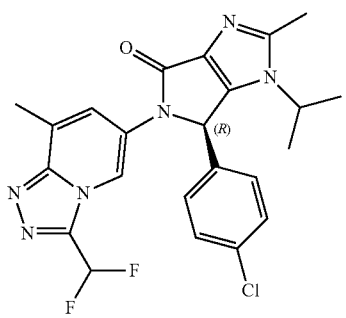

The title compound (45 mg, 51% yield) was obtained enantiomerically pure (>99% ee) after chiral preparative chromatography (system: Gilson PLC2020; column: Chiralcel OD-H, 20×250 mm; mobile phase: heptane/EtOH/MeOH 70:15:15; flow: 10 mL/min; temperature: 38° C.; detection UV: 220 nm) of the racemic mixture 6-(4-chlorophenyl)-5-(3-(difluoromethyl)-8-methyl-[1,2,4]triazolo[4,3-a]pyridin-6-yl)-1-isopropyl-2-methyl-5,6-dihydropyrrolo[3,4-d]imidazol-4(1H)-one (Example 131).

(R)-6-(4-chlorophenyl)-5-(3-(difluoromethyl)-8-methyl-[1,2,4]triazolo[4,3-a]pyridin-6-yl)-1-isopropyl-2-methyl-5,6-dihydropyrrolo[3,4-d]imidazol-4(1H)-one. t$_R$: 7.66 min (analytical system: Shimadzu prominence HPLC system; column: Chiralcel OD-H, 4.6×250 mm; mobile phase: Heptane/EtOH/MeOH 60:20:20; flow: 1.0 mL/min; temperature: 35° C.; detection UV: 220 nm).

(S)-6-(4-chlorophenyl)-5-(3-(difluoromethyl)-8-methyl-[1,2,4]triazolo[4,3-a]pyridin-6-yl)-1-isopropyl-2-methyl-5,6-dihydropyrrolo[3,4-d]imidazol-4(1H)-one. t$_R$: 4.30 min (analytical system: Shimadzu prominence HPLC system; column: Chiralcel OD-H, 4.6×250 mm; mobile phase: Heptane/EtOH/MeOH 60:20:20; flow: 1.0 mL/min; temperature: 35° C.; detection UV: 220 nm).

EXAMPLE 147

6-(4-chlorophenyl)-5-(3-(difluoromethyl)-8-methyl-[1,2,4]triazolo[4,3-a]pyridin-6-yl)-2-(3,6-dihydro-2H-pyran-4-yl)-1-isopropyl-5,6-dihydropyrrolo[3,4-d]imidazol-4(1H)-one

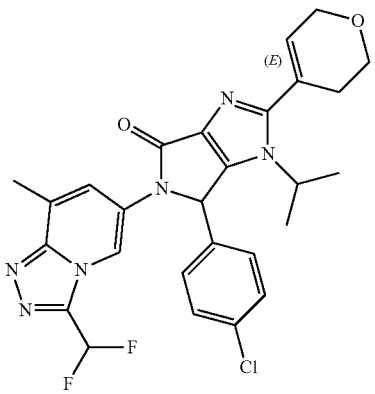

The title compound was prepared in analogy to the procedure described for Example 1 using 2-bromo-6-(4-chlorophenyl)-5-(3-(difluoromethyl)-8-methyl-[1,2,4]triazolo[4,3-a]pyridin-6-yl)-1-isopropyl-5,6-dihydropyrrolo[3,4-d]imidazol-4(1H)-one (Step 131.6) and 2-3,6-dihydro-2H-pyran-4-boronic acid pinacol ester as starting materials. Purification of the crude material by flash chromatography (ISCO system; 40 g column SiO$_2$; solvent A: hexanes; solvent B: EtOAc; gradient (% B): 0% for 5 min, 0-50% for 15 min, 50% for 10 min, 50-100% for 30 min; flow 40 mL/min followed by SFC chromatography (Thar 100; column: PFP, 25 cm, Ø 3 cm, 5 μm, 60 Å; gradient: 13% B for 12 min, 13-50% B in 1 min, 50% B for 1.5 min, 50%-13% B in 1 min, 13% B for 0.5 min; A: scCO$_2$, B: MeOH; flow: 100 mL/min) afforded the title compound as a white powder. t$_R$: 0.98 min (LC-MS 2); ESI-MS: 539.3 [M+H]$^+$/537.3 [M−H]$^−$ (LC-MS 2). $^1$H NMR (400 MHz, DMSO-d6) δ ppm ppm 0.63 (d, J=6.60 Hz, 3 H) 1.48 (d, J=6.72 Hz, 3 H) 2.55 (s, 3 H) 3.18 (d, J=5.14 Hz, 2 H) 3.74-3.94 (m, 2 H) 4.09 (q, J=5.18 Hz, 1 H) 4.26 (dd, J=6.11, 2.81 Hz, 2 H) 4.64 (quin, J=6.72 Hz, 1 H) 6.12 (br. s, 1 H) 6.83 (s, 1 H) 7.34-7.50 (m, 4 H) 7.54-7.88 (m, 2 H) 8.69 (s, 1H).

EXAMPLE 148

6-(4-chlorophenyl)-5-(3-(difluoromethyl)-8-methyl-[1,2,4]triazolo[4,3-b]pyridazin-6-yl)-1-isopropyl-2-(2-methoxypyridin-3-yl)-5,6-dihydropyrrolo[3,4-d]imidazol-4(1H)-one

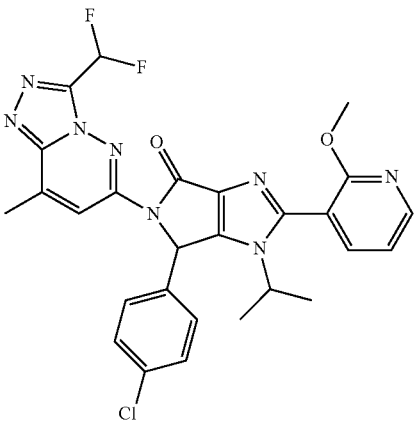 [SMILES: COc1ncccc1-c1nc2c(n1C(C)C)C(c1ccc(Cl)cc1)N(c1cc(C)c3nnc(C(F)F)n3n1)C2=O]

The title compound was prepared in analogy to the procedure described for Example 1 using 2-bromo-6-(4-chlorophenyl)-5-(3-(difluoromethyl)-8-methyl-[1,2,4]triazolo[4,3-b]pyridazin-6-yl)-1-isopropyl-5,6-dihydropyrrolo[3,4-d]imidazol-4(1H)-one (Step 148.6) and 2-methoxy-3-pyridine boronic acid as starting materials. Purification of the crude material by SFC chromatography (Thar 100; column: PFP, 25 cm, Ø 3 cm, 5 μm, 60 Å; gradient: 9% B for 1 min, 9-14% B in 1 min, 14-50% B in 3 min, 50% B for 3 min, 50%-9% B in 1 min, 9% B for 0.5 min; A: scCO$_2$, B: MeOH; flow: 100 mL/min) afforded the title compound. $t_R$: 1.12 min (LC-MS 2); ESI-MS: 565.1 [M+H]$^+$.

Step 148.1:
6-chloro-3-hydrazinyl-4-methylpyridazine 3,6-dichloro-4-methylpyridazine (Combi-Blocks) (60 g, 361 mmol) was dissolved in hydrazine monohydrate (Aldrich) (335 ml, 5411 mmol) and the solution was stirred at 80° C. for 1 h, forming a white precipitate. The reaction mixture is dilutes with water and the precipitated products isolated by filtration. The solid crude product is suspended in EtOH and left in an ultra sound bath for 1 h. The desired product (22.4 g) was obtained after filtration and drying under vacuum as a beige solid. $t_R$: 0.31 min (LC-MS 2); ESI-MS: 160.0 [M+H]$^+$ (LC-MS 2). $^1$H NMR (400 MHz; DMSO-d6) 5 ppm 7.83 (br.s, 1 H) 7.32 (s, 1 H) 4.49 (br.s, 2 H) 2.05 (s, 3 H).

Step 148.2: 6-chloro-3-(difluoromethyl)-8-methyl-[1,2,4]triazolo[4,3-b]pyridazine To a beige suspension of 6-chloro-3-hydrazinyl-4-methylpyridazine (Step 148.1) (22.44 g, 127 mmol) in dioxane (250 ml) was added difluoroacetic acid (Aldrich) (9.40 ml, 146 mmol) and the reaction mixture was stirred at rt for 5 min, then heated-up to 120° C. for 2.5 hr. With heating the suspension turned into a red-orange solution. The reaction mixture was cooled to rt. Et$_2$O (80 mL) was added and the suspension was stirred for 2 hours at 0° C. Precipitated solids were isolated by filtration, suspended in hexanes and filtered again. After repeated washings with hexanes the tiltle compound was obtained as an orange solid. $t_R$: 0.72 min (LC-MS 2); ESI-MS: 219.2 [M+H]$^+$ (LC-MS 2). $^1$H NMR (400 MHz; DMSO-d6) 5 ppm 7.66 (t, 1 H) 7.60 (s, 1 H) 2.71 (s, 3H) 2.51 (s, 3H).

Step 148.3: 3-(difluoromethyl)-8-methyl-[1,2,4]triazolo[4,3-b]pyridazin-6-amine 6-chloro-3-(difluoromethyl)-8-methyl-[1,2,4]triazolo[4,3-b]pyridazine (Step 148.2) (3.0 g, 13.7 mmol) was suspended in aqueous NH3 solution (24% wt; 41 mL) and copper idodide (135 mg, 0.79 mmol) was added. The reaction was heated at 100° C. for 18 h. It was allowed to cool to ambient temperature and the precipitated product isolated by filtration and dried under vacuum to give an orange powder. $t_R$: 0.45 min (LC-MS 2); ESI-MS: 200.2 [M+H]$^+$/198.2 [M–H]$^-$ (LC-MS 2).

Step 148.4: ethyl 2-bromo-54(4-chlorophenyl)((3-(difluoromethyl)-8-methyl-[1,2,4]triazolo[4,3-b]pyridazin-6-yl)amino)methyl)-1-isopropyl-1H-imidazole-4-carboxylate The title compound was prepared in analogy to the procedure described for Step 1.9 using ethyl 2-bromo-5-((4-chlorophenyl)(hydroxy)methyl)-1-isopropyl-1H-imidazole-4-carboxylate (Step 9.6) and 3-(difluoromethyl)-8-methyl-[1,2,4]triazolo[4,3-b]pyridazin-6-amine (Step 148.3). Purification of the crude material by flash chromatography (ISCO system; 80 g column SiO$_2$; solvent A: DCM; solvent B: MeOH; gradient (% B): 0%-10% for 45 min afforded the title compound as a yellow oil. $t_R$: 1.15 min (LC-MS 2); ESI-MS: 584.3 [M+H]$^+$ (LC-MS 2).

Step 148.5: 2-bromo-54(4-chlorophenyl)((3-(difluoromethyl)-8-methyl-[1,2,4]triazolo[4,3-b]pyridazin-6-yl)amino)methyl)-1-isopropyl-1H-imidazole-4-carboxylic acid The title compound was prepared in analogy to the procedure described in Step 1.10 using ethyl 2-bromo-54(4-chlorophenyl)((3-(difluoromethyl)-8-methyl-[1,2,4]triazolo[4,3-b]pyridazin-6-yl)amino)methyl)-1-isopropyl-1H-imidazole-4-carboxylate (Step 148.4). as starting material. $t_R$: 0.97 min (LC-MS 2); ESI-MS: ESI-MS: 556.2 [M+H]$^+$/554.2 [M–H]$^-$ (LC-MS 2).

Step 148.6: 2-bromo-6-(4-chlorophenyl)-5-(3-(difluoromethyl)-8-methyl-[1,2,4]triazolo[4,3-b]pyridazin-6-yl)-1-isopropyl-5,6-dihydropyrrolo[3,4-d]imidazol-4(1H)-one The title compound was prepared in analogy to the procedure described in Step 1.11 using 2-bromo-54(4-chlorophenyl)((3-(difluoromethyl)-8-methyl-[1,2,4]triazolo[4,3-b]pyridazin-6-yl)amino)methyl)-1-isopropyl-1H-imidazole-4-carboxylic acid (Step 148.5). Crystallization in MeOH/sonication afforded the desired product as beige crystals. $t_R$: 1.13 min (LC-MS 2); ESI-MS: 538.3 [M+H]$^+$/ESI-MS: 534.2 [M–H]$^-$ (LC-MS2).

EXAMPLE 149

6-(4-chlorophenyl)-5-(3-(difluoromethyl)-8-methyl-[1,2,4]triazolo[4,3-b]pyridazin-6-yl)-1-isopropyl-2-(6-methoxypyridin-3-yl)-5,6-dihydropyrrolo[3,4-d]imidazol-4(1H)-one

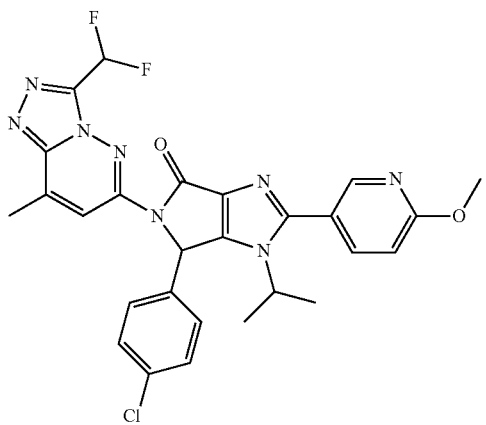

The title compound was prepared in analogy to the procedure described for Example 1 using 2-bromo-6-(4-chlorophenyl)-5-(3-(difluoromethyl)-8-methyl-[1,2,4]triazolo[4,3-b]pyridazin-6-yl)-1-isopropyl-5,6-dihydropyrrolo[3,4-d]imidazol-4(1H)-one (Step 148.6) and 2-methoxy-5- pyridine boronic acid as starting materials. Purification of the crude material by SFC chromatography (Thar 100; column: PFP, 25 cm, Ø 3 cm, 5 µm, 60 Å; gradient: 11% B for 1 min, 11-16% B in 6 min, 11-50% B in 1 min, 50% B for 1.5 min, 50%-11% B in 1 min, 11% B for 0.5 min; A: scCO₂, B: MeOH; flow: 100 mL/min) afforded the title compound. $t_R$: 1.14 min (LC-MS 2); ESI-MS: 565.1 [M+H]⁺.

EXAMPLE 150

6-(4-chlorophenyl)-5-(3-(difluoromethyl)-8-methyl-[1,2,4]triazolo[4,3-b]pyridazin-6-yl)-1-isopropyl-2-methyl-5,6-dihydropyrrolo[3,4-d]imidazol-4(1H)-one

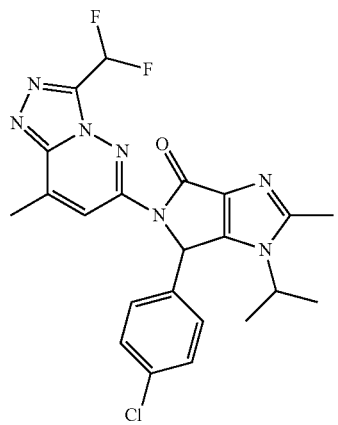

The title compound was prepared in analogy to the procedure described for Example 1 using 2-bromo-6-(4-chlorophenyl)-5-(3-(difluoromethyl)-8-methyl-[1,2,4]triazolo[4,3-b]pyridazin-6-yl)-1-isopropyl-5,6-dihydropyrrolo[3,4-d]imidazol-4(1H)-one (Step 148.6) and trimethylboroxin as starting materials. Purification of the crude material by SFC chromatography (Thar 100; column: PFP, 25 cm, Ø 3 cm, 5 µm, 60 Å; gradient: 9% B for 1 min, 9-14% B in 6 min, 14-50% B in 1 min, 50% B for 1.5 min, 50%-9% B in 1 min, 9% B for 0.5 min; A: scCO₂, B: MeOH; flow: 100 mL/min) afforded the title compound. $t_R$: 1.01 min (LC-MS 2); ESI-MS: 472.2 [M+H]⁺/ESI-MS: 470.2 [M–H]⁻.

EXAMPLE 151

(R)-6-(4-chlorophenyl)-5-(3-(difluoromethyl)-8-methyl-[1,2,4]triazolo[4,3-a]pyridin-6-yl)-1-isopropyl-2-(2-methoxypyridin-3-yl)-5,6-dihydropyrrolo[3,4-d]imidazol-4(1H)-one

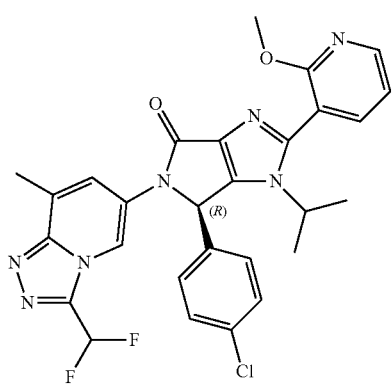

The title compound (98 mg, 45% yield) was obtained enantiomerically pure (>99% ee) after chiral preparative chromatography (system: VWR LaPrep system; column: Chiralpak AD, 20 µM; 7.65×39.3 cm; mobile phase: Heptane/EtOH 50:50; flow: 100 mL/min; temperature: 38° C.; detection UV: 220 nm) of the racemic mixture of 6-(4-chlorophenyl)-5-(3-(difluoromethyl)-8-methyl-[1,2,4]triazolo[4,3-a]pyridin-6-yl)-1-isopropyl-2-(2-methoxypyridin-3-yl)-5,6-dihydropyrrolo[3,4-d]imidazol-4(1H)-one (Example 132).

(R)-6-(4-chlorophenyl)-5-(3-(difluoromethyl)-8-methyl-[1,2,4]triazolo[4,3-a]pyridin-6-yl)-1-isopropyl-2-(2-methoxypyridin-3-yl)-5,6-dihydropyrrolo[3,4-d]imidazol-4(1H)-one. $t_R$: 13.19 min (analytical system: Agilent HPLC system; column: Chiralpak AD-H, 4.6×250 mm; mobile phase: Heptane/EtOH 50:50; flow: 1.0 mL/min; temperature: 35° C.; detection UV: 220 nm).

(S)-6-(4-chlorophenyl)-5-(3-(difluoromethyl)-8-methyl-[1,2,4]triazolo[4,3-a]pyridin-6-yl)-1-isopropyl-2-(2-methoxypyridin-3-yl)-5,6-dihydropyrrolo[3,4-d]imidazol-4(1H)-one. $t_R$: 4.17 min (analytical system: Agilent HPLC system; column: Chiralpak AD-H, 4.6×250 mm; mobile phase: Heptane/EtOH 50:50; flow: 1.0 mL/min; temperature: 35° C.; detection UV: 220 nm).

EXAMPLE 152

(R)-6-(4-chlorophenyl)-2-(3,6-dihydro-2H-pyran-4-yl)-5-(1,5-dimethyl-6-oxo-1,6-dihydropyridin-3-yl)-5,6-dihydropyrrolo[3,4-d]imidazol-4(1H)-one

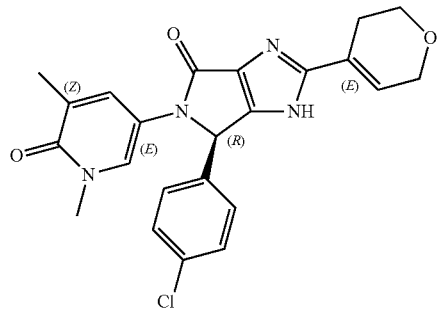

The title compound (16 mg, 35% yield) was obtained enantiomerically pure (>99% ee) after chiral preparative chromatography (system: Gilson 215 prep; column: Chiralpak IC, 5 µM; 250×20 mm; mobile phase: Heptane/EtOH/MeOH 50:25:25; flow: 12 mL/min; temperature: 38° C.; detection UV: 220 nm) of the racemic mixture of 6-(4-chlorophenyl)-2-(3,6-dihydro-2H-pyran-4-yl)-5-(1,5-dimethyl-6-oxo-1,6-dihydropyridin-3-yl)-5,6-dihydropyrrolo[3,4-d]imidazol-4(1H)-one (Example 134).

(R)-6-(4-chlorophenyl)-2-(3,6-dihydro-2H-pyran-4-yl)-5-(1,5-dimethyl-6-oxo-1,6-dihydropyridin-3-yl)-5,6-dihydropyrrolo[3,4-d]imidazol-4(1H)-one. $t_R$: 11.39 min (analytical system: Agilent 1200; column: Chiralpak IC, 4.6×250 mm; mobile phase: Heptane/EtOH 50:50; flow: 1.0 mL/min; temperature: 35° C.; detection UV: 220 nm).

(S)-6-(4-chlorophenyl)-2-(3,6-dihydro-2H-pyran-4-yl)-5-(1,5-dimethyl-6-oxo-1,6-dihydropyridin-3-yl)-5,6-dihydropyrrolo[3,4-d]imidazol-4(1H)-one. $t_R$: 14.84 min (analytical system: Agilent 1200; column: Chiralpak IC, 4.6×250 mm; mobile phase: Heptane/EtOH 50:50; flow: 1.0 mL/min; temperature: 35° C.; detection UV: 220 nm).

EXAMPLE 153

(R)-6-(4-chlorophenyl)-5-(3-(difluoromethyl)-8-methyl-[1,2,4]triazolo[4,3-a]pyridin-6-yl)-2-(2-methoxypyridin-3-yl)-5,6-dihydropyrrolo[3,4-d]imidazol-4(1H)-one

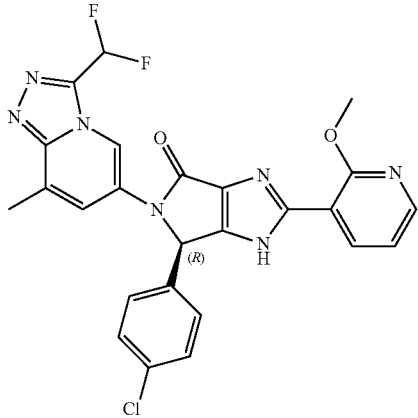

The title compound (25 mg, 50% yield) was obtained enantiomerically pure (>99% ee) after chiral preparative chromatography (system: Gilson 215 prep; column: Chiralcel OD-H, 5 µM; 250×20 mm; mobile phase: Heptane/EtOH/MeOH 60:20:20; flow: 12 mL/min; temperature: 38° C.; detection UV: 220 nm) of the racemic mixture of 6-(4-chlorophenyl)-5-(3-(difluoromethyl)-8-methyl-[1,2,4]triazolo[4,3-a]pyridin-6-yl)-2-(2-methoxypyridin-3-yl)-5,6-dihydropyrrolo[3,4-d]imidazol-4(1H)-one (Example 140).

(R)-6-(4-chlorophenyl)-5-(3-(difluoromethyl)-8-methyl-[1,2,4]triazolo[4,3-a]pyridin-6-yl)-2-(2-methoxypyridin-3-yl)-5,6-dihydropyrrolo[3,4-d]imidazol-4(1H)-one. $t_R$: 6.44 min (analytical system: Agilent 1200 DAD; column: Chiralpak OD-H, 4.6×250 mm; mobile phase: Heptane/EtOH/MeOH 60:20:20; flow: 1.0 mL/min; temperature: 35° C.; detection UV: 220 nm).

(S)-6-(4-chlorophenyl)-5-(3-(difluoromethyl)-8-methyl-[1,2,4]triazolo[4,3-a]pyridin-6-yl)-2-(2-methoxypyridin-3-yl)-5,6-dihydropyrrolo[3,4-d]imidazol-4(1H)-one. $t_R$: 4.89 min (analytical system: Agilent 1200 DAD; column: Chiralpak OD-H, 4.6×250 mm; mobile phase: Heptane/EtOH/MeOH 60:20:20; flow: 1.0 mL/min; temperature: 35° C.; detection UV: 220 nm).

EXAMPLE 154

(R)-6-(4-chlorophenyl)-5-(3,7-dimethyl-3H-[1,2,3]triazolo[4,5-b]pyridin-5-yl)-1-isopropyl-2-(6-methoxypyridin-3-yl)-5,6-dihydropyrrolo[3,4-d]imidazol-4(1H)-one The title compound (73 mg, 45% yield) was obtained enantiomerically pure (>99% ee) after chiral preparative chromatography (system: Sepiatec Prep 100; column: Chiralpak IA, 30×250 mm; mobile phase: scCO$_2$/EtOH 60:40; flow: 100 g/min; temperature: 38° C.; detection UV: 220 nm) of the racemic mixture of 6-(4-chlorophenyl)-5-(3,7-dimethyl-3H-[1,2,3]triazolo[4,5-b]pyridin-5-yl)-1-isopropyl-2-(6-methoxypyridin-3-yl)-5,6-dihydropyrrolo[3,4-d]imidazol-4(1H)-one (Example 138).

(R)-6-(4-chlorophenyl)-5-(3-(difluoromethyl)-8-methyl-[1,2,4]triazolo[4,3-a]pyridin-6-yl)-2-(2-methoxypyridin-3-yl)-5,6-dihydropyrrolo[3,4-d]imidazol-4(1H)-one. $t_R$: 5.49 min (analytical system: Thar/Waters SFC Investigator MS (ZQ); column: Chiralpak IA, 4.6×250 mm; mobile phase: scCO$_2$/EtOH 60:40; flow: 4.0 mL/min; temperature: 35° C.; detection UV: 220 nm).

(S)-6-(4-chlorophenyl)-5-(3-(difluoromethyl)-8-methyl-[1,2,4]triazolo[4,3-a]pyridin-6-yl)-2-(2-methoxypyridin-3-yl)-5,6-dihydropyrrolo[3,4-d]imidazol-4(1H)-one. $t_R$: 4.22 min (analytical system: Thar/Waters SFC Investigator MS (ZQ); column: Chiralpak IA, 4.6×250 mm; mobile phase: scCO$_2$/EtOH 60:40; flow: 4.0 mL/min; temperature: 35° C.; detection UV: 220 nm).

EXAMPLE 155

6-(4-chlorophenyl)-5-(1,5-dimethyl-6-oxo-1,6-dihydropyridin-3-yl)-2-(2-methoxypyridin-3-yl)-5,6-dihydropyrrolo[3,4-d]imidazol-4(1H)-one The title compound was prepared in analogy to the procedure described in Example 1 using 1-allyl-2-bromo-6-(4-chlorophenyl)-5-(1,5-dimethyl-6-oxo-1,6-dihydropyridin-3-yl)-5,6-dihydropyrrolo[3,4-d]imidazol-4(1H)-one (Step 4.6) and 2-methoxy-3-pyridinylboronic acid at 100° C. for 16 hr. After workup, the palladium was removed using a polymer supported benzyl mercaptan resin (PL-BnSH MP-resin) and the resulting crude product was purified by silica gel column chromatography (ISCO system; column: 40 g; solvent A: hexanes; solvent B: EtOAc; gradient (% B): 0% for 15 min, 0-15% for 5 min, 15% for 10 min. Then solvents are switched. solvent A: EtOAc; solvent B: MeOH; gradient (% B) 0-10% for 20 min; flow 40 mL/min.). $t_R$: 0.92 min (LC-MS 2); ESI-MS: 462.3 [M+H]$^+$ (LC-MS 2). $^1$H NMR (400 MHz, DMSO-d6) δ ppm 1.93-1.99 (m, 3 H) 3.36-3.41 (m, 3 H) 3.95-4.10 (m, 3 H) 6.13-6.24 (m, 1 H) 7.07-7.21 (m, 1 H) 7.22-7.33 (m, 2 H) 7.36-7.49 (m, 3 H) 7.65-7.78 (m, 1 H) 8.22-8.29 (m, 1 H) 8.32-8.50 (m, 1 H) 12.58-13.08 (m, 1 H).

EXAMPLE 156

(R)-6-(4-chlorophenyl)-5-(1,5-dimethyl-6-oxo-1,6-dihydropyridin-3-yl)-2-(2-methoxypyridin-3-yl)-5,6-dihydropyrrolo[3,4-d]imidazol-4(1H)-one

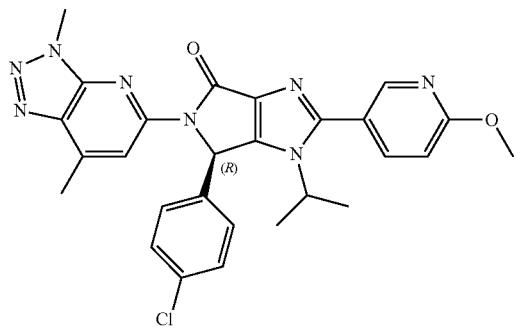

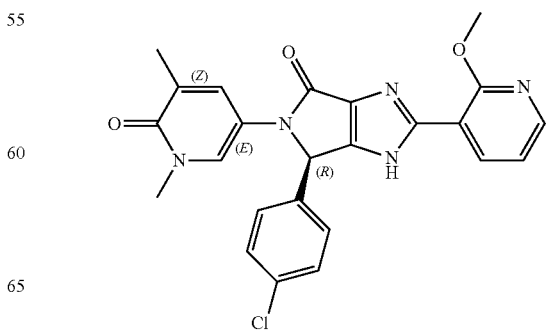

The title compound (25 mg, 43% yield) was obtained enantiomerically pure (>99% ee) after chiral preparative chromatography (system: Gilson PLC 2020; column: Chiralpak IC, 5 μm 20×250 mm; mobile phase: heptane/EtOH/MeOH 60:20:20; flow: 10 mL/min; temperature: 38° C.; detection UV: 220 nm) of the racemic mixture of 6-(4-chlorophenyl)-5-(1,5-dimethyl-6-oxo-1,6-dihydropyridin-3-yl)-2-(2-methoxypyridin-3-yl)-5,6-dihydropyrrolo[3,4-d]imidazol-4(1H)-one (Example 155).

(R)-6-(4-chlorophenyl)-5-(1,5-dimethyl-6-oxo-1,6-dihydropyridin-3-yl)-2-(2-methoxypyridin-3-yl)-5,6-dihydropyrrolo[3,4-d]imidazol-4(1H)-one. $t_R$: 21.02 min (analytical system: Shimadzu prominence HPLC system; column: Chiralpak IC, 5 μm 4.6×250 mm; mobile phase: heptane/EtOH/MeOH 60:20:20; flow: 1.0 mL/min; temperature: 35° C.; detection UV: 220 nm).

(S)-6-(4-chlorophenyl)-5-(1,5-dimethyl-6-oxo-1,6-dihydropyridin-3-yl)-2-(2-methoxypyridin-3-yl)-5,6-dihydropyrrolo[3,4-d]imidazol-4(1H)-one. $t_R$: 17.27 min (analytical system: Shimadzu prominence HPLC system; column: Chiralpak IC, 5 μm 4.6×250 mm; mobile phase: heptane/EtOH/MeOH 60:20:20; flow: 1.0 mL/min; temperature: 35° C.; detection UV: 220 nm).

EXAMPLE 157

6-(4-chlorophenyl)-5-(3,7-dimethyl-3H-[1,2,3]triazolo[4,5-b]pyridin-5-yl)-1-isopropyl-2-(2-methoxypyridin-3-yl)-5,6-dihydropyrrolo[3,4-d]imidazol-4(1H)-one

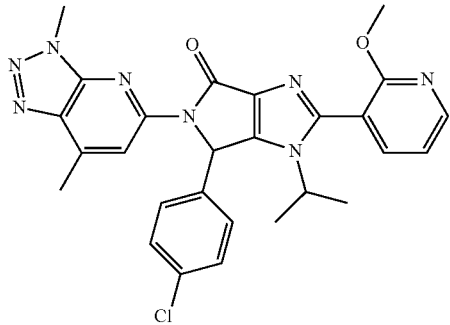 [SMILES: COc1ncccc1-c1nc2c(n1C(C)C)C(c1ccc(Cl)cc1)N(c1cc(C)c3nnn(C)c3n1)C2=O]

The title compound was prepared in analogy to the procedure described for Example 1 using 2-bromo-6-(4-chlorophenyl)-5-(3,7-dimethyl-3H-[1,2,3]triazolo[4,5-b]pyridin-5-yl)-1-isopropyl-5,6-dihydropyrrolo[3,4-d]imidazol-4(1H)-one (Step 138.8) and 2-methoxy-3-pyridineboronic acid. The title compound was obtained after tituration of the crude material with MeOH as a beige powder. $t_R$: 1.17 min (LC-MS 2); ESI-MS: 503.2 [M+H]$^+$/501.2 [M−H]$^-$ (LC-MS 2).

EXAMPLE 158

(R)-6-(4-chlorophenyl)-5-(3,7-dimethyl-3H-[1,2,3]triazolo[4,5-b]pyridin-5-yl)-1-isopropyl-2-(2-methoxypyridin-3-yl)-5,6-dihydropyrrolo[3,4-d]imidazol-4(1H)-one

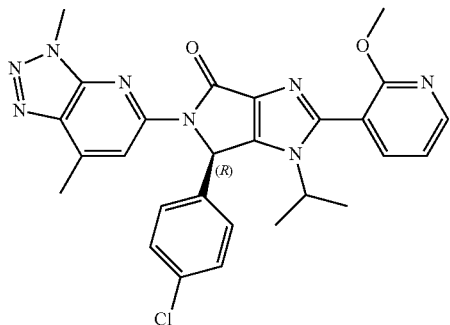

The title compound (70 mg, 42% yield) was obtained enantiomerically pure (>99% ee) after chiral preparative chromatography (system: Sepiatec Prep 100; column: Chiralpak IA, 30×250 mm; mobile phase: scCO$_2$/EtOH 80:20; flow: 100 g/min; temperature: 38° C.; detection UV: 220 nm) of the racemic mixture 6-(4-chlorophenyl)-5-(3,7-dimethyl-3H-[1,2,3]triazolo[4,5-b]pyridin-5-yl)-1-isopropyl-2-(2-methoxypyridin-3-yl)-5,6-dihydropyrrolo[3,4-d]imidazol-4(1H)-one (Example 157).

(R)-6-(4-chlorophenyl)-5-(3,7-dimethyl-3H-[1,2,3]triazolo[4,5-b]pyridin-5-yl)-1-isopropyl-2-(2-methoxypyridin-3-yl)-5,6-dihydropyrrolo[3,4-d]imidazol-4(1H)-one. $t_R$: 4.57 min (analytical system: Thar/Waters SFC Investigator MS (ZQ); column: Chiralpak IA, 4.6×250 mm; mobile phase: scCO$_2$/EtOH 75:25; flow: 4.0 mL/min; temperature: 35° C.; detection UV: 220 nm).

(S)-6-(4-chlorophenyl)-5-(3,7-dimethyl-3H-[1,2,3]triazolo[4,5-b]pyridin-5-yl)-1-isopropyl-2-(2-methoxypyridin-3-yl)-5,6-dihydropyrrolo[3,4-d]imidazol-4(1H)-one. $t_R$: 3.75 min (analytical system: Thar/Waters SFC Investigator MS (ZQ); column: Chiralpak IA, 4.6×250 mm; mobile phase: scCO$_2$/EtOH 75:25; flow: 4.0 mL/min; temperature: 35° C.; detection UV: 220 nm).

EXAMPLE 159

(R)-6-(4-chlorophenyl)-5-(3-(difluoromethyl)-8-methyl-[1,2,4]triazolo[4,3-a]pyridin-6-yl)-2-(2,4-dimethoxypyrimidin-5-yl)-1-isopropyl-5,6-dihydropyrrolo[3,4-d]imidazol-4(1H)-one

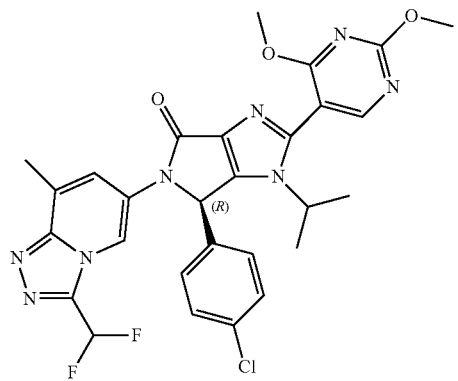

6-(4-chlorophenyl)-5-(3-(difluoromethyl)-8-methyl-[1,2,4]triazolo[4,3-a]pyridin-6-yl)-2-(2,4-dimethoxypyrimidin-5-yl)-1-isopropyl-5,6-dihydropyrrolo[3,4-d]imidazol-4(1H)-one The title compound (42 mg, 37% yield) was obtained enantiomerically pure (>99% ee) after chiral preparative chromatography (system: MGII preparative SFC; column: Chiralcel OD-H, 30×250 mm; mobile phase: scCO$_2$/EtOH 60:40; flow: 50 mL/min; temperature: 38° C.; detection UV: 220 nm) of the racemic mixture 6-(4-chlorophenyl)-5-(3-(difluoromethyl)-8-methyl-[1,2,4]triazolo[4,3-a]pyridin-6-yl)-2-(2,4-dimethoxypyrimidin-5-yl)-1-isopropyl-5,6-dihydropyrrolo[3,4-d]imidazol-4(1H)-one (Example 143).

(R)-6-(4-chlorophenyl)-5-(3-(difluoromethyl)-8-methyl-[1,2,4]triazolo[4,3-a]pyridin-6-yl)-2-(2,4-dimethoxypyrimidin-5-yl)-1-isopropyl-5,6-dihydropyrrolo[3,4-d]imidazol-4(1H)-one $t_R$: 5.78 min (analytical system: Thar/Waters SFC Investigator MS (ZQ); column: ChiralCel OD-3, 4.6×150 mm; mobile phase: scCO$_2$/EtOH 60:40; flow: 2.4 mL/min; temperature: 35° C.; detection UV: 220 nm).

(S)-6-(4-chlorophenyl)-5-(3-(difluoromethyl)-8-methyl-[1,2,4]triazolo[4,3-a]pyridin-6-yl)-2-(2,4-dimethoxypyrimidin-5-yl)-1-isopropyl-5,6-dihydropyrrolo[3,4-d]imidazol-4(1H)-one $t_R$: 2.71 min (analytical system: Thar/Waters SFC Investigator MS (ZQ); column: ChiralCel OD-3, 4.6×150 mm; mobile phase: scCO$_2$/EtOH 60:40; flow: 2.4 mL/min; temperature: 35° C.; detection UV: 220 nm).

EXAMPLE 160

6-(4-chlorophenyl)-2-(3,6-dihydro-2H-pyran-4-yl)-5-(3,7-dimethyl-3H-[1,2,3]triazolo[4,5-b]pyridin-5-yl)-1-isopropyl-5,6-dihydropyrrolo[3,4-d]imidazol-4(1H)-one

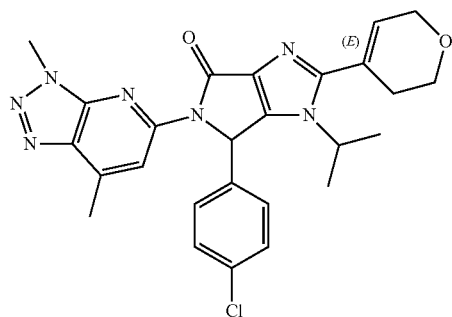 [SMILES: Cc1cc(N2C(=O)c3nc(C4=CCOCC4)n(C(C)C)c3C2c2ccc(Cl)cc2)nc2c1nnn2C]

The title compound was prepared in analogy to the procedure described for Example 1 using 2-bromo-6-(4-chlorophenyl)-5-(3,7-dimethyl-3H[1,2,3]triazolo[4,5-b]pyridin-5-yl)-1-isopropyl-5,6-dihydropyrrolo[3,4-d]imidazol-4(1H)-one (Step 138.8) and 3,6-dihydro-2H-pyran-4-boronic acid pinacol ester. After workup, the palladium was removed using a polymer supported benzyl mercaptan resin (PL-BnSH MP-resin) and the resulting crude product was purified by silica gel column chromatography (ISCO system; column: 40 g; solvent A: hexanes; solvent B: EtOAc; gradient (% B): 0% for 15 min, 0-15% for 5 min, 15% for 10 min. $t_R$: 1.09 min (LC-MS 2); ESI-MS: 504.4 [M+H]$^+$. $^1$H NMR (400 MHz, DMSO-d6) δ ppm 0.62 (d, J=6.72 Hz, 3 H) 1.50 (d, J=6.85 Hz, 3 H) 2.31-2.45 (m, 1 H) 2.56-2.66 (m, 1 H) 2.68 (s, 3 H) 3.72-3.97 (m, 2 H) 4.18-4.38 (m, 5 H) 4.64 (quin, J=6.76 Hz, 1 H) 6.14 (br. s, 1 H) 6.82 (s, 1 H) 7.41 (d, J=8.56 Hz, 2 H) 7.55 (br. s, 2 H) 8.26 (s, 1 H).

EXAMPLE 161

6-(4-chlorophenyl)-5-(3-(difluoromethyl)-8-methyl-[1,2,4]triazolo[4,3-b]pyridazin-6-yl)-2-(3,6-dihydro-2H-pyran-4-yl)-1-isopropyl-5,6-dihydropyrrolo[3,4-d]imidazol-4(1H)-one

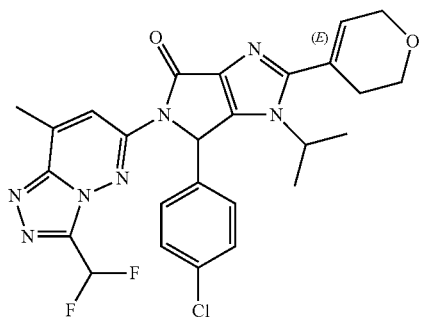 [SMILES: Cc1cc(N2C(=O)c3nc(C4=CCOCC4)n(C(C)C)c3C2c2ccc(Cl)cc2)nn2c(C(F)F)nnc12]

The title compound was prepared in analogy to the procedure described for Example 1 using 2-bromo-6-(4-chlorophenyl)-5-(3-(difluoromethyl)-8-methyl-[1,2,4]triazolo[4,3-b]pyridazin-6-yl)-1-isopropyl-5,6-dihydropyrrolo[3,4-d]imidazol-4(1H)-one (Step 148.6) and 3,6-dihydro-2H-pyran-4-boronic acid pinacol ester as starting materials. Purification of the crude material by SFC chromatography (Thar 100; column: PFP, 25 cm, Ø 3 cm, 5 μm, 60 Å; gradient: 9% B for 1 min, 9-14% B in 6 min, 14-50% B in 1 min, 50% B for 1.5 min, 50%-9% B in 1 min, 9% B for 0.5 min; A: scCO$_2$, B: MeOH; flow: 100 mL/min) afforded the title compound. $t_R$: 1.05 min (LC-MS 2); ESI-MS: 540.2. [M+H]$^+$ (LC-MS 2). $^1$H NMR (400 MHz, DMSO-d6) δ ppm 0.61 (d, J=6.72 Hz, 3 H) 1.47 (d, J=6.85 Hz, 3 H) 2.31-2.46 (m, 1 H) 2.56-2.74 (m, 4 H) 3.72-3.94 (m, 2 H) 4.15-4.35 (m, 2 H) 4.64 (quin, J=6.76 Hz, 1 H) 6.15 (br. s, 1 H) 6.62 (s, 1 H) 7.42 (d, J=8.68 Hz, 2 H) 7.52 (br. s, 2 H) 7.58-7.91 (m, 1 H) 8.36 (s, 1 H).

EXAMPLE 162

6-(4-chlorophenyl)-2-(3,6-dihydro-2H-pyran-4-yl)-5-(3,7-dimethyl-3H-[1,2,3]triazolo[4,5-b]pyridin-5-yl)-5,6-dihydropyrrolo[3,4-d]imidazol-4(1H)-one

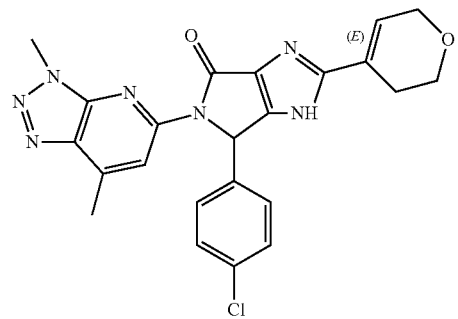 [SMILES: Cc1cc(N2C(=O)c3nc(C4=CCOCC4)[nH]c3C2c2ccc(Cl)cc2)nc2c1nnn2C]

The title compound was prepared in analogy to the procedure described for Example 1 using 1-allyl-2-bromo-6-(4-chlorophenyl)-5-(3,7-dimethyl-3H-[1,2,3]triazolo[4,5-b]pyridin-5-yl)-5,6-dihydropyrrolo[3,4-d]imidazol-4(1H)- one (Step 162.3) and 3,6-dihydro-2H-pyran-4-boronic acid pinacol ester as starting materials. Purification of the crude material by SFC chromatography (Thar 100; column: PFP, 25 cm, Ø 3 cm, 5 μm, 60 Å; gradient: 9% B for 1 min, 9-14% B in 6 min, 14-50% B in 1 min, 50% B for 1.5 min, 50%-9% B in 1 min, 9% B for 0.5 min; A: scCO₂, B: MeOH; flow: 100 mL/min) afforded the title compound. $t_R$: 1.00 min (LC-MS 2); ESI-MS: 462.1 [M+H]⁺/ESI-MS: 460.1 [M−H]⁻ (LC-MS 2). ¹H NMR (400 MHz, DMSO-d6) δ 8.25 (s, 1H), 7.40 (d, J=8.5 Hz, 2H), 7.32 (d, J=8.5 Hz, 2H), 5.73 (s, 1H), 4.21 (t, J=4.2 Hz, 2H), 4.09 (s, 3H), 3.81-3.67 (m, 2H), 2.67 (s, 4H), 2.30 (d, J=1.8 Hz, 1H).

Step 162.1: ethyl 1-allyl-2-bromo-54(4-chlorophenyl)((3,7-dimethyl-3H-[1,2,3]triazolo[4,5-b]pyridin-5-yl)amino)methyl)-1H-imidazole-4-carboxylate

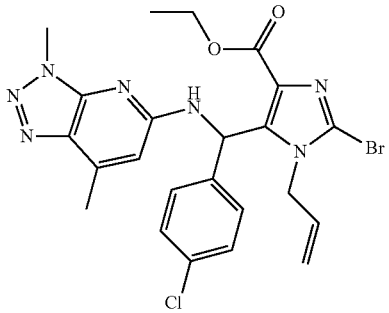 [SMILES: C=CCn1c(Br)nc(C(=O)OCC)c1C(Nc1cc(C)c2nnn(C)c2n1)c1ccc(Cl)cc1]

The title compound was prepared in analogy to the procedure described in Step 1.9 using ethyl 1-allyl-2-bromo-5-((4-chlorophenyl)(hydroxy)methyl)-1H-imidazole-4-carboxylate (Step 1.8) and 3,7-dimethyl-3H-[1,2,3]triazolo[4,5-b]pyridin-5-amine (Step 138.5) as starting materials. The crude product was purified by silica gel column chromatography (CH₂Cl₂/MeOH 0-15% MeOH) to afford the title product as brownish foam. $t_R$: 1.18 min (LC-MS 2); ESI-MS: 546.2 [M+H]⁺ (LC-MS 2).

The title compound was prepared in analogy to the procedure described in Step 1.10 using ethyl 1-allyl-2-bromo-54(4-chlorophenyl)((3,7-dimethyl-3H-[1,2,3]triazolo[4,5-b]pyridin-5-yl)amino)methyl)-1H-imidazole-4-carboxylate (Step 162.1). $t_R$: 0.98 min (LC-MS 2); ESI-MS: 518.1 [M+H]⁺; ESI-MS: 514.1 [M−H]⁻ (LC-MS 2).

Step 162.3: 1-allyl-2-bromo-6-(4-chlorophenyl)-5-(3,7-dimethyl-3H-[1,2,3]triazolo[4,5-b]pyridin-5-yl)-5,6-dihydropyrrolo[3,4-d]imidazol-4(1H)-one The title compound was prepared in analogy to the procedure described in Step 1.11 using 1-allyl-2-bromo-54(4-chlorophenyl)((3,7-dimethyl-3H-[1,2,3]triazolo[4,5-b]pyridin-5-yl)amino)methyl)-1H-imidazole-4-carboxylic acid (Step 162.2). $t_R$: 0.90 min (LC-MS 2); ESI-MS: 473/475 [M+H]⁺ (LC-MS2)

EXAMPLE 163

6-(4-chlorophenyl)-5-(3,7-dimethyl-3H-[1,2,3]triazolo[4,5-b]pyridin-5-yl)-2-(2-methoxypyridin-3-yl)-5,6-dihydropyrrolo[3,4-d]imidazol-4(1H)-one

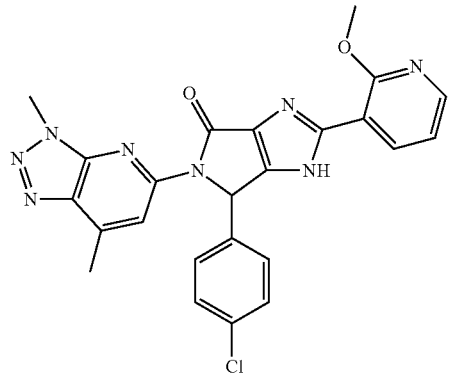 [SMILES: COc1ncccc1-c1nc2c([nH]1)C(c1ccc(Cl)cc1)N(c1cc(C)c3nnn(C)c3n1)C2=O]

The title compound was prepared in analogy to the procedure described for Example 1 using 1-allyl-2-bromo-6-(4-chlorophenyl)-5-(3,7-dimethyl-3H-[1,2,3]triazolo[4,5-b]pyridin-5-yl)-5,6-dihydropyrrolo[3,4-d]imidazol-4(1H)-one (Step 162.3) and 2-methoxy-3-pyridine boronic acid as starting materials. purified by silica gel column chromatography (ISCO system; column: 40 g; solvent A: CH2Cl2; solvent B: MeOH; gradient (% B): 0% for 15 min, 0-10% for 5 min, 10% for 10 min. flow: 35 mL/min) afforded the title compound. $t_R$: 1.13 min (LC-MS 2); ESI-MS: 487.2 [M+H]⁺/ESI-MS: 485.0 [M−H]⁻ (LC-MS 2).

EXAMPLE 164

(R)-6-(4-chlorophenyl)-2-(3,6-dihydro-2H-pyran-4-yl)-5-(3,7-dimethyl-3H-[1,2,3]triazolo[4,5-b]pyridin-5-yl)-1-isopropyl-5,6-dihydropyrrolo[3,4-d]imidazol-4(1H)-one

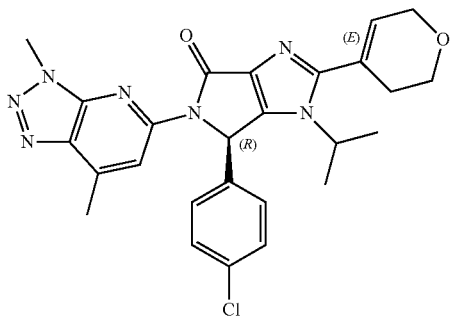

The title compound (165 mg, 42% yield) was obtained enantiomerically pure (>99% ee) after chiral preparative chromatography (system: Sepiatec Prep 100; column: Chiralpak IA, 30×250 mm; mobile phase: scCO₂/EtOH 80:20; flow: 100 g/min; temperature: 38° C.; detection UV: 220 nm) of the racemic mixture 6-(4-chlorophenyl)-2-(3,6-dihydro-2H-pyran-4-yl)-5-(3,7-dimethyl-3H-[1,2,3]triazolo[4,5-b]pyridin-5-yl)-1-isopropyl-5,6-dihydropyrrolo[3,4-d]imidazol-4(1H)-one (Example 161).

(R)-6-(4-chlorophenyl)-2-(3,6-dihydro-2H-pyran-4-yl)-5-(3,7-dimethyl-3H-[1,2,3]triazolo[4,5-b]pyridin-5-yl)-1-isopropyl-5,6-dihydropyrrolo[3,4-d]imidazol-4(1H)-one. $t_R$: 4.57 min (analytical system: Thar/Waters SFC Investigator MS (ZQ); column: Chiralpak IA, 4.6×250 mm; mobile phase: scCO$_2$/EtOH 75:25; flow: 4.0 mL/min; temperature: 35° C.; detection UV: 220 nm).

(S)-6-(4-chlorophenyl)-2-(3,6-dihydro-2H-pyran-4-yl)-5-(3,7-dimethyl-3H-[1,2,3]triazolo[4,5-b]pyridin-5-yl)-1-isopropyl-5,6-dihydropyrrolo[3,4-d]imidazol-4(1H)-one. $t_R$: 3.75 min (analytical system: Thar/Waters SFC Investigator MS (ZQ); column: Chiralpak IA, 4.6×250 mm; mobile phase: scCO$_2$/EtOH 75:25; flow: 4.0 mL/min; temperature: 35° C.; detection UV: 220 nm).

EXAMPLE 165

(R)-6-(4-chlorophenyl)-2-(3,6-dihydro-2H-pyran-4-yl)-5-(3,7-dimethyl-3H-[1,2,3]triazolo[4,5-b]pyridin-5-yl)-5,6-dihydropyrrolo[3,4-d]imidazol-4(1H)-one

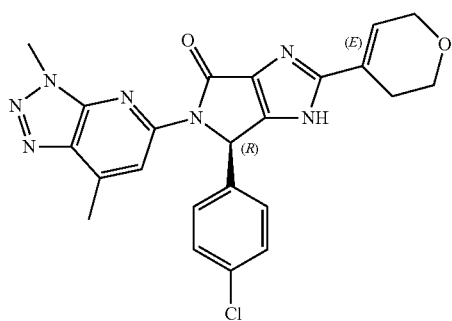

The title compound (45 mg, 45% yield) was obtained enantiomerically pure (>99% ee) after chiral preparative chromatography (system: Gilson 215; column: Chiralpak IC, 20×250 mm; mobile phase: heptane/CH$_2$Cl$_2$/EtOH 60:35:5; flow: 12 mL/min; temperature: 38° C.; detection UV: 220 nm) of the racemic mixture 6-(4-chlorophenyl)-2-(3,6-dihydro-2H-pyran-4-yl)-5-(3,7-dimethyl-3H-[1,2,3]triazolo[4,5-b]pyridin-5-yl)-5,6-dihydropyrrolo[3,4-d]imidazol-4(1H)-one (Example 162).

(R)-6-(4-chlorophenyl)-2-(3,6-dihydro-2H-pyran-4-yl)-5-(3,7-dimethyl-3H[1,2,3]triazolo[4,5-b]pyridin-5-yl)-5,6-dihydropyrrolo[3,4-d]imidazol-4(1H)-one. $t_R$: 18.02 min (analytical system: Shimadzu; column: Chiralpak IC, 4.6×250 mm; mobile phase: heptane/CH$_2$Cl$_2$/EtOH 60:35:5; flow: 1.0 mL/min; temperature: 35° C.; detection UV: 220 nm).

(S)-6-(4-chlorophenyl)-2-(3,6-dihydro-2H-pyran-4-yl)-5-(3,7-dimethyl-3H-[1,2,3]triazolo[4,5-b]pyridin-5-yl)-5,6-dihydropyrrolo[3,4-d]imidazol-4(1H)-one. $t_R$: 21.36 min (analytical system: Shimadzu; column: Chiralpak IC, 4.6×250 mm; mobile phase: heptane/CH$_2$Cl$_2$/EtOH 60:35:5; flow: 1.0 mL/min; temperature: 35° C.; detection UV: 220 nm).

EXAMPLE 166

(R)-6-(4-chlorophenyl)-5-(3,7-dimethyl-3H-[1,2,3]triazolo[4,5-b]pyridin-5-yl)-2-(2-methoxypyridin-3-yl)-5,6-dihydropyrrolo[3,4-d]imidazol-4(1H)-one

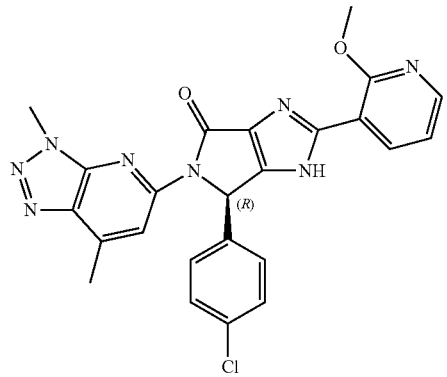

The title compound (35 mg, 35% yield) was obtained enantiomerically pure (>99% ee) after chiral preparative chromatography (system: Gilson215; column: Chiralpak IC, 20×250 mm; mobile phase: heptane/CH$_2$Cl$_2$/EtOH 60:30:10; flow: 12 mL/min; temperature: 38° C.; detection UV: 220 nm) of the racemic mixture 6-(4-chlorophenyl)-5-(3,7-dimethyl-3H-[1,2,3]triazolo[4,5-b]pyridin-5-yl)-2-(2-methoxypyridin-3-yl)-5,6-dihydropyrrolo[3,4-d]imidazol-4(1H)-one. (Example 163).

(R)-6-(4-chlorophenyl)-5-(3,7-dimethyl-3H-[1,2,3]triazolo[4,5-b]pyridin-5-yl)-2-(2-methoxypyridin-3-yl)-5,6-dihydropyrrolo[3,4-d]imidazol-4(1H)-one. $t_R$: 11.62 min (analytical system: Shimadzu; column: Chiralpak IC, 4.6×250 mm; mobile phase: heptane/CH$_2$Cl$_2$/EtOH 60:30:10; flow: 1.0 mL/min; temperature: 35° C.; detection UV: 220 nm).

(S)-6-(4-chlorophenyl)-5-(3,7-dimethyl-3H-[1,2,3]triazolo[4,5-b]pyridin-5-yl)-2-(2-methoxypyridin-3-yl)-5,6-dihydropyrrolo[3,4-d]imidazol-4(1H)-one. $t_R$: 8.09 min (analytical system: Shimadzu; column: Chiralpak IC, 4.6×250 mm; mobile phase: heptane/CH$_2$Cl$_2$/EtOH 60:30:10; flow: 1.0 mL/min; temperature: 35° C.; detection UV: 220 nm).

EXAMPLE 167

(R)-6-(4-chlorophenyl)-2-(3,6-dihydro-2H-pyran-4-yl)-5-(3,8-dimethyl-[1,2,4]triazolo[4,3-a]pyridin-6-yl)-5,6-dihydropyrrolo[3,4-d]imidazol-4(1H)-one

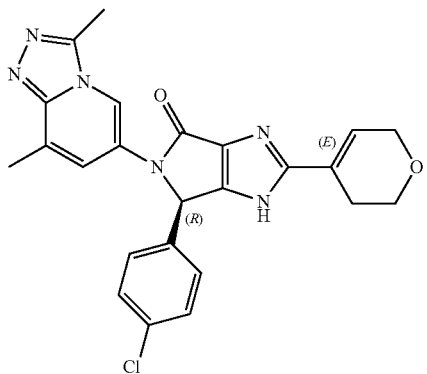

The title compound (20 mg, 35% yield) was obtained enantiomerically pure (>99% ee) after chiral preparative chromatography (system: Sepiatec Prep 100; column: Chiralpak IA, 30×250 mm; mobile phase: scCO$_2$/EtOH 80:20; flow: 100 g/min; temperature: 38° C.; detection UV: 220 nm) of the racemic mixture of 6-(4-chlorophenyl)-2-(3,6-dihydro-2H-pyran-4-yl)-5-(3,8-dimethyl-[1,2,4]triazolo[4,3-a]pyridin-6-yl)-5,6-dihydropyrrolo[3,4-d]imidazol-4(1H)-one. (Example 116).

(R)-6-(4-chlorophenyl)-2-(3,6-dihydro-2H-pyran-4-yl)-5-(3,8-dimethyl-[1,2,4]triazolo[4,3-a]pyridin-6-yl)-5,6-dihydropyrrolo[3,4-d]imidazol-4(1H)-one t$_R$: 3.70 min (analytical system: Thar/Waters SFC Investigator MS (ZQ); column: Chiralpak IA, 4.6×250 mm; mobile phase: scCO$_2$/EtOH 75:25; flow: 4.0 mL/min; temperature: 35° C.; detection UV: 220 nm).

(S)-6-(4-chlorophenyl)-2-(3,6-dihydro-2H-pyran-4-yl)-5-(3,8-dimethyl-[1,2,4]triazolo[4,3-a]pyridin-6-yl)-5,6-dihydropyrrolo[3,4-d]imidazol-4(1H)-one. t$_R$: 6.02 min (analytical system: Thar/Waters SFC Investigator MS (ZQ); column: Chiralpak IA, 4.6×250 mm; mobile phase: scCO$_2$/EtOH 75:25; flow: 4.0 mL/min; temperature: 35° C.; detection UV: 220 nm).

EXAMPLE 168

(R)-6-(4-chlorophenyl)-5-(3-(difluoromethyl)-8-methyl-[1,2,4]triazolo[4,3-b]pyridazin-6-yl)-1-isopropyl-2-(2-methoxypyridin-3-yl)-5,6-dihydropyrrolo[3,4-d]imidazol-4(1H)-one

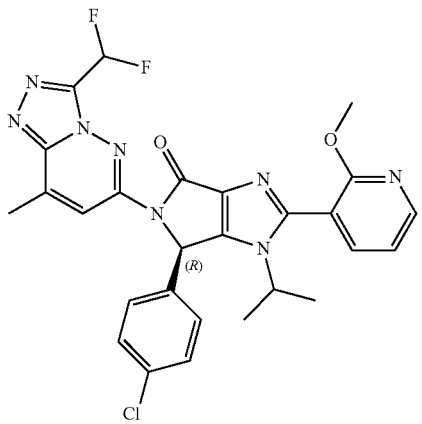

The title compound (45 mg, 45% yield) was obtained enantiomerically pure (>99% ee) after chiral preparative chromatography (system: Gilson 215; column: Chiralpak IC, 20×250 mm; mobile phase: heptane/CH$_2$Cl$_2$/EtOH 60:35:5; flow: 12 mL/min; temperature: 38° C.; detection UV: 220 nm) of the racemic mixture of 6-(4-chlorophenyl)-5-(3-(difluoromethyl)-8-methyl-[1,2,4]triazolo[4,3-b]pyridazin-6-yl)-1-isopropyl-2-(2-methoxypyridin-3-yl)-5,6-dihydropyrrolo[3,4-d]imidazol-4(1H)-one (Example 148).

(R)-6-(4-chlorophenyl)-5-(3-(difluoromethyl)-8-methyl-[1,2,4]triazolo[4,3-b]pyridazin-6-yl)-1-isopropyl-2-(2-methoxypyridin-3-yl)-5,6-dihydropyrrolo[3,4-d]imidazol-4(1H)-one. t$_R$: 7.37 min (analytical system: Agilent HPLC system; column: Chrialcel ODH, 4.6×250 mm; mobile phase: heptane/MeOH/EtOH 60:20:20; flow: 1.0 mL/min; temperature: 35° C.; detection UV: 220 nm).

(S)-6-(4-chlorophenyl)-5-(3-(difluoromethyl)-8-methyl-[1,2,4]triazolo[4,3-b]pyridazin-6-yl)-1-isopropyl-2-(2-methoxypyridin-3-yl)-5,6-dihydropyrrolo[3,4-d]imidazol-4(1H)-one t$_R$: 12.73 min (analytical system: Agilent HPLC system; column: Chrialcel ODH, 4.6×250 mm; mobile phase: heptane/MeOH/EtOH 60:20:20; flow: 1.0 mL/min; temperature: 35° C.; detection UV: 220 nm).

EXAMPLE 169

6-(4-chlorophenyl)-5-(3,8-dimethyl-[1,2,4]triazolo[4,3-b]pyridazin-6-yl)-1-isopropyl-2-(1-methylpiperidin-4-yl)-5,6-dihydropyrrolo[3,4-d]imidazol-4(1H)-one

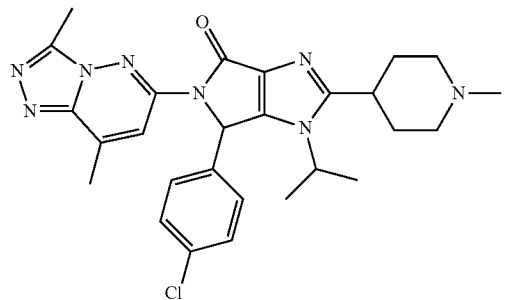 [SMILES: Cc1cc(N2C(=O)c3nc(C4CCN(C)CC4)n(C(C)C)c3C2c2ccc(Cl)cc2)nn2c(C)nnc12]

The title compound was prepared in analogy to the procedure described in Example 101 using 6-(4-chlorophenyl)-1-isopropyl-2-(1-methylpiperidin-4-yl)-5,6-dihydropyrrolo[3,4-d]imidazol-4(1H)-one (Step 103.5). Purification by preparative HPLC (gradient 5-100% CH$_3$CN in 20 min), followed by basic workup gave the title product. t$_R$: 0.70 min (LC-MS 2); ESI-MS: 519 [M+H]$^+$ (LC-MS 2).

Step 169.1: ethyl 5-(azido(4-chlorophenyl)methyl)-1-isopropyl-2-(1-methyl-1,2,3,6-tetrahydropyridin-4-yl)-1H-imidazole-4-carboxylate

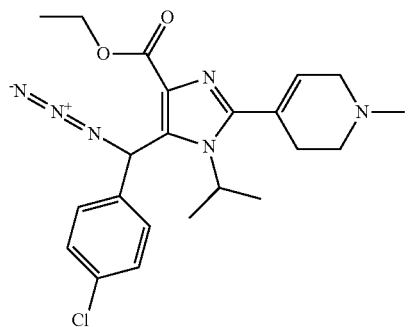

The title compound was prepared in analogy to the procedure described for Example 1 using ethyl 5-(azido(4-chlorophenyl)methyl)-2-bromo-1-isopropyl-1H-imidazole-4-carboxylate (Step 100.1) and 1-methyl-1,2,3,6,-tetrahydropyridin-4-boronic acid pinacolester under heating at 85° C. for 7 hr. The reaction mixture was diluted with CH$_2$Cl$_2$ and H$_2$O. The aq. layer was separated off and extracted with CH$_2$Cl$_2$. Combined extracts were dried over Na$_2$SO$_4$, filtered and concentrated under reduced pressure. The crude product was purified by silica gel column chromatography

[CH₂Cl₂/(CH₂Cl₂/EtOH/N H₃ 18:4:1) 0-100% (CH₂Cl₂/EtOH/NH₃ 18:4:1)]. $t_R$: 0.95 min (LC-MS 2); ESI-MS: 443 [M+H]⁺.

Step 169.2: ethyl 5-(amino(4-chlorophenyl)methyl)-1-isopropyl-2-(1-methyl-1,2,3,6-tetrahydropyridin-4-yl)-1H-imidazole-4-carboxylate

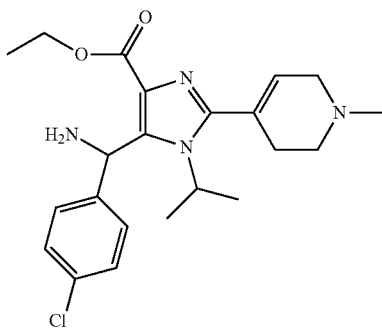 [SMILES: CCOC(=O)c1nc(C2=CCN(C)CC2)n(C(C)C)c1C(N)c1ccc(Cl)cc1]

Hydrogenation of ethyl 5-(azido(4-chlorophenyl)methyl)-1-isopropyl-2-(1-methyl-1,2,3,6-tetrahydropyridin-4-yl)-1H-imidazole-4-carboxylate (215 mg, 0.49 mmol) in EtOH (20 mL) in presence of Raney nickel (0.07 g) during 20 hr, filtration and concentration of the filtrate gave the title compound. $t_R$: 0.52 min (LC-MS 2); ESI-MS: 417 [M+H]⁺ (LC-MS 2).

Step 169.3: 5-(amino(4-chlorophenyl)methyl)-1-isopropyl-2-(1-methyl-1,2,3,6-tetrahydropyridin-4-yl)-1H-imidazole-4-carboxylic acid

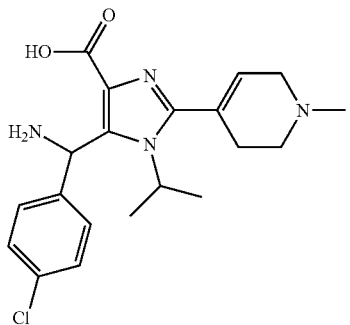 [SMILES: CC(C)n1c(C2=CCN(C)CC2)nc(C(=O)O)c1C(N)c1ccc(Cl)cc1]

The title compound was prepared in analogy to the procedure described in Step 1.10 using ethyl 5-(amino(4-chlorophenyl)methyl)-1-isopropyl-2-(1-methyl-1,2,3,6-tetrahydropyridin-4-yl)-1H-imidazole-4-carboxylate at 50° C. The reaction mixture was acidified with 4 N HCl and then concentrated. The residue was stirred in CH₂Cl₂/MeOH 4:1. The suspension was filtered and the filtrate concentrated. $t_R$: 0.43 min (LC-MS 2); ESI-MS: 389 [M+H]⁺ (LC-MS 2).

Step 169.4: 6-(4-chlorophenyl)-1-isopropyl-2-(1-methyl-1,2,3,6-tetrahydropyridin-4-yl)-5,6-dihydropyrrolo[3,4-d]imidazol-4(1H)-one

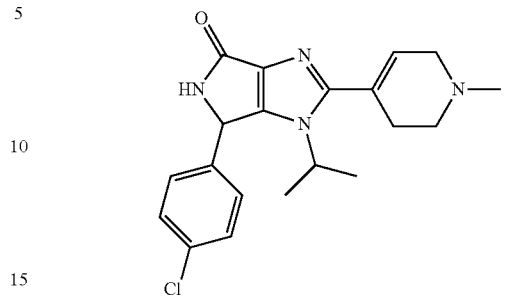

The title compound was prepared in analogy to the procedure described in Step 1.11 using 5-(amino(4-chlorophenyl)methyl)-1-isopropyl-2-(1-methyl-1,2,3,6-tetrahydropyridin-4-yl)-1H-imidazole-4-carboxylic acid. The reaction mixture was diluted with CH₂Cl₂ and aq. NaHCO₃. The aq. layer was separated off and extracted with CH₂Cl₂. Combined extracts were washed with brine and dried over Na₂SO₄, filtered and concentrated under reduced pressure. Purification by preparative HPLC (gradient 5-100% CH₃CN in 20 min), followed by basic workup gave the title product. $t_R$: 0.60 min (LC-MS 2); ESI-MS: 371 [M+H]⁺ (LC-MS 2).

Step 169.5: 6-(4-chlorophenyl)-1-isopropyl-2-(1-methylpiperidin-4-yl)-5,6-dihydropyrrolo[3,4-d]imidazol-4(1H)-one

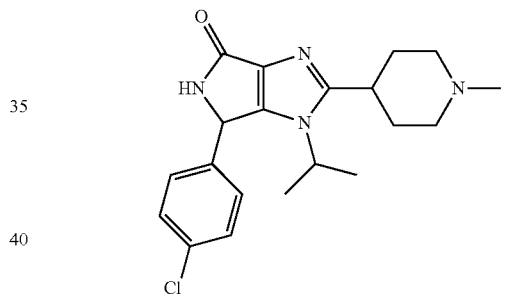

Hydrogenation of 6-(4-chlorophenyl)-1-isopropyl-2-(1-methyl-1,2,3,6-tetrahydropyridin-4-yl)-5,6-dihydropyrrolo[3,4-d]imidazol-4(1H)-one (51 mg, 0.138 mmol) in EtOH (15 mL) in presence of Pt/C 5% (110 mg) during 61 h, filtration and concentration of the filtrate gave the title compound. $t_R$: 0.62 min (LC-MS 2); ESI-MS: 373 [M+H]⁺ (LC-MS 2).

EXAMPLE 170

6-(4-chlorophenyl)-5-(3,8-dimethyl-[1,2,4]triazolo[4,3-b]pyridazin-6-yl)-1-isopropyl-2-(tetrahydrofuran-3-yl)-5,6-dihydropyrrolo[3,4-d]imidazol-4(1H)-one

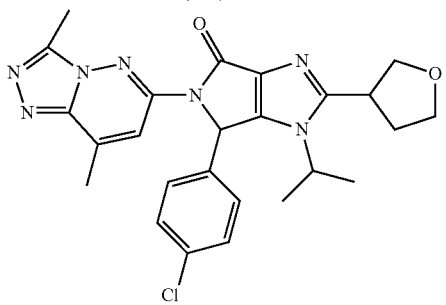

6-(4-Chlorophenyl)-1-isopropyl-2-(tetrahydrofuran-3-yl)-5,6-dihydropyrrolo[3,4-d]imidazol-4(1H)-one (Step 170.4) (90 mg, 0.26 mmol) was dissolved in dioxane (5 mL) under an Ar-atmosphere. 6-Chloro-3,8-dimethyl-[1,2,4]triazolo[4,3-b]pyridazine (Step 18.2) (95 mg, 0.52 mmol), Pd$_2$(dba)$_3$ (47.7 mg, 0.052 mmol), XantPhos (60.2 mg, 0.104 mmol) and Cs$_2$CO$_3$ (170 mg, 0.52 mmol) were added and the resulting mixture was heated up and stirred at 85° C. for 10 hr. The cooled mixture was filtered and the residue washed with dioxane. The filtrate was concentrated. Purification by silica gel column chromatography [CH$_2$Cl$_2$/(CH$_2$Cl$_2$/EtOH 9:1) 0-50% (CH$_2$Cl$_2$/EtOH 9:1)] and finally by preparative HPLC (gradient 30-100% CH$_3$CN in 20 min), followed by basic workup yielded the title compound as a mixture of diastereomers (66 mg, 51% yield). $t_R$: 0.93/0.95 min (LC-MS 2); ESI-MS: 492 [M+H]$^+$ (LC-MS 2).

Step 170.1: ethyl 5-(azido(4-chlorophenyl)methyl)-1-isopropyl-2-(tetrahydrofuran-3-yl)-1H-imidazole-4-carboxylate

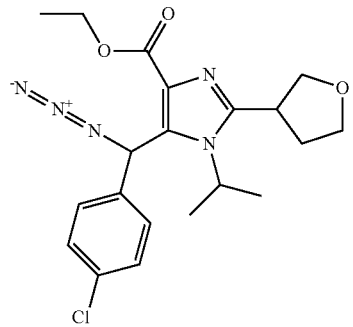

Ethyl 5-((4-chlorophenyl)(hydroxy)methyl)-1-isopropyl-2-(tetrahydrofuran-3-yl)-1H-imidazole-4-carboxylate (Step 99.3) (310 mg, 0.79 mmol) was dissolved in CH$_2$Cl$_2$ (6 mL). TEA (0.547 mL, 3.95 mmol) was added and the resulting mixture was cooled down to −5° C. After portionwise addition of methanesulfonic anhydride (275 mg, 1.58 mmol), the reaction mixture was stirred for 30 min. Then tetrabutylammonium azide (449 mg, 1.58 mmol) was added. The mixture was allowed to warm up to rt. After 16 h it was diluted with CH$_2$Cl$_2$ and H$_2$O. The aq. layer was separated off and extracted with CH$_2$Cl$_2$. Combined extracts were washed with brine and dried over Na$_2$SO$_4$, filtered and concentrated under reduced pressure. Purification by silica gel column chromatography (hexane/TBME 10-80% TBME) gave the title product (221 mg, 67% yield). $t_R$: 1.28 min (LC-MS 2); ESI-MS: 418 [M+H]$^+$ (LC-MS 2).

Step 170.2: ethyl 5-(amino(4-chlorophenyl)methyl)-1-isopropyl-2-(tetrahydrofuran-3-yl)-1H-imidazole-4-carboxylate

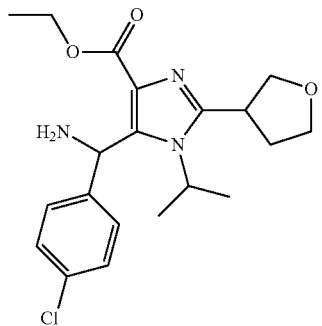 [SMILES: CCOC(=O)c1nc(C2CCOC2)n(C(C)C)c1C(N)c1ccc(Cl)cc1]

Hydrogenation of ethyl 5-(azido(4-chlorophenyl)methyl)-1-isopropyl-2-(tetrahydrofuran-3-yl)-1H-imidazole-4-carboxylate (219 mg, 0.524 mmol) in EtOH (15 mL) in presence of Raney nickel (0.07 g), filtration and concentration of the filtrate gave the title compound as a mixture of diastereomers. $t_R$: 0.75/0.76 min (LC-MS 2); ESI-MS: 392 [M+H]$^+$ (LC-MS 2).

Step 170.3: 5-(amino(4-chlorophenyl)methyl)-1-isopropyl-2-(tetrahydrofuran-3-yl)-1H-imidazole-4-carboxylic acid

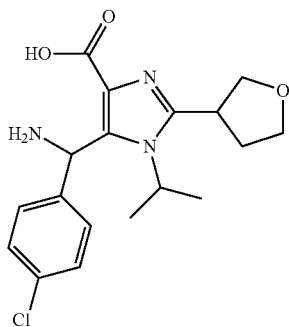 [SMILES: CC(C)n1c(C2CCOC2)nc(C(=O)O)c1C(N)c1ccc(Cl)cc1]

The title compound was prepared in analogy to the procedure described in Step 1.10 using ethyl 5-(amino(4-chlorophenyl)methyl)-1-isopropyl-2-(tetrahydrofuran-3-yl)-1H-imidazole-4-carboxylate at 40° C. The reaction mixture was acidified with 4 N HCl and then extracted with 2 portions of 5 mL EtOAc. The org. layers were washed with brine (4 mL), dried over Na$_2$SO$_4$, filtered and concentrated under reduced pressure giving the title compound as a mixture of diastereomers. $t_R$: 0.58/0.60 min (LC-MS 2); ESI-MS: 364 [M+H]$^+$ (LC-MS 2).

Step 170.4: 6-(4-chlorophenyl)-1-isopropyl-2-(tetrahydrofuran-3-yl)-5,6-dihydropyrrolo[3,4-d]imidazol-4(1H)-one

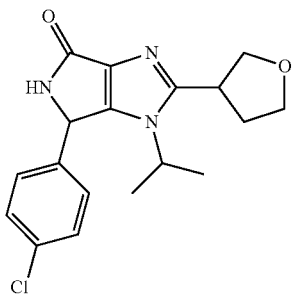 [SMILES: CC(C)n1c(C2CCOC2)nc2c1C(c1ccc(Cl)cc1)NC2=O]

The title compound was prepared in analogy to the procedure described in Step 1.11 using 5-(amino(4-chlorophenyl)methyl)-1-isopropyl-2-(tetrahydrofuran-3-yl)-1H-imidazole-4-carboxylic acid. The reaction mixture was diluted with CH$_2$Cl$_2$ and aq. NaHCO$_3$. The aq. layer was separated off and extracted with CH$_2$Cl$_2$. Combined extracts were washed with brine and dried over Na$_2$SO$_4$, filtered and concentrated under reduced pressure. Purification by silica gel column chromatography [CH$_2$Cl$_2$/(CH$_2$Cl$_2$/MeOH 9:1) 0-75% (CH$_2$Cl$_2$/MeOH 9:1)] gave the title compound. $t_R$: 0.85 min (LC-MS 2); ESI-MS: 346 [M+H]$^+$ (LC-MS 2).

EXAMPLE 171

(6R)-6-(4-chlorophenyl)-5-(3,8-dimethyl-[1,2,4]triazolo[4,3-b]pyridazin-6-yl)-1-isopropyl-2-(tetrahydrofuran-3-yl)-5,6-dihydropyrrolo[3,4-d]imidazol-4(1H)-one

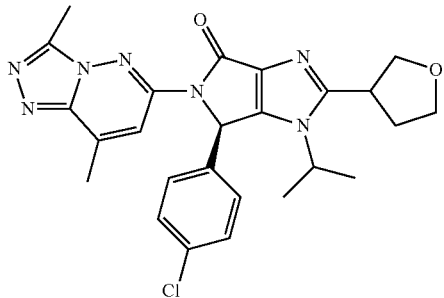 [SMILES: Cc1cc(N2C(=O)c3nc(C4CCOC4)n(C(C)C)c3[C@H]2c2ccc(Cl)cc2)nn2c(C)nnc12]

Chiral preparative chromatography (Chiralpak IC 5 μm, 250×30 mm; mobile phase: heptane/CH$_2$Cl$_2$/EtOH 30:50:20+0.05% Et$_2$NH; flow rate: 15 mL/min; detection 275 nm) of the racemic diastereomeric mixture of 6-(4-chlorophenyl)-5-(3,8-dimethyl-[1,2,4]triazolo[4,3-b]pyridazin-6-yl)-1-isopropyl-2-(tetrahydrofuran-3-yl)-5,6-dihydropyrrolo[3,4-d]imidazol-4(1H)-one (78 mg) gave the two enantiomerically pure diastereomeric title compounds (diast.A: 20 mg, >99% ee; diast.B: 21 mg, >99% ee). The second pair of enantiomerically pure diastereomeric compounds {(6S)-6-(4-chlorophenyl)-5-(3,8-dimethyl-[1,2,4]triazolo[4,3-b]pyridazin-6-yl)-1-isopropyl-2-(tetrahydrofuran-3-yl)-5,6-dihydropyrrolo[3,4-d]imidazol-4(1H)-one: diast.A: 20 mg, >99% ee; diast.B: 16 mg, >99% ee} was obtained via the same separation. $^1$H NMR diast.A (600 MHz, DMSO-d$_6$) δ 8.16 (m, 1H), 7.50 (br. s, 2H), 7.44 (d, 2H), 6.66 (s, 1H), 4.59 (m, 1H), 4.08 (t, 1H), 3.88 (m, 2H), 3.83 (q, 1H), 3.70 (m, 1H), 2.68 (s, 3H), 2.56 (s, 3H), 2.33 (m, 1H), 2.17 (m, 1H), 1.45 (d, 3H), 0.58 (d, 3H). $^1$H NMR diast.B (600 MHz, DMSO-d$_6$) δ 8.16 (m, 1H), 7.51 (br. s, 2H), 7.44 (d, 2H), 6.65 (s, 1H), 4.56 (m, 1H), 4.11 (t, 1H), 3.93 (m, 1H), 3.83 (m, 2H), 3.69 (m, 1H), 2.67 (s, 3H), 2.56 (s, 3H), 2.25 (m, 2H), 1.44 (d, 3H), 0.59 (d, 3H).

EXAMPLE 172

(6R)-6-(4-chlorophenyl)-5-(1,4-dimethyl-1H-benzo[d][1,2,3]triazol-6-yl)-1-isopropyl-2-(tetrahydrofuran-3-yl)-5,6-dihydropyrrolo[3,4-d]imidazol-4(1H)-one

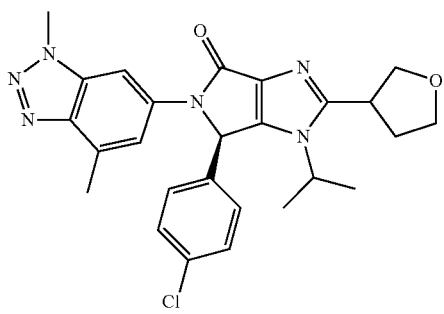 [SMILES: Cc1cc(N2C(=O)c3nc(C4CCOC4)n(C(C)C)c3[C@H]2c2ccc(Cl)cc2)cc2c1nnn2C]

Chiral preparative chromatography (Chiralpak IC 7.65×37.5 cm; mobile phase: heptane/CH$_2$Cl$_2$/EtOH 50:33:17+0.05% Et$_2$NH, then CH$_2$Cl$_2$/EtOH 50:50+0.05% Et$_2$NH; flow rate: 90 mL/min; detection 230 nm) of the racemic diastereomeric mixture of 6-(4-chlorophenyl)-5-(1,4-dimethyl-1H-benzo[d][1,2,3]triazol-6-yl)-1-isopropyl-2-(tetrahydrofuran-3-yl)-5,6-dihydropyrrolo[3,4-d]imidazol-4(1H)-one (Example 99; 478 mg) gave the two enantiomerically pure diastereomeric title compounds (diast.A: 105 mg, >99% ee; diast.B: 110 mg, >99% ee). The second pair of enantiomerically pure diastereomeric compounds {(6S)-6-(4-chlorophenyl)-5-(1,4-dimethyl-1H-benzo[d][1,2,3]triazol-6-yl)-1-isopropyl-2-(tetrahydrofuran-3-yl)-5,6-dihydropyrrolo[3,4-d]imidazol-4(1H)-one: diast.A: 95 mg, >99% ee; diast.B: 105 mg, >99% ee} was obtained via the same separation. $^1$H NMR diast.A (600 MHz, DMSO-d$_6$) δ 7.78 (m, 1H), 7.49 (s, 1H), 7.40 (br. s, 2H), 7.36 (d, 2H), 6.75 (s, 1H), 4.61 (m, 1H), 4.23 (s, 3H), 4.09 (t, 1H), 3.90 (m, 2H), 3.84 (q, 1H), 3.69 (m, 1H), 2.61 (s, 3H), 2.33 (m, 1H), 2.18 (m, 1H), 1.49 (d, 3H), 0.59 (d, 3H). $^1$H NMR diast.B (600 MHz, DMSO-d$_6$) δ 7.78 (m, 1H), 7.49 (s, 1H), 7.41 (br. s, 2H), 7.36 (d, 2H), 6.75 (s, 1H), 4.58 (m, 1H), 4.23 (s, 3H), 4.12 (t, 1H), 3.94 (m, 1H), 3.83 (m, 2H), 3.69 (m, 1H), 2.60 (s, 3H), 2.27 (m, 2H), 1.48 (d, 3H), 0.60 (d, 3H).

Assays

The activity of a compound according to the present invention can be assessed by the following methods.

TR-FRET In-Vitro Binding Assays for BRD2, BRD3, and BRD4:

All assays were performed in 384 well microtiter plates. Each assay plate contained 8-point serial dilutions for 40 test compounds, plus 16 high- and 16 low controls. Liquid handling and incubation steps were done on an Innovadyne Nanodrop Express equipped with a robotic arm (Thermo CatX, Perkin Elmer/Caliper Twister II) and an incubator (Liconic STX40, Thermo Cytomat 2C450). The assay plates were prepared by addition of 50 nl per well of compound solution in 90% DMSO HummingBird nanodispenser (Zinsser Analytic). The assay was started by stepwise addition of 4.5 μl per well of bromo domain protein (50 mM HEPES, pH 7.5, 0.005% Tween20, 0.1% BSA, 50 mM NaCl, 45 nM His-Brd2(60-472) or 45 nM His-Brd3(20-477) or 45 nM His-Brd4(44-477) all proteins produced in-house) and 4.5μl per well of peptide solution (50 mM HEPES, pH 7.5, 0.005% Tween20, 0.1% BSA, 50 mM NaCl, 60 nM acetyl-histone H4 (AcK 5, 8, 12, 16) (Biosyntan GmbH)). Reactions were incubated at 30° C. for 35 minutes. Subsequently 4.5 μl per well detection mix (50 mM HEPES, pH 7.5, 0.005% Tween20, 0.1% BSA, 50 mM NaCl, 3 nM Eu-labeled anti-His6 antibody, 21 nM streptavidin-allophycocyanin) were added. After 35 minutes incubation at 30° C., plates were measured in a Perkin Elmer EnVision multilabel reader. Concentrations causing 50% inhibition (IC50 values) were determined from percent inhibition values at different compound concentrations by non-linear regression analysis.

AlphaScreen In-Vitro Binding Assay for CREBBP

In order to assess bromodomain selectivity, we set up a binding assay using the bromodomain encoded by the CREBBP gene. Compounds were tested in the CREBBP assay with a similar protocol, however using AlphaScreen (Amplified Luminescent Proximity Homogeneous Assay, Perkin Elmer) as detection readout instead of TR-FRET. The assay was started by stepwise addition of 4.5μl per well of bromo domain protein (50 mM HEPES, pH 7.5, 0.005% Tween20, 0.02% BSA, 150 mM NaCl, 324 nM His-CREBBP(1081-1197) (custom production at Viva Biotech Ltd.)) and 4.5μl per well of peptide solution (50 mM HEPES, pH 7.5, 0.005% Tween20, 0.02% BSA, 150 mM NaCl, 120 nM acetyl-histone H4 (AcK 5, 8, 12) (Biosyntan GmbH)). Reactions were incubated at 30° C. for 35 minutes. Subsequently 4.5 µl per well detection mix (50 mM HEPES, pH 7.5, 0.005% Tween20, 0.02% BSA, 150 mM NaCl, 45 µg/ml Ni-chelate acceptor beads, 45 µg/mlstreptavidin-donor beads) (Perkin Elmer)) were added. After 60 minutes incubation at room temperature, plates were measured in a Perkin Elmer EnVision multilabel reader. IC50 values were determined from percent inhibition values at different compound concentrations by non-linear regression analysis.

For further bromodomain selectivity profiling, additional panel assays were performed using analog protocols with minor modifications specific for the individual assay, using either TR-FRET or AlphaScreen for detection.

Preparation of Compound Dilutions

Test compounds were dissolved in DMSO (10 mM) and transferred into 1.4 mL flat bottom or V-shaped Matrix tubes carrying a unique 2D matrix. The stock solutions were stored at +2° C. if not used immediately. For the test procedure the vials were defrosted and identified by a scanner whereby a working sheet was generated that guided the subsequent working steps.

Compound dilutions were made in 96 well plates. This format enabled the assay of maximally 40 individual test compounds at 8 concentrations (single points) including 4 reference compounds, if desired (known BET inhibitors from the prior art, for this and other assays of the type disclosed herein). The dilution protocol included the production of "pre-dilution plates", "master plates" and "assay plates".

Pre-Dilution Plates: 96 polypropylene well plates were used as pre-dilution plates. A total of 4 pre-dilution plates were prepared including 10 test compounds each on the plate positions A1-A10, one standard compound at A11 and one DMSO control at A12. All dilution steps were done on a HamiltonSTAR robot.

Master Plates: 30 µL of individual compound dilutions including standard compound and controls of the 4 "pre-dilution plates" were transferred into a 384 "master plate" including the following concentrations 10000, 3003, 1000, 300, 100, 30, 10 and 3 µM, respectively in 90% of DMSO.

Assay Plates: Identical "assay plates" were then prepared by pipetting 50 nL each of compound dilutions of the "master plates" into 384-well "assay plates" by means of a HummingBird 384-channel dispenser. These plates were used directly for the assay which was performed in a total volume of 13.55 µL. This led to a final compound concentration of 37, 11, 3.7, 1.1, 0.37, 0.11, 0.037 and 0.011 µM and a final DMSO concentration of 0.37% in the assay.

Cell Growth Inhibition Assay

The human leukemia cell lines MV-4-11, THP-1 and K-562 were employed to characterize the effect of BET inhibitors on cellular proliferation and viability. Cells were obtained from the American Type Culture Collection (ATCC) and cultured at 37° C. in a humidified 5% $CO_2$ incubator in the following media: MV-4-11: DMEM high glucose (Animed #1-26F01-I), 10% FCS (Animed #2-01F26-I), 4 mM L-Glutamine (Animed #5-10K50), 1 mM Sodium Pyruvate (Animed # G03625P), 1× Penicillin-Streptomycin (Animed # F12478P); K-562: Iscove's MEM (Animed #1-28F16-I), 10% FCS (Animed #2-01F26-I), 4 mM L-Glutamine (Animed #5-10K50), 1× Penicillin-Streptomycin (Animed # F12478P); THP-1: RPMI-1640 (Animed #1-41F01-I), 10% FCS (Animed #2-01F26-I), 2 mM L-Glutamine (Animed #5-10K50), 10 mM HEPES (Animed #5-31F100), 1 mM Sodium Pyruvate (Animed # G03625P), 1x Penicillin-Streptomycin (Animed # F12478P). The AML lines MV-4-11 and THP-1 are very sensitive to BET inhibitors and show massive cell death upon BET inhibition (Zuber et al., Nature, 478 (2011), 524-8). Compound-mediated suppression of cell proliferation/viability was assessed by quantification of cellular ATP levels using the CellTiter-Glo (CTG) reagent (Promega). Briefly, cells were seeded in 20 µl fresh medium into 384-well plates, followed by addition of 5 µl medium containing compound dilutions at 5-fold their final intended concentration. Dose-response effects were assessed by 3-fold serial dilutions of the test compound, starting at 10 µM. Following incubation of the cells for 4 days at 37° C. and 5% $CO_2$, the effect of inhibitors on cell viability was quantified following addition of 20 µl CTG and luminescence quantification (integration time: 100 ms) as per vendor manual, using a correspondingly equipped Tecan M200 multi-mode platereader (TECAN, Switzerland). For data analysis, the assay background value determined in wells containing medium, but no cells, was subtracted from all data points. To enable differentiation of cytotoxic from cytostatic compounds, the number of viable cells is assessed relative to that observed at the time of compound addition using a separate cell plate (day 0). The effect of a particular test compound concentration on cell proliferation/viability is expressed as percentage of the background- and day 0-corrected luminescence reading obtained for cells treated with vehicle only (DMSO, 0.1% final concentration), which is set as 100%, whereas that luminescence reading for wells containing medium is set as −100%. Compound concentrations leading to half-maximal (1050) and total growth inhibition (TGI) were determined using standard four parameter curve fitting.

Nut-Foci Formation Assay

HCC2494 NUT midline carcinoma cells (expressing BRD4-NUT-fusion) were obtained from the University of Texas Southwestern and cultured in RPMI-1640 medium containing 10% Foetal Calf Serum at 37° C. in a humidified 5% $CO_2$ incubator.

Compound-mediated inhibition of BRD4 activity was monitored by quantification of the number and intensity of nuclear BRD4-NUT foci using automated immunofluorescence microscopy. Briefly, 5000 cells in 20 µl fresh medium were seeded into Poly-D-Lysine-precoated 384-well plates and incubated overnight at 37° C. and 5% $CO_2$, followed by addition of 5 µl medium containing compound dilutions at 5-fold their final intended concentration. Dose-response effects were assessed by 3-fold serial dilutions of the test compound, starting at 10 µM. Following incubation of the cells for 24 hours at 37° C. and 5% $CO_2$, the cells were fixed by incubation with 3.7% formaldehyde for 10 min, followed by immunofluorescence staining using rabbit anti-NUT (Cell Signaling Technologies, Cat#3625) as primary, and AlexaFluor488-labeled goat anti-rabbit (Invitrogen, Cat#A11008) as secondary antibody (latter complemented with 1 µg/mL Hoechst33342 as DNA dye). Assay plates were imaged using the appropriate filter sets on the Cellomics VTi automated fluorescence microscopy platform (ThermoFisher Scientific) and the population average of the number of NUT-foci per nucleus is quantified using the Cellomics Spot Detection BioApplication image analysis algorithm (ThermoFisher Scientific). The effect of a particular test compound concentration on NUT-foci number and intensity is expressed as percentage of the value obtained for cells treated with vehicle only (DMSO, 0.1% final concentration), which was set as 100. Compound concentrations leading to half-maximal (IC50) inhibition of the aforementioned readout parameters were determined using standard four parameter curve fitting.

Using the biochemical and cellular assays as described in this application compounds of the invention exhibit inhibitory efficacy in accordance to Tables 1 and 2, provided infra.

TABLE 1

Biochemical IC50 values*

IC50 (μM)

| Example | BRD4 | BRD2 | BRD3 | CREBBP |
|---|---|---|---|---|
| 1 | 0.046 | 0.067 | 0.053 | 7 |
| 2 | 0.02 | 0.033 | 0.015 | 8.6 |
| 3 | 0.015 | 0.027 | 0.012 | 2.6 |
| 4 | 0.064 | 0.068 | 0.068 | 1.4 |
| 5 | 0.03 | 0.032 | 0.038 | 0.56 |
| 6 | 0.092 | 0.088 | 0.088 | 2.7 |
| 7 | 0.056 | 0.06 | 0.048 | 1.5 |
| 8 | 0.086 | 0.091 | 0.079 | 0.97 |
| 9 | 0.034 | 0.043 | 0.034 | >37 |
| 10 | 0.045 | 0.06 | 0.059 | 6.3 |
| 11 | 0.018 | 0.041 | 0.025 | 5.7 |
| 12 | 0.02 | 0.043 | 0.021 | 8.9 |
| 13 | 0.037 | 0.041 | 0.039 | 4.5 |
| 14 | 0.016 | 0.033 | 0.015 | 2.3 |
| 15 | 0.037 | 0.048 | 0.041 | 16.1 |
| 16 | 0.045 | 0.049 | 0.047 | >24.05 |
| 17 | 0.041 | 0.1 | 0.075 | >37 |
| 18 | 0.013 | 0.019 | 0.011 | 27.7 |
| 19 | 0.22 | | | |
| 20 | 0.63 | 0.71 | 0.61 | 24.6 |
| 21 | 0.772 | 1.095 | 0.84 | 34.8 |
| 22 | 0.495 | 0.6066667 | 0.6033333 | >37 |
| 23 | 0.052 | 0.055 | 0.068 | |
| 24 | 0.0425 | 0.03 | 0.0415 | 0.455 |
| 25 | 0.099 | 0.12 | 0.079 | |
| 26 | 0.14 | 0.17 | 0.14 | |
| 27 | 0.12 | 0.14 | 0.096 | |
| 28 | 0.117 | 0.104 | 0.0936667 | 3.4 |
| 29 | 0.11 | 0.081 | 0.1 | 0.8 |
| 30 | 0.12 | 0.092 | 0.1 | 1 |
| 31 | 0.047 | 0.045 | 0.037 | |
| 32 | 0.17 | 0.18 | 0.13 | |
| 33 | 0.1 | 0.065 | 0.066 | 0.51 |
| 34 | 0.06525 | 0.09825 | 0.0765 | 1.6666667 |
| 35 | 0.021 | 0.043 | 0.035 | >37 |
| 36 | 0.15 | 0.1635 | 0.16 | 2.5 |
| 37 | 0.166 | 0.2745 | 0.1645 | 4.1 |
| 38 | 0.078 | 0.0925 | 0.076 | 2 |
| 39 | 0.0285 | 0.024 | 0.032 | 0.91 |
| 40 | | | | |
| 41 | 0.016 | 0.0155 | 0.017 | 0.43 |
| 42 | 0.069 | 0.065 | 0.061 | 3.4 |
| 43 | 0.064 | 0.0595 | 0.055 | 32.3 |
| 44 | 0.039 | 0.033 | 0.039 | 1 |
| 45 | 0.016 | 0.017 | 0.017 | 1 |
| 46 | 0.078 | 0.084 | 0.077 | 2 |
| 47 | 0.04 | 0.039 | 0.038 | 1.1 |
| 48 | 0.027 | 0.041 | 0.033 | 3.05 |
| 49 | 0.035 | 0.056 | 0.042 | 2.205 |
| 50 | 0.027 | 0.041 | 0.0235 | 5.4 |
| 51 | 0.0195 | 0.04 | 0.025 | 6.4 |
| 52 | 0.035 | 0.08 | 0.063 | >37 |
| 53 | 0.092 | 0.22 | 0.2 | >37 |
| 54 | 0.059 | 0.12 | 0.098 | >37 |
| 55 | 0.056 | 0.11 | 0.092 | >37 |
| 56 | 0.13 | 0.29 | 0.21 | >37 |
| 57 | <0.011 | <0.011 | <0.011 | 5.1 |
| 58 | 0.055 | 0.078 | 0.038 | 10.35 |
| 59 | 0.03 | 0.048 | 0.034 | 5.7 |
| 60 | 0.0315 | 0.096 | 0.0535 | 21.9 |
| 61 | 0.0245 | 0.1 | 0.0515 | 17.9 |
| 62 | 0.12 | 0.15 | 0.086 | 31.35 |
| 63 | 0.072 | 0.24 | 0.0965 | 21.9 |
| 64 | 0.043 | 0.12 | 0.058 | 10.15 |
| 65 | 0.024 | 0.05 | 0.0275 | 4 |
| 66 | 0.0315 | 0.086 | 0.066 | 3.45 |
| 67 | 0.017 | 0.038 | 0.0205 | 5.2 |
| 68 | 0.03 | 0.077 | 0.0445 | 5 |
| 69 | 0.012 | 0.024 | 0.013 | 6.1 |
| 70 | 0.0175 | 0.032 | 0.017 | 6.65 |
| 71 | 0.0185 | 0.033 | 0.018 | 4.3 |
| 72 | 0.012 | 0.023 | <0.011 | 5.1 |
| 73 | 0.058 | 0.15 | 0.0925 | 16.1 |
| 74 | 0.032 | 0.14 | 0.061 | 10.3 |
| 75 | 0.017 | 0.027 | 0.024 | 4.9 |
| 76 | 0.054 | 0.097 | 0.064 | 2.05 |
| 77 | <0.024 | 0.052 | 0.039 | 1.44 |
| 78 | 0.028 | 0.048 | 0.031 | 4.3 |
| 79 | 0.026 | 0.046 | 0.0215 | 3.4 |
| 80 | 0.013 | 0.017 | 0.012 | 1.45 |
| 81 | <0.011 | <0.011 | <0.011 | 1.5 |
| 82 | <0.011 | 0.013 | <0.011 | 1.075 |
| 83 | 0.024 | 0.065 | 0.03 | >37 |
| 84 | 0.018 | 0.036 | 0.024 | 3.5 |
| 85 | 0.015 | 0.029 | 0.02 | 3.65 |
| 86 | <0.011 | 0.019 | <0.011 | 3.8 |
| 87 | 0.014 | 0.025 | 0.014 | 1.8 |
| 88 | 0.039 | 0.075 | 0.043 | 15 |
| 89 | 0.015 | 0.035 | 0.013 | 8.35 |
| 90 | 0.03 | 0.067 | 0.037 | 13.1 |
| 91 | 0.0345 | 0.095 | 0.045 | 17.5 |
| 92 | <0.011 | 0.027 | 0.027 | 5.8 |
| 93 | 0.0215 | | 0.034 | 2.7 |
| 94 | 0.0715 | | 0.046 | 8.05 |
| 95 | 0.0265 | | 0.029 | 1.95 |
| 96 | 0.039 | | 0.0335 | 3.95 |
| 97 | 0.0235 | 0.058 | 0.0355 | 15.65 |
| 98 | 0.015 | 0.028 | 0.023 | 2.9 |
| 99 | 0.016 | | 0.018 | 0.96 |
| 100 | 0.0265 | 0.063 | 0.025 | >37 |
| 101 | 0.023 | 0.034 | 0.024 | 19.6 |
| 102 | 0.015 | 0.02 | 0.017 | 17.4 |
| 103 | <0.011 | <0.011 | <0.011 | >37 |
| 104 | 0.0245 | 0.041 | 0.033 | 2.8 |
| 105 | 0.013 | | 0.017 | 2 |
| 106 | 0.0405 | 0.09 | 0.0415 | 7.2 |
| 107 | 0.023 | 0.028 | 0.023 | 1.45 |
| 108 | 0.061 | 0.18 | 0.074 | 9.75 |
| 109 | 0.022 | 0.038 | 0.019 | 4.35 |
| 110 | <0.011 | 0.012 | <0.011 | 35.9 |
| 111 | 0.014 | 0.033 | 0.02 | 8.9 |
| 112 | <0.011 | 0.013 | <0.011 | 0.775 |
| 113 | 0.2 | 0.1 | 0.1015 | >37 |
| 114 | 0.038 | 0.087 | 0.1 | 12.9 |
| 115 | 0.048 | 0.068 | 0.066 | |
| 116 | 0.041 | | 0.058 | 2.25 |
| 117 | 0.0245 | | 0.03 | 2.7 |
| 118 | <0.011 | 0.014 | 0.012 | 1.085 |
| 119 | | | | |
| 120 | 0.0205 | 0.0355 | 0.0295 | 5.1333333 |
| 121 | 0.029 | 0.029 | 0.027 | 4.4 |
| 122 | 0.019 | 0.0215 | 0.026 | 2.6166667 |
| 123 | 0.065 | 0.097 | 0.087 | 5.5 |
| 124 | 0.038 | 0.094 | 0.039 | 3.8 |
| 125 | | | | 34.9 |
| 126 | 0.1043333 | 0.385 | 0.2833333 | 25.9 |
| 127 | 0.12 | 0.36 | 0.48 | >37 |
| 128 | 0.0845 | 0.22 | 0.136 | 16.45 |
| 129 | 1.84 | 4.7 | 2.32 | >37 |
| 130 | 0.18 | 0.23 | 0.16 | 2.4 |
| 131 | 0.028 | 0.049 | 0.031 | >37 |
| 132 | <0.011 | 0.019 | 0.012 | 27.5 |
| 133 | 0.023 | 0.035 | 0.0195 | 5.4 |
| 134 | 0.038 | 0.08 | 0.035 | 1.68 |
| 135 | 0.031 | 0.053 | 0.037 | 3.85 |
| 136 | 0.03 | | 0.032 | 2.6 |
| 137 | 0.0845 | | 0.089 | |
| 138 | 0.011 | 0.026 | 0.011 | >37 |
| 139 | 0.0325 | 0.086 | 0.042 | >37 |

TABLE 1-continued

Biochemical IC50 values*

| Example | BRD4 IC50 (μM) | BRD2 | BRD3 | CREBBP |
|---|---|---|---|---|
| 140 | 0.029 | 0.042 | 0.028 | >37 |
| 141 | 0.0235 | 0.047 | 0.021 | >37 |
| 142 | 0.04 | 0.096 | 0.036 | 1.75 |
| 143 | 0.019 | 0.034 | 0.018 | >37 |
| 144 | 0.023 | 0.026 | 0.022 | >37 |
| 145 | 0.028 | 0.054 | 0.029 | >37 |
| 146 | <0.011 | 0.02 | 0.012 | >37 |
| 147 | 0.013 | 0.06 | 0.044 | 34.3 |
| 148 | 0.023 | 0.036 | 0.022 | >37 |
| 149 | 0.016 | 0.022 | 0.021 | >37 |
| 150 | 0.038 | 0.094 | 0.039 | >37 |
| 151 | 0.011 | 0.014 | 0.014 | 13.9 |
| 152 | 0.025 |  | 0.0225 | 0.525 |
| 153 | 0.013 | 0.025 | 0.023 | 28.9 |
| 154 | 0.019 | 0.042 | 0.019 | >37 |
| 155 |  |  |  |  |
| 156 | 0.025 | 0.032 | 0.0295 | 0.26 |
| 157 |  |  |  |  |
| 158 | <0.011 | 0.016 | <0.011 | >37 |
| 159 | <0.011 | 0.016 | 0.012 | 12.55 |
| 160 | <0.011 |  | <0.011 | >37 |
| 161 | 0.015 | 0.03 | 0.016 | >37 |
| 162 | 0.0115 |  | 0.013 | >37 |
| 163 | 0.013 |  | 0.016 | >37 |
| 164 | <0.011 |  | <0.011 | 11.25 |
| 165 | 0.019 |  | 0.018 | 14.75 |
| 166 | 0.013 |  | 0.012 | 33.1 |
| 167 | 0.035 | 0.063 | 0.053 | 1.65 |
| 168 | <0.011 | 0.017 | <0.011 | >37 |
| 169 | 0.019 | 0.025 | 0.033 | >37 |
| 170 | 0.031 |  | 0.043 | >37 |
| 171 | 0.012 |  | <0.011 | 17.8 |
| 172 | 0.013 |  | 0.017 | 0.98 |

*Values from either single determination or n ≥ 2 independent determinations

TABLE 2

Cellular IC50 values*

| Example | MV-4-11 GI50 (μM) | MV-4-11 TGI (μM) | THP-1 GI50 (μM) | THP-1 TGI (μM) | K-562 GI50 (μM) | K-562 TGI (μM) | HCS Brd4-NUT IC50 (μM) |
|---|---|---|---|---|---|---|---|
| 1 | 0.02635 | 0.05235 | 0.0384 | 0.0799 | 0.1595 | >10 | 0.02795 |
| 2 | 0.0138 | 0.02865 | 0.0234 | 0.04095 | 0.09595 | >10 | 0.01453 |
| 3 | 0.008195 | 0.01445 | 0.0137 | 0.02755 | 0.05515 | >10 | 0.01235 |
| 4 | 0.0695 | 0.116 | 0.11 | 0.207 | 0.254 | >10 | 0.0747 |
| 5 | 0.0371 | 0.0739 | 0.06 | 0.106 | 0.221 | >10 | 0.067 |
| 6 | 0.0601 | 0.102 | 0.161 | 0.324 | 0.23 | >10 | 0.0863 |
| 7 | 0.0446 | 0.085 | 0.0655 | 0.111 | 0.17 | >10 | 0.0735 |
| 8 | 0.051 | 0.098 | 0.152 | 0.314 | 0.309 | >10 | 0.092 |
| 9 | 0.0484 | 0.0942 | 0.0987 | 0.175 | 0.258 | >10 | 2.0865 |
| 10 | 0.0297 | 0.0785 | 0.1585 | 0.302 | 0.3265 | >10 | 0.1795 |
| 11 | 0.04845 | 0.09775 | 0.0909 | 0.2025 | 0.33 | >10 | 0.11 |
| 12 | 0.04225 | 0.07845 | 0.2635 | 0.715 | 1.035 | >10 | 0.3735 |
| 13 | 0.01129 | 0.02715 | 0.0261 | 0.05945 | 0.114 | >10 | 0.01614 |
| 14 | 0.0204 | 0.0388 | 0.066 | 0.12 | 0.203 | >10 | 0.0409 |
| 15 | 0.042 | 0.08625 | 0.0719 | 0.132 | 0.3175 | >10 | 0.08005 |
| 16 | 0.0743 | 0.1255 | 0.22 | 0.37 | 0.5625 | >10 | 0.2625 |
| 17 | 0.1665 | 0.3165 | 0.3225 | 0.7045 | 1.085 | >10 | 0.323 |
| 18 | 0.01125 | 0.02695 | 0.01595 | 0.0356 | 0.09095 | >10 | 0.007555 |
| 19 |  |  |  |  |  |  |  |
| 20 |  |  |  |  |  | >10 |  |
| 21 |  |  |  |  |  |  |  |
| 22 |  |  |  |  |  |  |  |
| 23 | 0.0875 | 0.143 | 0.158 | 0.311 | 0.381 | >10 |  |
| 24 |  |  |  |  |  |  |  |
| 25 | 0.0657 | 0.0904 | 0.118 | 0.209 | 0.528 | >10 |  |
| 26 |  |  |  |  |  |  |  |
| 27 | 0.0827 | 0.142 | 0.195 | 0.433 | 0.861 | >10 | 0.2795 |
| 28 | 0.0979 | 0.136 | 0.208 | 0.384 | 0.908 | >10 |  |
| 29 |  |  |  |  |  |  |  |
| 30 |  |  |  |  |  |  |  |
| 31 | 0.0364 | 0.0599 | 0.0794 | 0.125 | 0.349 | >10 |  |
| 32 |  |  |  |  |  |  |  |
| 33 |  |  |  |  |  |  |  |
| 34 | 0.0366 | 0.0766 | 0.0649 | 0.109 | 0.219 | >10 |  |
| 35 | 0.226 | 0.384 | 0.289 | 0.462 | 0.946 | >10 |  |
| 36 | 0.0598 | 0.104 | 0.115 | 0.235 | 0.25 | >10 |  |
| 37 | 0.0669 | 0.105 | 0.1 | 0.195 | 0.32 | >10 |  |
| 38 | 0.0301 | 0.0489 | 0.0749 | 0.118 | 0.271 | >10 | 0.02455 |
| 39 | 0.01165 | 0.0239 | 0.02625 | 0.0481 | 0.072 | >10 | 0.0211 |
| 40 |  |  |  |  |  |  |  |
| 41 | 0.00672 | 0.011 | 0.0138 | 0.0306 | 0.0452 | >10 | 0.007 |
| 42 | 0.0535 | 0.1023 | 0.07435 | 0.126 | 0.2735 | >10 | 0.06415 |
| 43 | 0.06615 | 0.09955 | 0.09045 | 0.1625 | 0.3565 | >10 | 0.05285 |

TABLE 2-continued

Cellular IC50 values*

| Example | MV-4-11 GI50 (μM) | MV-4-11 TGI (μM) | THP-1 GI50 (μM) | THP-1 TGI (μM) | K-562 GI50 (μM) | K-562 TGI (μM) | HCS Brd4-NUT IC50 (μM) |
|---|---|---|---|---|---|---|---|
| 44 | | | | | | | |
| 45 | 0.0225 | 0.0439 | 0.0328 | 0.0605 | 0.126 | >10 | 0.0497 |
| 46 | 0.0653 | 0.108 | 0.145 | 0.305 | 0.499 | >10 | 0.226 |
| 47 | 0.04255 | 0.1028 | 0.07435 | 0.141 | 0.305 | >10 | 0.0813 |
| 48 | 0.0105 | 0.0245 | 0.0565 | 0.109 | 0.351 | >10 | |
| 49 | 0.191 | 0.32 | 0.989 | 1.47 | 2.04 | >10 | |
| 50 | 0.0288 | 0.0571 | 0.233 | 0.495 | 0.575 | >10 | |
| 51 | 0.0224 | 0.0479 | 0.212 | 0.612 | 0.439 | >10 | |
| 52 | 0.271 | 0.409 | 0.981 | 1.92 | 2.48 | >10 | 0.71 |
| 53 | 0.505 | 0.939 | 1.27 | 3.74 | 7.99 | >10 | 1.33 |
| 54 | 2.1 | 3.6 | 3.71 | >10 | >10 | >10 | 3.39 |
| 55 | 0.706 | 1.06 | 2 | 4.41 | 7.25 | >10 | 2.8 |
| 56 | 0.816 | 1.34 | 1.24 | 3.67 | 3.23 | >10 | 1.21 |
| 57 | 0.0405 | 0.0688 | 0.0836 | 0.193 | 0.572 | >10 | 0.0912 |
| 58 | 0.02375 | 0.04875 | 0.09945 | 0.2075 | 0.3665 | >10 | |
| 59 | 0.0178 | 0.0349 | 0.041 | 0.114 | 0.117 | >10 | |
| 60 | 0.03405 | 0.0631 | 0.06905 | 0.132 | 0.2795 | >10 | |
| 61 | 0.0282 | 0.0551 | 0.0654 | 0.149 | 0.116 | >10 | |
| 62 | 0.04185 | 0.08025 | 0.1635 | 0.3315 | 0.391 | >10 | |
| 63 | 0.0882 | 0.141 | 0.192 | 0.369 | 0.458 | >10 | |
| 64 | 0.0351 | 0.0546 | 0.0843 | 0.155 | 0.156 | >10 | |
| 65 | 0.0193 | 0.03895 | 0.1375 | 0.2995 | 0.298 | >10 | |
| 66 | 0.2325 | 0.43 | 1.755 | 5.86 | 5.545 | >10 | |
| 67 | 0.165 | 0.3325 | 1.275 | 3.275 | 5.405 | >10 | |
| 68 | 0.0213 | 0.0371 | 0.2585 | 0.458 | 1.3825 | >10 | |
| 69 | 0.03155 | 0.05845 | 0.0634 | 0.1675 | 0.184 | >10 | |
| 70 | 0.02955 | 0.0413 | 0.05985 | 0.188 | 0.353 | >10 | |
| 71 | 0.0313 | 0.0445 | 0.0637 | 0.1385 | 0.228 | >10 | |
| 72 | 0.0458 | 0.0969 | 0.222 | 0.746 | 1.34 | >10 | |
| 73 | 0.0306 | 0.0527 | 0.09365 | 0.2545 | 0.2995 | >10 | |
| 74 | 0.03815 | 0.05925 | 0.0579 | 0.121 | 0.1575 | >10 | |
| 75 | 0.7805 | 1.125 | 1.605 | 8.63 | 8.65 | >10 | |
| 76 | 0.0233 | 0.0388 | 0.09565 | 0.266 | 0.3145 | >10 | |
| 77 | 0.00493 | 0.00936 | 0.00794 | 0.0217 | 0.0215 | >10 | |
| 78 | 0.00454 | 0.00958 | 0.0144 | 0.0388 | 0.0496 | >10 | |
| 79 | 0.00558 | 0.0111 | 0.007925 | 0.0179 | 0.02955 | >10 | |
| 80 | 0.00414 | 0.00945 | 0.00553 | 0.0154 | 0.0288 | >10 | |
| 81 | 0.00342 | 0.005405 | 0.003825 | 0.0107 | 0.0195 | >10 | |
| 82 | 0.00157 | 0.00603 | 0.00254 | 0.00982 | 0.00896 | >10 | |
| 83 | 0.0239 | 0.0464 | 0.0271 | 0.0722 | 0.105 | >10 | |
| 84 | 0.0146 | 0.0294 | 0.044 | 0.0998 | 0.0732 | >10 | |
| 85 | 0.0163 | 0.0325 | 0.138 | 0.37 | 0.277 | >10 | |
| 86 | 0.02075 | 0.043 | 0.057 | 0.155 | 0.2495 | >10 | |
| 87 | 0.00854 | 0.01445 | 0.02755 | 0.0792 | 0.1665 | >10 | |
| 88 | 0.0237 | 0.03985 | 0.04275 | 0.11215 | 0.1715 | >10 | |
| 89 | 0.01034 | 0.0208 | 0.01495 | 0.04045 | 0.0636 | >10 | |
| 90 | 0.0162 | 0.03175 | 0.08275 | 0.271 | 0.27 | >10 | |
| 91 | 0.02745 | 0.0637 | 0.1225 | 0.334 | 0.353 | >10 | |
| 92 | 0.0153 | 0.03365 | 0.02395 | 0.0784 | 0.10985 | >10 | |
| 93 | 0.01595 | 0.032 | 0.02125 | 0.06935 | 0.10365 | >10 | |
| 94 | 0.0406 | 0.0687 | 0.04745 | 0.09435 | 0.2695 | >10 | |
| 95 | 0.02805 | 0.042 | 0.017 | 0.0524 | 0.0857 | >10 | |
| 96 | 0.0793 | 0.1206 | 0.20195 | 0.27355 | 0.351 | >10 | |
| 97 | 0.0384 | 0.0902 | 0.1475 | 0.432 | 0.5955 | >10 | |
| 98 | 0.126 | 0.282 | 0.472 | 2.14 | 3.63 | >10 | |
| 99 | | | | | | | |
| 100 | 0.004965 | 0.0138 | 0.007225 | 0.0267 | 0.04285 | >10 | |
| 101 | 0.001865 | 0.00411 | 0.003495 | 0.01105 | 0.01555 | >10 | |
| 102 | 0.00138 | 0.004435 | 0.00295 | 0.01051 | 0.0134 | >10 | |
| 103 | 0.00209 | 0.003945 | 0.003465 | 0.01055 | 0.01239 | >10 | |
| 104 | 0.008215 | 0.0187 | 0.02125 | 0.05395 | 0.05335 | >10 | |
| 105 | 0.01076 | 0.02195 | 0.01235 | 0.02785 | 0.09025 | >10 | |
| 106 | 0.0193 | 0.0347 | 0.0501 | 0.0868 | 0.0925 | >10 | |
| 107 | 0.00484 | 0.00971 | 0.01125 | 0.02375 | 0.0418 | >10 | |
| 108 | 0.0207 | 0.04295 | 0.04735 | 0.113 | 0.132 | >10 | |
| 109 | 0.006285 | 0.01535 | 0.0119 | 0.0358 | 0.052 | >10 | |
| 110 | 0.00448 | 0.011 | 0.00694 | 0.0216 | 0.0306 | >10 | |
| 111 | 0.01855 | 0.04465 | 0.0402 | 0.0921 | 0.09005 | >10 | |
| 112 | 0.00172 | 0.00461 | 0.00479 | 0.00984 | 0.0172 | >10 | |
| 113 | 0.125 | 0.186 | 0.171 | 0.3595 | 0.3585 | >10 | |
| 114 | 0.0777 | 0.1585 | 0.1175 | 0.3005 | 0.268 | >10 | |
| 115 | 0.0103 | 0.0177 | 0.0234 | 0.0581 | 0.102 | >10 | 0.0205 |

TABLE 2-continued

Cellular IC50 values*

| Example | MV-4-11 GI50 (μM) | MV-4-11 TGI (μM) | THP-1 GI50 (μM) | THP-1 TGI (μM) | K-562 GI50 (μM) | K-562 TGI (μM) | HCS Brd4-NUT IC50 (μM) |
|---|---|---|---|---|---|---|---|
| 116 | 0.07145 | 0.1175 | 0.09105 | 0.166 | 0.3295 | >10 | |
| 117 | 0.06955 | 0.112 | 0.08105 | 0.129 | 0.207 | >10 | |
| 118 | 0.0021 | 0.00379 | 0.00512 | 0.0125 | 0.0284 | >10 | 0.0034 |
| 119 | | | | | | | |
| 120 | | | | | | | |
| 121 | 0.0108 | 0.0209 | 0.009 | 0.0201 | 0.0481 | >10 | 0.00307 |
| 122 | | | | | | | |
| 123 | | | | | | | |
| 124 | 0.0562 | 0.09675 | 0.0663 | 0.1345 | 0.257 | >10 | |
| 125 | 0.809 | 1.12 | 2.14 | 3.92 | 5.29 | >10 | 1.95 |
| 126 | 0.408 | 0.592 | 0.947 | 1.7 | 2.27 | >10 | |
| 127 | 0.209 | 0.317 | 0.377 | 0.966 | 1.72 | >10 | 0.408 |
| 128 | 0.1885 | 0.3505 | 0.371 | 0.947 | 1.23 | >10 | |
| 129 | 0.209 | 0.343 | 0.6625 | 1.08 | 1.07 | >10 | |
| 130 | 0.167 | 0.3905 | 0.526 | 1.21 | 1.945 | >10 | |
| 131 | 0.0164 | 0.0295 | 0.0238 | 0.055 | 0.0875 | >10 | |
| 132 | 0.009435 | 0.0189 | 0.01255 | 0.03315 | 0.0518 | >10 | |
| 133 | 0.0351 | 0.0608 | 0.0656 | 0.1375 | 0.1415 | >10 | |
| 134 | 0.0724 | 0.141 | 0.1205 | 0.399 | 0.61 | >10 | |
| 135 | 0.06495 | 0.1115 | 0.265 | 0.964 | 0.806 | >10 | |
| 136 | 0.07665 | 0.114 | 0.07935 | 0.1795 | 0.227 | >10 | |
| 137 | 0.09025 | 0.1245 | 0.1008 | 0.213 | 0.2535 | >10 | |
| 138 | 0.007975 | 0.013 | 0.00937 | 0.0236 | 0.0372 | >10 | |
| 139 | 0.05755 | 0.0992 | 0.0407 | 0.1155 | 0.2145 | >10 | |
| 140 | 0.03845 | 0.0668 | 0.0636 | 0.1245 | 0.18 | >10 | |
| 141 | 0.07325 | 0.1115 | 0.07695 | 0.179 | 0.2015 | >10 | |
| 142 | | | | | | | |
| 143 | 0.00919 | 0.0161 | 0.0113 | 0.03065 | 0.04405 | >10 | |
| 144 | 0.03085 | 0.0469 | 0.04625 | 0.09295 | 0.11625 | >10 | |
| 145 | 0.014 | 0.02695 | 0.0222 | 0.0476 | 0.07025 | >10 | |
| 146 | 0.009565 | 0.01505 | 0.011035 | 0.02975 | 0.04685 | >10 | |
| 147 | 0.00812 | 0.01625 | 0.01185 | 0.03355 | 0.05195 | >10 | |
| 148 | 0.00647 | 0.0131 | 0.00999 | 0.02495 | 0.06955 | >10 | |
| 149 | 0.02645 | 0.0435 | 0.0333 | 0.0839 | 0.14765 | >10 | |
| 150 | 0.009635 | 0.0242 | 0.0173 | 0.0464 | 0.0753 | >10 | |
| 151 | 0.003735 | 0.008015 | 0.006845 | 0.01745 | 0.0241 | >10 | |
| 152 | 0.0344 | 0.0573 | 0.0627 | 0.1355 | 0.244 | >10 | |
| 153 | 0.0256 | 0.0386 | 0.01835 | 0.0443 | 0.09505 | >10 | |
| 154 | 0.00364 | 0.008305 | 0.004675 | 0.0122 | 0.02145 | >10 | |
| 155 | | | | | | | |
| 156 | 0.02535 | 0.05135 | 0.04335 | 0.099 | 0.122 | >10 | |
| 157 | 0.0106 | 0.01515 | 0.008825 | 0.02475 | 0.05685 | >10 | |
| 158 | 0.00164 | 0.00329 | 0.002 | 0.005065 | 0.008735 | >10 | |
| 159 | 0.00586 | 0.0156 | 0.0121 | 0.0315 | 0.0405 | >10 | |
| 160 | 0.00595 | 0.0049733 | 0.0046 | 0.0063833 | 0.0258333 | >7 | |
| 161 | 0.00599 | 0.01365 | 0.00609 | 0.01365 | 0.0752 | >10 | |
| 162 | 0.0043667 | 0.01112 | 0.00503 | 0.0105367 | 0.0409667 | >7 | |
| 163 | 0.01553 | 0.02905 | 0.01578 | 0.02575 | 0.0533 | >10 | |
| 164 | 0.000887 | 0.00183 | 0.00112 | 0.00243 | 0.013245 | >10 | |
| 165 | 0.00412 | 0.01274 | 0.004 | 0.01567 | 0.0479 | >10 | |
| 166 | 0.005425 | 0.00815 | 0.00754 | 0.01128 | 0.0846 | >10 | |
| 167 | 0.03365 | 0.05785 | 0.1029 | 0.1885 | 0.537 | >10 | |
| 168 | 0.00299 | 0.0077 | 0.00565 | 0.0189 | 0.0308 | >10 | |
| 169 | 0.001945 | 0.005325 | 0.01155 | 0.03295 | 0.0559 | >10 | |
| 170 | | | | | | | |
| 171 | | | | | | | |
| 172 | 0.00522 | 0.010325 | 0.006275 | 0.01226 | 0.01955 | >10 | |

*Values from either single determination or n ≥ 2 independent determinations

The invention claimed is:
1. A compound of formula (I) or a pharmaceutically acceptable salt thereof,

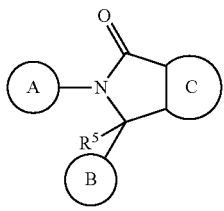

wherein
A is selected from:

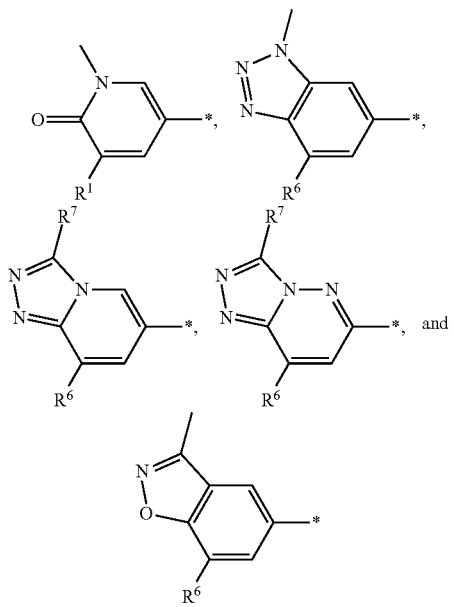

B is selected from

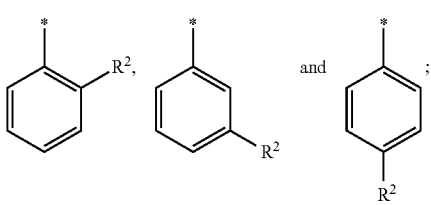

C is

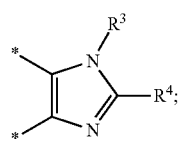

R¹ is selected from H, halo and methyl;
R² is selected from halo, cyano, methyl, —CF₃ and —O(C₁-C₄alkyl);
R³ is selected from H, methyl, ethyl, n-propyl, iso-propyl, n-butyl, sec-butyl, iso-butyl, tert-butyl, cyclopropyl, cyclobutyl, cyclopentyl, and methoxyethyl;
R⁴ is selected from:
methyl, cyclopropyl, cyclobutyl, cyclopentyl,

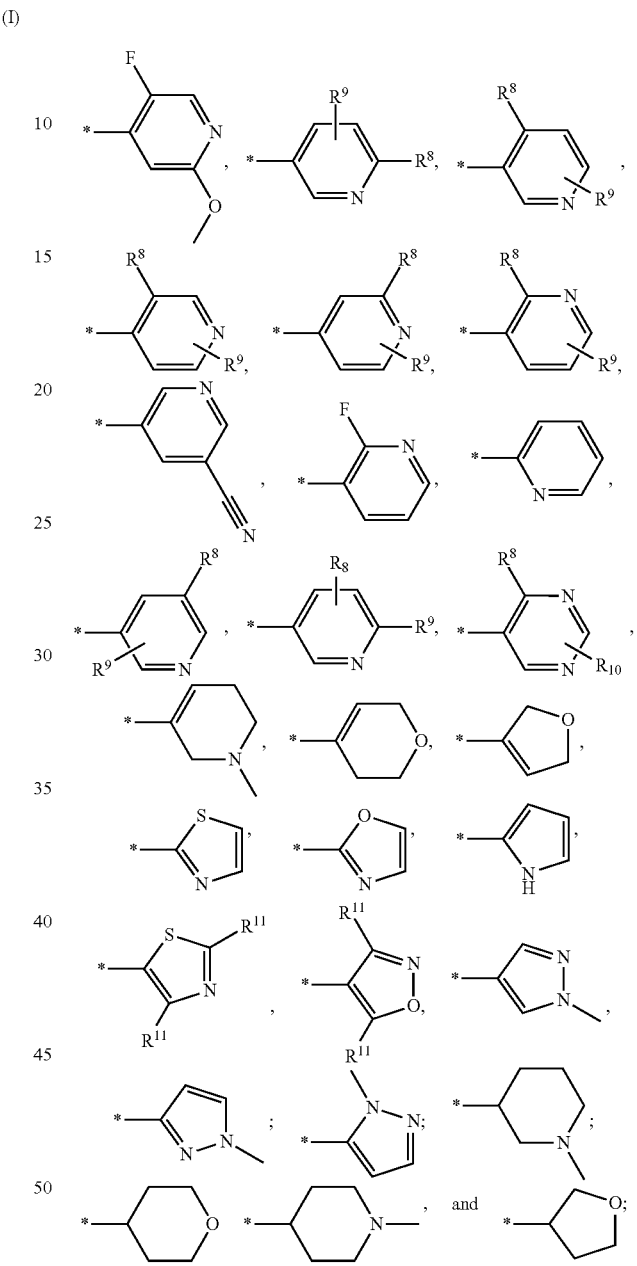

wherein
R⁸ is independently selected from OCH₃, OH and OCF₃;
R⁹ is selected from H and halo;
R¹⁰ is selected from H, O(C₁-C₄)alkyl, and OH;
each R¹¹ is independently selected from H, and CH₃;
R⁵ is H;
R⁶ is selected from methyl and methoxy; and
R⁷ is selected from methyl, —CH₂F and —CHF₂;
and wherein * indicates the point of attachment to the remainder of the molecule.

2. A compound of formula (I), or a pharmaceutically acceptable salt thereof, according to claim 1, wherein A is selected from:

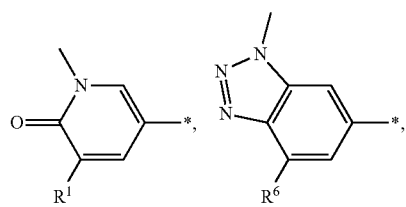
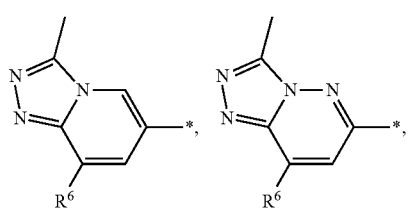
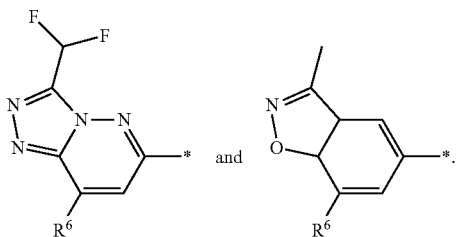

3. A compound of formula (I), or a pharmaceutically acceptable salt thereof, according to claim 1, wherein B is

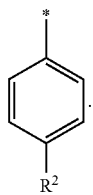

4. A compound of formula (I), or a pharmaceutically acceptable salt thereof, according to claim 1, wherein $R^4$ is selected from: methyl, cyclopropyl, cyclobutyl, cyclopentyl,

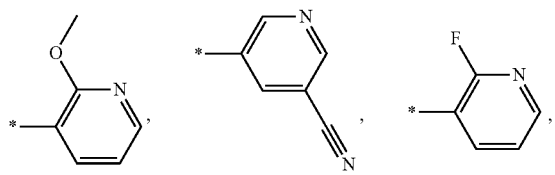

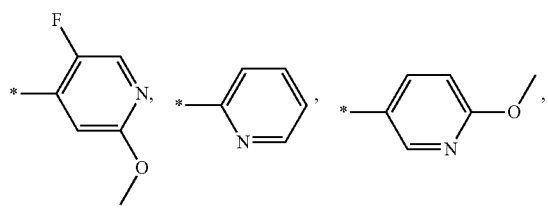

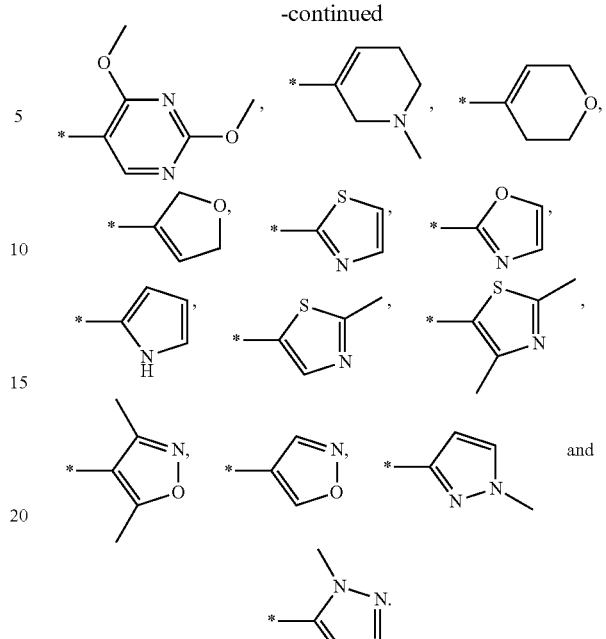

5. A compound of formula (I), or a pharmaceutically acceptable salt thereof, according to claim 1, which is selected from:

Example 3: 6-(4-chlorophenyl)-5-(3,7-dimethyl-3H-benzo[d][1,2,3]triazol-5-yl)-3-isopropyl-2-methyl-5,6-dihydropyrrolo[3,4-d]imidazol-4(3H)-one;

Example 6: 6-(4-chlorophenyl)-5-(1,5-dimethyl-6-oxo-1,6-dihydropyridin-3-yl)-2-(6-methoxypyridin-3-yl)-3-methyl-5,6-dihydropyrrolo[3,4-d]imidazol-4(3H)-one;

Example 7: (R)-6-(4-chlorophenyl)-5-(1,5-dimethyl-6-oxo-1,6-dihydropyridin-3-yl)-2-(6-methoxypyridin-3-yl)-3-methyl-5,6-dihydropyrrolo[3,4-d]imidazol-4(3H)-one;

Example 36: 6-(4-chlorophenyl)-5-(1,5-dimethyl-6-oxo-1,6-dihydropyridin-3-yl)-2-(5-fluoro-2-methoxypyridin-4-yl)-3-propyl-5,6-dihydropyrrolo[3,4-d]imidazol-4(3H)-one;

Example 37: 5-(4-(4-chlorophenyl)-5-(1,5-dimethyl-6-oxo-1,6-dihydropyridin-3-yl)-6-oxo-1-propyl-1,4,5,6-tetrahydropyrrolo[3,4-d]imidazol-2-yl)nicotinonitrile;

Example 38: 6-(4-chlorophenyl)-5-(1,5-dimethyl-6-oxo-1,6-dihydropyridin-3-yl)-3-ethyl-2-(6-methoxypyridin-3-yl)-5,6-dihydropyrrolo[3,4-d]imidazol-4(3H)-one;

Example 39: (R)-6-(4-chlorophenyl)-5-(1,5-dimethyl-6-oxo-1,6-dihydropyridin-3-yl)-3-ethyl-2-(6-methoxypyridin-3-yl)-5,6-dihydropyrrolo[3,4-d]imidazol-4(3H)-one;

Example 40: 6-(4-chlorophenyl)-5-(1,5-dimethyl-6-oxo-1,6-dihydropyridin-3-yl)-3-ethyl-2-(2-methoxypyridin-3-yl)-5,6-dihydropyrrolo[3,4-d]imidazol-4(3H)-one;

Example 41: (R)-6-(4-chlorophenyl)-5-(1,5-dimethyl-6-oxo-1,6-dihydropyridin-3-yl)-3-ethyl-2-(2-methoxypyridin-3-yl)-5,6-dihydropyrrolo[3,4-d]imidazol-4(3H)-one;

Example 42: 6-(4-chlorophenyl)-5-(1,5-dimethyl-6-oxo-1,6-dihydropyridin-3-yl)-3-ethyl-2-(1-methyl-1H-pyrazol-5-yl)-5,6-dihydropyrrolo[3,4-d]imidazol-4(3H)-one;

Example 44: 6-(4-chlorophenyl)-5-(1,5-dimethyl-6-oxo-1,6-dihydropyridin-3-yl)-3-isopropyl-2-(2-methoxypyridin-3-yl)-5,6-dihydropyrrolo[3,4-d]imidazol-4(3H)-one;

Example 45: (R)-6-(4-chlorophenyl)-5-(1,5-dimethyl-6-oxo-1,6-dihydropyridin-3-yl)-3-isopropyl-2-(2-methoxypyridin-3-yl)-5,6-dihydropyrrolo[3,4-d]imidazol-4(3H)-one;

Example 46: 6-(4-chlorophenyl)-2-cyclopropyl-5-(1,5-dimethyl-6-oxo-1,6-dihydropyridin-3-yl)-5,6-dihydropyrrolo[3,4-d]imidazol-4(3H)-one; and Example 47: R- 6-(4-chlorophenyl)-2-cyclopropyl-5-(1,5-dimethyl-6-oxo-1,6-dihydropyridin-3-yl)-5,6-dihydropyrrolo[3,4-d]imidazol-4(3H)-one.

6. A pharmaceutical composition comprising a therapeutically effective amount of a compound according to claim 1 or a pharmaceutically acceptable salt thereof and one or more pharmaceutically acceptable carriers.

7. A combination comprising a therapeutically effective amount of a compound according to claim 1 or a pharmaceutically acceptable salt thereof and one or more therapeutically active agents.

8. A method of modulating BET protein activity in a subject, wherein the method comprises administering to the subject a therapeutically effective amount of the compound according to claim 1 or a pharmaceutically acceptable salt thereof.

9. A method of claim 8, wherein said subject having a cancer.

10. A compound, or a pharmaceutically acceptable salt thereof, which is

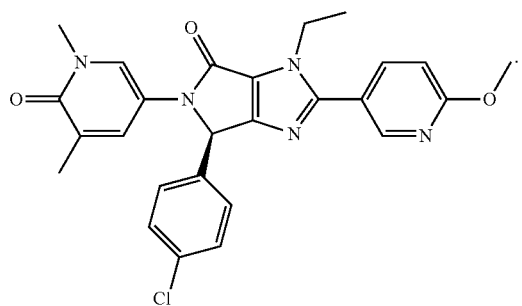 [SMILES: CCn1c(-c2ccc(OC)nc2)nc2c1C(=O)N(c1cc(C)c(=O)n(C)c1)[C@@H]2c1ccc(Cl)cc1]

11. A compound, or a pharmaceutically acceptable salt thereof, which is

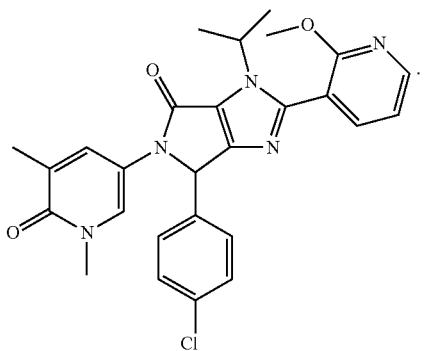 [SMILES: COc1ncccc1-c1nc2c(n1C(C)C)C(=O)N(c1cc(C)c(=O)n(C)c1)C2c1ccc(Cl)cc1]

12. A compound, or a pharmaceutically acceptable salt thereof, which is

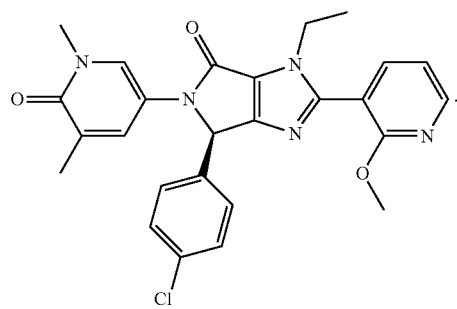 [SMILES: CCn1c(-c2cccnc2OC)nc2c1C(=O)N(c1cc(C)c(=O)n(C)c1)[C@@H]2c1ccc(Cl)cc1]

13. A compound, or a pharmaceutically acceptable salt thereof, which is

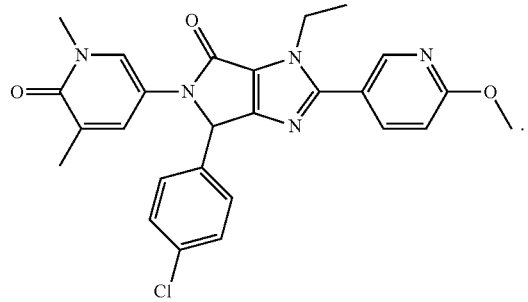 [SMILES: CCn1c(-c2ccc(OC)nc2)nc2c1C(=O)N(c1cc(C)c(=O)n(C)c1)C2c1ccc(Cl)cc1]

* * * * *